US009379361B2

(12) United States Patent
Tsurutani et al.

(10) Patent No.: US 9,379,361 B2
(45) Date of Patent: Jun. 28, 2016

(54) ORGANIC ELECTROLUMINESCENT ELEMENT, ORGANIC ELECTROLUMINESCENT LIGHTING DEVICE AND ORGANIC ELECTROLUMINESCENT DISPLAY DEVICE

(71) Applicant: MITSUBISHI CHEMICAL CORPORATION, Chiyoda-ku (JP)

(72) Inventors: Yasuyuki Tsurutani, Kanagawa (JP); Hideki Gorohmaru, Kanagawa (JP); Ichiro Imada, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 14/551,768

(22) Filed: Nov. 24, 2014

(65) Prior Publication Data

US 2015/0076483 A1    Mar. 19, 2015

Related U.S. Application Data

(63) Continuation of application No. PCT/JP2013/064286, filed on May 22, 2013.

(30) Foreign Application Priority Data

May 24, 2012 (JP) ................................. 2012-118717

(51) Int. Cl.
*H01L 51/50* (2006.01)
*H01L 51/56* (2006.01)
(Continued)

(52) U.S. Cl.
CPC .............. *H01L 51/56* (2013.01); *C07C 211/54* (2013.01); *C07C 211/61* (2013.01); *C07D 401/14* (2013.01); *C07D 403/10* (2013.01);
(Continued)

(58) Field of Classification Search
None
See application file for complete search history.

(56) References Cited

U.S. PATENT DOCUMENTS 7,453,200 B2    11/2008    Jou et al.
2007/0015006 A1   1/2007    Lee et al.
(Continued)

FOREIGN PATENT DOCUMENTS

EP    2 362 460 A1    8/2011
JP    2003-86370 A    3/2003
(Continued)

OTHER PUBLICATIONS

Extended European Search Report issued Jul. 20, 2015, in European Patent Application No. 13794122.5 filed May 22, 2013.
(Continued)

*Primary Examiner* — Gregory Clark
(74) *Attorney, Agent, or Firm* — Oblon, McClelland, Maier & Neustadt, L.L.P.

(57) ABSTRACT

An organic electroluminescent element comprising: an anode; a cathode; a luminescent layer provided between the anode and the cathode; and a hole injecting and transporting layer provided between the anode and the cathode and adjacent to the luminescent layer, wherein at least the luminescent layer is formed by a wet film forming method, and contains a charge transporting material and a luminescent material, in which the charge transporting material contains a hole transporting material and an electron transporting material each having a specific partial structure, and the luminescent material contains at least three kinds of materials and has an emission spectrum having at least two kinds of emission maximums.

13 Claims, 1 Drawing Sheet

(51) Int. Cl.
C07D 401/14 (2006.01)
C07D 405/14 (2006.01)
C07D 403/10 (2006.01)
C07C 211/61 (2006.01)
C07D 403/14 (2006.01)
C07D 405/10 (2006.01)
C07D 409/14 (2006.01)
C09K 11/06 (2006.01)
H05B 33/14 (2006.01)
H01L 51/00 (2006.01)
C07C 211/54 (2006.01)

(52) U.S. Cl.
CPC ............ *C07D403/14* (2013.01); *C07D 405/10* (2013.01); *C07D 405/14* (2013.01); *C07D 409/14* (2013.01); *C09K 11/06* (2013.01); *H01L 51/0035* (2013.01); *H01L 51/0039* (2013.01); *H01L 51/0043* (2013.01); *H01L 51/0052* (2013.01); *H01L 51/0067* (2013.01); *H01L 51/0072* (2013.01); *H01L 51/0073* (2013.01); *H01L 51/0074* (2013.01); *H01L 51/0085* (2013.01); *H01L 51/0094* (2013.01); *H05B 33/14* (2013.01); *C09K 2211/1007* (2013.01); *C09K 2211/1029* (2013.01); *C09K 2211/1037* (2013.01); *C09K 2211/1092* (2013.01); *C09K 2211/1416* (2013.01); *C09K 2211/1425* (2013.01); *C09K 2211/1433* (2013.01); *C09K 2211/185* (2013.01); *H01L 51/5016* (2013.01); *H01L 51/5036* (2013.01); *H01L 51/5056* (2013.01); *H01L 51/5072* (2013.01); *H01L 51/5088* (2013.01); *H01L 2251/5384* (2013.01)

(56) References Cited

U.S. PATENT DOCUMENTS

| | | |
|---|---|---|
| 2008/0038586 A1 | 2/2008 | Nishizeki et al. |
| 2009/0167162 A1* | 7/2009 | Lin ..................... C07D 409/14 313/504 |
| 2010/0140605 A1 | 6/2010 | Shibata et al. |
| 2011/0084601 A1 | 4/2011 | Nakayama et al. |
| 2011/0114926 A1 | 5/2011 | Okabe et al. |
| 2011/0204348 A1 | 8/2011 | Nishizeki et al. |
| 2014/0326975 A1 | 11/2014 | Tsurutani et al. |

FOREIGN PATENT DOCUMENTS

| | | | |
|---|---|---|---|
| JP | 2007-27679 A | 2/2007 | |
| JP | 2007-220459 A | 8/2007 | |
| JP | 2011-253722 | * 12/2011 | ............. H01L 51/50 |
| JP | 2011-253722 A | 12/2011 | |
| WO | WO 2006/008976 A1 | 1/2006 | |
| WO | WO 2010/001830 A1 | 1/2010 | |

OTHER PUBLICATIONS

International Search Report issued Aug. 13, 2013 in PCT/JP2013/064286 (with English language translation).

* cited by examiner

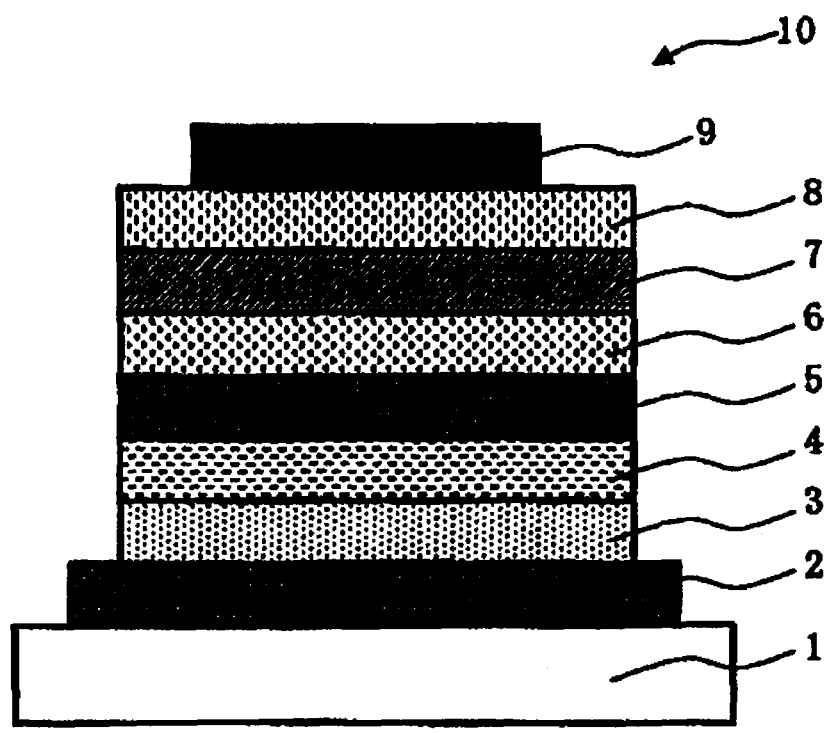

ORGANIC ELECTROLUMINESCENT ELEMENT, ORGANIC ELECTROLUMINESCENT LIGHTING DEVICE AND ORGANIC ELECTROLUMINESCENT DISPLAY DEVICE

TECHNICAL FIELD

The present invention relates to an organic electroluminescent element, an organic electroluminescent lighting device and an organic electroluminescent display device.

BACKGROUND ART

Since the introduction of laminate-type organic electroluminescent (hereinafter this may be abbreviated as "EL") elements into the market by Kodak using a vapor deposition method, organic EL displays have become actively developed and are now being put into practical use.

The laminate-type organic electroluminescent element of the type comprises plural organic layers (luminescent layer, hole injection layer, hole transport layer, electron transport layer, etc.) as laminated between the anode and the cathode therein. The laminate-type organic electroluminescent element of the type is self-luminous and therefore has a broad viewing angle and high visibility, and in addition, it is thin and therefore attracts special attention from the viewpoint of space saving.

Another characteristic feature of the organic electroluminescent element is the planar luminescent performance thereof different from that other luminescent diodes and cold-cathode tubes that have heretofore been put into practical use in the art. As applications that make use of the characteristic feature, there are mentioned backlights, lighting devices, full-color display devices using a color filter, etc.

Organic electroluminescent elements enable various light emissions depending on the combination of the constituent materials. For example, in case where luminescent materials for emission of red, green and blue are used, or in case where luminescent materials for emission of blue and yellow complementary to each other are used, white emission is possible; and in case where luminescent materials for emission of red and green, yellow emission is possible.

These days, in particular, applications of planar light sources such as lighting devices, backlights and others that utilize such color mixing systems are expected. For such lighting applications, preferred is use of a white light source and an electric lamp color light source.

For producing a white emitting element, for example, there is mentioned a method of adding plural kinds of luminescent materials for emission of red, green and blue are added to one layer, as described above. In case where an organic electroluminescent element is produced according to a vacuum vapor deposition process that employs the method, at least red, green and blue luminescent materials and a charge transporting material, totaling at least four different kinds of materials must be vapor-deposited all at a time. In a vacuum vapor deposition method, it is difficult to control vapor deposition of 3 or more different kinds of materials, and the method therefore has a problem in that the repetitive reproducibility is poor (PTL 1).

On the other hand, in case where an organic electroluminescent element is produced according to a wet film formation method, in general, the luminescent material is dissolved in a solvent (PTL 2). In this case, when organic metal complexes each having a ligand having the same basic skeleton are used as the red, green and blue luminescent materials, precipitates may form in the solution, and even when precipitates do not form in the solution, there may occur aggregation during coating or drying, and therefore there may be a possibility that the luminescent material of the type could not form uniform films along with the other luminescent materials and the charge-transporting material. Consequently, there may be a possibility of providing other problems of color shift and poor repetitive reproducibility.

Further, in a case where a luminescent layer is formed according to a wet film formation method, a polymer material may be used (PTL 3). However, the molecular weight of a polymer material is difficult to control and, as compared with a low-molecular material, it is impossible to sufficiently purify a polymer material. Accordingly, in a case where a phosphorus material is used as a luminescent material, there occurs a problem of reduction in the luminescent efficiency. Further, in a case where a luminescent layer is formed using a low-molecular material alone and where one compound alone is used as the charge-transporting material, it is considered that the crystallinity of the charge-transporting material is high and therefore could not have a sufficient amorphous structure. As a result, there may occur some problems of driving voltage increase and light emission efficiency reduction (PTL 4).

CITATION LIST

Patent Literature

PTL 1: JP-A 2007-027679
PTL 2: U.S. Pat. No. 7,453,200
PTL 3: WO2006/008976A1
PTL 4: WO2010/001830A1

SUMMARY OF INVENTION

Technical Problem

For the purpose of white emission mainly in lighting applications, there has been developed an element that uses plural luminescent materials; however, in an organic electroluminescent element containing three or more different kinds of luminescent materials, electric charges could not be uniformly given to the luminescent materials and positive or negative charges could reach only a part of the luminescent materials, and as a result, there occur some problems that the light emission efficiency may lower and the element durability may lower. In a case where a luminescent layer is formed according to a wet film formation method like in the present invention, there may occur other problems that the materials could not be mixed uniformly owing to the difference in solubility between the charge-transporting material and the luminescent material, or the materials could not be uniformly precipitated during film formation or drying but the individual materials may aggregate so that the light emission efficiency of the resultant element may lower.

Further, owing to the difference in solubility between other materials than charge-transporting materials, for example, luminescent materials and others, the materials could not be mixed uniformly or some concentration distribution may occur during film formation, thereby providing still other problems of light emission efficiency, etc. In particular, in case of using a few different kinds of luminescent materials and producing a white luminescent element by the wet film formation method through combination of emission wavelengths, when the materials could not be mixed and precipitated uniformly, there is a probability that the problem would provide some negative influence on not only the light emission efficiency, but also the light emission spectrum, repetitive reproducibility, etc.

Especially in an organic electroluminescent element containing plural luminescent materials, the present invention is to provide a high-efficiency organic electroluminescent element capable of being driven at a low driving voltage.

Solution to Problem

The present inventors have assiduously studied taking the above-mentioned problems into consideration and, as a result, have found that, in an organic electroluminescent element having an anode, a cathode, and a luminescent layer between the anode and the cathode, when a hole injecting and transporting layer is provided between the luminescent layer formed according to a wet film formation method and the anode and adjacent to the luminescent layer and, at the same time, when the luminescent layer is made to include a specific material, then the above-mentioned problems can be solved, and have completed the present invention.

Specifically, the gist of the present invention includes the following:

[1] An organic electroluminescent element comprising an anode, a cathode, and a luminescent layer between the anode and the cathode, wherein at least the luminescent layer is formed according to a wet film formation method, and contains a charge-transporting material and a luminescent material, in which the charge-transporting material includes a hole-transporting material and an electron-transporting material each having a partial structure represented by the following formula (2-A) or (2-B), the luminescent material includes at least three kinds of materials and has an emission spectrum having at least two kinds of emission maximums, and the organic electroluminescent element comprises a hole injecting and transporting layer provided between the anode and the luminescent layer and adjacent to the luminescent layer:

[Chem. 1]

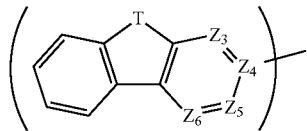

(2-A)

(In the formula (2-A), T represents an atom or an atomic group selected from —O—, —S—, —C(Ar$^{21}$)(Ar$^{22}$)—, —N(Ar$^{23}$)—, and —Si(Ar$^{24}$)(Ar$^{25}$)—, Ar$^{21}$ to Ar$^{25}$ each independently represent a hydrogen atom, or an aromatic ring group having from 3 to 30 carbon atoms and optionally having a substituent, (Ar$^{21}$ and Ar$^{22}$) and (Ar$^{24}$ and Ar$^{25}$) may bond to each other to form a ring structure, $Z_3$ to $Z_6$ each independently represent a group =CH— or a group =N—.)

[Chem. 2]

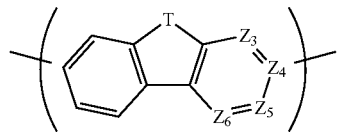

(2-B)

(In the formula (2-B), T represents an atom or an atomic group selected from —O—, —S—, —C(Ar$^{26}$)(Ar$^{27}$)—, —N(Ar$^{28}$)—, and —Si(Ar$^{29}$)(Ar$^{30}$)—, Ar$^{26}$ to Ar$^{30}$ each independently represent a hydrogen atom, or an aromatic ring group having from 3 to 30 carbon atoms and optionally having a substituent, (Ar$^{26}$ and Ar$^{27}$) and (Ar$^{29}$ and Ar$^{30}$) may bond to each other to form a ring structure, $Z_3$ to $Z_6$ each independently represent a group =CH— or a group =N—.)

[2] The organic electroluminescent element according to [1], wherein the hole-transporting material and the electron-transporting material have the same partial structure, and the same partial structure is a structure represented by the formula (2-A) or the formula (2-B).

[3] The organic electroluminescent element according to [1] or [2], wherein all the luminescent materials are a phosphorescent organic metal complex compound.

[4] The organic electroluminescent element according to [3], wherein all the organic metal complex compounds have a ligand having a basic skeleton represented by the following formula (IIIg), each of which may differ.

[Chem. 3]

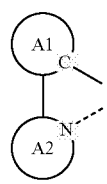

(IIIg)

(In the formula (IIIg), the ring A1 represents any of a benzene ring, a naphthalene ring, a benzothiophene ring or a phenanthrene ring, the ring A2 represents any of a pyridine ring, a quinoline ring, an isoquinoline ring, a quinoxaline ring, a quinazoline ring, a pyrrole ring, an imidazole ring, a benzothiazole ring or a benzisoquinoline ring.)

[5] The organic electroluminescent element according to [3] or [4], wherein the luminescent material includes three or more kinds of luminescent materials of the organic metal complex compounds, and the combination of the basic skeleton of the ligands in the individual organic metal complex compounds have differs between the three or more kinds of the organic metal complex compounds.

[6] The organic electroluminescent element according to any of [3] to [5], wherein at least one basic skeleton of the ligands of the organic metal complex compounds is selected from a group consisting of a phenylpyridine skeleton, a phenylquinoline skeleton, a phenylisoquinoline skeleton and a phenylimidazole skeleton.

[7] The organic electroluminescent element according to any of [3] to [6], wherein all the basic skeletons of the ligands of at least two organic metal complex compounds of the three or more organic metal complex compounds are selected from a phenylpyridine skeleton, a phenylquinoline skeleton, a phenylisoquinoline skeleton and a phenylimidazole skeleton.

[8] The organic electroluminescent element according to any of [1] to [7], wherein the hole injecting and transporting layer adjacent to the luminescent layer contains an arylamine polymer compound.

[9] The organic electroluminescent element according to [8], wherein the arylamine polymer compound contains a repeating unit having a partial structure represented by the following formula (10-C):

[Chem. 4]

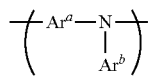
(10-C)

(In the formula (10-C), $Ar^a$ and $Ar^b$ each independently represent an aromatic ring group optionally having a substituent, and in each of the repeating units, $Ar^a$ and $Ar^b$ may differ from each other.)

[10] The organic electroluminescent element according to [8], wherein the arylamine polymer compound contains a repeating unit having a partial structure represented by the following formula (10-A):

[Chem. 5]

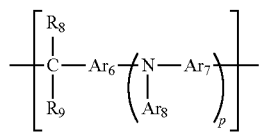
(10-A)

(In the formula (10-A), $Ar_6$ and $Ar_7$ each independently represent a divalent aromatic ring group optionally having a substituent, $Ar_8$ represents an aromatic ring group optionally having a substituent, $R_8$ and $R_9$ each independently represent a hydrogen atom, an alkyl group optionally having a substituent, an alkoxy group optionally having a substituent, or an aromatic ring group optionally having a substituent, $R_8$ and $R_9$ may bond to each other to form a ring, p indicates an integer of from 1 to 5, and when the formula (10-A) has plural $Ar_6$'s to $Ar_8$'s, $R_8$'s and $R_9$'s, these plural substituents may be the same or different.)

[11] The organic electroluminescent element according to [8], wherein the arylamine polymer compound contains a repeating unit having a partial structure represented by the following formula (10-B):

[Chem. 6]

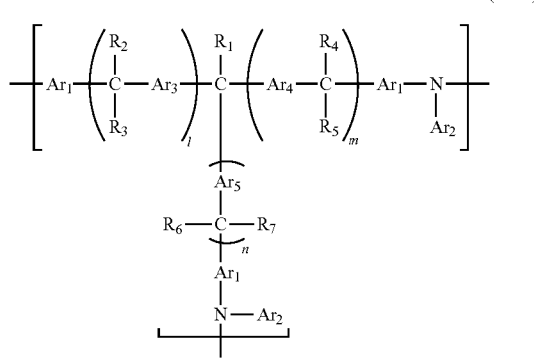
(10-B)

(In the formula (10-B), $Ar_1$, $Ar_3$, $Ar_4$ and $Ar_5$ each independently represent a divalent aromatic ring group optionally having a substituent, $Ar_2$ represents an aromatic ring group optionally having a substituent, $R_1$ represents an alkyl group optionally having a substituent or an alkoxy group optionally having a substituent, $R_2$ to $R_7$ each independently represent a hydrogen atom, an alkyl group optionally having a substituent, an alkoxy group optionally having a substituent, or an aromatic ring group optionally having a substituent, $R_2$ and $R_3$ may bond to each other to form a ring, $R_4$ and $R_5$ may bond to each other to form a ring, $R_6$ and $R_7$ may bond to each other to form a ring, l, m and n each independently indicate an integer of from 0 to 2, and when the formula (10-B) has plural $Ar_1$'s to $Ar_5$', $R_1$'s to $R_7$'s, these plural substituents may be the same or different.)

[12] The organic electroluminescent element according to any one of [1] to [11], which comprises at least two hole injecting and transporting layers between the anode and the luminescent layer.

[13] A display device comprising the organic electroluminescent element according to any one of [1] to [12].

[14] A lighting device comprising the organic electroluminescent element according to any one of [1] to [12].

Advantageous Effects of Invention

According to the present invention, there is provided an organic electroluminescent element capable of being driven at a low driving voltage and having a high power efficiency.

In addition, the organic electroluminescent element of the present invention is, making full use of the characteristics thereof as a planar luminescent element, applicable to lighting devices, while light sources (for example light sources for copiers, backlight sources for liquid-crystal displays and instruments, color filter display devices), sign boards, and marker lamps, and the technical value of the element is considered to be extremely high.

BRIEF DESCRIPTION OF DRAWING

FIG. 1 is a schematic cross-sectional view of one example of a configuration of the organic electroluminescent element of the present invention.

DESCRIPTION OF EMBODIMENTS

Embodiments of the present invention are described in detail hereinunder; however, the present invention is not limited to the following embodiments but can be carried out as various modifications falling within the scope and the spirit thereof. White or electric lamp color emission requires various kinds of luminescent materials. In particular, for attaining high efficiency in wet film formation, it is considered that uniform mixing of various kinds of luminescent materials is important, and it is further considered good not to deactivate that the luminescent energy of the materials. Consequently, it is considered that the embodiments of the present invention are favorable for white and electric lamp color emission.

[Organic Electroluminescent Element]

The organic electroluminescent element of the present invention is an organic electroluminescent element having an anode, a cathode, and a luminescent layer between the anode and the cathode, wherein at least the luminescent layer is formed according to a wet film formation method, the luminescent layer contains a charge-transporting material and a luminescent material, the charge-transporting material includes a hole-transporting material and an electron-transporting material each having a specific partial structure, the luminescent material includes at least three kinds of materials and has at least two kinds of emission maximums as the emission spectrum thereof, and a hole injecting and transporting layer is arranged between the anode and the luminescent layer and adjacent to the luminescent layer.

[Luminescent Layer]

In the present invention, the luminescent layer is a layer that is excited through recombination of the hole injected from the anode and the electron injected from the cathode between the electrodes given an electric field, thereby to be the main luminescent source in the element.

In the present invention, the luminescent layer contains a luminescent material and a charge-transporting material, in which, preferably, the luminescent material is a dopant and the charge-transporting material is a host.

<Luminescent Material>

The luminescent material is preferably a phosphorescent luminescent material, more preferably a phosphorescent organic metal complex compound emitting phosphorescent light particularly.

(Phosphorescent Luminescent Material)

Of luminescent materials, the phosphorescent luminescent material includes, for example, a Werner-type complex or organic metal complex compound that contains, as the center metal therein, a metal selected from Groups 7 to 11 of the Long Periodic Table (hereinafter unless otherwise specifically indicated, "Periodic Table" means Long Periodic Table).

The metal selected from Groups 7 to 11 of the Periodic Table includes preferably ruthenium, rhodium, palladium, silver, rhenium, osmium, iridium, platinum, gold, etc. Above all, more preferred is iridium or platinum, and most preferred is iridium from the viewpoint of high stability and high light emission efficiency of the compound.

In particular, as the phosphorescent organic metal complex of phosphorescent luminescent materials, preferred are compounds represented by the following formula (III) or formula (IV).

$$ML_{(q-j)}L'_j \quad (III)$$

(In the formula (III), M represents a metal, q indicates the valence of the metal. L and L' each represent a bidentate ligand, and plural L's and (L')'s, if any, each may be an independent different ligand. j indicates a number of 0, 1 or 2.)

[Chem. 7]

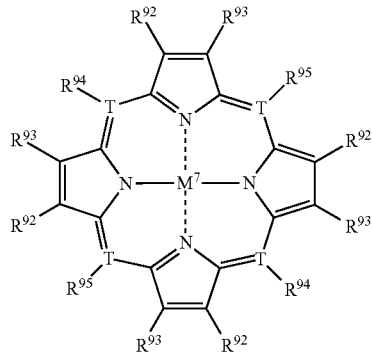

(IV)

(In the formula (IV), $M^7$ represents a metal, preferably ruthenium, rhodium, palladium, silver, rhenium, osmium, iridium, platinum, gold, etc. Above all, more preferred is iridium or platinum, and most preferred is iridium from the viewpoint of high stability and high light emission efficiency of the compound. T represents a carbon atom or a nitrogen atom. $R^{92}$ to $R^{95}$ each independently represent a substituent. However, when T is a nitrogen atom, the formula does not have $R^{94}$ and $R^{95}$.

Of the compounds represented by the formulae (III) and (IV), the compounds represented by the formula (III) are preferred as the phosphorescent organic metal complex of phosphorescent luminescent materials from the viewpoint of solubility, since the compounds represented by the formula (IV) have high planarity and are therefore easy to aggregate and have low solubility.

The compounds represented by the formula (III) are described below.

In the formula (III), M represents a metal selected from Groups 7 to 11 of the Periodic Table, and is preferably ruthenium, rhodium, palladium, silver, rhenium, osmium, iridium, platinum, gold, etc. Above all, more preferred is iridium or platinum, and most preferred is iridium from the viewpoint of high stability and high light emission efficiency of the compound.

In the formula (III), L represents a ligand having a partial structure represented by the following formula (IIIg) (hereinafter this may be referred to as "partial structure (IIIg)"). L' represent an auxiliary ligand to be mentioned below.

[Chem. 8]

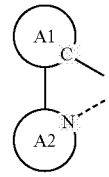

(IIIg)

In the partial structure (IIIg) of the ligand, the ring A1 represents an aromatic ring group optionally having a substituent. The aromatic ring group in the present invention may be an aromatic hydrocarbon ring group or an aromatic heterocyclic group. Preferred is an aromatic hydrocarbon group.

The aromatic hydrocarbon ring group is a 5- or 6-membered, single ring or 2- to 5-condensed ring having one free atomic valence. Here, in the present invention, the free atomic valence is one capable of forming a bond with any other free atomic valence, as described in Organic Chemistry, Biochemical Nomenclature (Vol. 1) (revised version of 2nd edition, issued by Nanko-do in 1992).

Specific examples of the aromatic hydrocarbon ring group include a benzene ring, a naphthalene ring, an anthracene ring, a phenanthrene ring, a fluorene ring and the like having one free atomic valence. Preferred are a benzene ring, a naphthalene ring and a phenanthrene ring.

The aromatic heterocyclic group is a 5- or 6-membered, single ring or 2- to 4-condensed ring having one free atomic valence.

The aromatic ring of the ring A1 is preferably a benzene ring, a naphthalene ring, a phenanthrene ring or a benzothiophene ring. Above all, more preferred are a benzene ring and a naphthalene ring, and most preferred is a benzene ring.

In the partial structure (IIIg) of the ligand, the ring A2 is a nitrogen-containing aromatic heterocyclic group optionally having a substituent.

The nitrogen-containing aromatic heterocyclic group includes a 5- or 6-membered, single ring or 2- to 4-condensed ring having one free atomic valence.

Specific examples of the substituent are a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a furopyrrole ring, a thienofuran ring, a benzisoxazole ring, a benzothiazole ring, a benzisothiazole ring, a benzimidazole ring, a pyridine ring, a pyrazine ring, a pyridazine ring, a pyrimidine ring, a triazine ring, a quinoline ring, an isoquinoline ring, a benzisoquinoline ring, a quinoxaline ring, a phenanthridine ring, a benzimidazole ring, a perimidine ring, a quinazoline ring, a quinazolinone ring and the like having one free atomic valence. Of those, more preferred are a pyridine ring, a quinoline ring, an isoquinoline ring, a quinoxaline ring, a quinazoline ring, a pyrrole ring, an imidazole ring, a benzothiazole ring and a benzisoquinoline ring. Even more preferred are a pyridine ring, a quinoline ring, an isoquinoline ring, a quinoxaline ring, a quinazoline ring and an imidazole ring; and most preferred are a pyridine ring, a quinoline ring, an isoquinoline ring and an imidazole ring.

The substituent that the ring A1 or the ring A2 may have includes a fluorine atom, an alkyl group having from 1 to 20 carbon atoms, an alkoxy group having from 1 to 20 carbon atoms, a trialkylsilyl group in which the alkyl group has from 1 to 20 carbon atoms, an alkylcarbonyl group having from 1 to 20 carbon atoms, an arylcarbonyl group having from 1 to 20 carbon atoms, an alkylamino group having from 1 to 20 carbon atoms, an arylamino group having from 1 to 20 carbon atoms, an aromatic hydrocarbon group having from 6 to 20 carbon atoms, and an aromatic heterocyclic group having from 3 to 19 carbon atoms. Of those, preferred are an alkyl group having from 1 to 20 carbon atoms, an aromatic hydrocarbon group having from 6 to 20 carbon atoms, and an aromatic heterocyclic group having from 3 to 19 carbon atoms, from the viewpoint of solubility and heat resistance of the compound.

These groups except fluorine atom may be further substituted with any of a fluorine atom, an alkyl group having from 1 to 8 carbon atoms, an alkoxy group having form 1 to 8 carbon atoms, a trialkylsilyl group in which the alkyl group has from 1 to 8 carbon atoms, an alkylcarbonyl group having from 1 to 8 carbon atoms, an arylcarbonyl group having from 1 to 14 carbon atoms, an alkylamino group having from 1 to 16 carbon atoms, an arylamino group having from 1 to 14 carbon atoms, an aromatic hydrocarbon group having from 6 to 14 carbon atoms, or an aromatic heterocyclic group having from 3 to 13 carbon atoms.

In the present invention, the basic skeleton of the ligand that constitutes the organic metal complex is determined by the molecular structure of the ligand that directly coordinates with the center metal of the complex. For example, in the compound number 51 to be given below, the basic skeleton indicates the phenylpyridine skeleton that directly coordinates with the center metal Ir. The picolinate structure is an auxiliary ligand and is not considered as the basic skeleton-having ligand. The auxiliary ligand is a ligand in which the atom not included in the aromatic ring group except the substituent directly bonds to the center metal atom, and does not correspond to the partial structure (IIIg). One organic metal complex having plural ligands may have plural basic skeletons.

In the formula (III), the bidentate ligand L' may have a partial structure mentioned below. This corresponds to the above-mentioned auxiliary ligand. In the following formulae, "Ph" means a phenyl group.

[Chem. 9]

L':

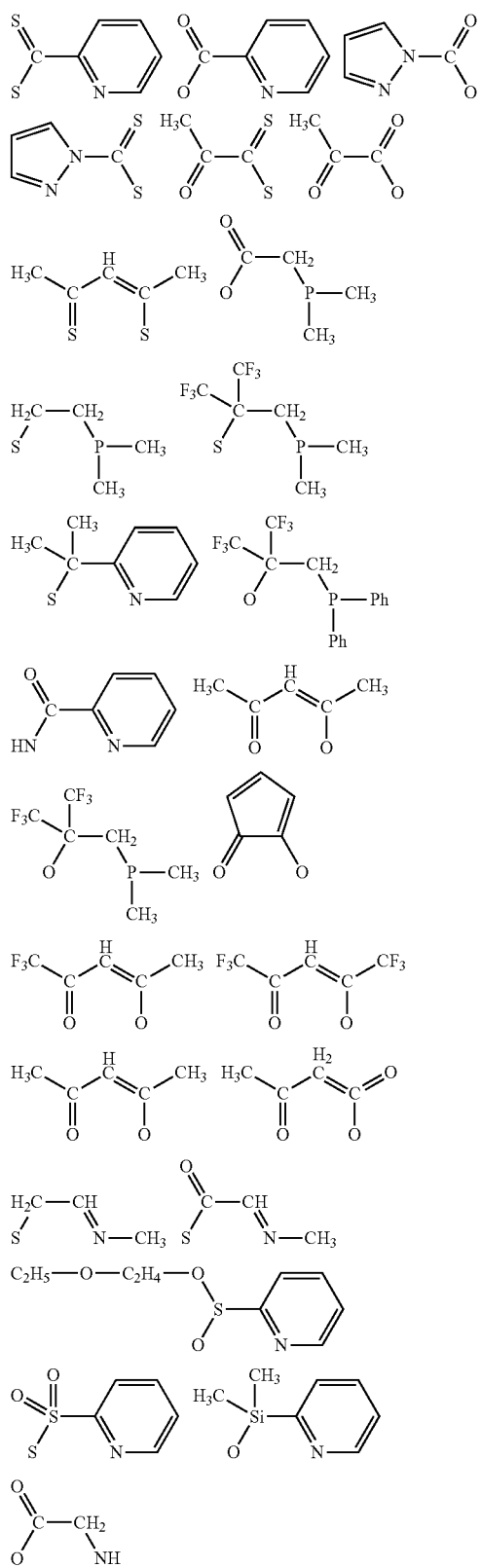

Above all, more preferred structures for L' are as shown below, from the viewpoint of the stability of the complex.

[Chem. 10]

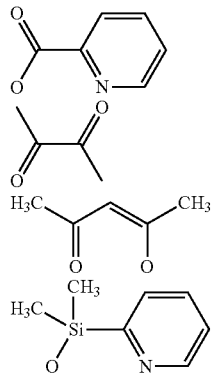

As the compounds represented by the formula (III), more preferably mentioned are the compounds represented by the following formulae (IIIa) and (IIIc).

[Chem. 11]

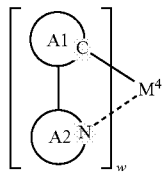
(IIIa)

(In the formula (IIIa), $M^4$ represents the same metal as M, w indicates the valence of the metal, the ring A1 is the same as the ring A1 in the partial structure (IIIg), and the ring A2 is the same as the ring A2 in the partial structure (IIIg).)

[Chem. 12]

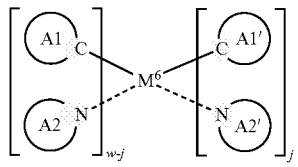
(IIIc)

(In the formula (IIIc), $M^6$ represents the same metal as M, w indicates the valence of the metal, j indicates 0, 1 or 2, the ring A1 and the ring A1' each are independently the same as the ring A1 in the partial structure (IIIg), and the ring A2 and the ring A2' each are independently the same as the ring A2 in the partial structure (IIIg).)

The compounds described in WO2005/019373 are also usable as the luminescent materials here.

Concretely, the basic skeleton of the ligand includes a phenylpyridine skeleton, a phenylquinoline skeleton, a phenylisoquinoline skeleton, a phenylimidazole skeleton, a pyridylpyridine skeleton, a naphthylpyridine skeleton, a pyridylbenzothiophene skeleton, a phenylbenzothiazole skeleton, an isoquinolylbenzothiophene skeleton, a phenylquinoxaline skeleton, a phenylbenzisoquinoline skeleton, a phenylpyrazole skeleton, a phenyltetrazole skeleton, a phenylbenzimidazole skeleton, etc. From the viewpoint of the stability of the compound, the light emission efficiency of the element and the easiness in production, preferred are a phenylpyridine skeleton, a phenylquinoline skeleton, a phenylisoquinoline skeleton, a phenylimidazole skeleton, a naphthylpyridine skeleton, a phenylquinoxaline skeleton, a phenylbenzisoquinoline skeleton, a phenylpyrazole skeleton, and a phenylbenzimidazole skeleton. More preferred are a phenylpyridine skeleton, a phenylquinoline skeleton, a phenylisoquinoline skeleton, a phenylimidazole skeleton, a naphthylpyridine skeleton, and a phenylquinoxaline skeleton; and most preferred are a phenylpyridine skeleton, a phenylquinoline skeleton, a phenylisoquinoline skeleton, and a phenylimidazole skeleton.

Next described are the compounds represented by the formula (IV).

In the formula (IV), $M^7$ represents a metal. Specific examples of the metal include the metals mentioned hereinabove as the metal selected from Groups 7 to 11 of the Periodic Table. Above all, $M^7$ is preferably ruthenium, rhodium, palladium, silver, rhenium, osmium, iridium, platinum or gold, and more preferably a divalent metal such as platinum, palladium, etc.

In the formula (IV), $R^{92}$ and $R^{93}$ each independently represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, or an aromatic ring group.

Further, when T is a carbon atom, $R^{94}$ and $R^{95}$ each independently represent the substituent mentioned above for $R^{92}$ and $R^{93}$. When T is a nitrogen atom, the formula does not have $R^{94}$ and $R^{95}$.

$R^{92}$ to $R^{95}$ may further have a substituent. When these have a substituent, the type of the substituent is not specifically defined, and they may have any optional substituent.

Further, any two or more groups of $R^{92}$ to $R^{95}$ may bond to each other to form a ring.

Specific examples of the phosphorescent luminescent material are shown below; however, the phosphorescent luminescent material for use in the present invention is not whatsoever limited to the following.

[Chem. 13]

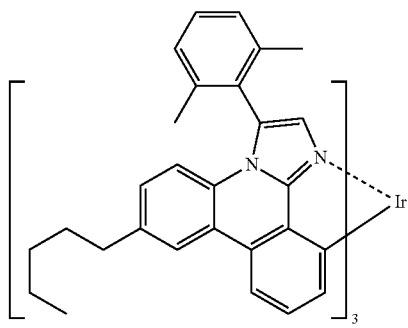

26

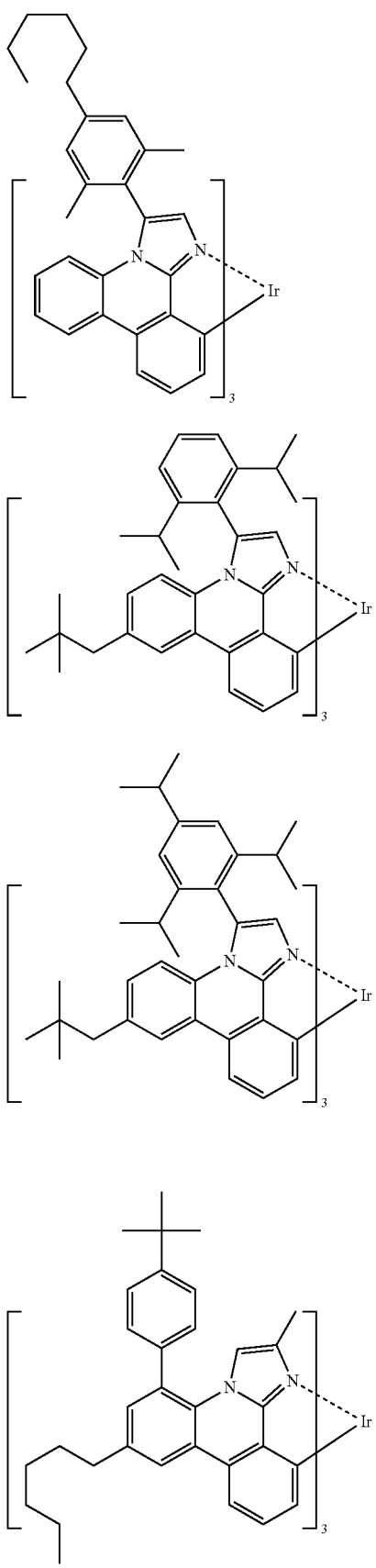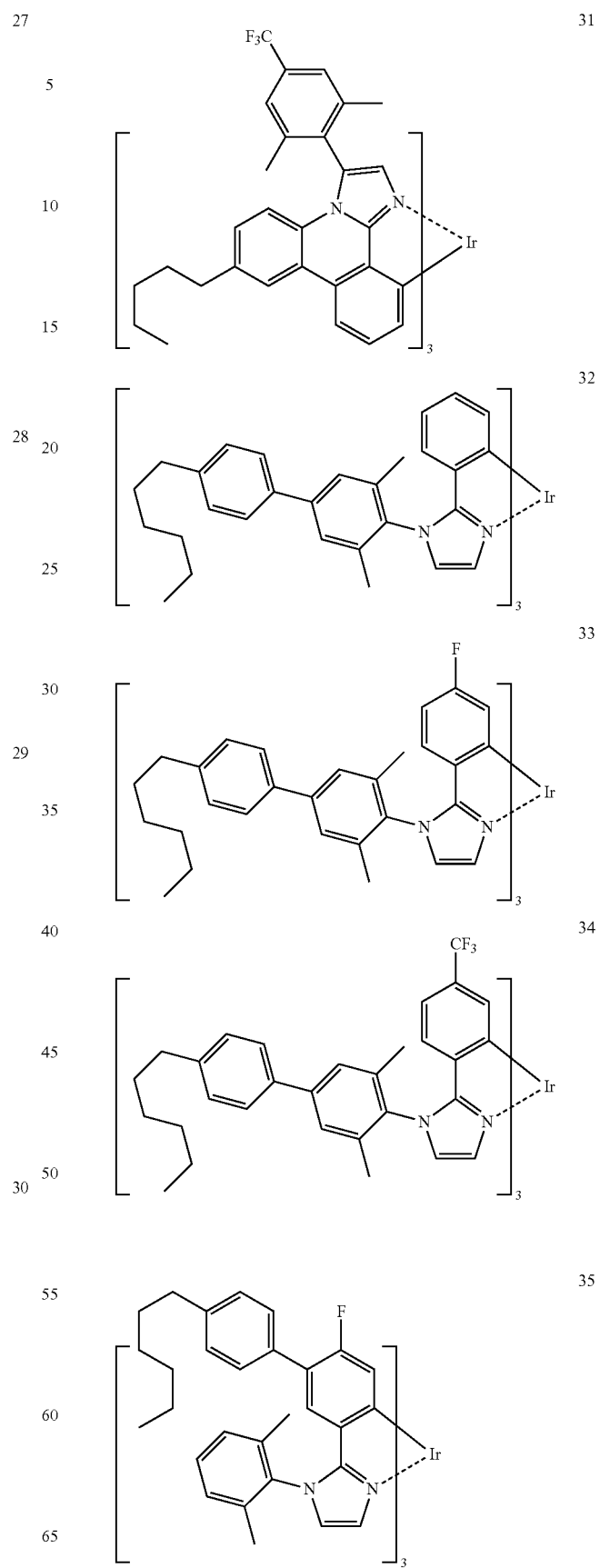

-continued
36
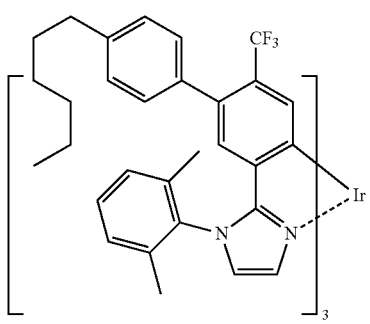
37
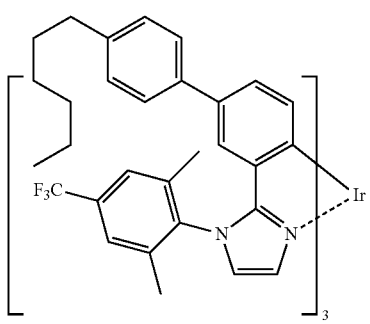
38
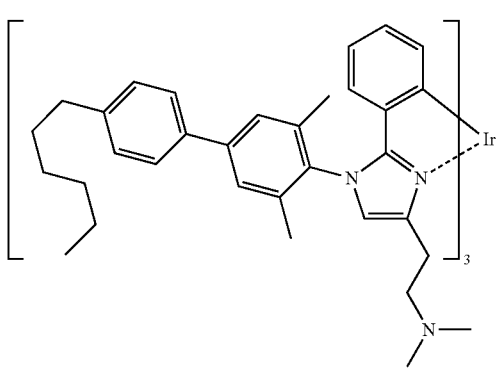
39
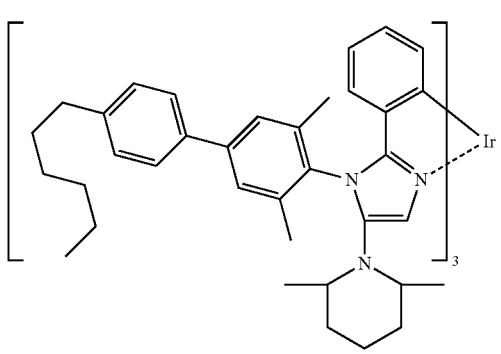
-continued
40
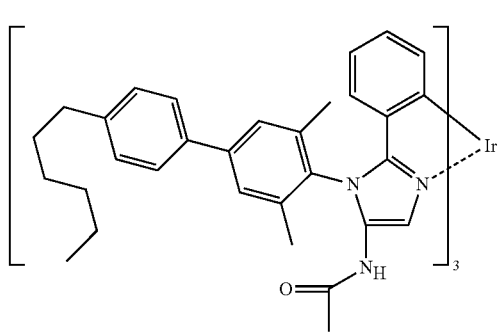
[Chem. 14]
41
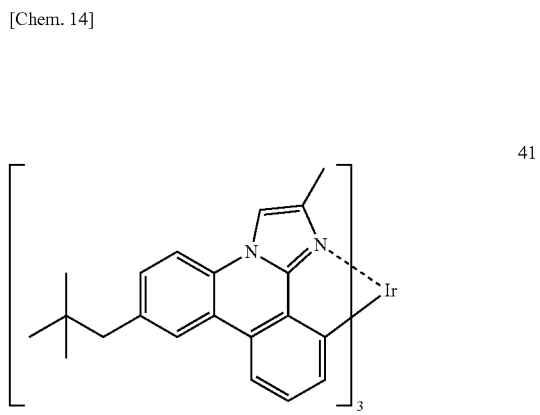
42
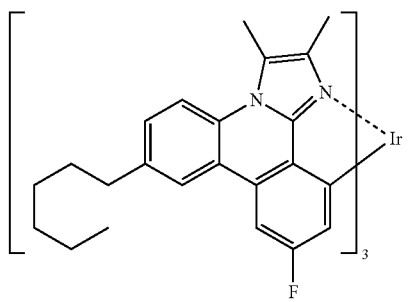
43
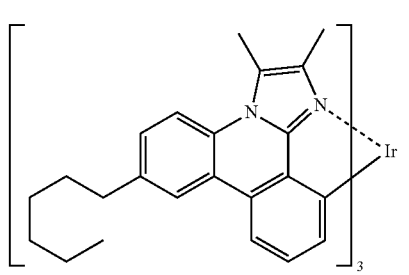

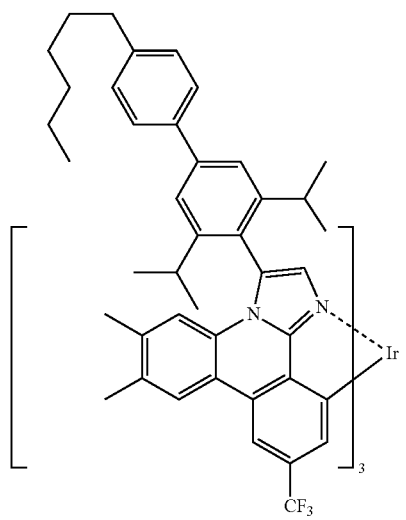
44
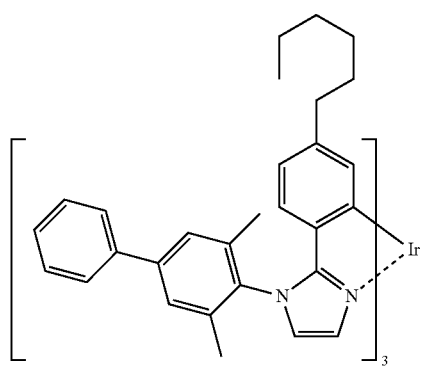
45
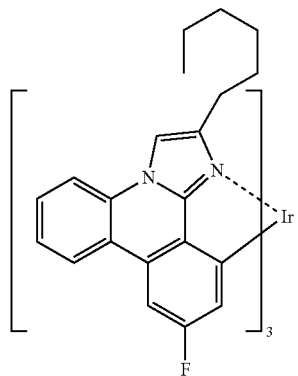
46
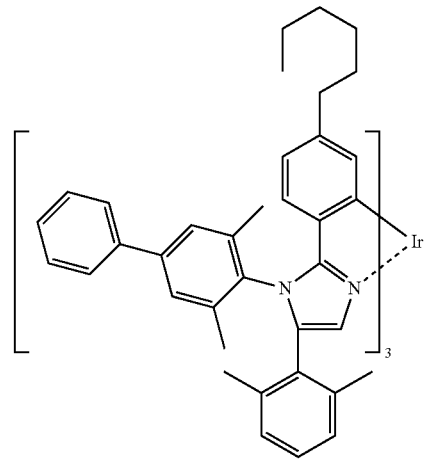
47
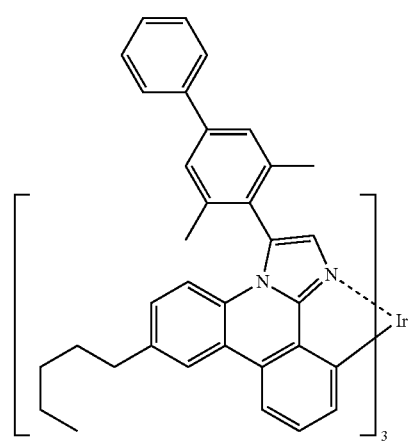
48
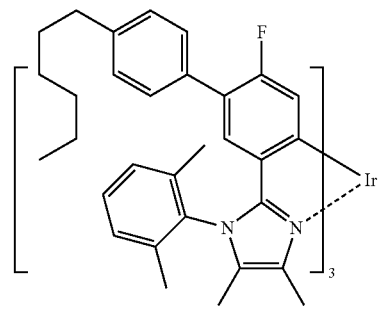
49
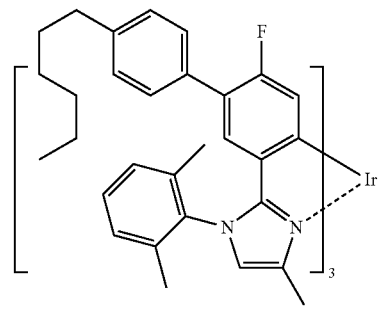
50

-continued
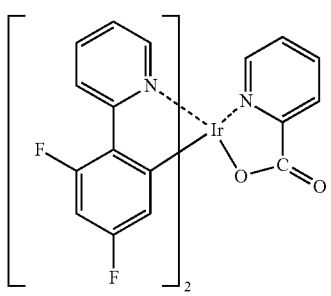
[Chem. 15]
[Chem. 16]
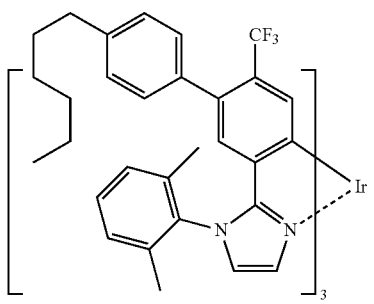
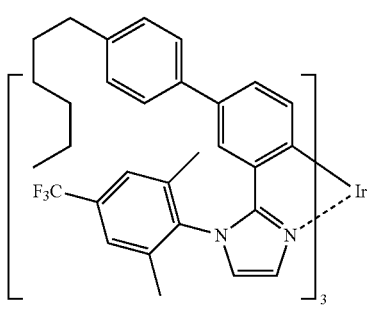
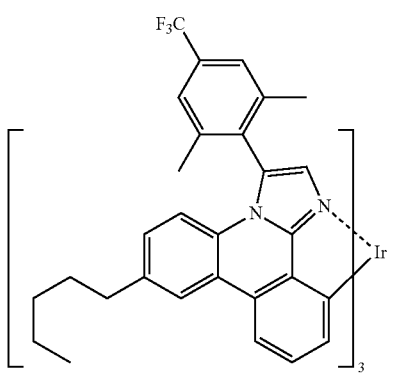
-continued
51
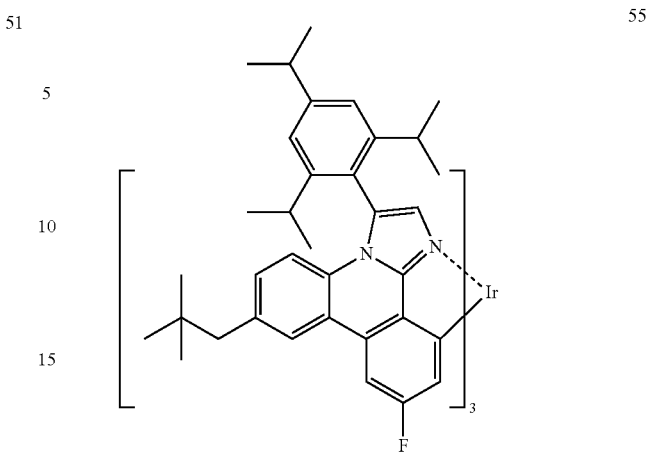
52
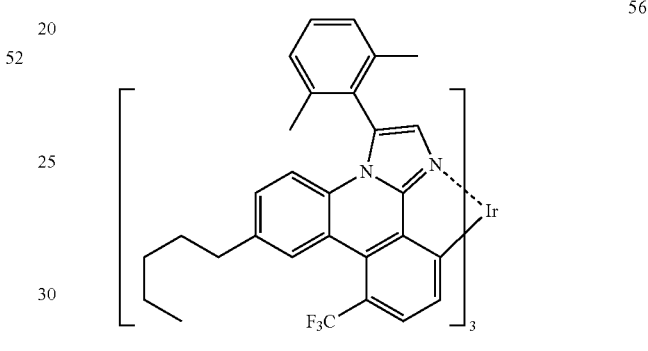
53
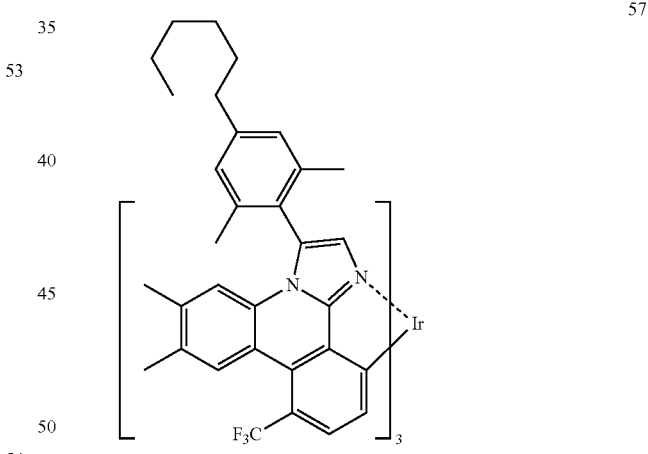
54
55
56
57
58
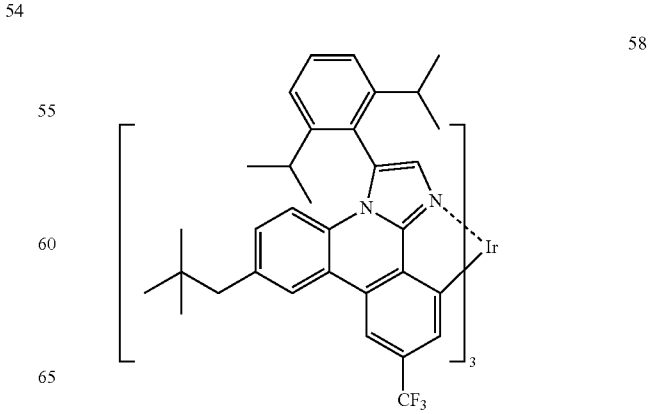

-continued
59
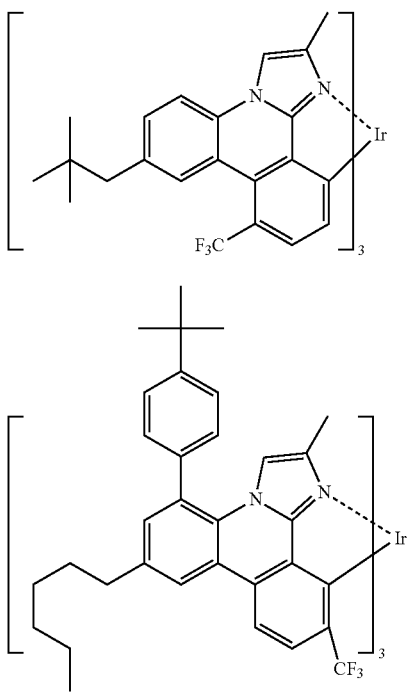
[Chem. 17]
61
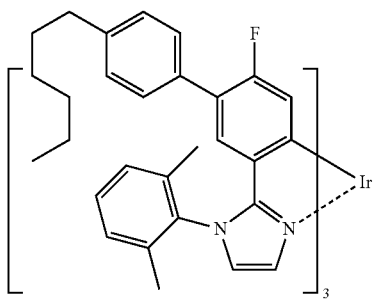
62
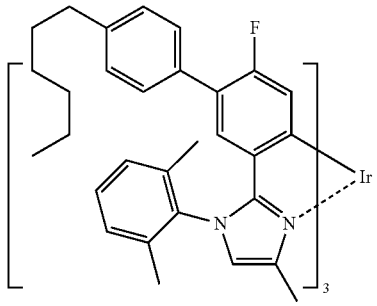
63
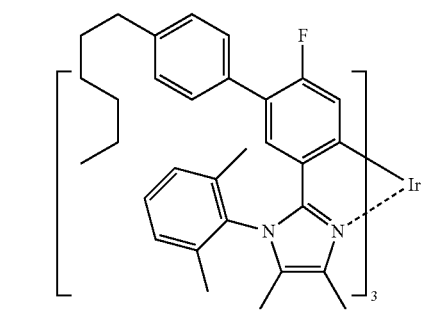
-continued
64
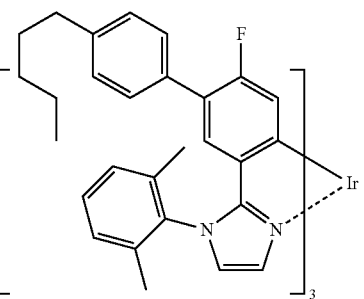
65
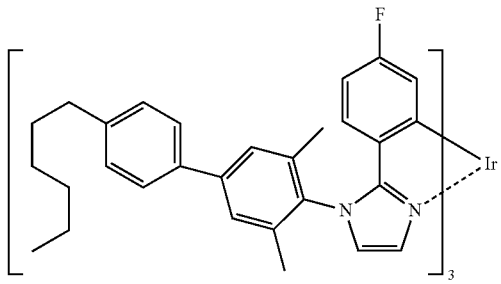
66
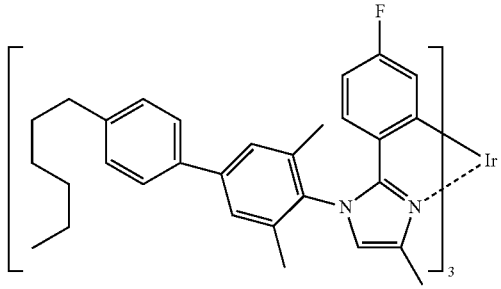
67
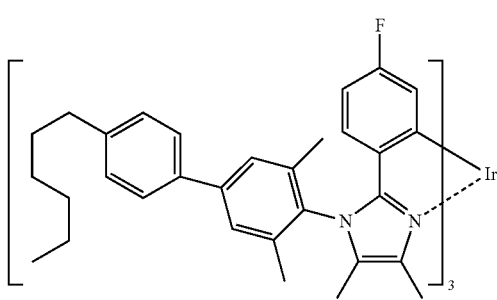
68
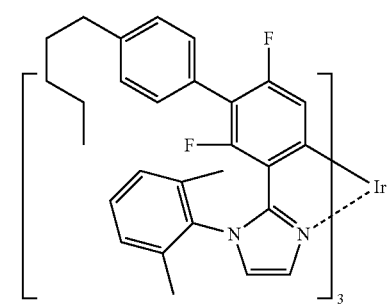

69
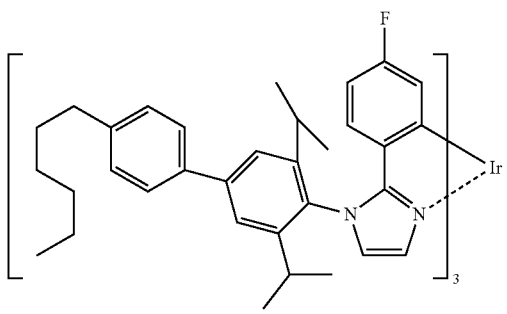
70
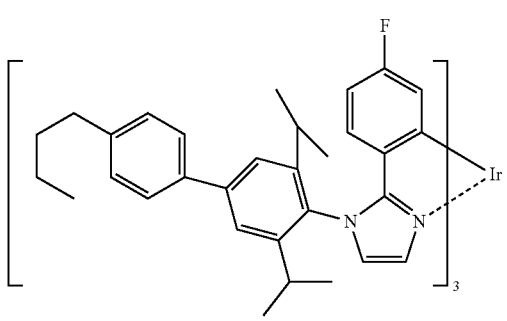
71
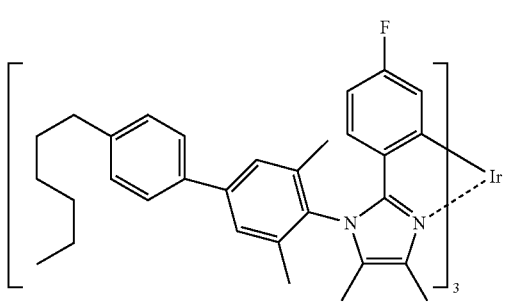
72
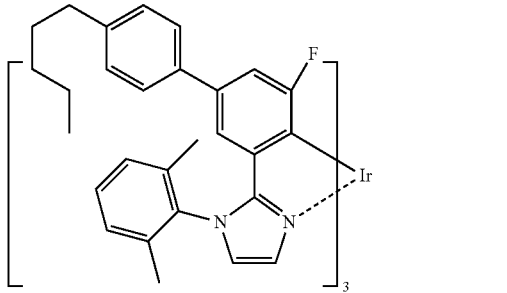
73
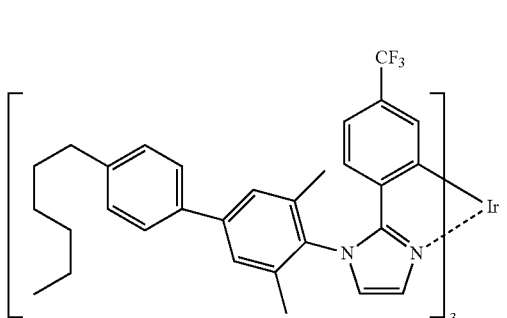
74
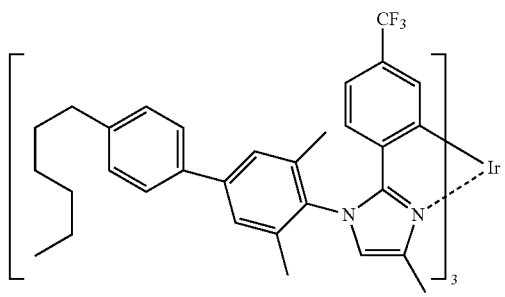
75
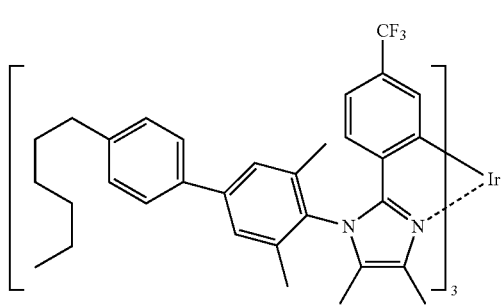
76
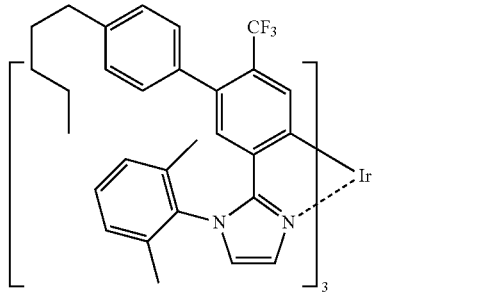
77
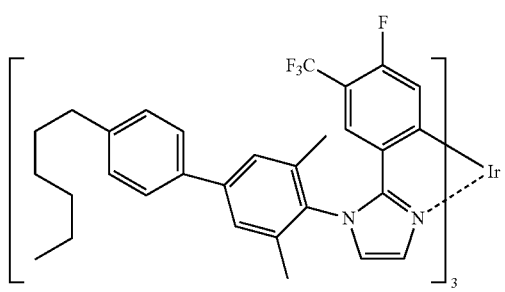
78
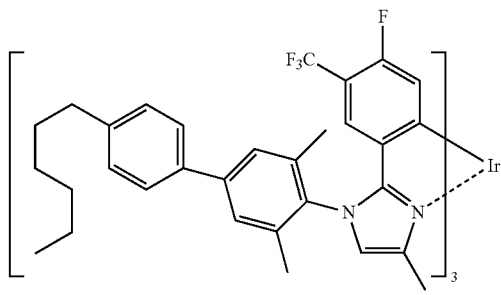

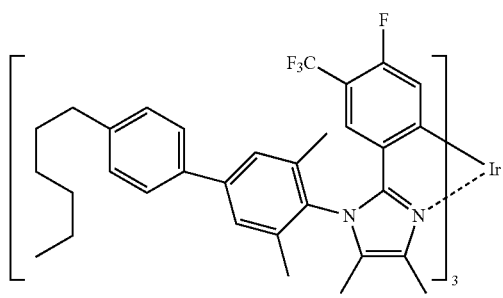
79
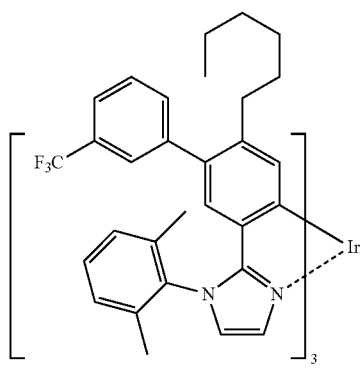
80
[Chem. 18]
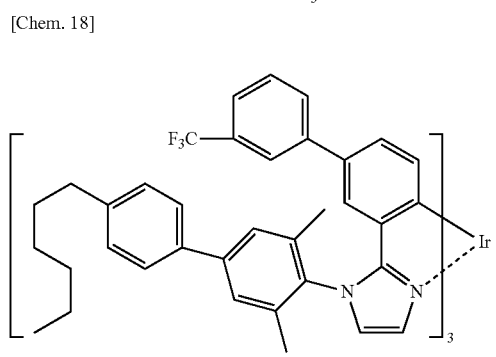
81
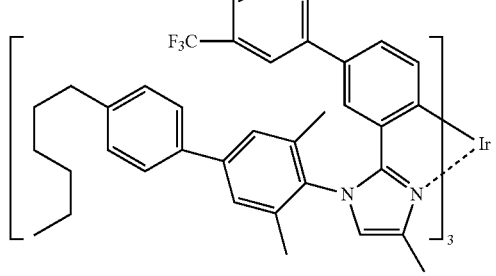
82
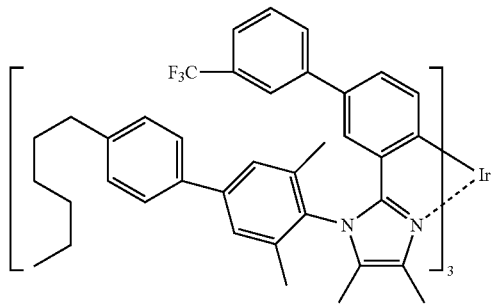
83
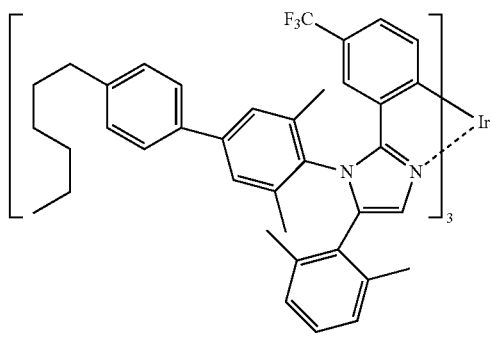
84
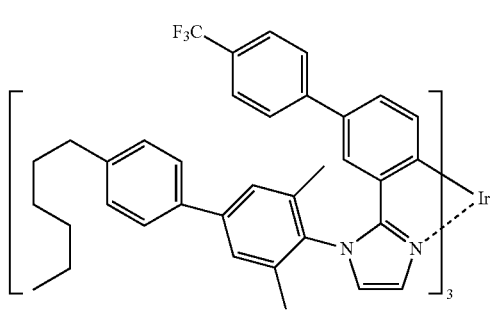
85
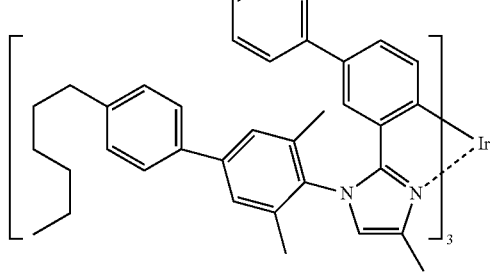
86
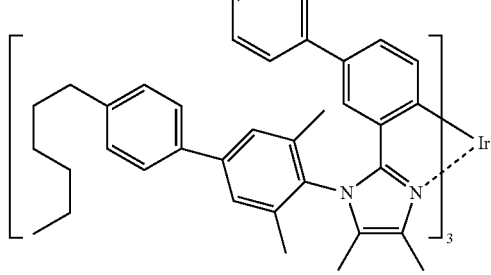
87
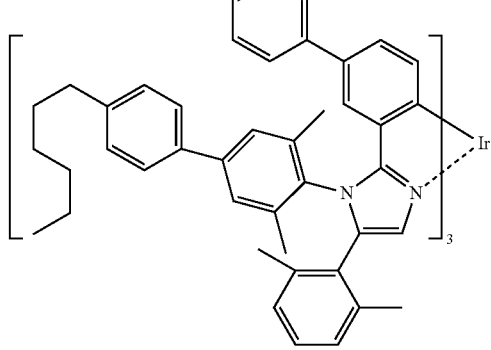
88

89
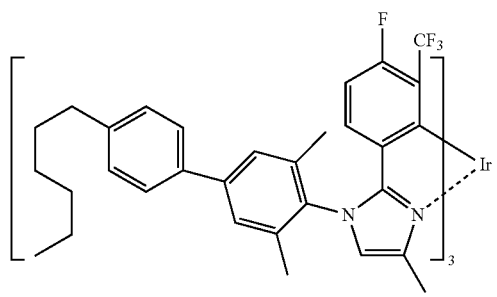
94
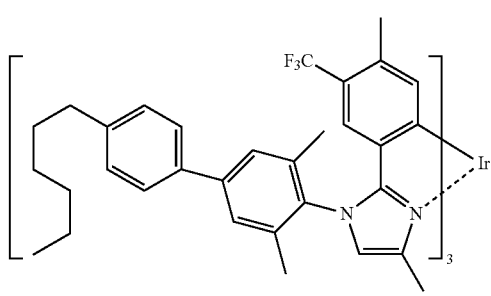
90
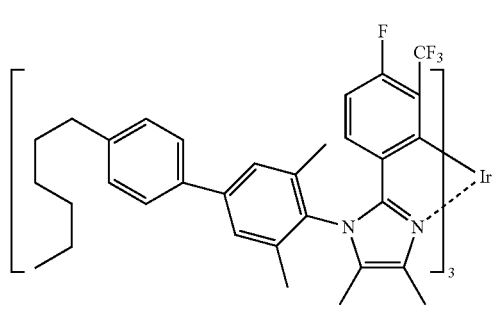
95
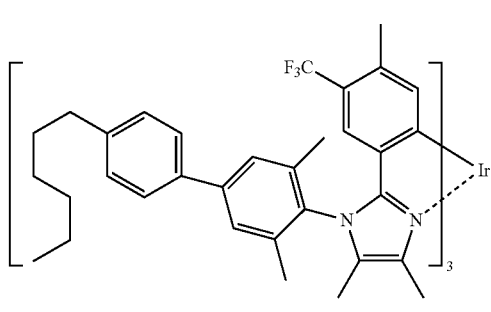
91
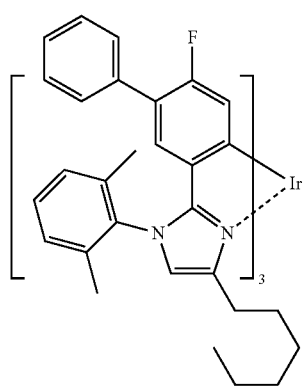
96
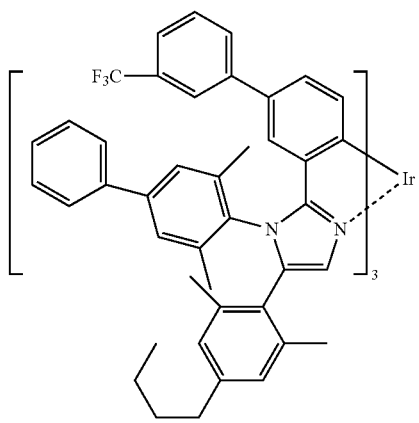
92
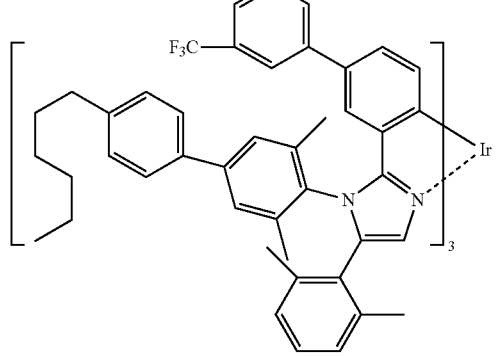
97
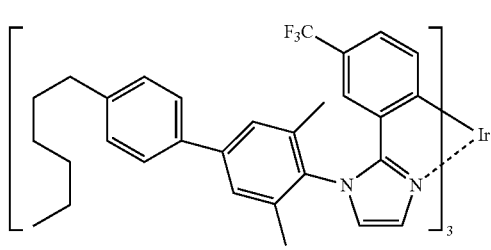
93
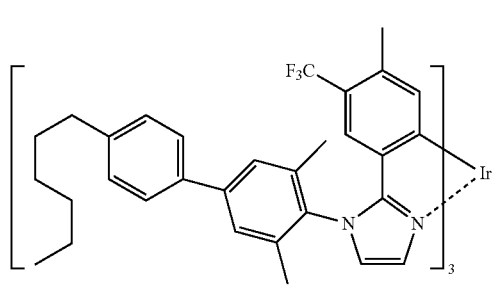
98
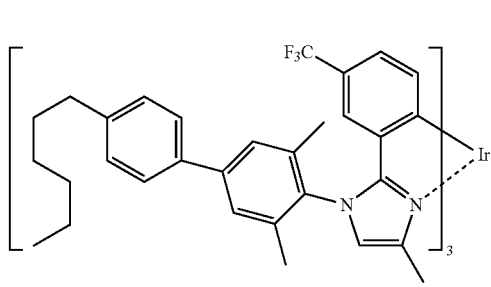

99
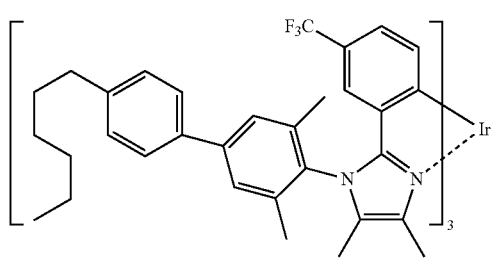
100
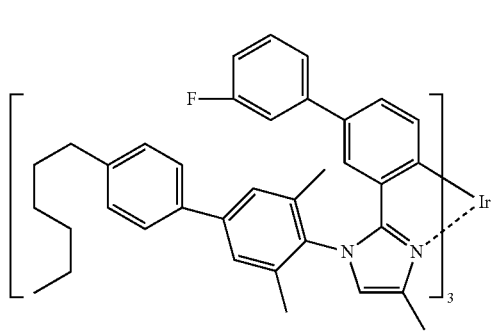
[Chem. 19]
101
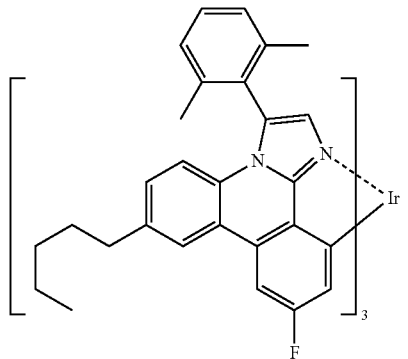
102
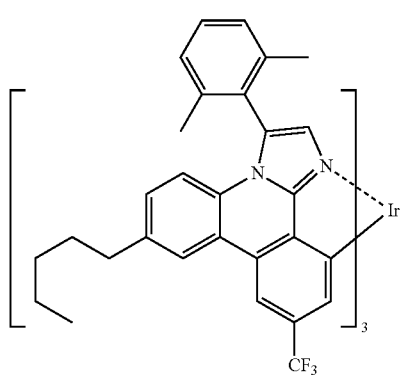
103
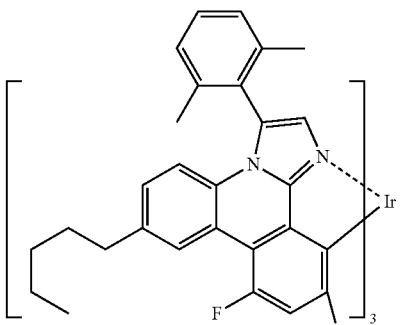
104
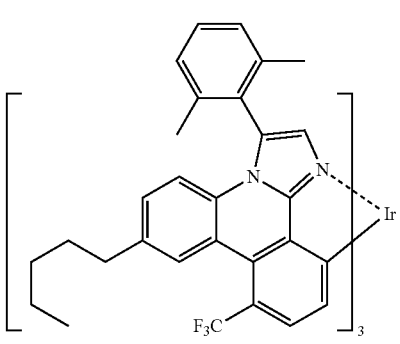
105
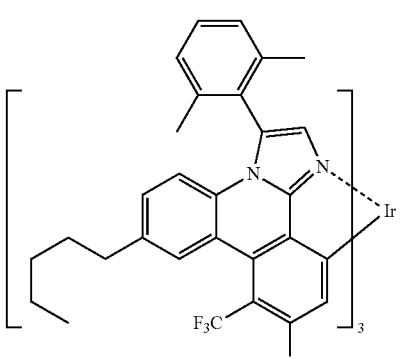
106
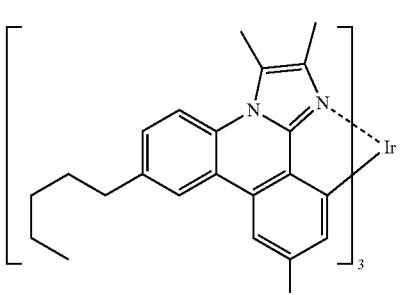
107
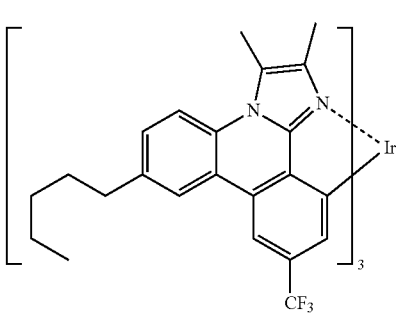

108 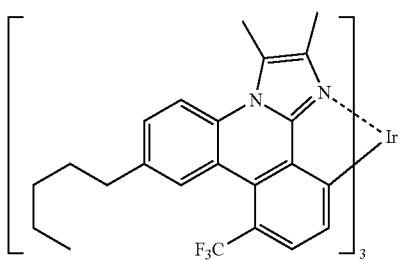
109 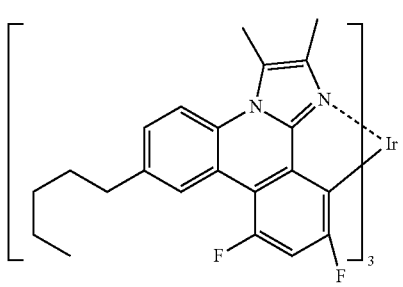
110 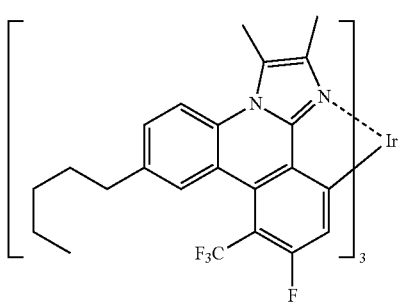
111 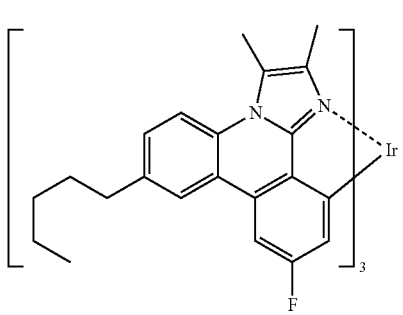
112 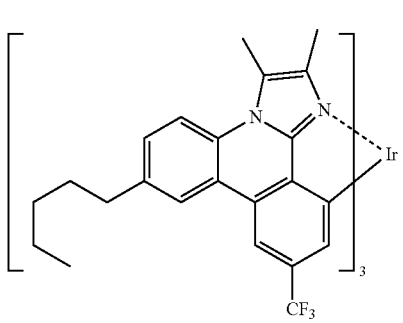
113 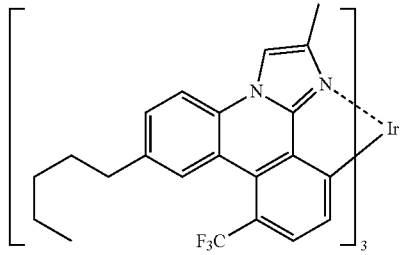
114 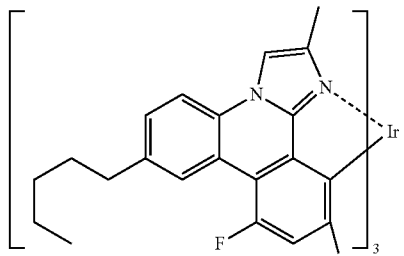
115 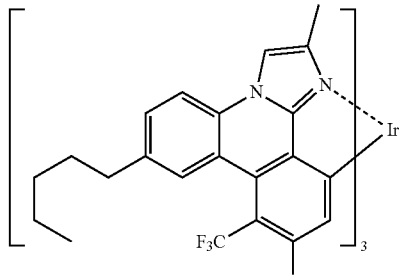
116 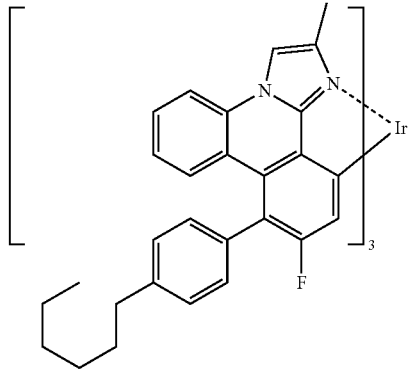
117 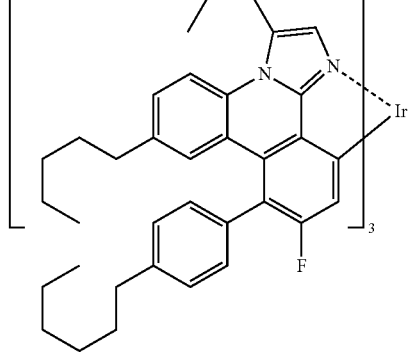

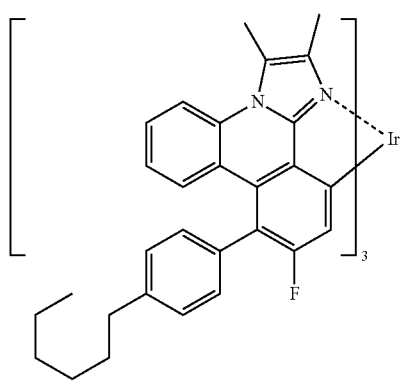
118
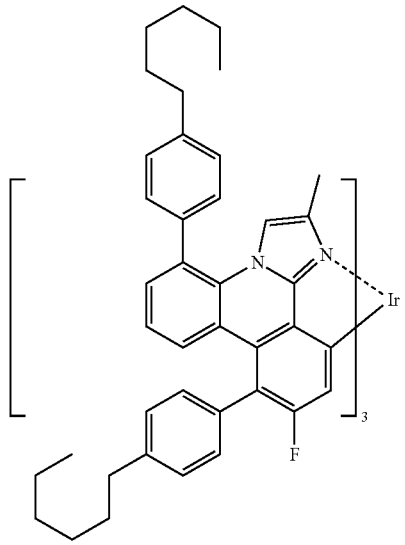
119
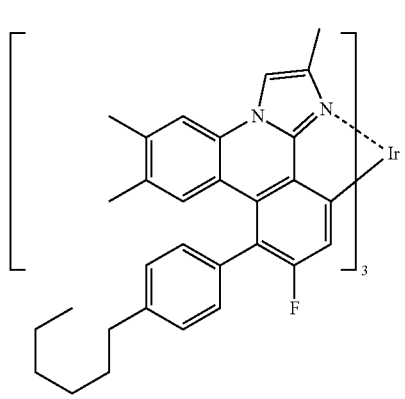
120
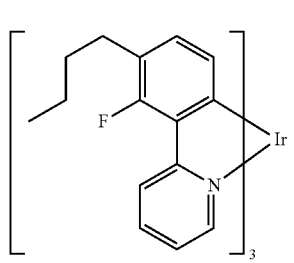
121
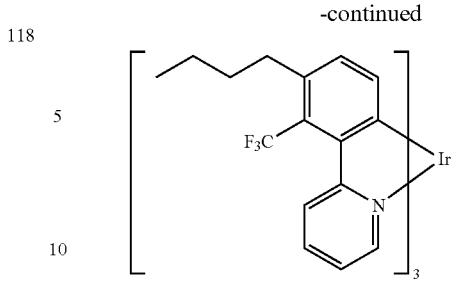
122
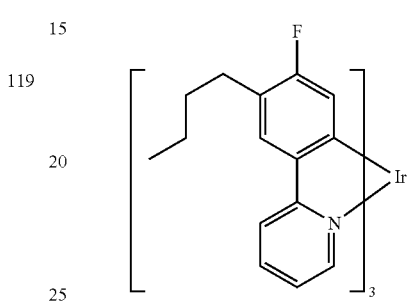
123
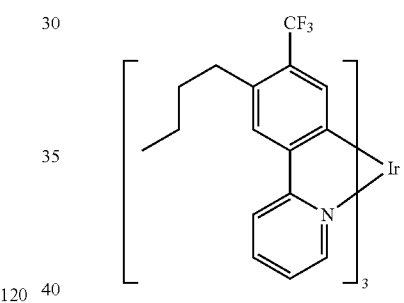
124
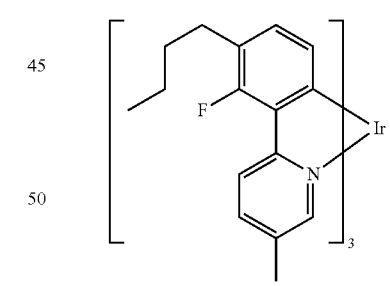
125
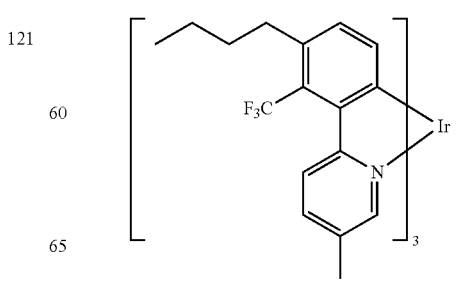
126

-continued
127 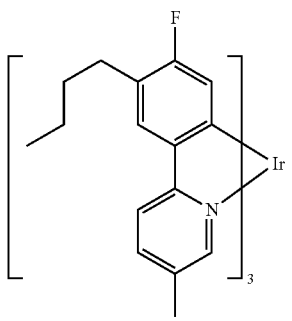
128 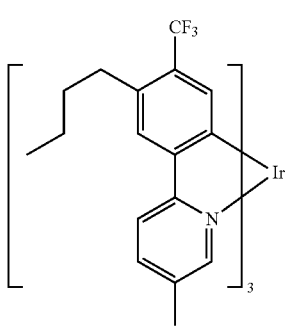
129 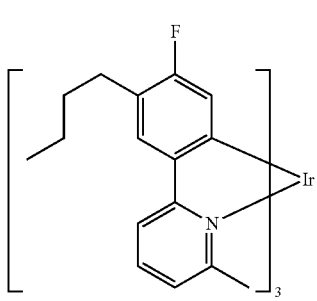
130 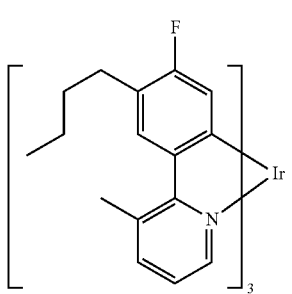
131 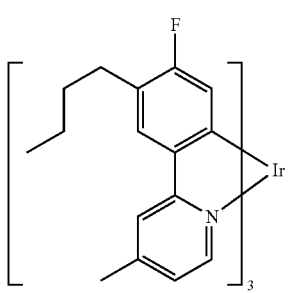
132 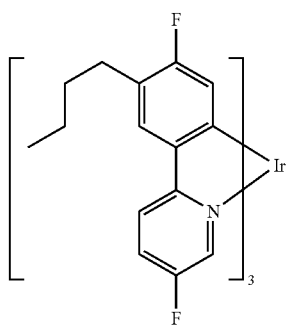
133 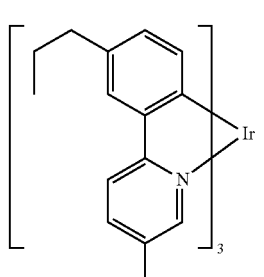
134 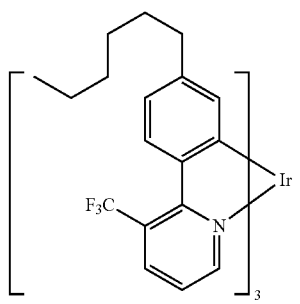
135 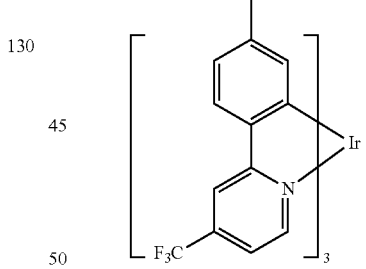
136 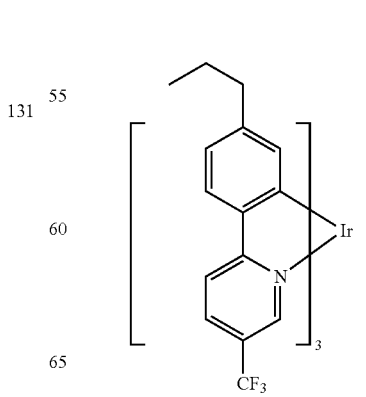

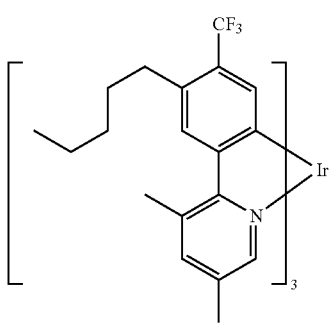
137
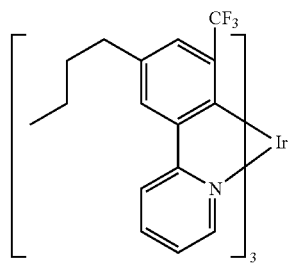
142
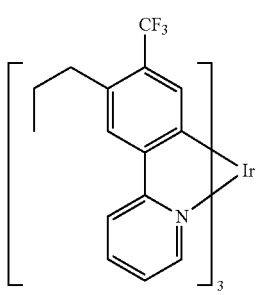
138
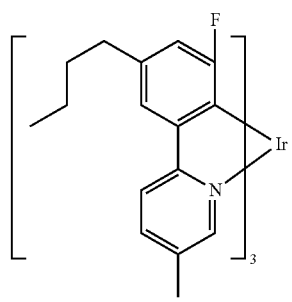
143
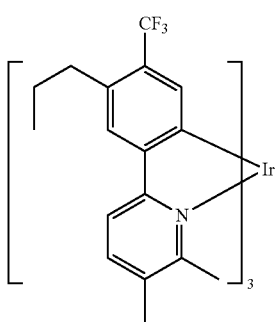
139
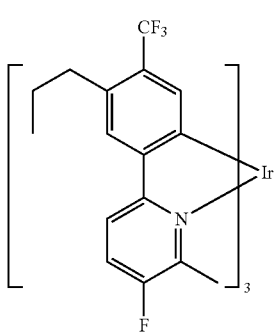
140
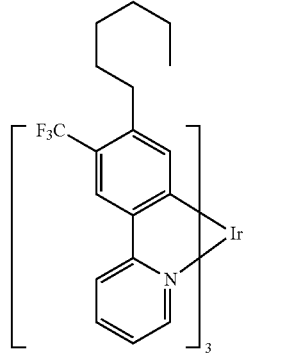
144
[Chem. 20]
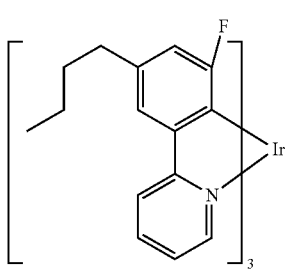
141
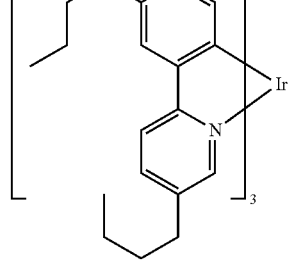
145

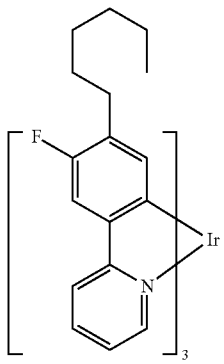
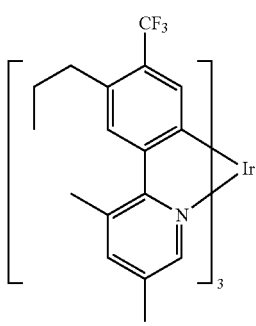
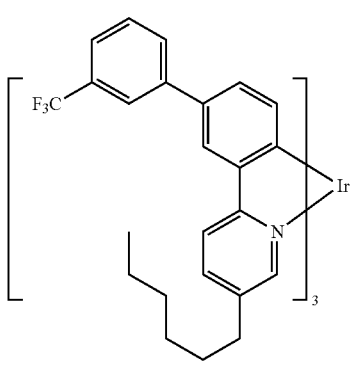
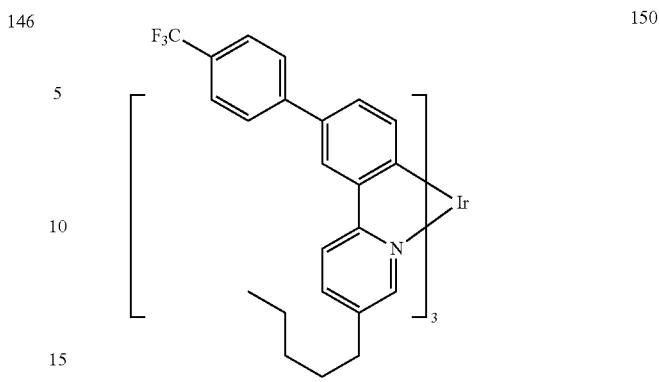
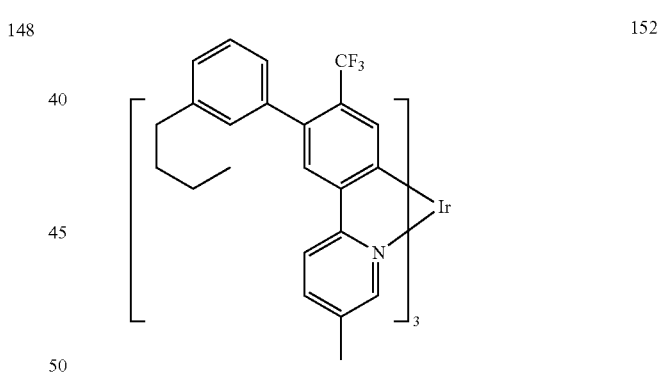
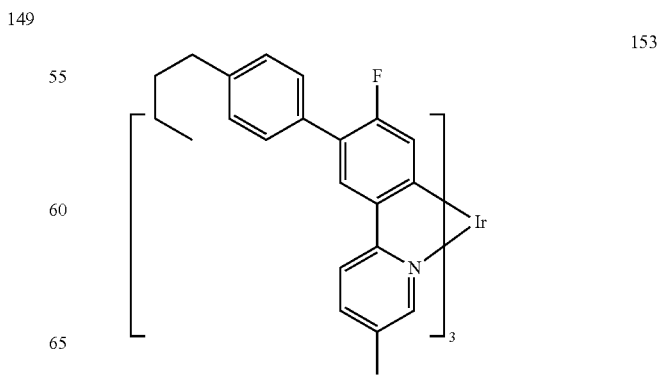

154
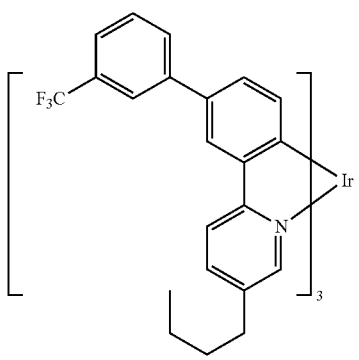
155
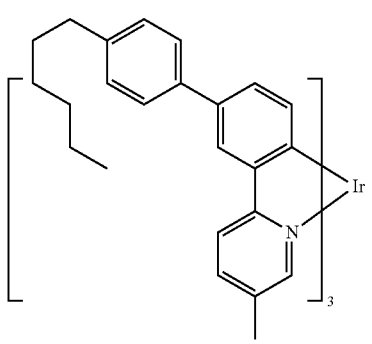
156
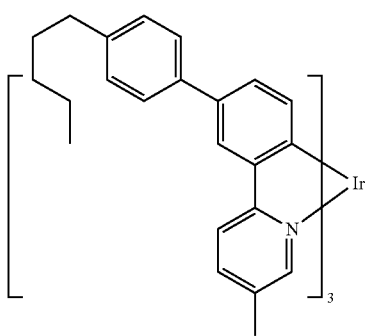
157
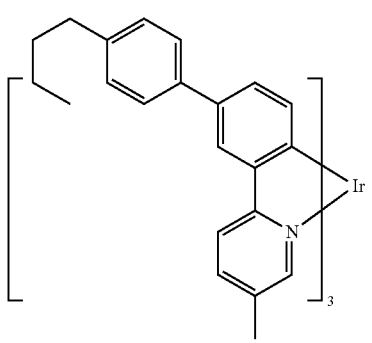
158
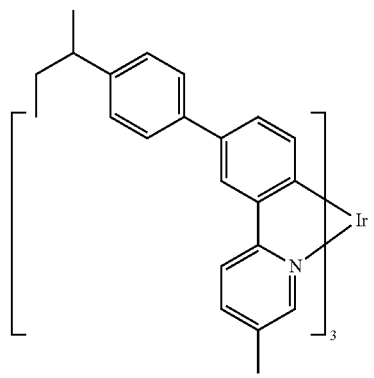
159
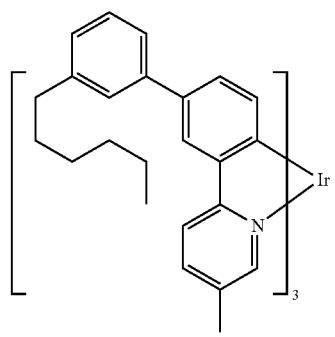
160
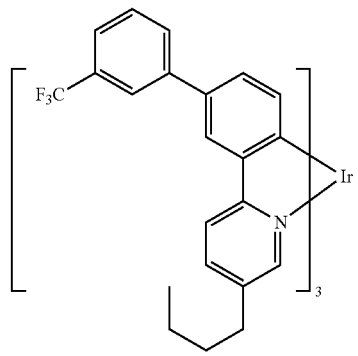
161
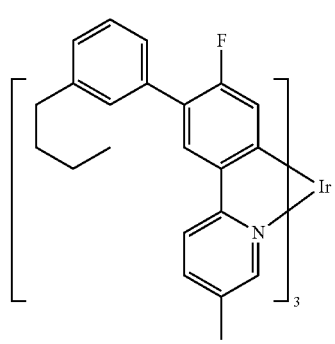

-continued
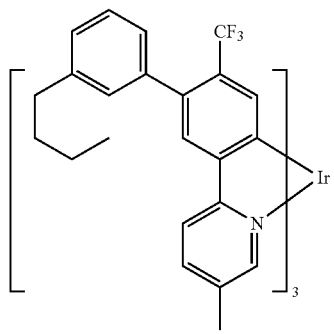
162
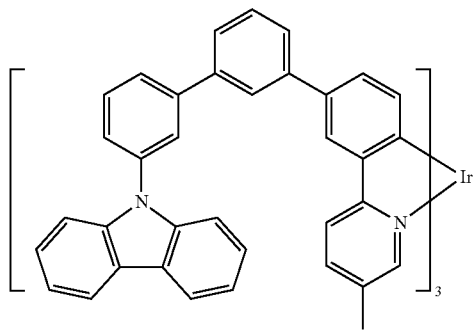
163
[Chem. 21]
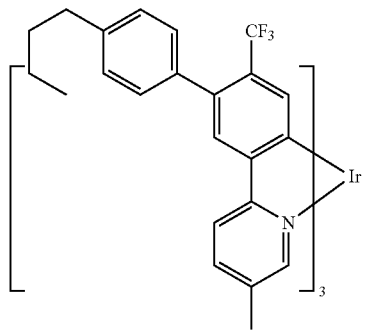
164
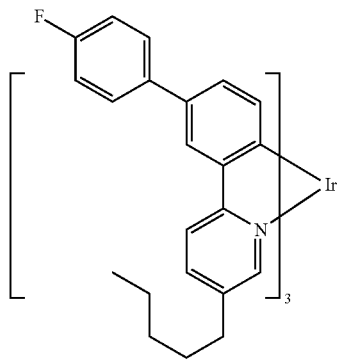
165
-continued
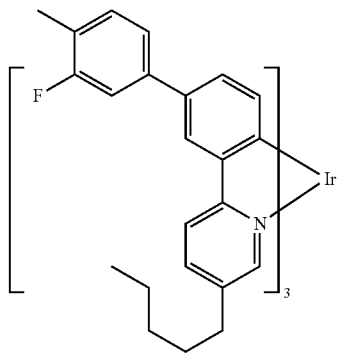
166
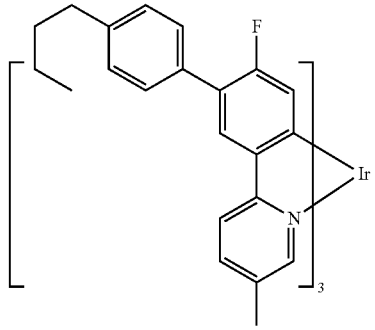
167
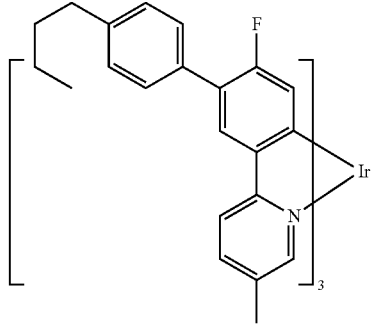
168
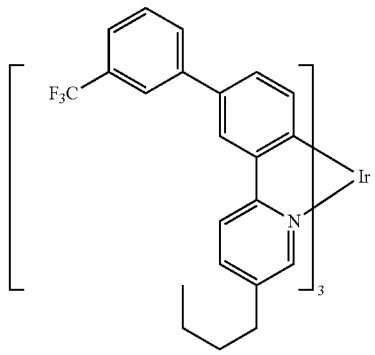
169

-continued
170 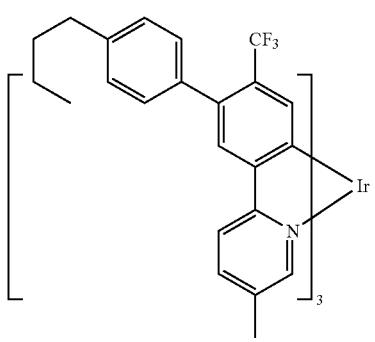
171 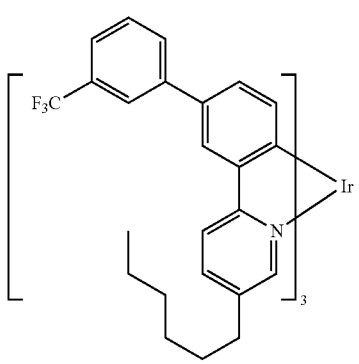
172 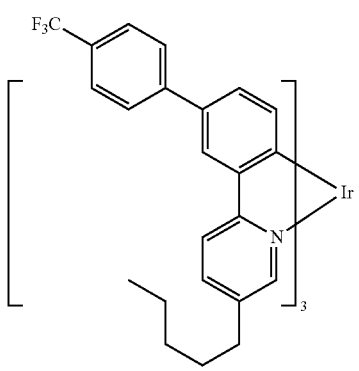
173 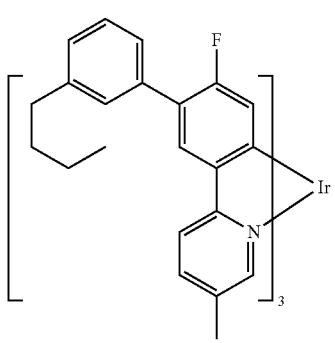
-continued
174 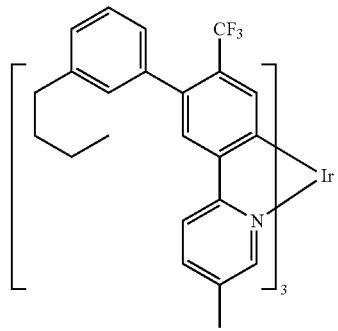
175 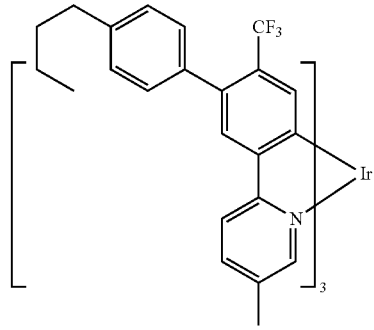
176 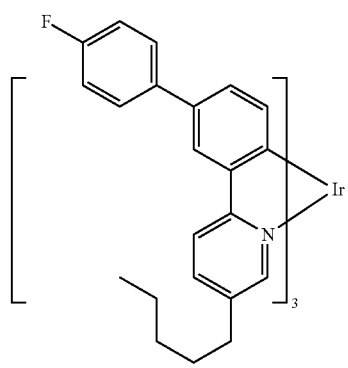
177 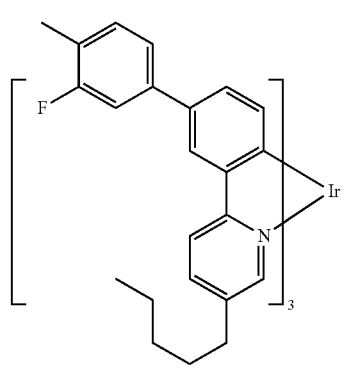

[Chem. 22]
178 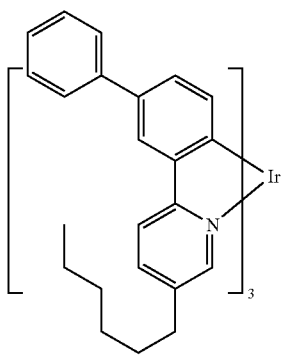
179 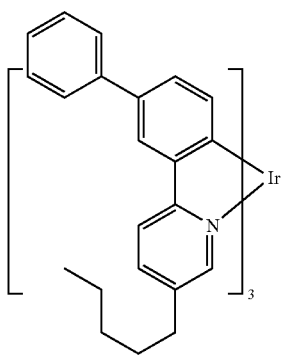
180 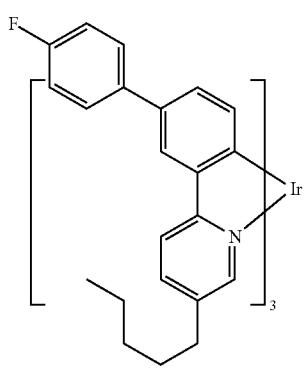
181 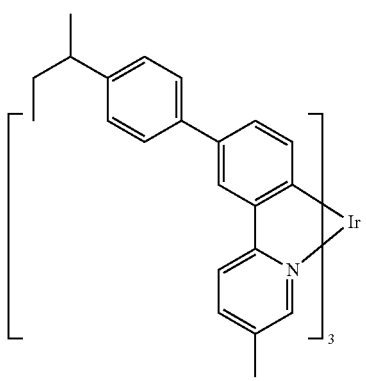
182 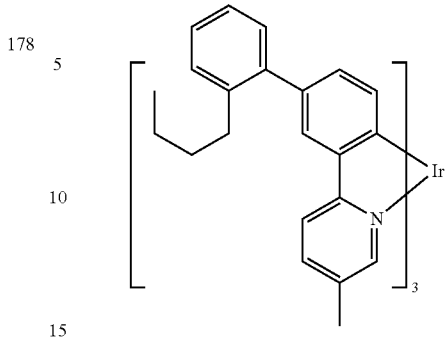
183 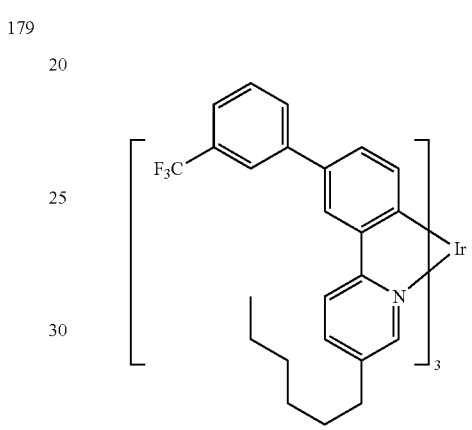
184 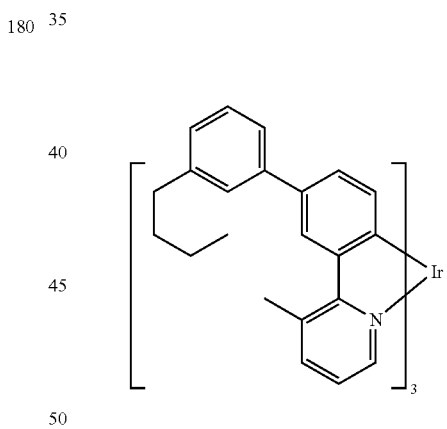
185 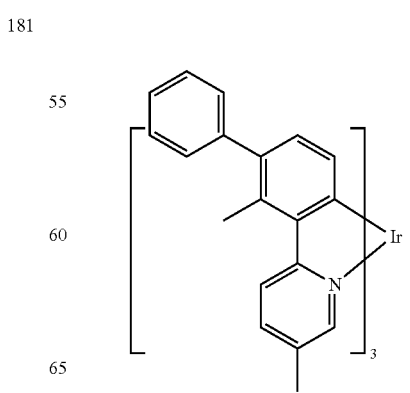

186
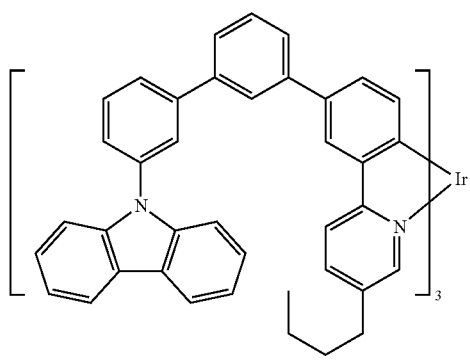
187
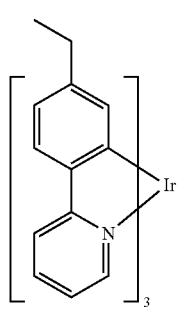
188
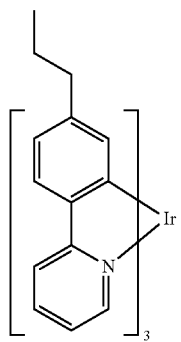
189
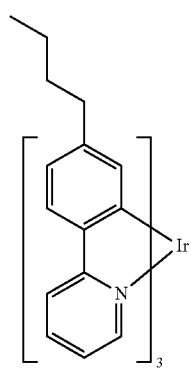
190
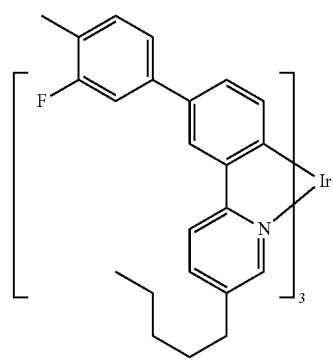
191
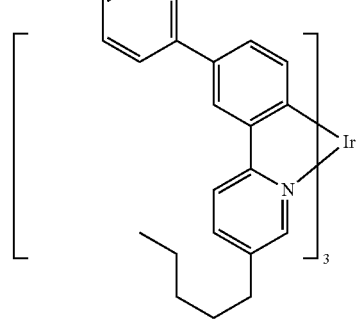
[Chem. 23]
192
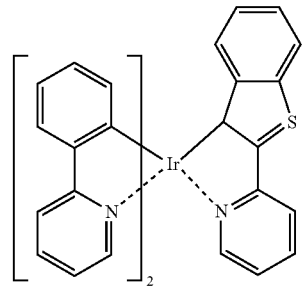
193
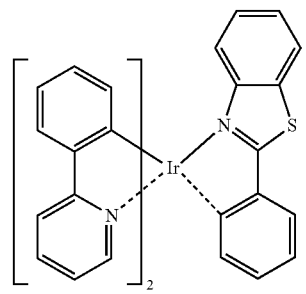
194
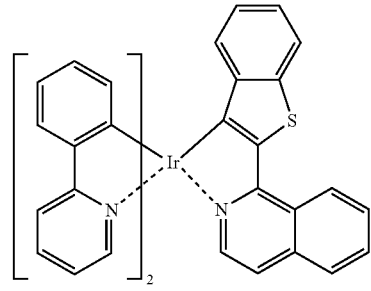

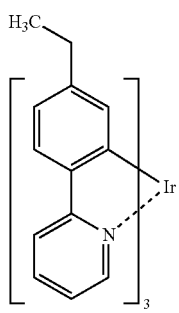
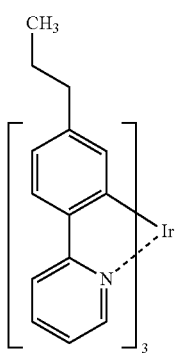
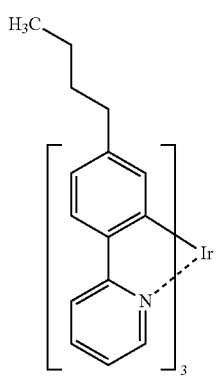
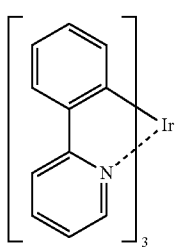
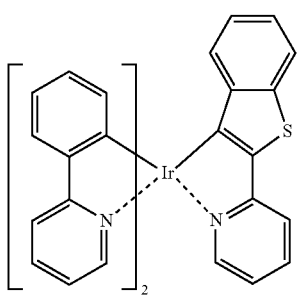
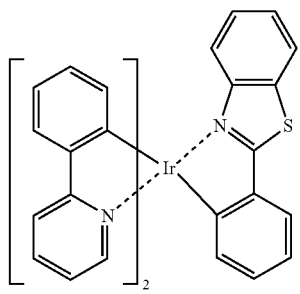
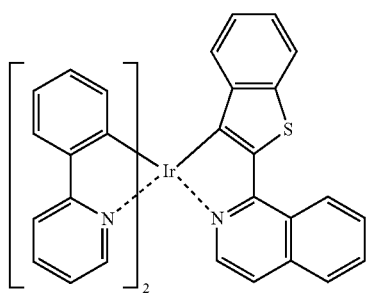
[Chem. 24]
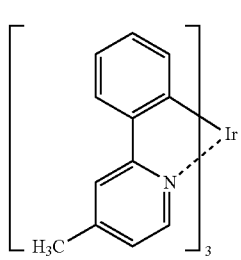
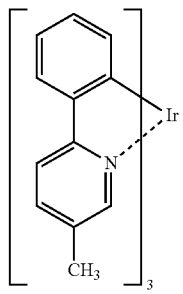
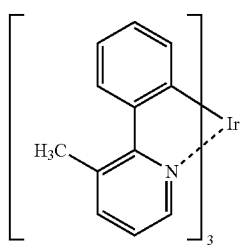

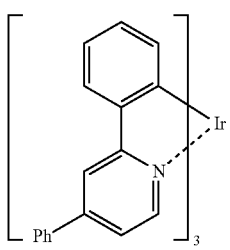 205
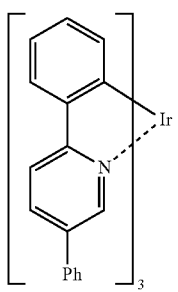 206
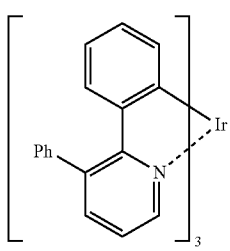 207
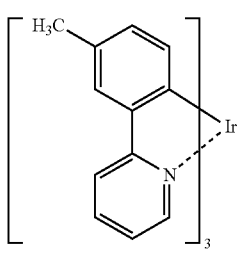 208
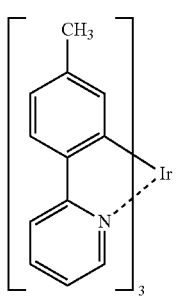 209
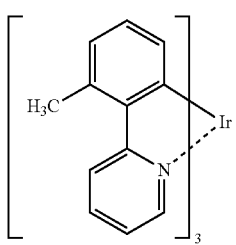 210
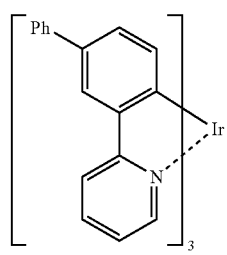 211
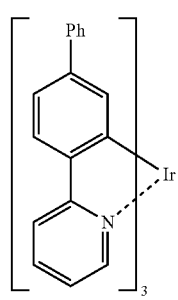 212
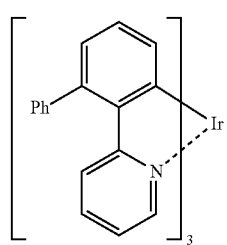 213
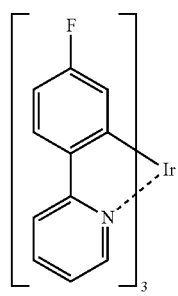 214
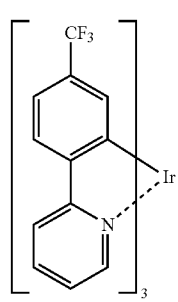 215

[Chem. 25]
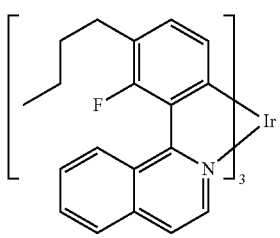  216
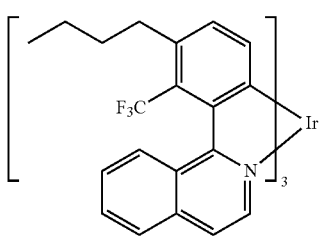  217
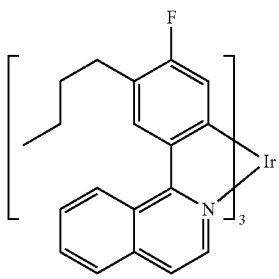  218
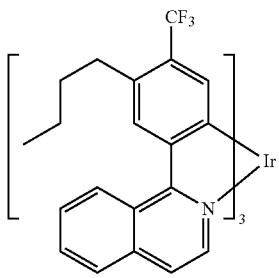  219
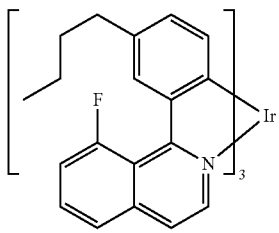  220
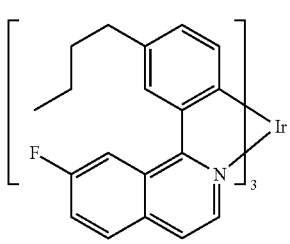  221
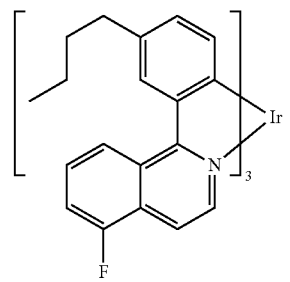  222
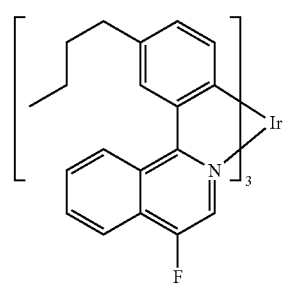  223
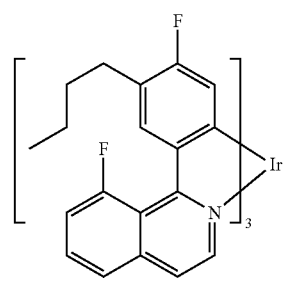  224
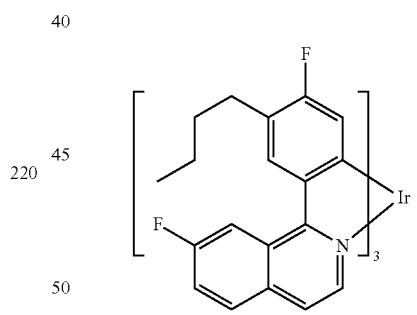  225
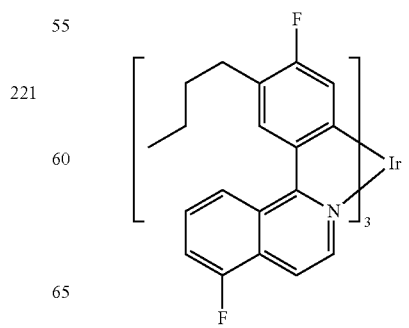  226

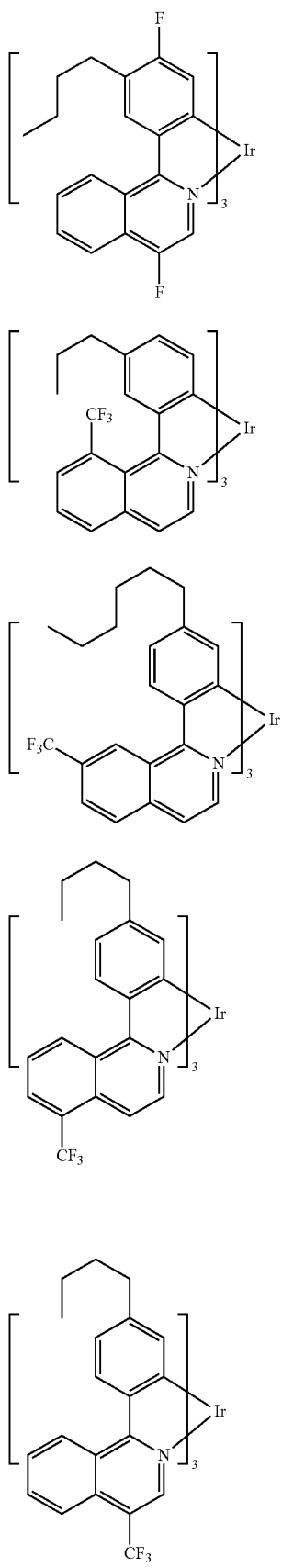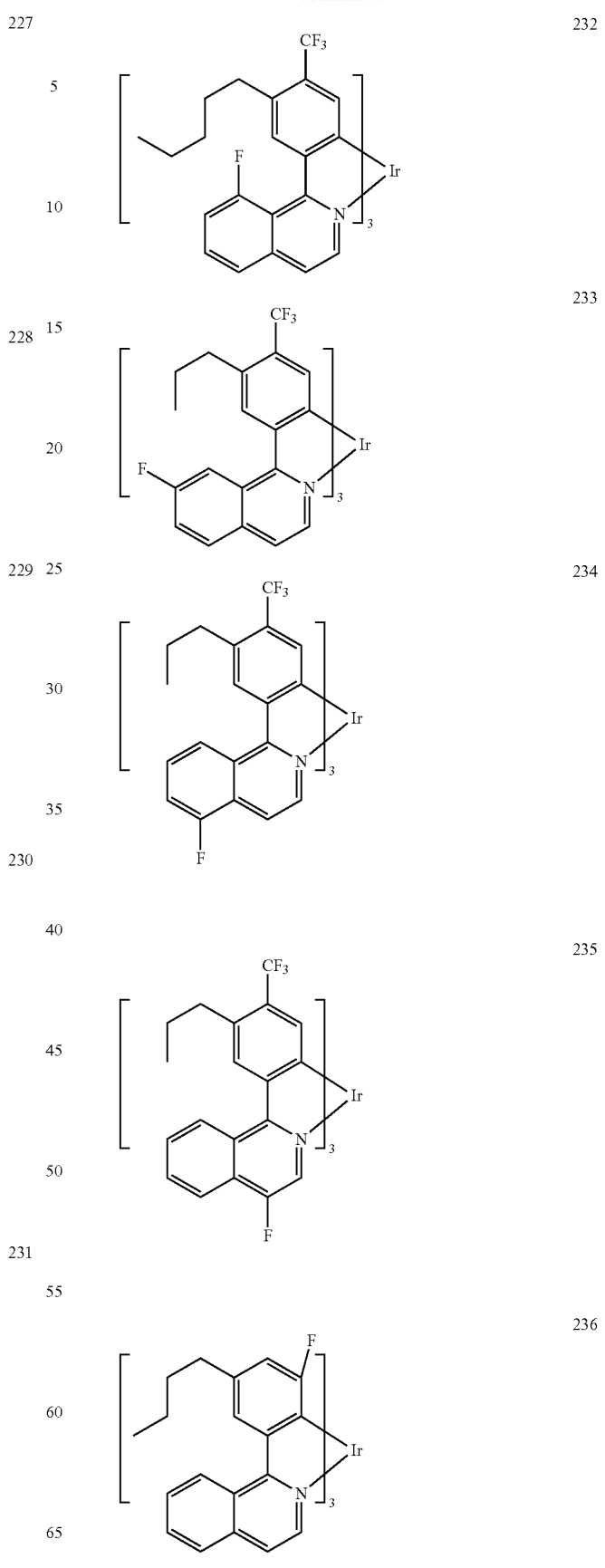

237 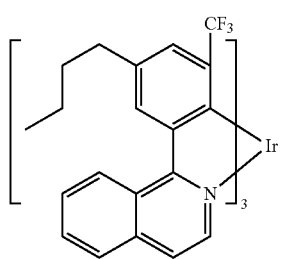
238 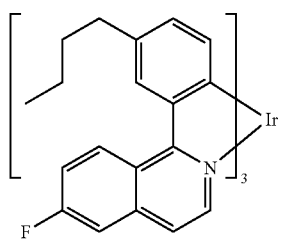
[Chem. 26]
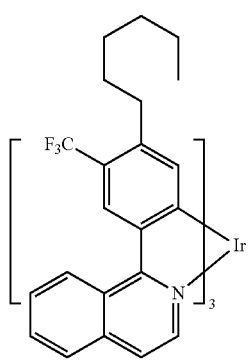
240 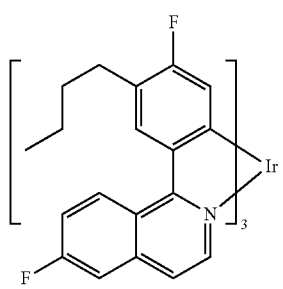
241 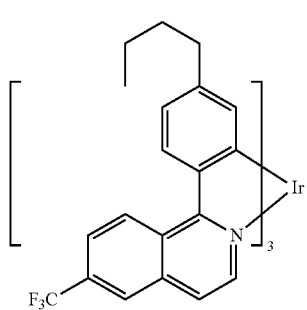
242 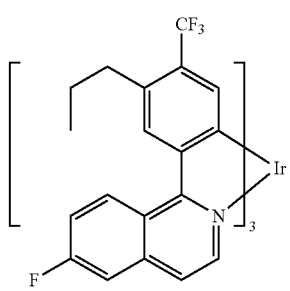
243 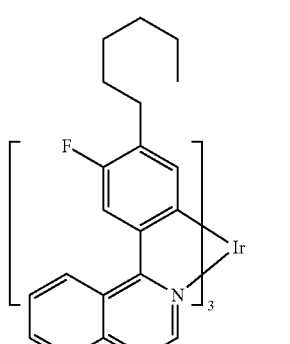
244 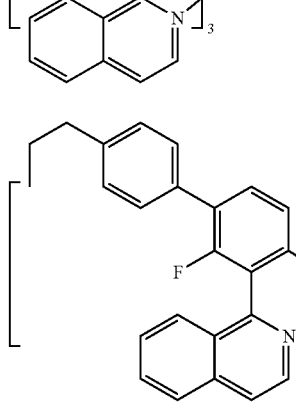
245 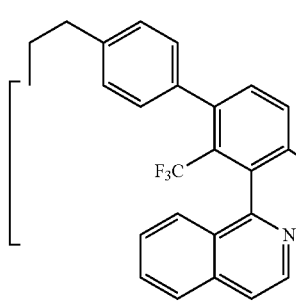
246 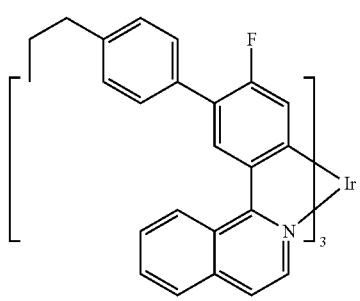

247
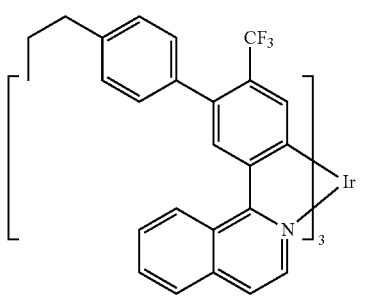
248
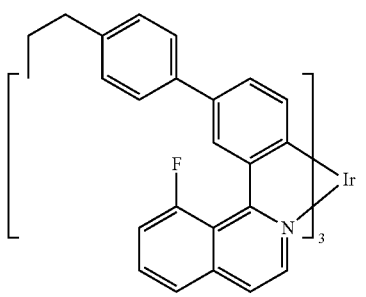
249
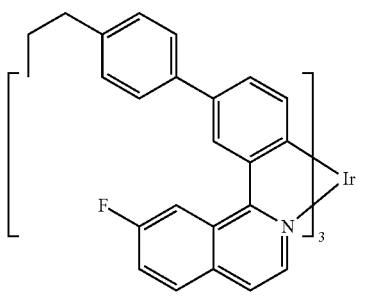
250
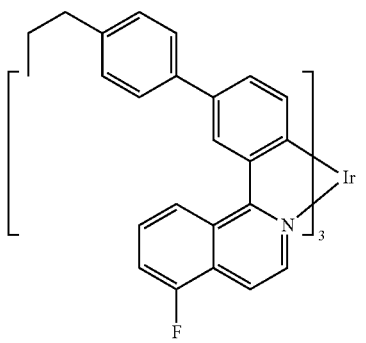
251
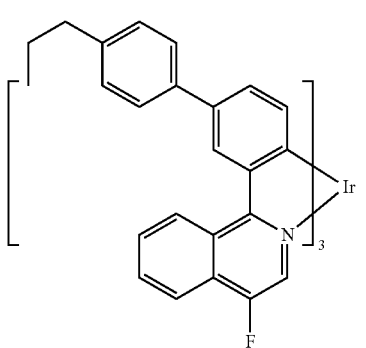
252
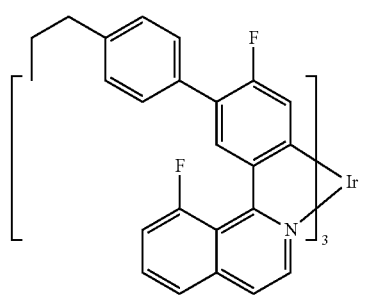
253
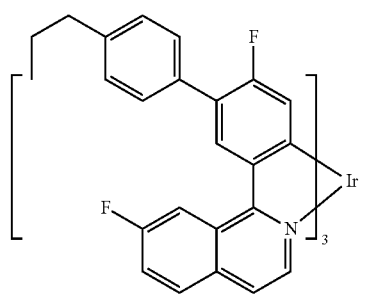
254
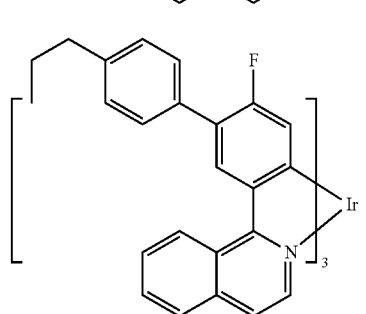
255
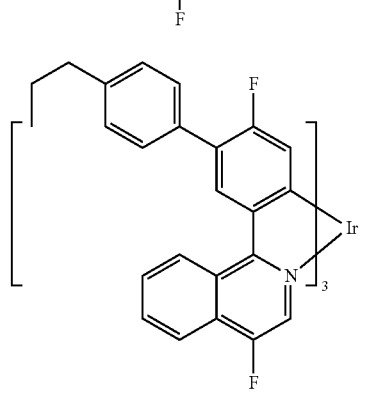
256
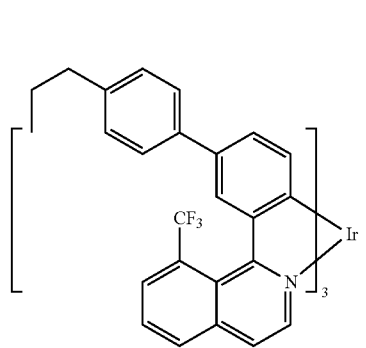

-continued
257 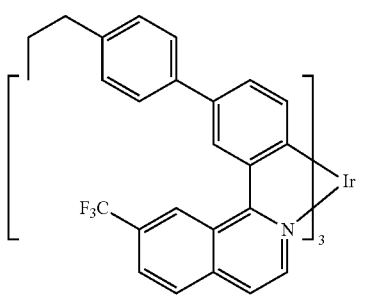
258 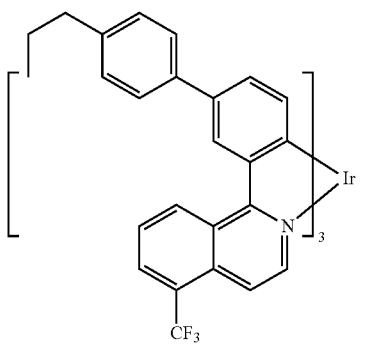
259 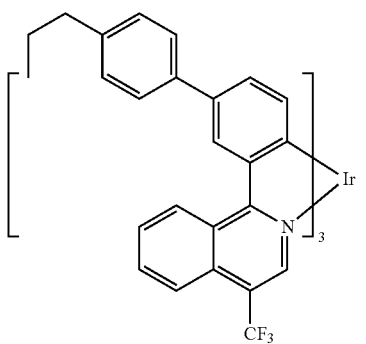
260 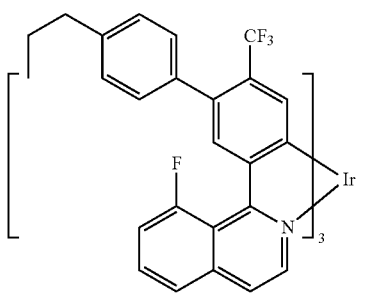
261 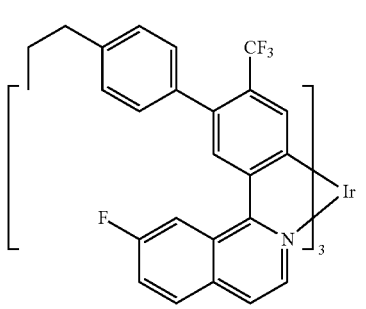
262 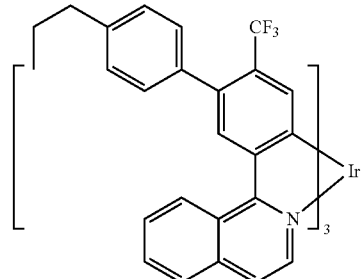
263 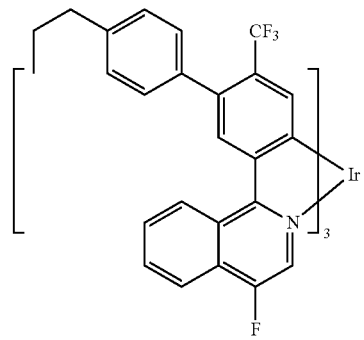
[Chem. 27]
264 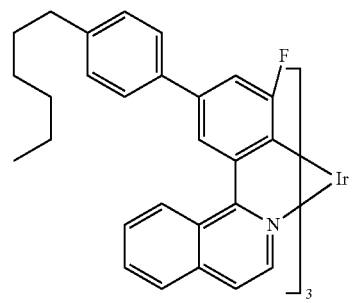
265 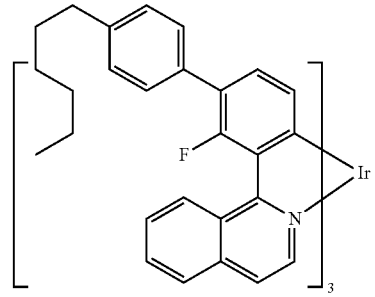
266 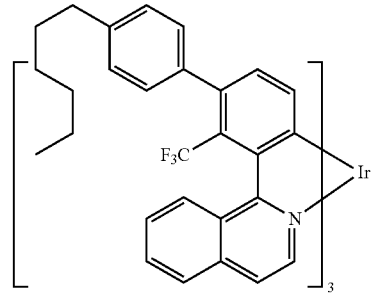

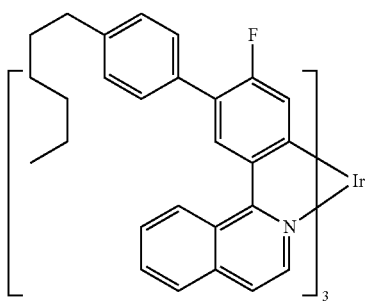 267
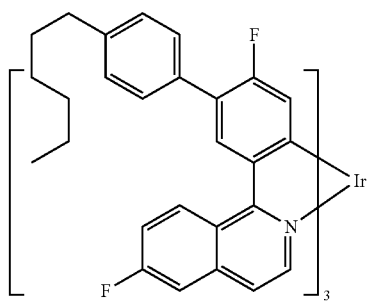 272
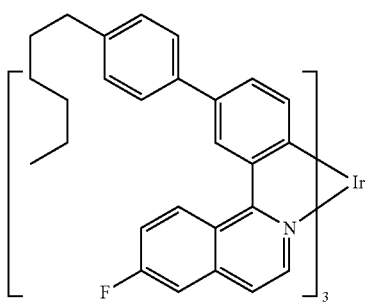 268
273
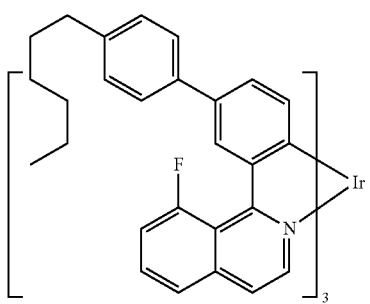 269
274
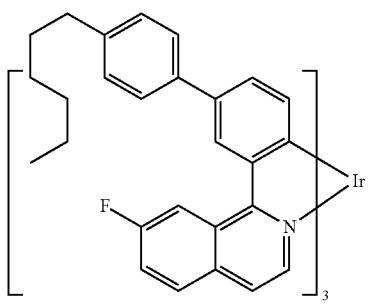 270
275
271
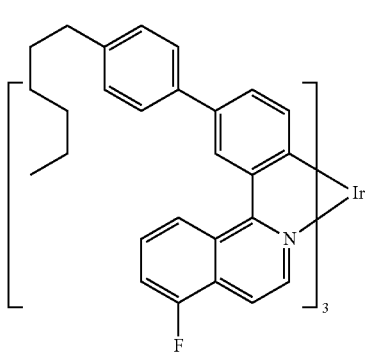
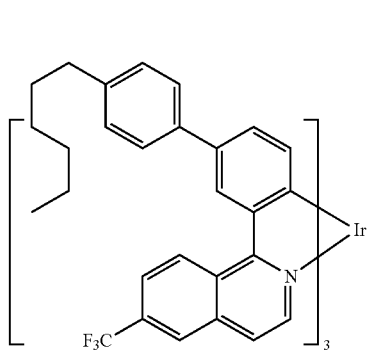 276

277
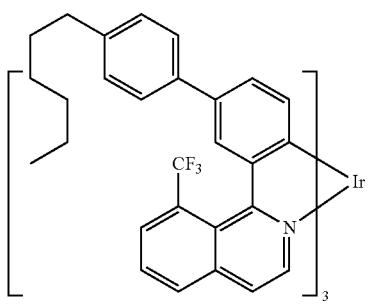
278
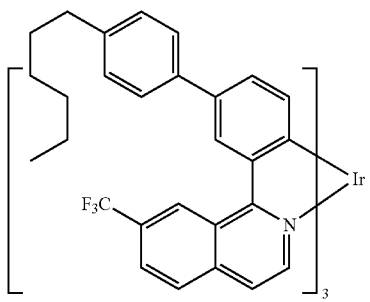
279
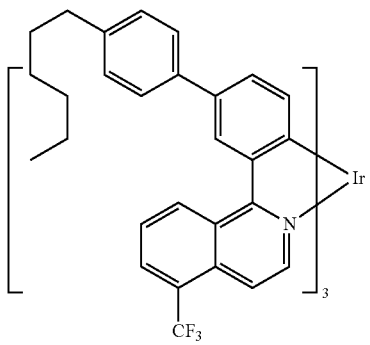
280
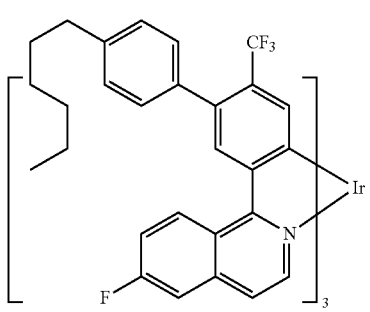
281
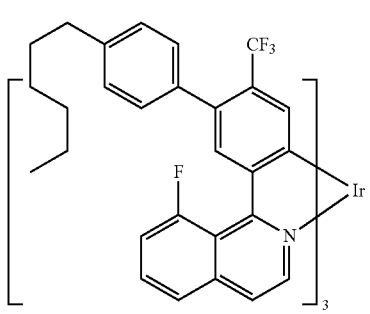
282
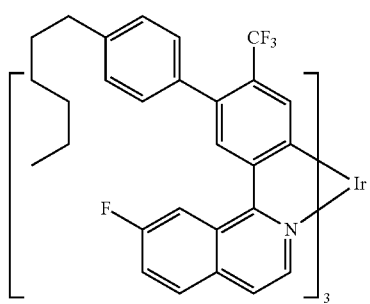
283
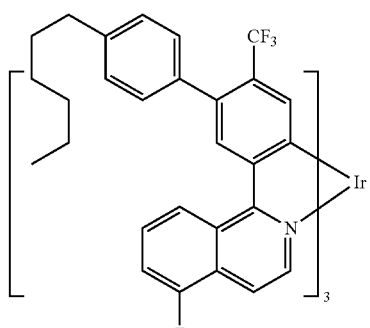
284
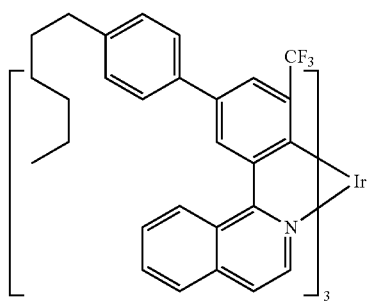
285
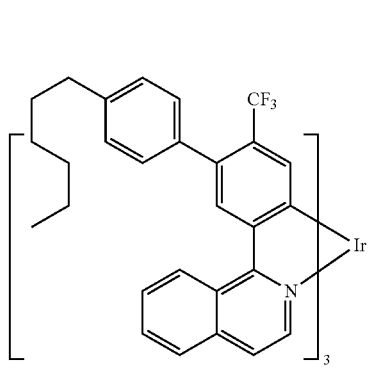
286
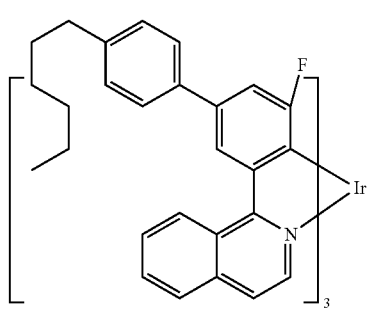

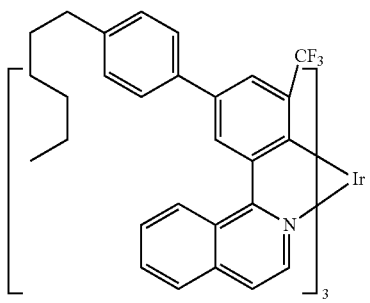
287
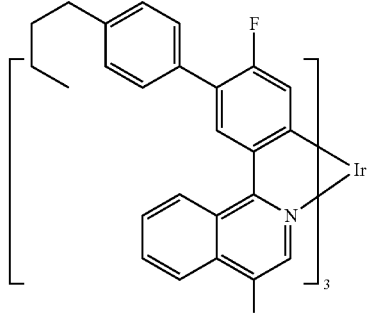
292
[Chem. 28]
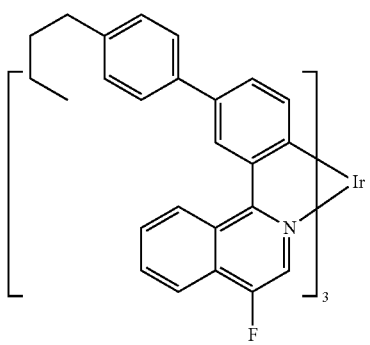
288
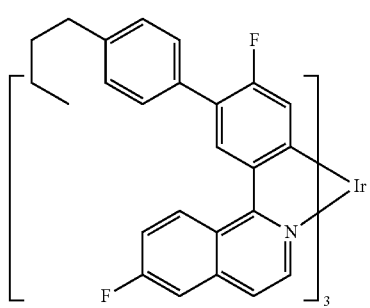
293
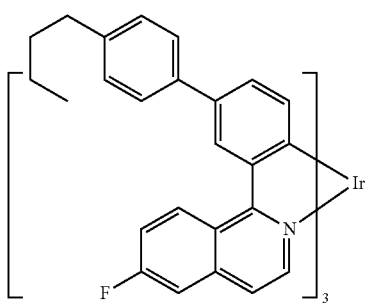
289
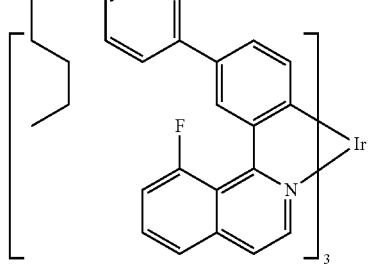
294
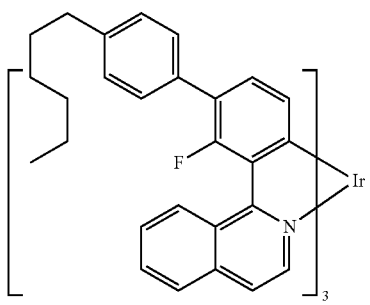
290
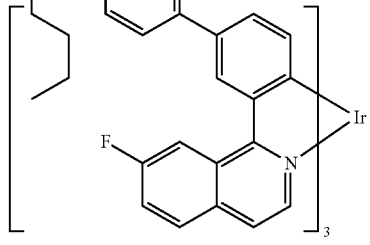
295
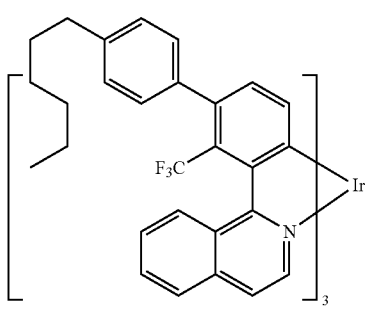
291
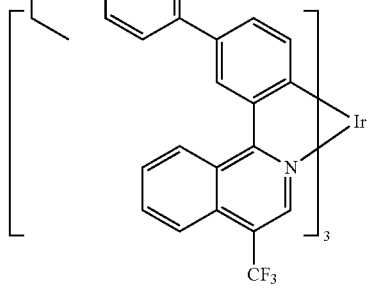
296

297
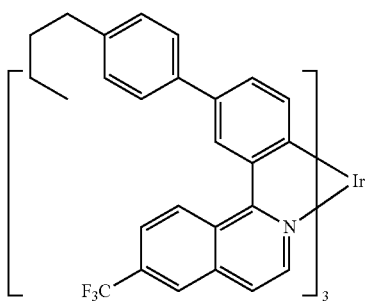
298
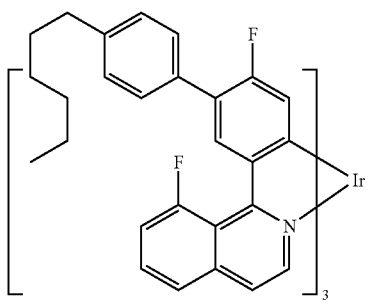
299
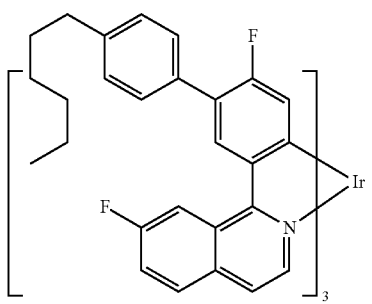
300
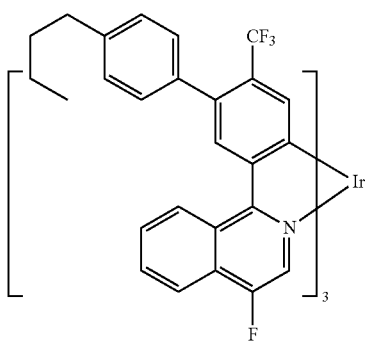
301
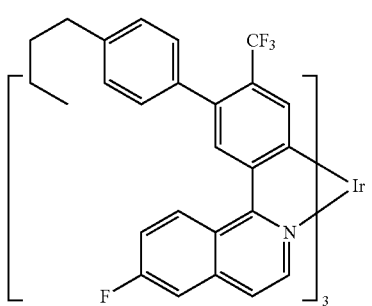
302
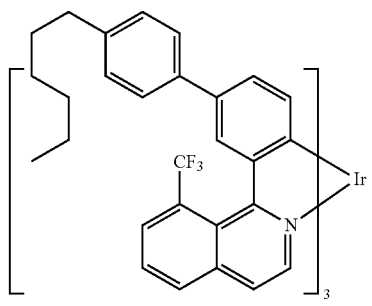
303
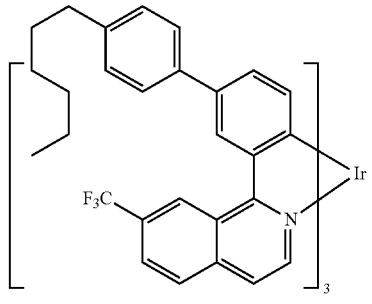
304
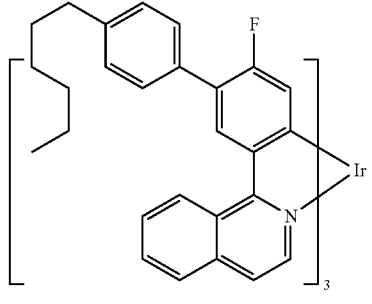
305
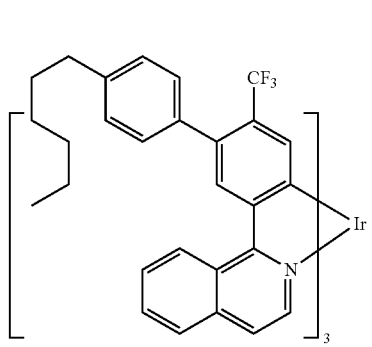
306
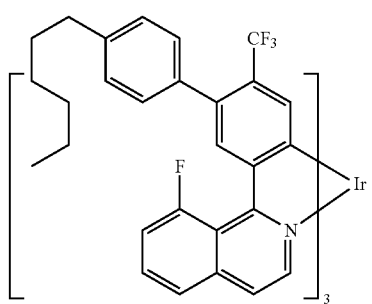

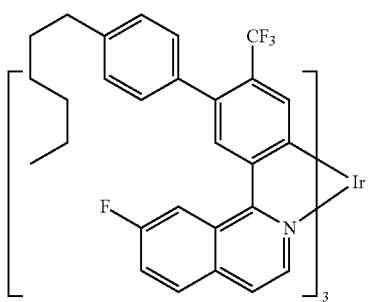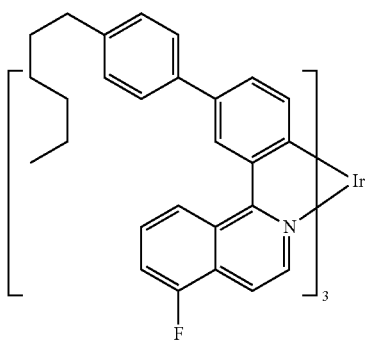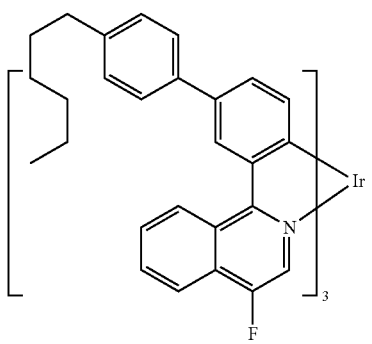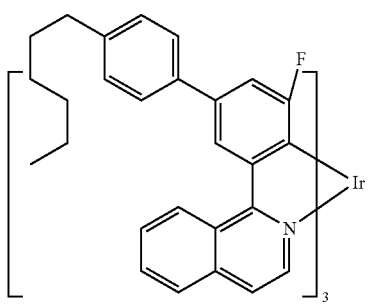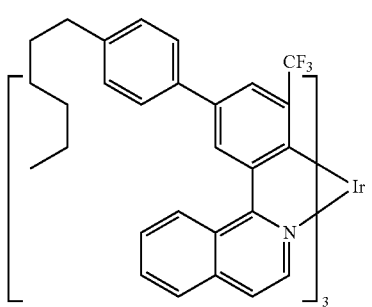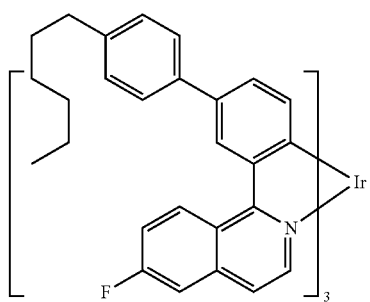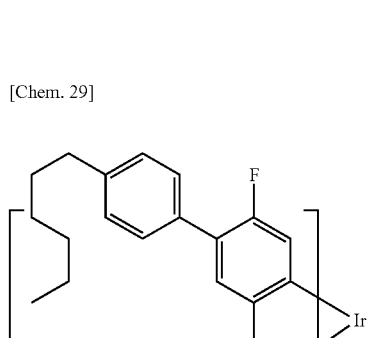
[Chem. 29]
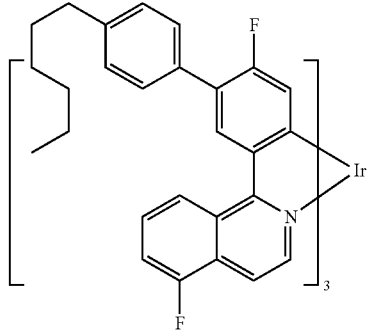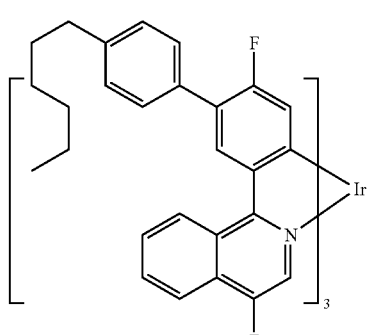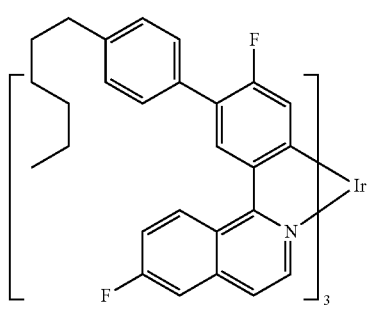

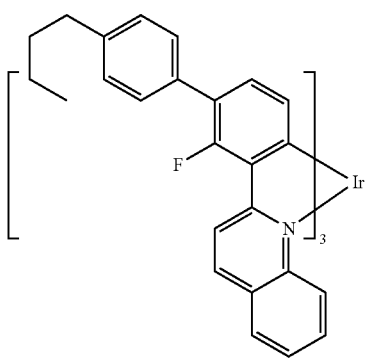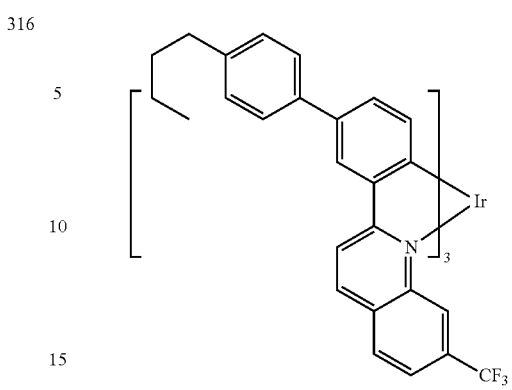

324
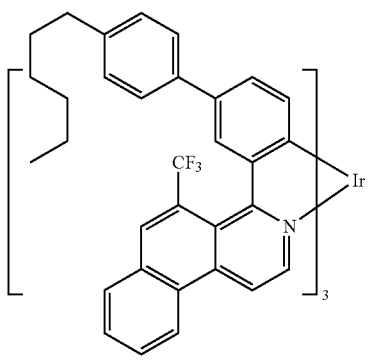
325
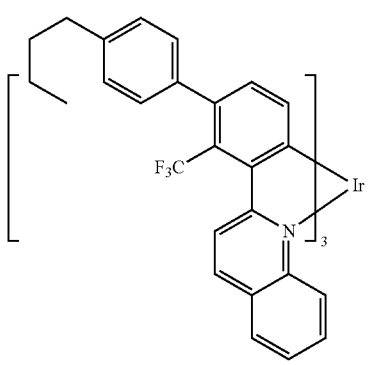
326
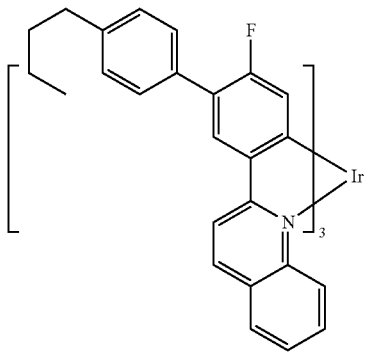
327
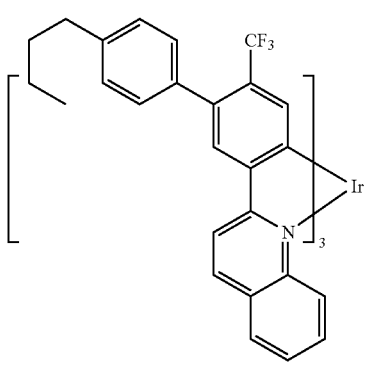
328
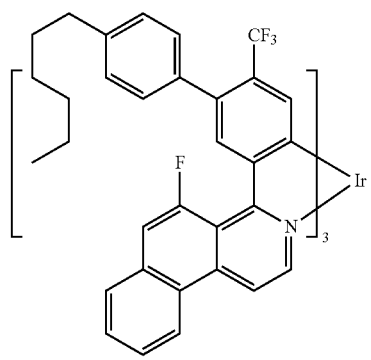
329
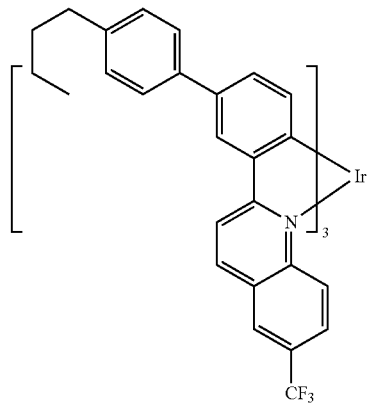
330
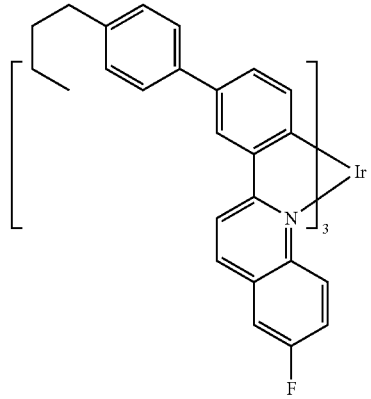
331
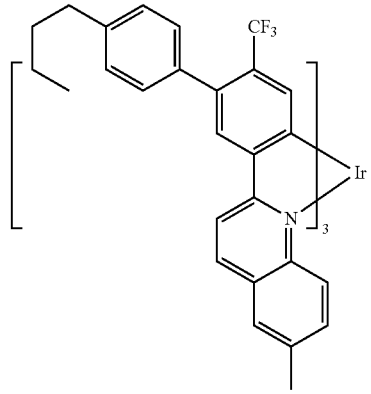

-continued
332
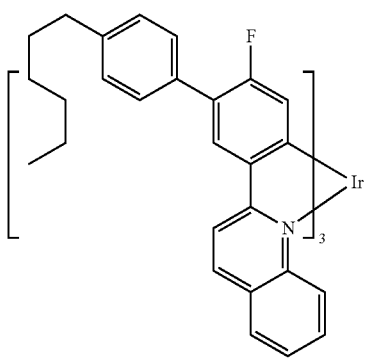
333
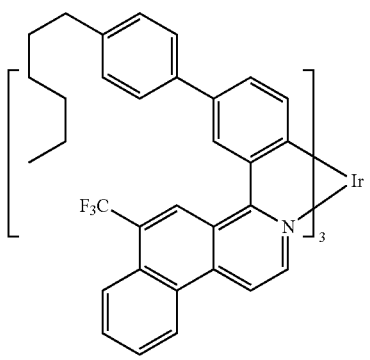
334
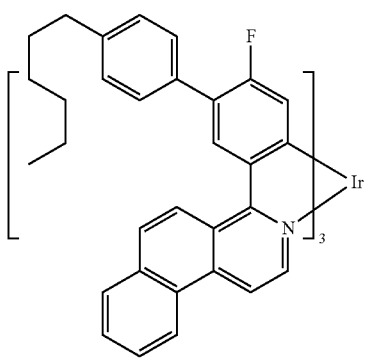
335
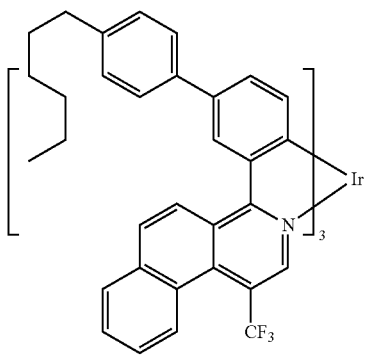
[Chem. 30]
336
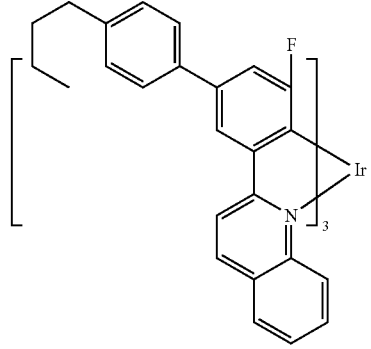
337
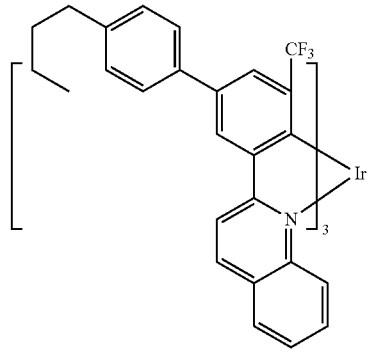
338
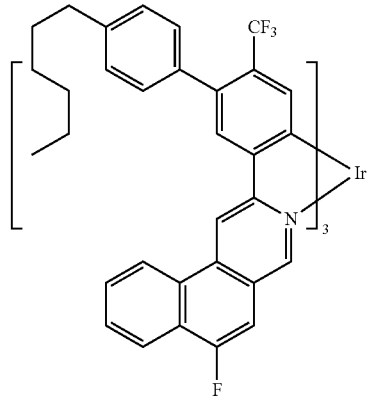
339
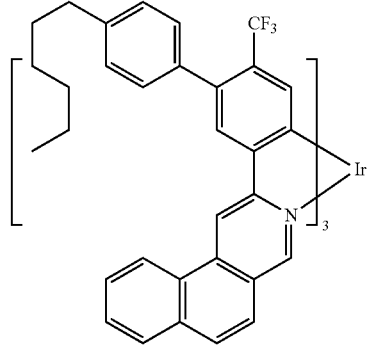

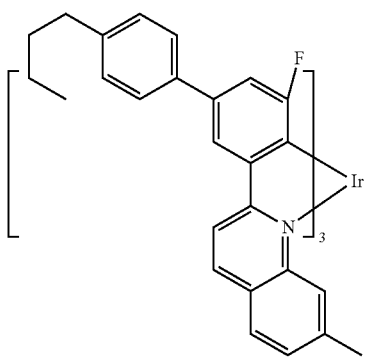
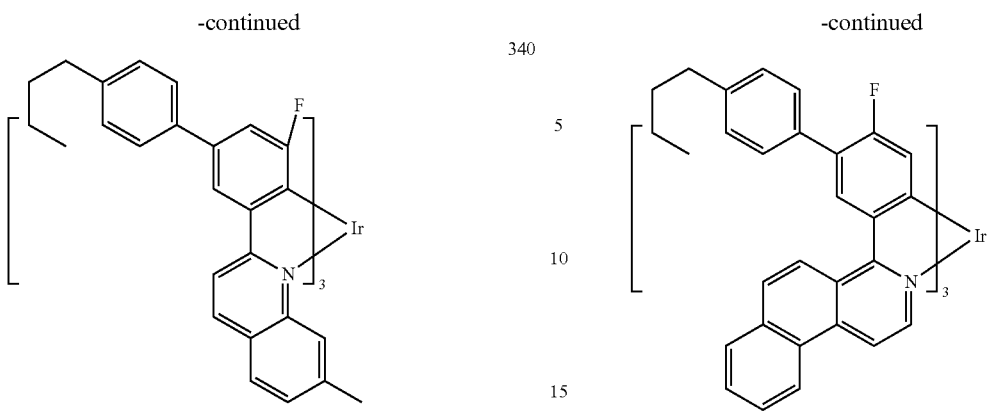
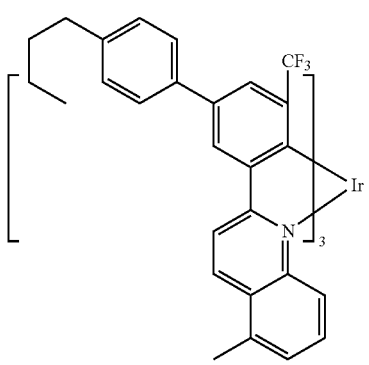
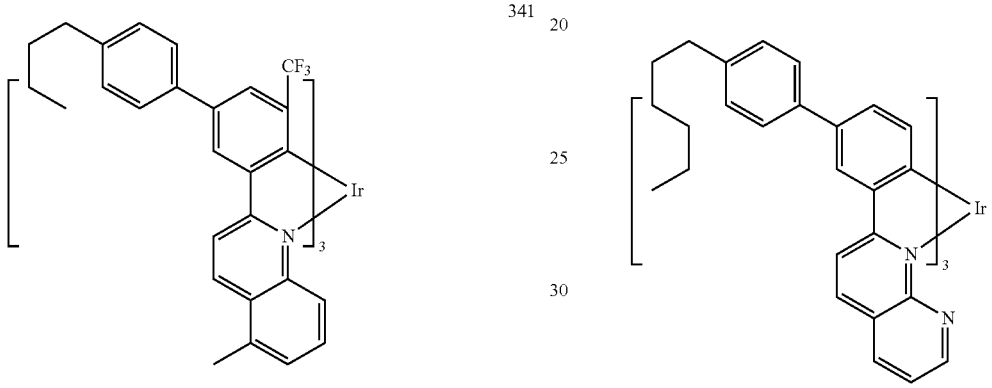
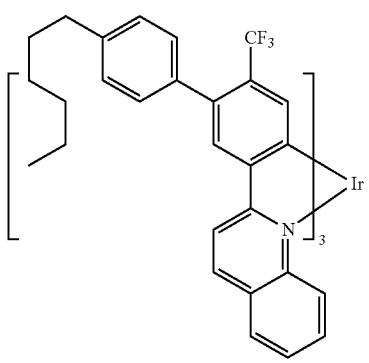
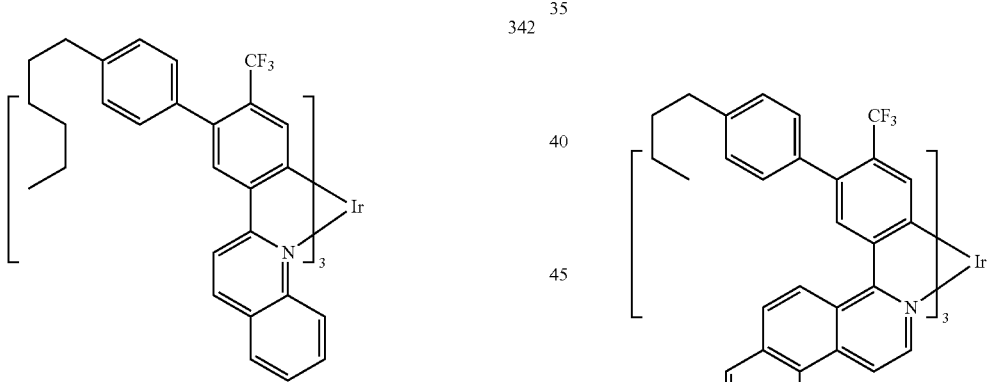
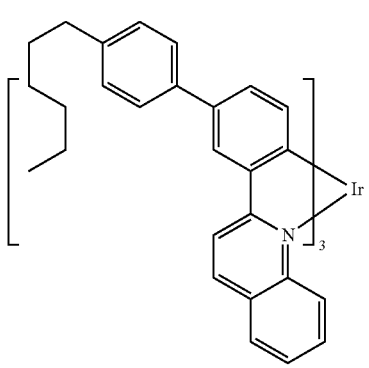
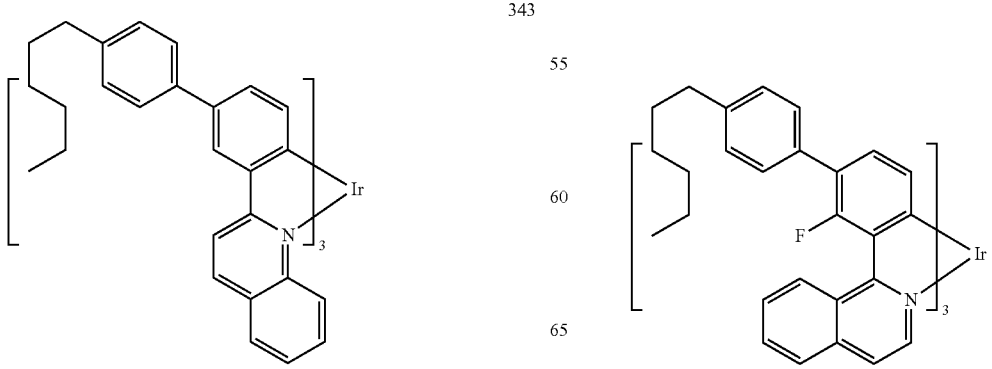

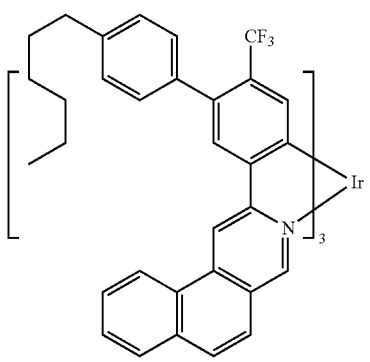
348
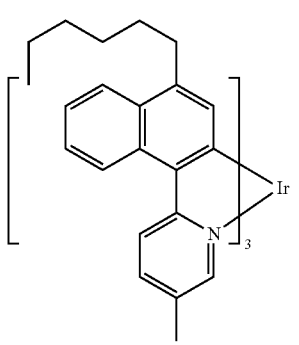
349
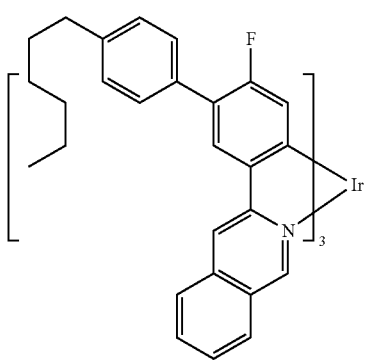
350
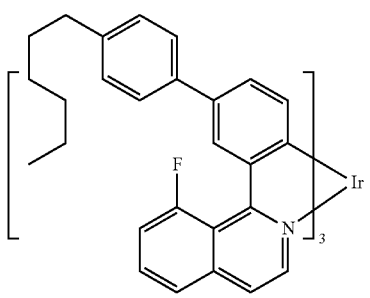
351
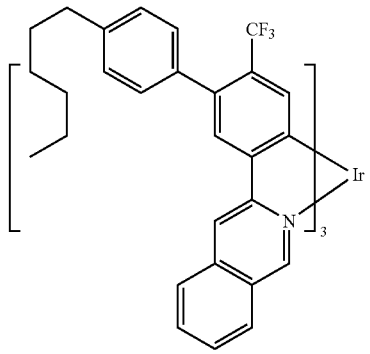
352
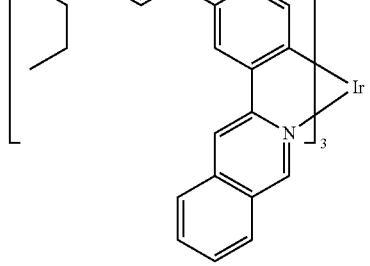
353
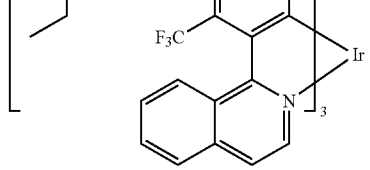
354
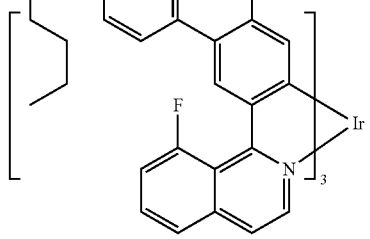
355
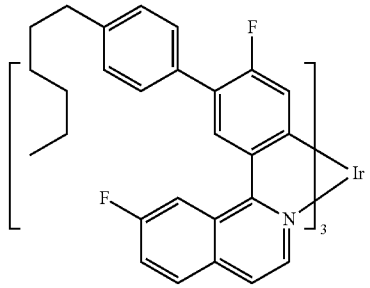
356

85
-continued
357
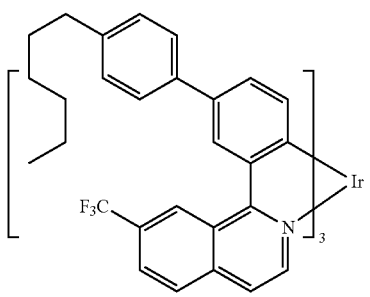
358
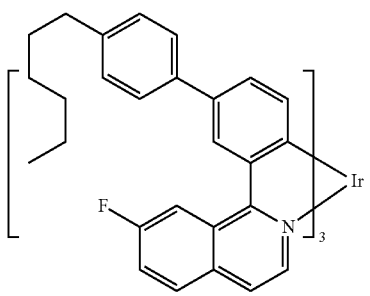
359
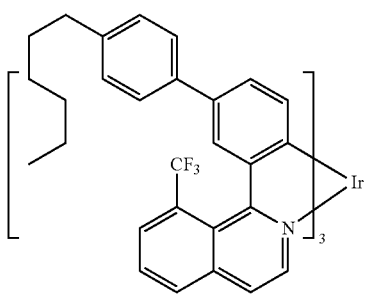
[Chem. 31]
360
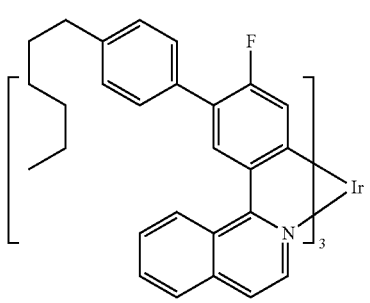
361
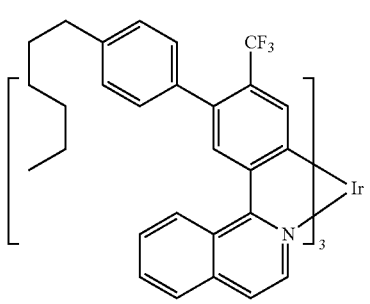
86
-continued
362
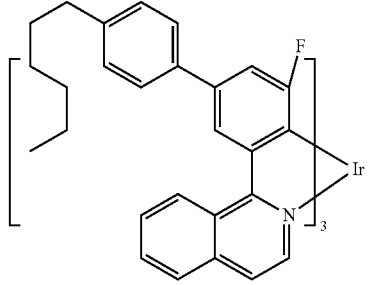
363
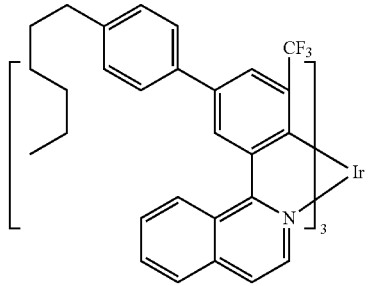
364
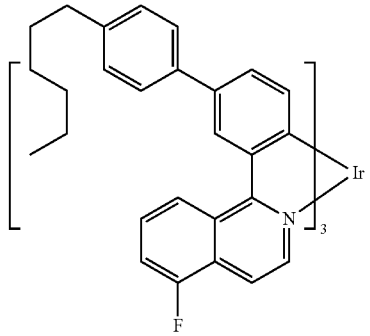
365
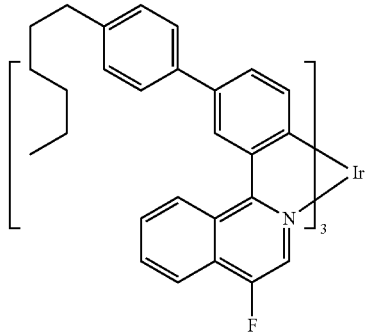
366
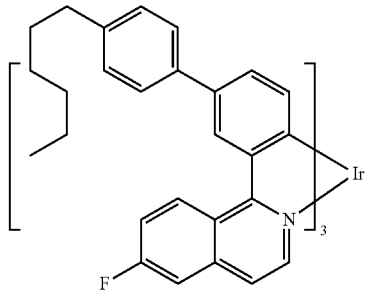

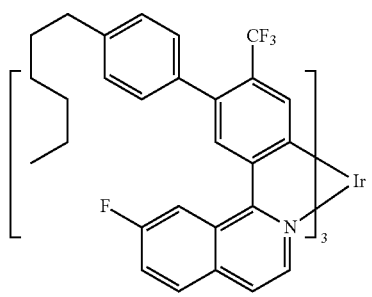
367
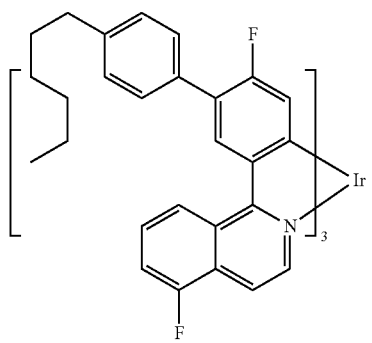
368
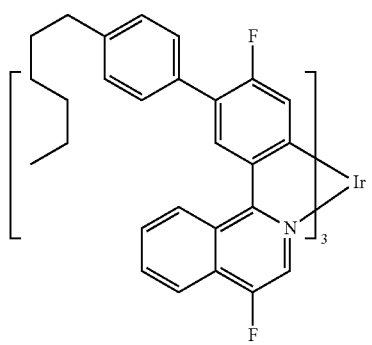
369
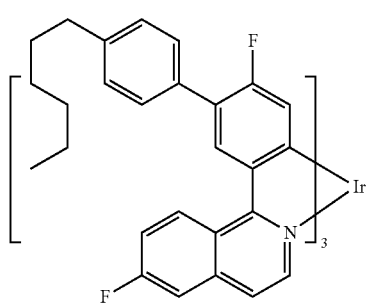
370
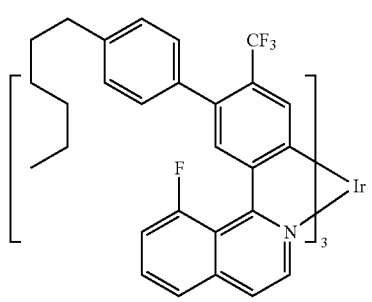
371
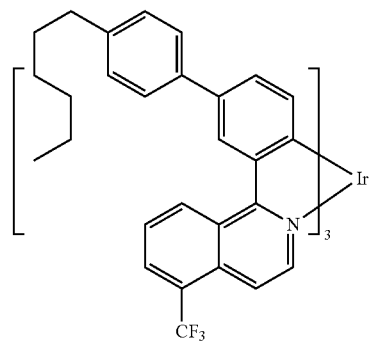
372
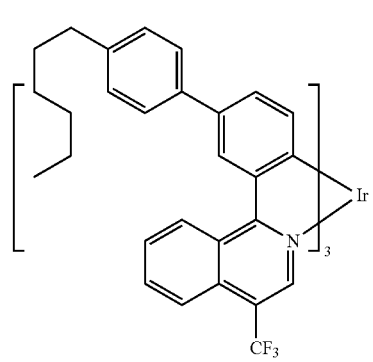
373
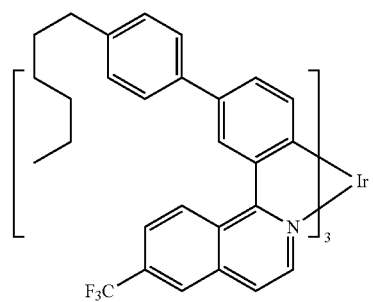
374
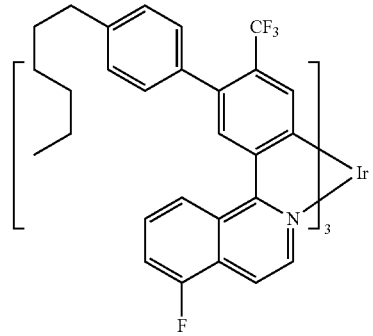
375

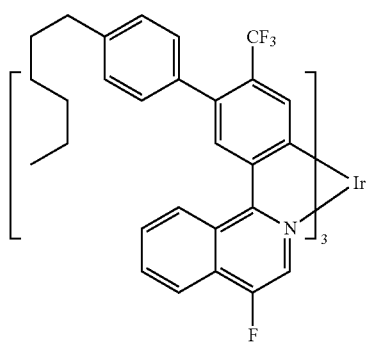
376
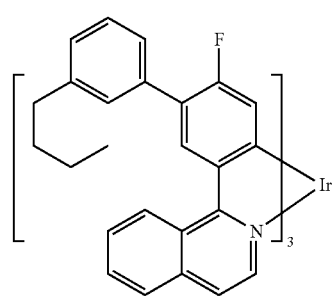
382
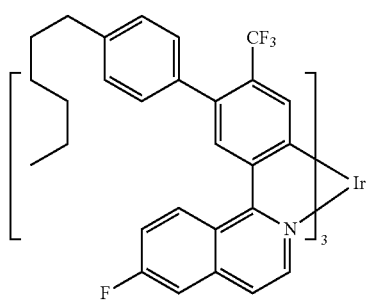
378
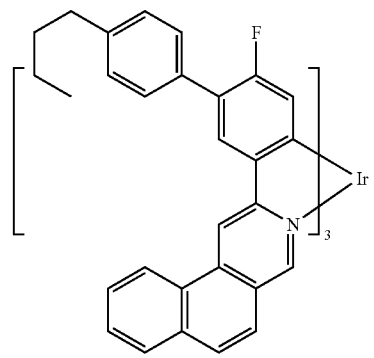
383
[Chem. 32]
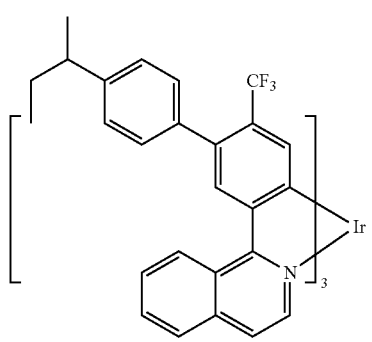
379
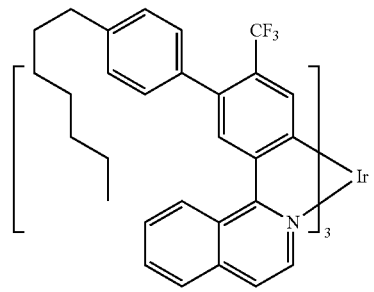
384
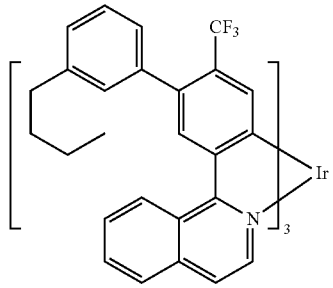
380
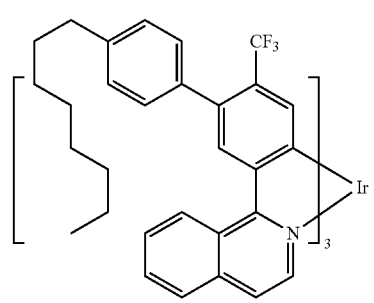
385
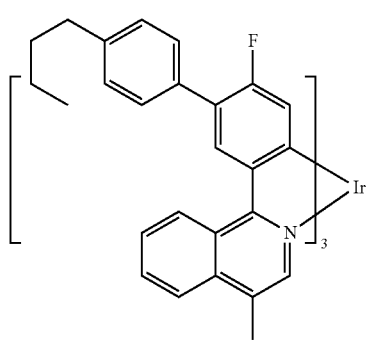
381
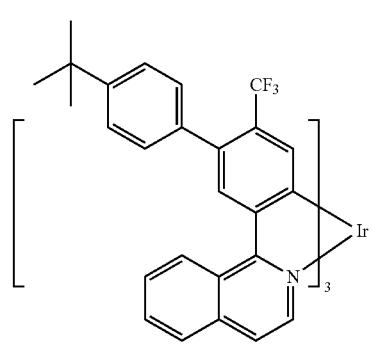
386

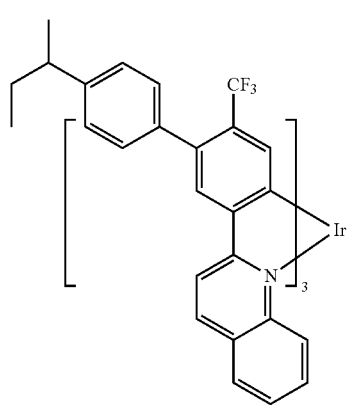
387
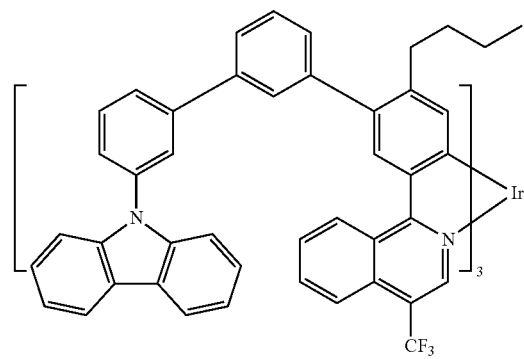
392
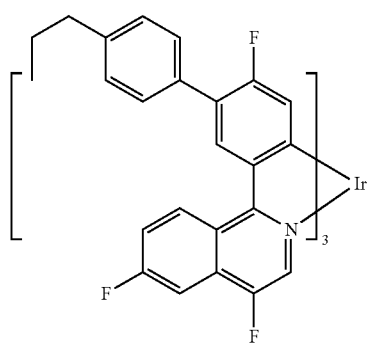
389
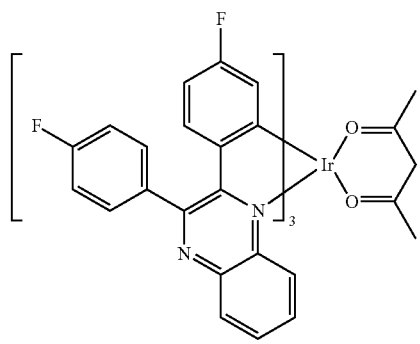
393
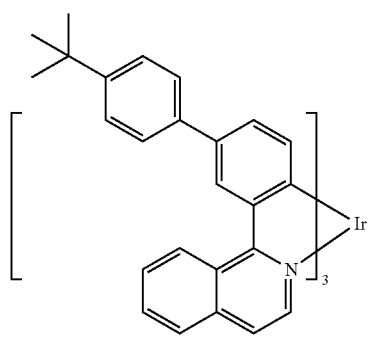
390
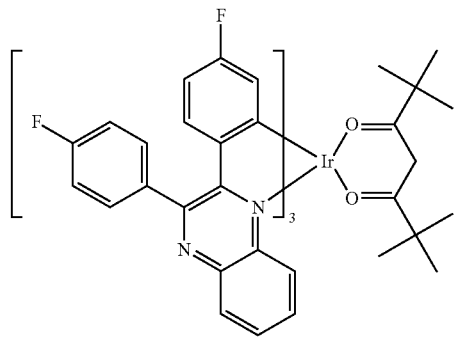
394
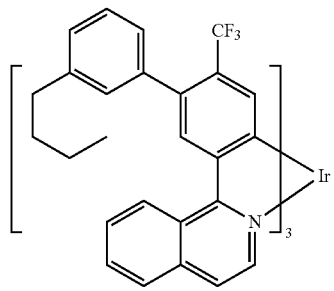
391
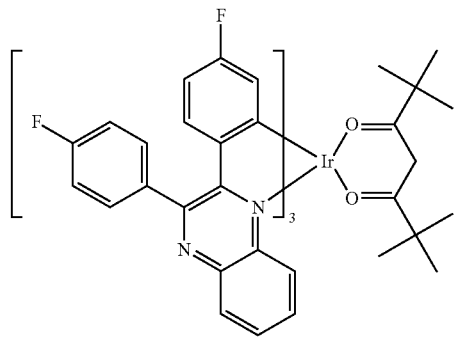
395

396 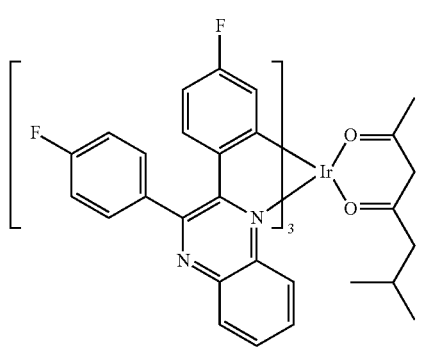
397 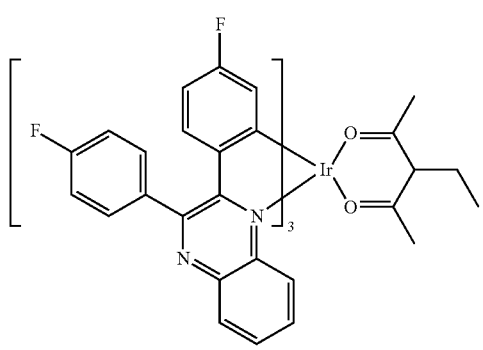
398 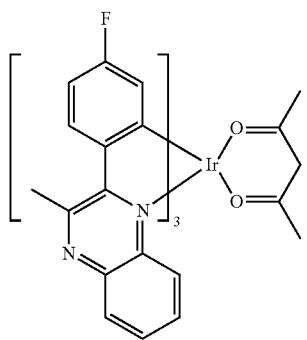
399 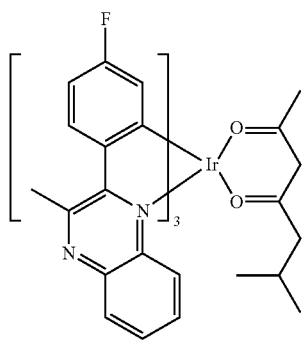
400 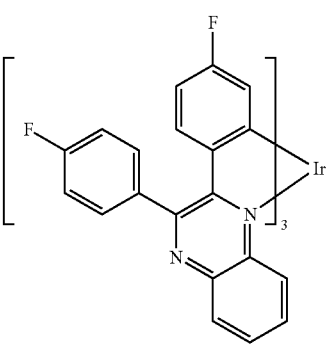
401 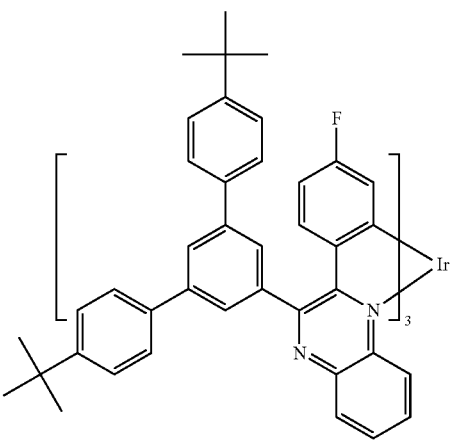
402 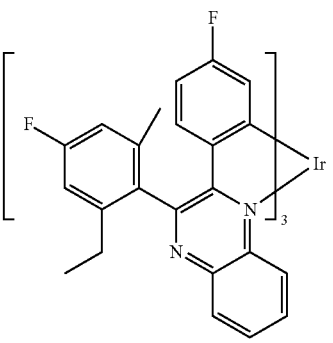
403 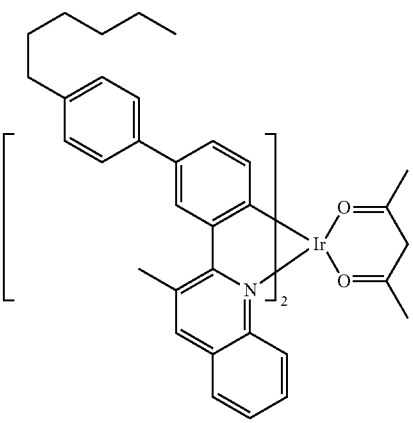

95
-continued
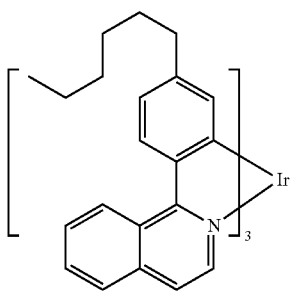
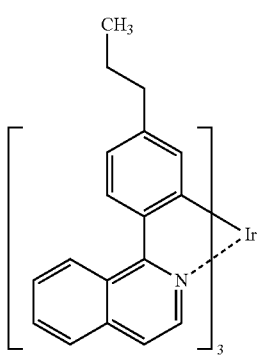
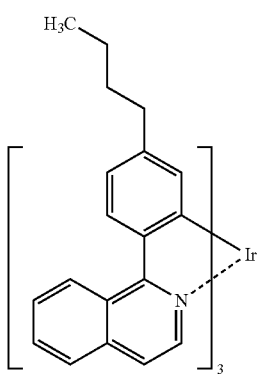
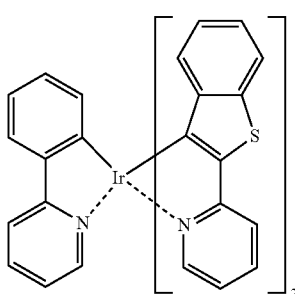
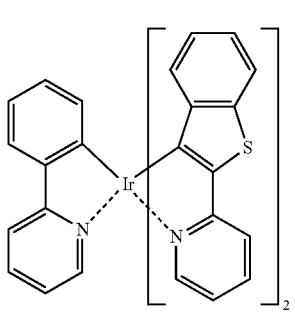
96
-continued
404
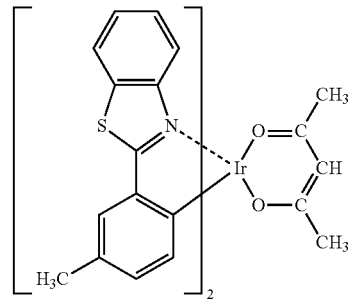
405
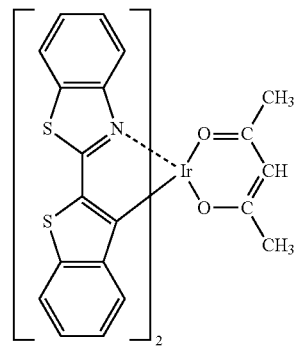
406
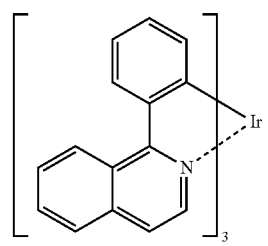
407
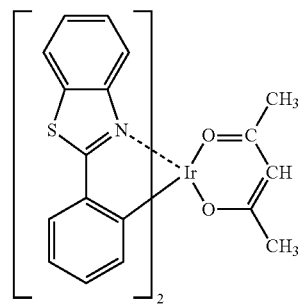
408
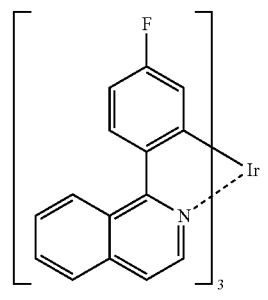
409
410
411
412
413

[Chem. 34]
-continued

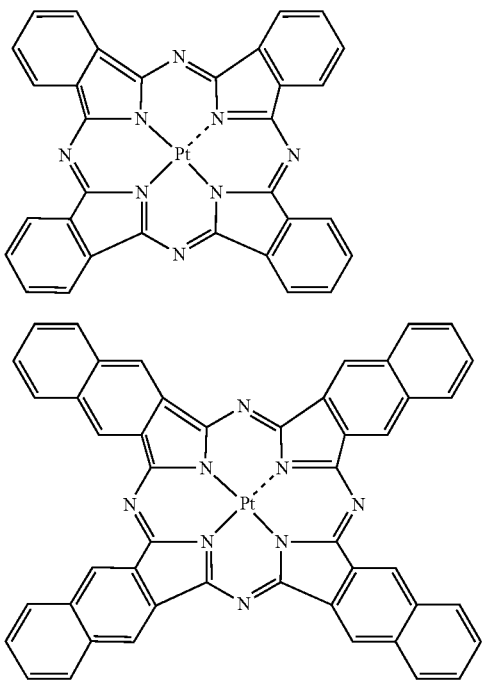

414

415

<Molecular Weight of Luminescent Material>

The molecular weight of the compound to be used as the luminescent material in the present invention is generally at most 10000, preferably at most 5000, more preferably at most 4000, and is generally at least 400, preferably at least 500, more preferably at least 550.

When the molecular weight of the luminescent material is too small, then the heat resistance may be significantly low, or the material may be a cause of gas generation, or the material may lower the film quality in film formation, or the migration of the material may cause morphology change in the organic electroluminescent element. On the other hand, when the molecular weight of the luminescent material is too large, then the organic compound may be difficult to purify, or a lot of time may be taken in dissolving the material in solvent.

When the molecular weight of the luminescent material falls within the above range, then the glass transition temperature, the melting point and the decomposition temperature of the material could be high and the heat resistance of the luminescent layer material and the luminescent layer formed of the material is good. Other advantages are that the film quality does not lower owing to recrystallization or migration of molecules, the impurity concentration does not increase owing to thermal decomposition of the material, the element performance would hardly degrade, and the purification of the material is easy.

<Selection of Luminescent Material>

In the present invention, the luminescent layer uses three or more kinds of luminescent materials and has at least two kinds of emission maximums as the emission spectrum thereof. In a case where the layer comprises three kinds of luminescent materials, the spectrum of each luminescent material contained in the luminescent layer may partly overlap with that of another so that the spectra of the two luminescent materials could apparently have one peak. In particular, from the viewpoint of the general color rendering index (Ra) and the color reproducibility, it is more desirable that at least two maximum emission wavelengths exist in two of regions from 440 to 500 nm, from 510 to 590 nm, and from 570 to 660 nm. Further, it is desirable that the emission maximums are three or more, and more desirably at least three maximum emission wavelengths exists in each region of from 440 to 500 nm, from 510 to 590 nm, and from 570 to 660 nm. Most preferably at least three maximum emission wavelengths exist in each region of from 440 to 500 nm, from 510 to 550 nm, and from 580 to 660 nm.

Further in the present invention, from the viewpoint of preventing precipitation in a solution state, it is more desirable that at least three luminescent materials differing from each other in point of the basic skeleton of the ligand in the organic metal complex of the luminescent material are used in the luminescent layer. When the ligand of the organic metal complex for the luminescent material has the partial structure (IIIg) and when plural kinds of the luminescent materials differing from each other in the basic skeleton therein are used, the materials would hardly precipitate and therefore the element performance may better. When plural complexes each having the same basic skeleton are used, then they may aggregate together and may precipitate, and even when they do not precipitate, the emission efficiency of the element may often worsen.

In case where the ligand of the organic metal complex compound has plural basic skeletons, it will be good that the combination of the plural basic skeletons could differ from the combination of the basic skeletons of the ligand of any other organic metal complex compound. The combination of basic skeletons of a ligand means, in an organic metal complex compound having plural ligands where at least two ligands differ from each other in point of the basic skeleton thereof, the combination of the basic skeletons of the ligands that the organic metal complex compound has.

For example, in a case where the ligand of the first organic metal complex compound has a structure having a "phenylimidazole skeleton" alone as the basic skeleton, the ligand of the second organic metal complex compound has a structure having a "phenylpyridine skeleton" alone as the basic skeleton, and the ligands of the third organic metal complex compound are a ligand having a "phenylpyridine skeleton" as the basic skeleton and a ligand having a "phenylbenzimidazole skeleton" as the basic skeleton, it can be said that the basic skeleton of the ligand of the first organic metal complex compound, the basic skeleton of the ligand of the second organic metal complex compound and the combination of the ligands of the third organic metal complex compound differ from each other.

[Charge-Transporting Material]

The charge-transporting material for use in the present invention is a compound having charge transportability such as hole transportability, electron transportability, etc., and is a compound defined by a single molecular weight.

As the charge-transporting material, usable here is any compound that has heretofore been used in the luminescent layer of organic electroluminescent elements, and especially preferred is a compound used as a host in the luminescent layer.

As the charge-transporting material, concretely, there are mentioned aromatic amine compounds, phthalocyanine compounds, porphyrin compounds, oligothiophene compounds, polythiophene compounds, benzylphenyl compounds, compounds with a tertiary amine bonded via a fluorene group, hydrazone compounds, silazane compounds, silanamine compounds, phosphamine compounds, quinacridone compounds, anthracene compounds, pyrene compounds, carbazole compounds, pyridine compounds, styryl compounds, phenanthroline compounds, oxadiazole compounds, silol compounds, etc.

The charge-transporting material is categorized into two main kinds of a hole-transporting material (hole-transporting compound) and an electron-transporting material (electron-transporting compound), and the luminescent layer in the present invention contains both a hole-transporting material and an electron-transporting material as the charge-transporting material.

In the luminescent layer, one alone or two or more different kinds of hole-transporting materials (compounds) may be used either alone or as combined in any desired combination mode and in any desired ratio. Also in the luminescent layer, one alone or two or more different kinds of electron-transporting materials (compounds) may be used either alone or as combined in any desired combination mode and in any desired ratio.

<Molecular Weight of Charge-Transporting Material>

The molecular weight of the compound to be used as the charge-transporting material in the present invention is generally at most 1500, preferably at most 1000, more preferably at most 800, and is generally at least 300, preferably at least 400, more preferably at least 480.

When the molecular weight of the charge-transporting material falls within the above range, then the glass transition temperature, the melting point and the decomposition temperature of the material could be high and the heat resistance of the luminescent layer material and the luminescent layer formed of the material is good. Other advantages are that the film quality does not lower owing to recrystallization or migration of molecules, the impurity concentration does not increase owing to thermal decomposition of the material, the element performance would hardly degrade, and the purification of the material is easy.

PREFERRED EXAMPLES

Preferably, the charge-transporting material is a compound represented by the following general formula (1-A), (1-B), (1-C), (1-D), (1-E) or (1-F).

[Chem. 35]

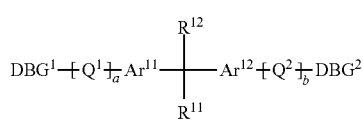

(1-A)

(In the formula (1-A), $Ar^{11}$ and $Ar^{12}$ each independently represent an aromatic ring group having from 3 to 30 carbon atoms and optionally having a substituent, $Q^1$ and $Q^2$ each independently represent a single bond or an aromatic ring compound having from 3 to 30 carbon atoms and optionally having a substituent, $DBG^1$ and $DBG^2$ each independently represent a structure represented by the following general formula (2-A), $R^{11}$ and $R^{12}$ each independently represent an alkyl group optionally having a substituent, or an aromatic ring group having from 3 to 30 carbon atoms and optionally having a substituent, and these $R^{11}$ and $R^{12}$ may bond to each other to form a cyclic structure. The indices a and b each independently indicate an integer of from 1 to 3. When a and b each are 2 or more, plural $Q^1$'s and $Q^2$'s may be the same or different.)

In the above formula (1-A), one preferred example of $Ar^{11}$ and $Ar^{12}$ is an aromatic ring group having from 3 to 30 carbon atoms and having two free valences. More preferred are a benzene ring and a naphthalene rings each having two free atomic valences, from the viewpoint of the stability of the compound; and even more preferred is a benzene ring having two free atomic valences.

Preferred examples of $Q^1$ and $Q^2$ are a single bond and an aromatic group having from 3 to 30 carbon atoms and having two free atomic valences. More preferred are a benzene ring, a naphthalene ring, an anthracene ring, a pyrene ring, a triphenylene ring, a phenanthrene ring, a pyridine ring, a pyrimidine ring, a triazine ring, a carbazole ring, a dibenzofuran ring and a dibenzothiophene ring each having two free atomic valences. From the viewpoint of the durability of the compound, especially preferred are a benzene ring, a naphthalene ring, a phenanthrene ring and a triphenylene ring each having two free atomic valences; and most preferred is a benzene ring having two free atomic valences since the compound is considered to have a further higher triplet energy level. From the viewpoint of the charge transportability, preferred are a pyridine ring, a pyrimidine ring, a triazine ring and a carbazole ring each having two free atomic valences; and especially preferred are a pyridine ring, a pyrimidine ring and a carbazole ring each having two free atomic valences.

Preferred examples of $R^{11}$ and $R^{12}$ are an alkyl group and an aromatic group having from 3 to 30 carbon atoms and having one free atomic valence. More preferred are a phenyl group, a naphthyl group, a pyridyl group, a methyl group, an ethyl group, a branched or linear propyl group, a butyl group, a pentyl group a hexyl group, a heptyl group, an octyl group and a nonyl group. From the viewpoint of solubility, especially preferred are a methyl group, an ethyl group, and a branched or linear propyl group, and a butyl group. Examples of the cyclic structure formed by $R^{11}$ and $R^{12}$ bonding to each other are a cyclobutane ring, a cyclopentane ring, a cyclohexane ring, a fluorene ring, an azafluorene ring, an indane ring, a tetralin ring, etc. Especially preferred are a cyclohexane ring, a fluorene ring, and an azafluorene ring, and most preferred is a cyclohexane ring.

The indices a and b each are preferably 1 or 2 from the viewpoint of the charge transportability, and most preferred is 1.

[Chem. 36]

(1-B)

(In the formula (1-B), $Ar^{13}$ represents an aromatic ring group having from 3 to 30 carbon atoms and having one free atomic valence and optionally having a substituent, $DBG^3$ represents a structure represented by the following general formula (2-A), $DBG^4$ represents a structure represented by the following general formula (2-B). The index c indicates an integer of from 1 to 5. When c is 2 or more, then plural $DBG^4$'s may be the same or different.)

In the above formula (1-B), a preferred example of $Ar^{13}$ is an aromatic ring group having from 3 to 30 carbon atoms and having one free atomic valence, and more preferred is a benzene ring, a naphthalene ring, an anthracene ring, a pyrene ring, a triphenylene ring, a phenanthrene ring, a pyridine ring, a pyrimidine ring, a triazine ring, a carbazole ring, a dibenzofuran ring or a dibenzothiophene ring having one free atomic valence. Especially preferred is a benzene ring, a carbazole ring, a dibenzofuran ring or a dibenzothiophene ring having one free atomic valence, since the compound is considered to have a further higher triplet energy level. Most preferred is a benzene ring having one free atomic valence. From the viewpoint of the charge transportability, preferred are a pyridine ring, a pyrimidine ring, a triazine ring, a carbazole ring, a dibenzofuran ring and a dibenzothiophene ring each having one free atomic valence; and especially preferred are a pyridine ring, a carbazole ring and a dibenzofuran ring each having one free atomic valence.

The index c is preferably from 1 to 3 from the viewpoint of easiness in purification of the compound, and especially preferred is 1 or 2.

[Chem. 37]

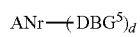

(1-C)

(In the formula (1-C), ANr represents a nitrogen-containing aromatic ring group having from 3 to 30 carbon atoms and having d's free atomic valences and optionally having a substituent, $DBG^5$ represents a structure represented by the following general formula (2-A) and optionally having a substituent. The index d indicates an integer of from 1 to 5. When d is 2 or more, plural $DBG^5$'s may be the same or different.)

In the above formula (1-C), a preferred example of ANr is a nitrogen-containing aromatic ring group having from 3 to 30 carbon atoms and having d's free atomic valences, and more preferred is a nitrogen-containing 5-membered ring, a nitrogen-containing 6-membered ring, a nitrogen-containing 6-5 condensed ring or a nitrogen-containing 6-5-6 condensed ring each having d's free atomic valences, since larger rings or condensed rings may worsen the solubility and the stability of the compound. More preferred examples are imidazole, pyrazole, pyridine, pyrimidine, triazine, quinoline, quinoxaline, quinazoline, benzimidazole, benzimidazolidinone, indole, carbazole and carboline each having d's free atomic valences. From the viewpoint of charge transportability, especially preferred are imidazole, pyrazole, pyridine, pyrimidine, triazine, benzimidazole, benzimidazolidinone and carbazole each having d's free atomic valences. Further, most preferred from the viewpoint of durability are pyridine, pyrimidine, triazine and carbazole each having d's free atomic valences.

The index d is preferably from 1 to 3 from the viewpoint of the stability of the compound.

[Chem. 38]

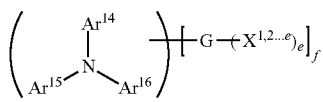

(1-D)

(In the formula (1-D), $Ar^{14}$ represents an aromatic ring group having from 3 to 30 carbon atoms and having from 1 to (f+1)'s free atomic valences and optionally having a substituent, $Ar^{15}$ and $Ar^{16}$ each independently represent a benzene ring or a pyridine ring having from 1 to (f+1)'s free atomic valences and optionally having a substituent. $Ar^{14}$ and $Ar^{15}$ may bond to each other to form a cyclic structure. G represents an atom selected from {C, N, Si}. $X^{1,2\cdots e}$ represents e's X's, or that is, $[X^1, X^2 \ldots X^e]$, and $[X^1, X^2 \ldots X^e]$ each independently represent a benzene ring or a pyridine ring having one free atomic valence. These $X^1$ and $X^2$ may bond to each other to form a cyclic structure. The index e indicates an integer of from 3 to 4, and the index f indicates an integer of from 1 to 3.)

In the above formula (1-D), a preferred example of $Ar^{14}$ is an aromatic ring group having from 3 to 30 carbon atoms and having from 1 to (f+1)'s free atomic valences. More preferred is a benzene ring, a naphthalene ring, an anthracene ring, a pyrene ring, a triphenylene ring, a phenanthrene ring, a pyridine ring, a pyrimidine ring, a triazine ring, a carbazole ring, a dibenzofuran ring or a dibenzothiophene ring each having from 1 to (f+1)'s free atomic valences. From the viewpoint of the durability of the compound, especially preferred is a benzene ring, a dibenzofuran ring or a dibenzothiophene ring having from 1 to (f+1)'s free atomic valences. From the viewpoint that the compound could have further higher triplet energy level, most preferred is a benzene ring having from 1 to (f+1)'s free atomic valences.

[Chem. 39]

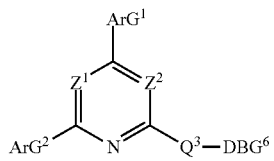

(1-E)

(In the formula (1-E), $ArG^1$ and $ArG^2$ each represent an aromatic ring group having from 3 to 30 carbon atoms and having one free atomic valence and optionally having a substituent, or a condensed atomic group of two or more aromatic rings having from 3 to 60 carbon atoms and having one free atomic valence and optionally having a substituent, $Q^3$ represents a single bond or an aralkyl group having from 3 to 60 carbon atoms and having two free atomic valences and optionally having a substituent, an aromatic ring having from 3 to 30 carbon atoms and having two free atomic valences and optionally having a substituent, or a substituent of a condensed atomic group of two or more aromatic rings having from 3 to 60 carbon atoms and having two free atomic valences and optionally having a substituent, $DBG^6$ represents a structure represented by the following general formula (2-A) and optionally having a substituent, $Z^1$ and $Z^2$ each independently represent a group =CH— or a group =N—.)

In the above formula (1-E), preferred examples of $ArG^1$ and $ArG^2$ are an aromatic ring group having from 3 to 30 carbon atoms and having one free atomic valence and a condensed atomic group of two or more aromatic rings having from 3 to 60 carbon atoms and having one free atomic valence. More preferred are a benzene ring, a naphthalene ring, a carbazole ring, an indolocarbazole ring, biphenyl, terphenyl, pyridylbenzene, naphthylbenzene, carbazolylbenzene and diphenylindolocarbazole each having one free atomic valence. From the viewpoint of durability, more preferred are a benzene ring, a carbazole ring, biphenyl, terphenyl, carbazolylbenzene and diphenylindolocarbazole each having one free atomic valence. As considered to have a further higher triplet energy level, especially preferred are a benzene ring, an indolocarbazole ring, biphenyl, terphenyl, carbazolylbenzene and diphenylindolocarbazole each having one free atomic valence. Most preferred are a benzene ring, biphenyl and terphenyl each having one free atomic valence.

$Q^3$ is preferably a single bond, a fluorene ring having two free atomic valences and optionally having a substituent, an aromatic ring group having from 3 to 30 carbon atoms and having two free atomic valences, or a substituent of a condensed atomic group of two or more aromatic rings having from 3 to 60 carbon atoms and having two free atomic valences. Especially preferred are a dialkyl-substituted fluorene ring, a benzene ring, a naphthalene ring, biphenyl and terphenyl each having two free atomic valences.

From the viewpoint of charge mobility, it is desirable that one of $Z^1$ and $Z^2$ is =N—.

[Chem. 40]

(1-F)

(In the formula (1-F), $DBG^7$ and $DBG^9$ each represent a structure represented by the following general formula (2-A), $DBG^8$ represents a structure represented by the following general formula (2-B). The index g indicates an integer of from 1 to 5. When g is 2 or more, plural $DBG^8$'s may be the same or different.)

In the above formula (1-F), the index g is preferably from 1 to 3 from the viewpoint of easiness in purifying the compound, more preferably 1 or 2.

[Chem. 41]

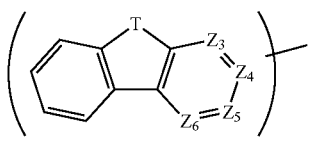

(2-A)

(In the formula (2-A), T represents an atom or an atomic group selected from {—O—, —S—, —C($Ar^{21}$)($Ar^{22}$)—, —N($Ar^{23}$)—, —Si($Ar^{24}$)($Ar^{25}$)—}, $Ar^{21}$ to $Ar^{25}$ each independently represent a hydrogen atom, or an aromatic ring group having from 3 to 30 carbon atoms and having one or two free atomic valences and optionally having a substituent, ($Ar^{21}$ and $Ar^{22}$) and ($Ar^{24}$ and $Ar^{25}$) may bond to each other to form a ring structure. $Z_3$ to $Z_6$ each independently represent a group =CH— or a group =N—.)

In the above formula (2-A), T is preferably —O—, —C($Ar^{21}$)($Ar^{22}$)— or —N($Ar^{23}$)— from the viewpoint of durability, and is especially preferably —O— or —N($Ar^{23}$)—. Preferred examples of $Ar^{21}$ to $Ar^{25}$ are a hydrogen atom, and an aromatic ring group having from 3 to 30 carbon atoms and having one or two free atomic valences. More preferred are a hydrogen atom, and a benzene ring and a pyridine ring each having one or two free atomic valences. Especially preferred are a hydrogen atom, and a benzene ring having one or two free atomic valences.

[Chem. 42]

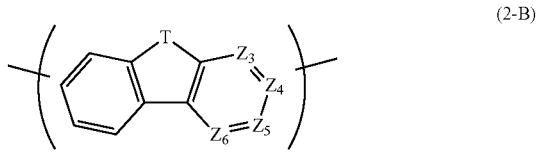

(2-B)

(In the formula (2-B), T represents an atom or an atomic group selected from {—O—, —S—, —C($Ar^{26}$)($Ar^{27}$)—, —N($Ar^{28}$)—, —Si($Ar^{29}$)($Ar^{30}$)—}, $Ar^{26}$ to $Ar^{30}$ each independently represent a hydrogen atom, or an aromatic ring group having from 3 to 30 carbon atoms and having one or two free atomic valences and optionally having a substituent, ($Ar^{26}$ and $Ar^{27}$) and ($Ar^{29}$ and $Ar^{30}$) may bond to each other to form a ring structure. $Z_3$ to $Z_6$ each independently represent a group =CH— or a group =N—.)

In the above formula (2-B), T is preferably —O—, —C($Ar^{26}$)($Ar^{27}$)— or —N($Ar^{28}$)— from the viewpoint of durability, and is especially preferably —O— or —N($Ar^{28}$)—. Preferred examples of $Ar^{26}$ to $Ar^{28}$ are a hydrogen atom, and an aromatic ring group having from 3 to 30 carbon atoms and having one or two free atomic valences. More preferred are a hydrogen atom, and a benzene ring and a pyridine ring each having one or two free atomic valences. Especially preferred are a hydrogen atom, and a benzene ring having one or two free atomic valences.

Specific examples of the charge-transporting material preferred for the present invention are shown below, however, the charge-transporting material for use in the present invention is not limited to the following compounds.

In the following, those with a sign "H" are hole-transporting materials and those with "E" are electron-transporting materials.

[Chem. 43]

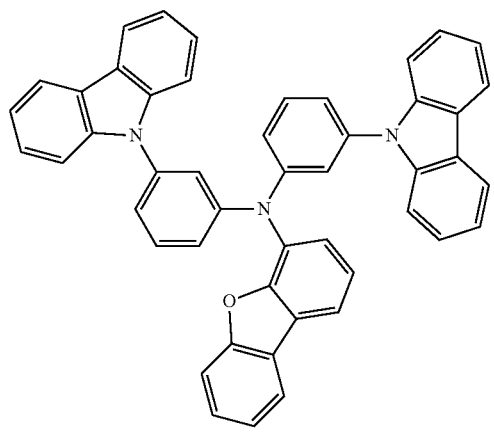

H2

E1
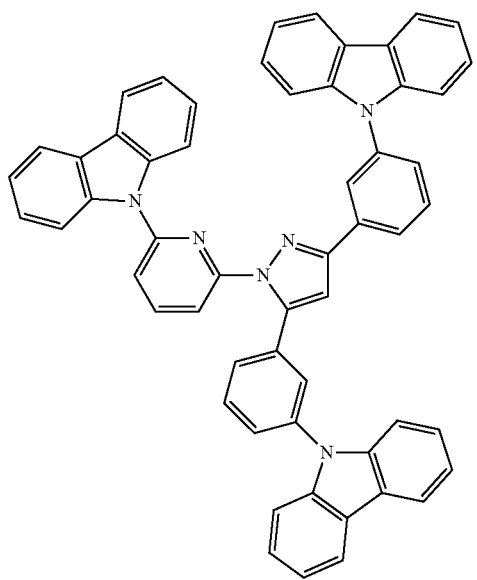
H3
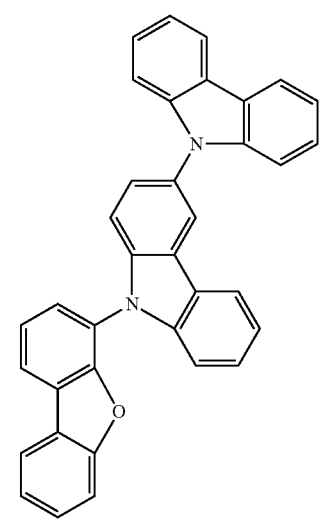
E2
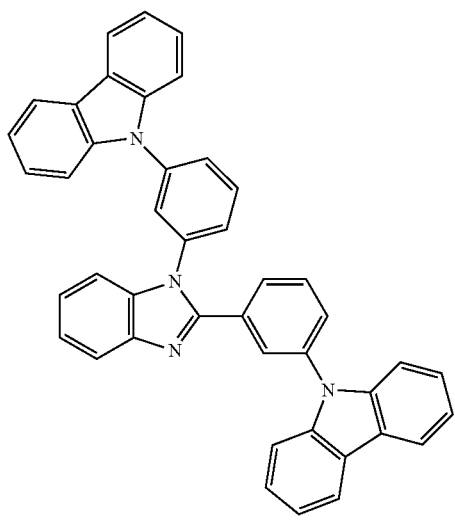
E3
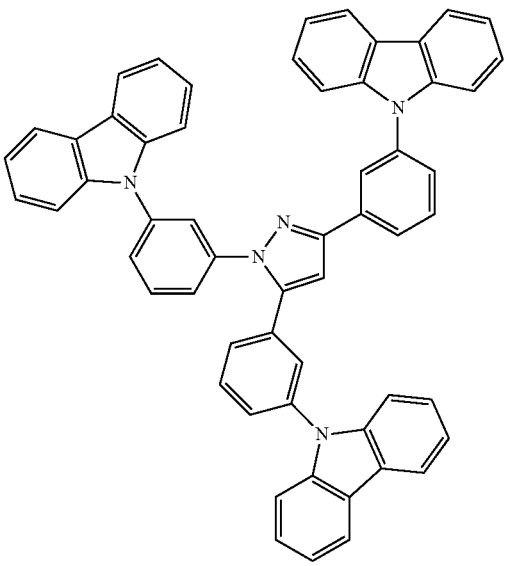
H4
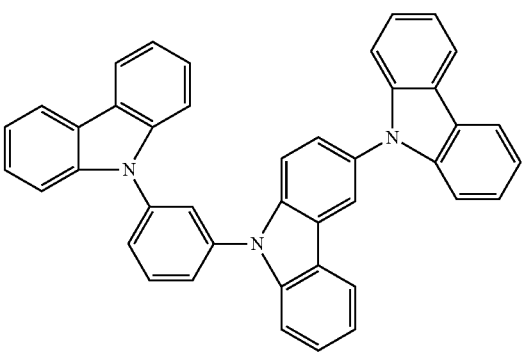
H5
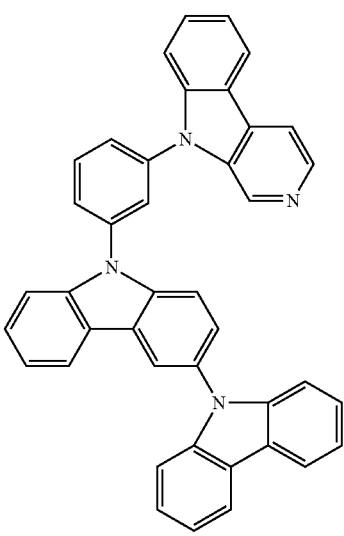

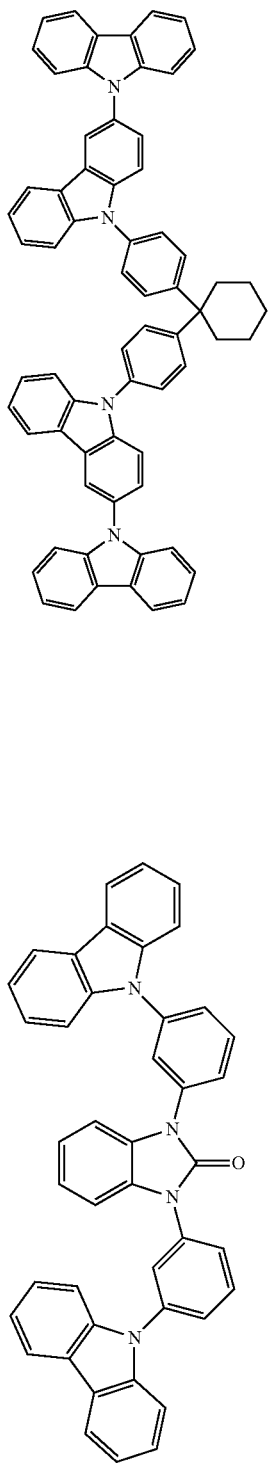
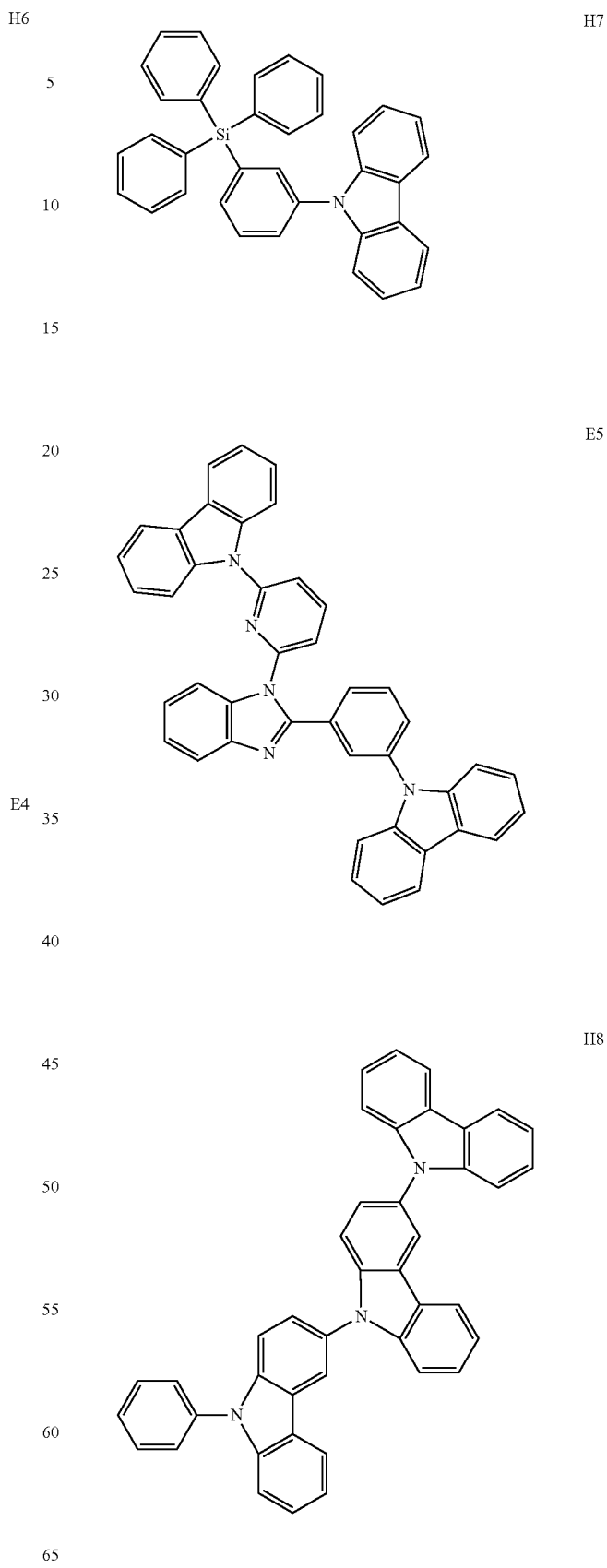

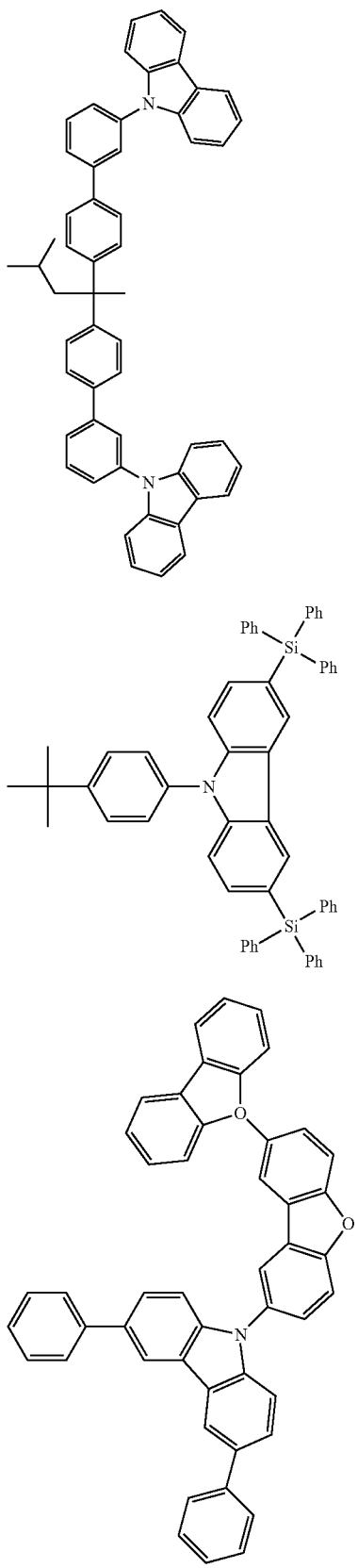
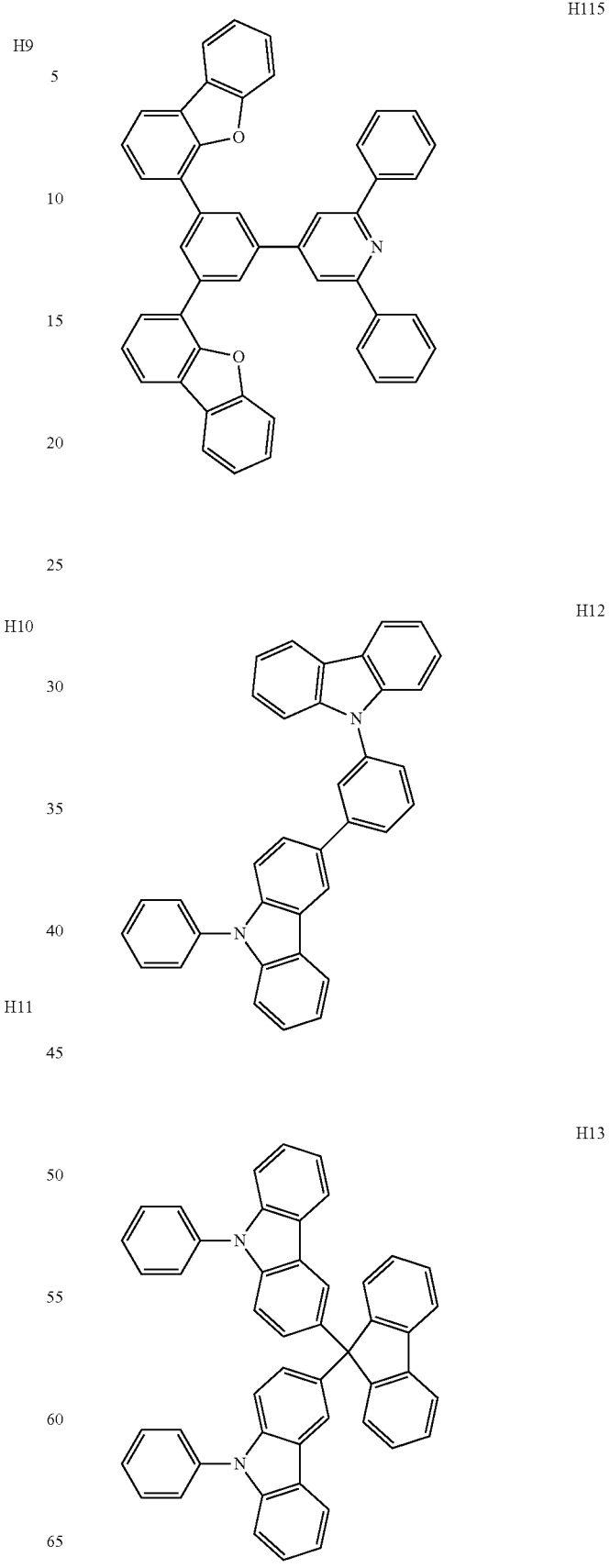

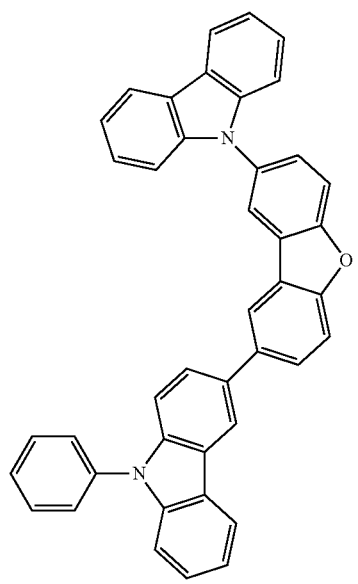
H14
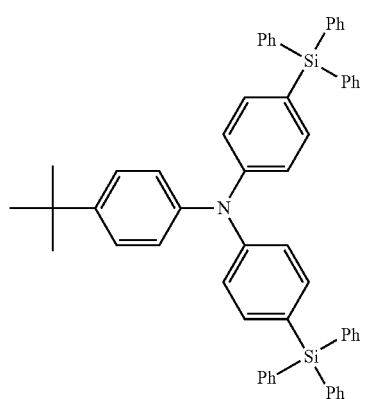
H16
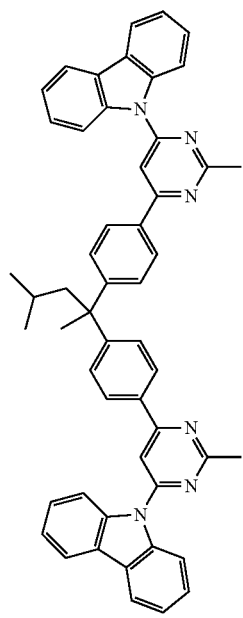
E7
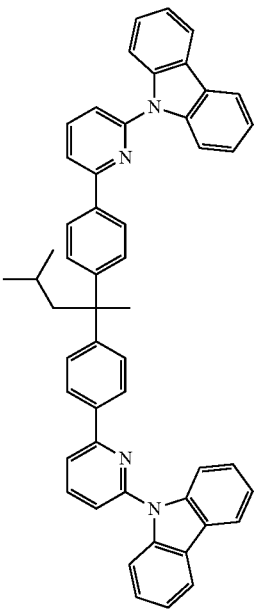
E8
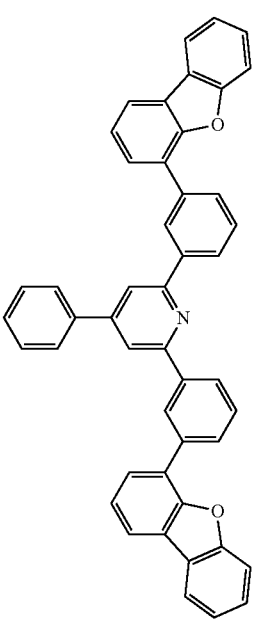
E9

[Chem. 45]
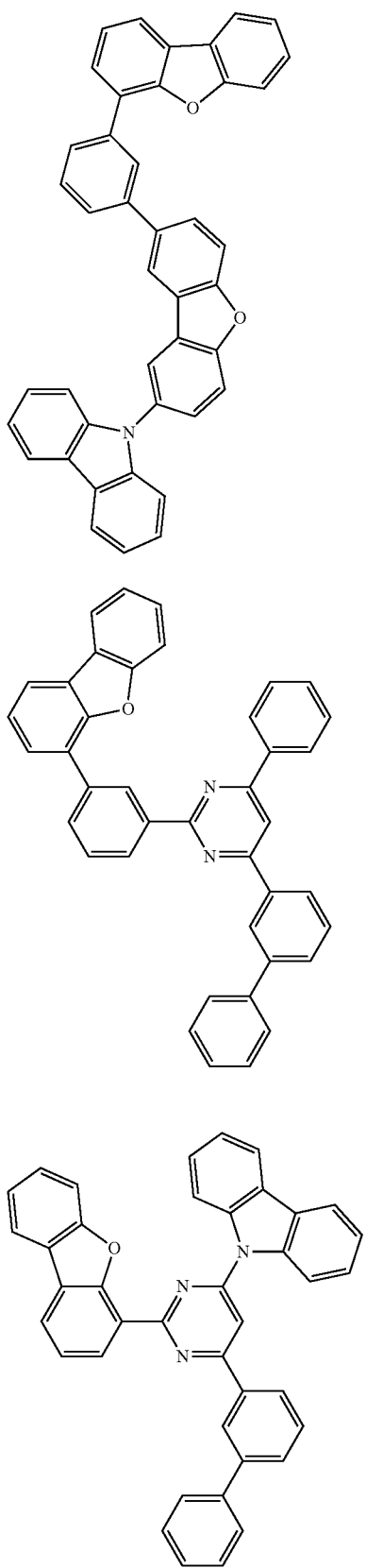
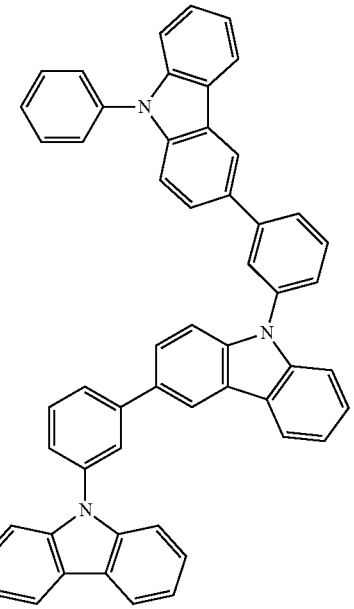
H17
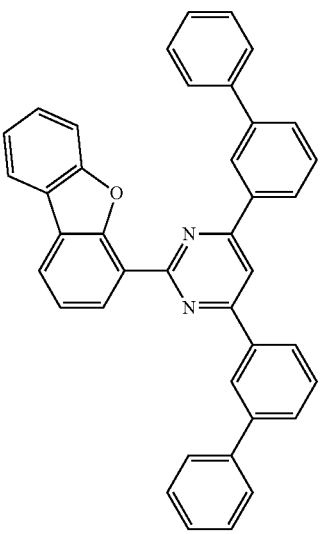
H18
E10
E12
E11

115
-continued
116
-continued
H19
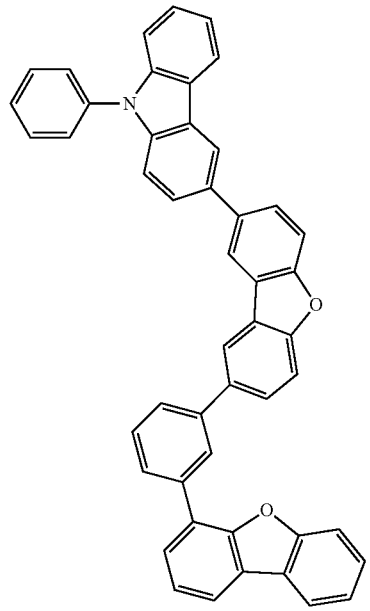
E13
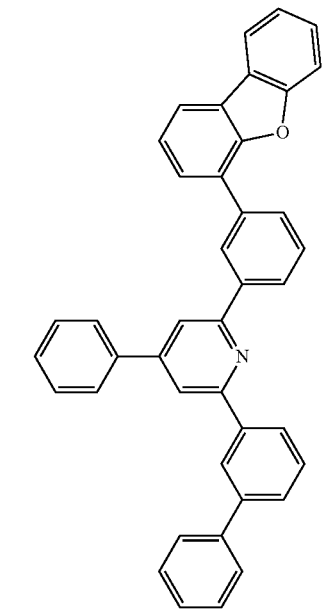
H20
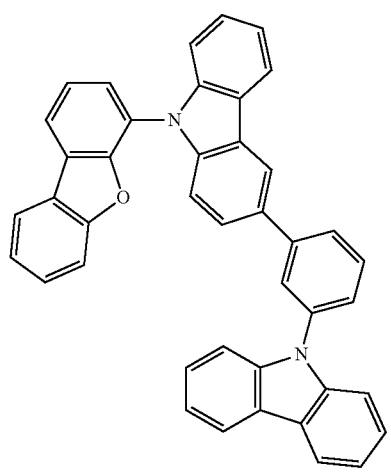
E14
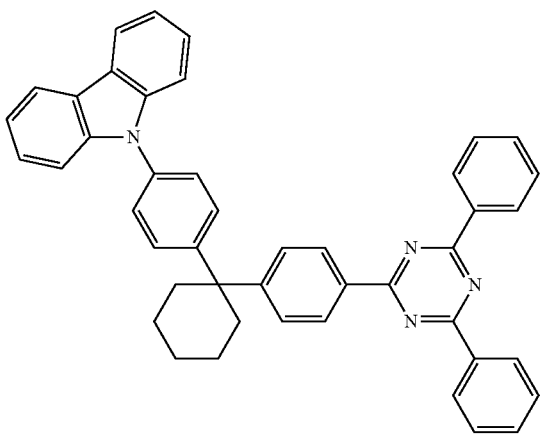
E15
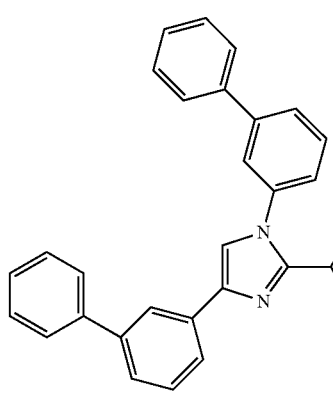

E16
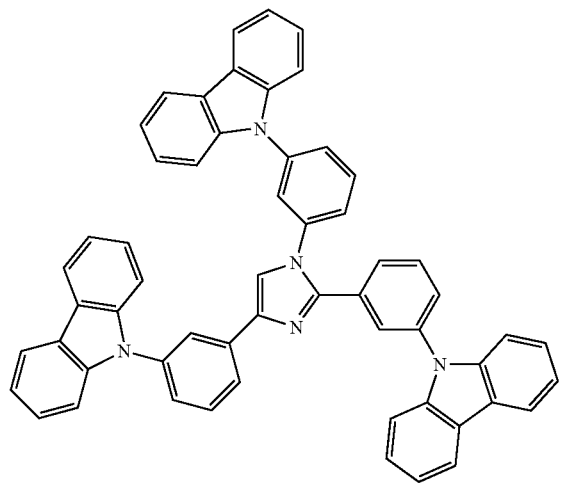
E17
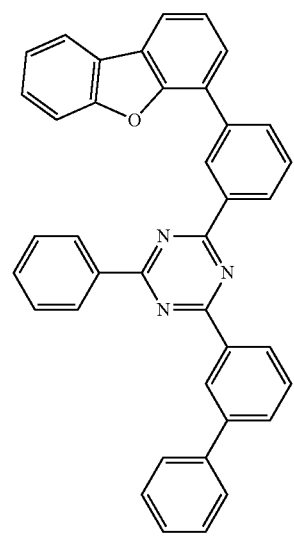
[Chem. 46]
H21
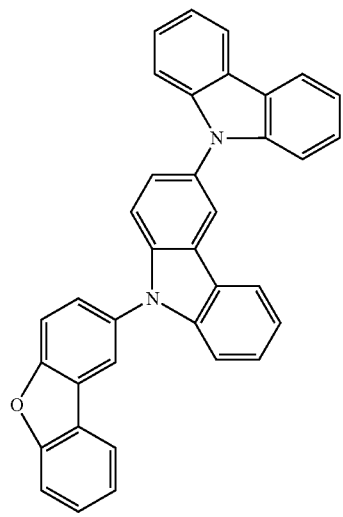
E18
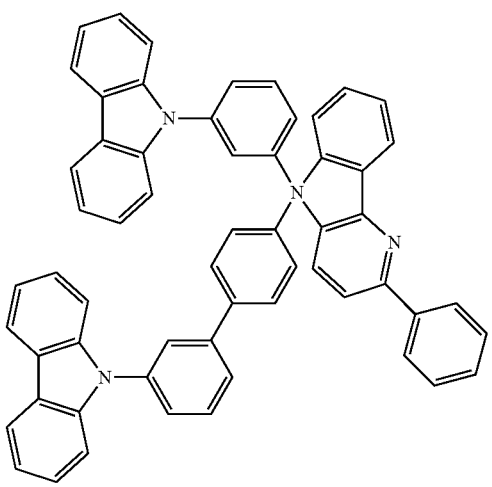
H22
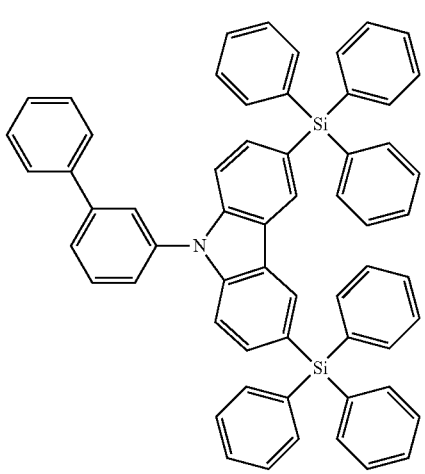
H23
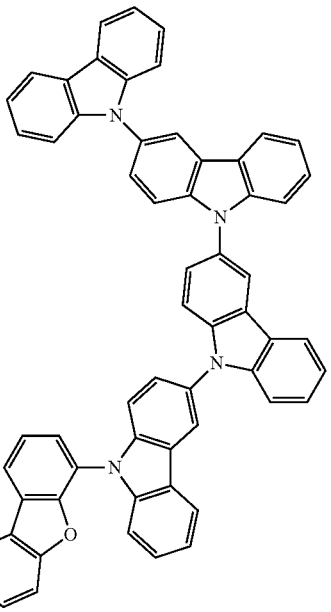

119
-continued
E19
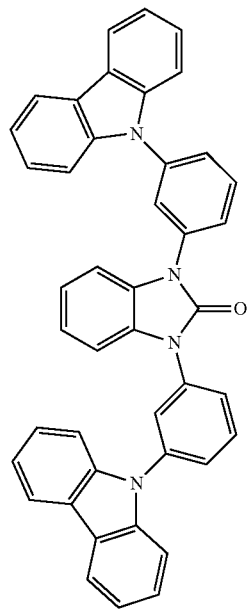
120
-continued
H26
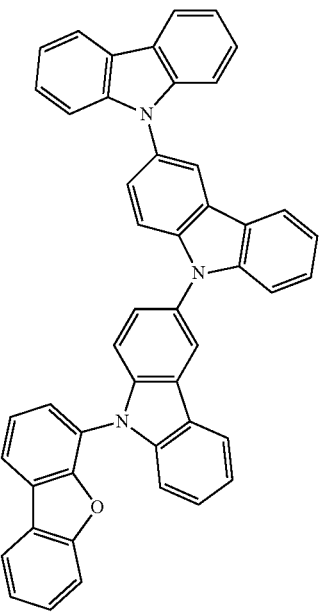
H25
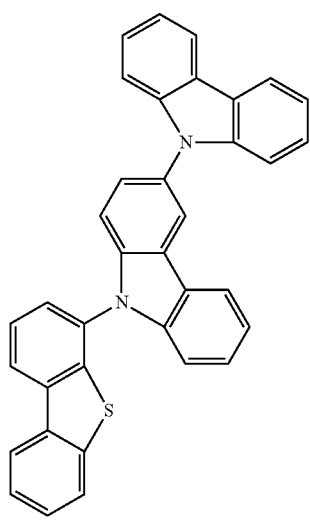
H28
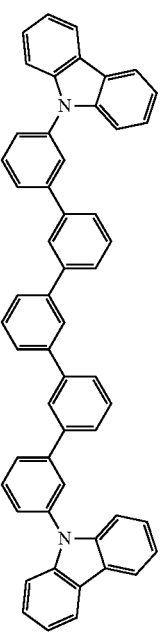

-continued
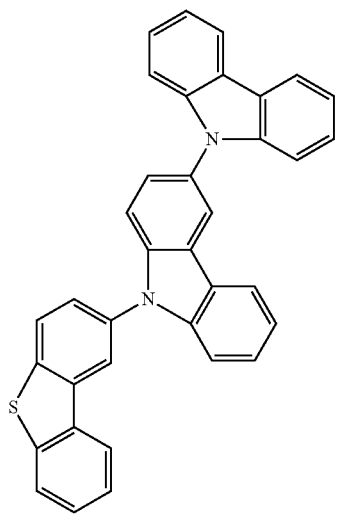
H29
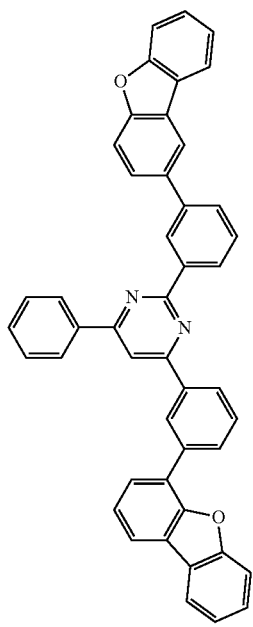
E20
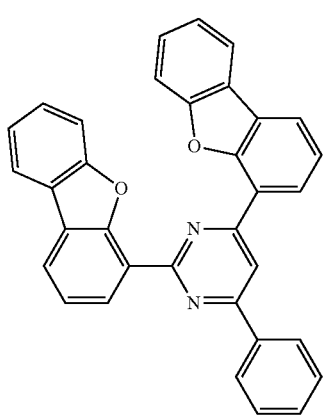
E21
-continued
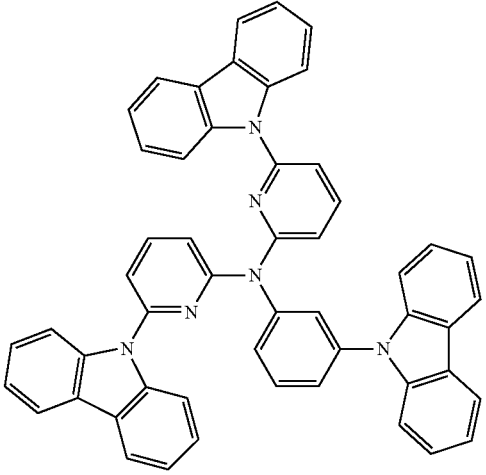
E22
[Chem. 47]
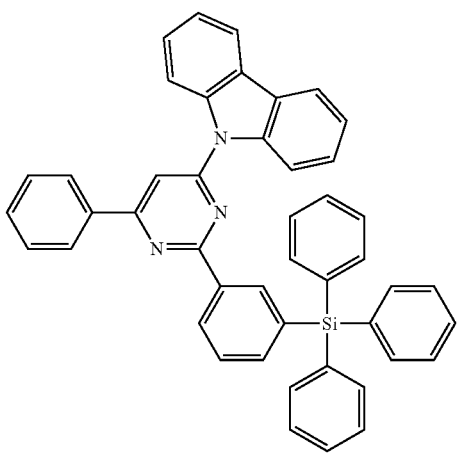
E24
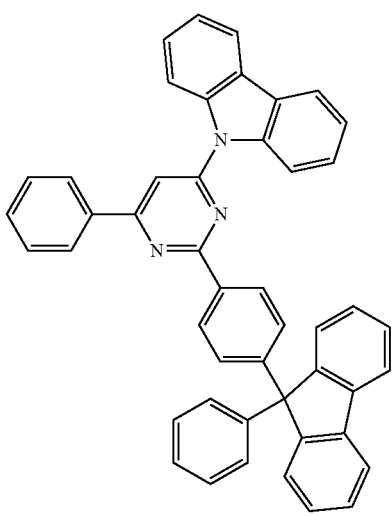
E25

-continued

E26

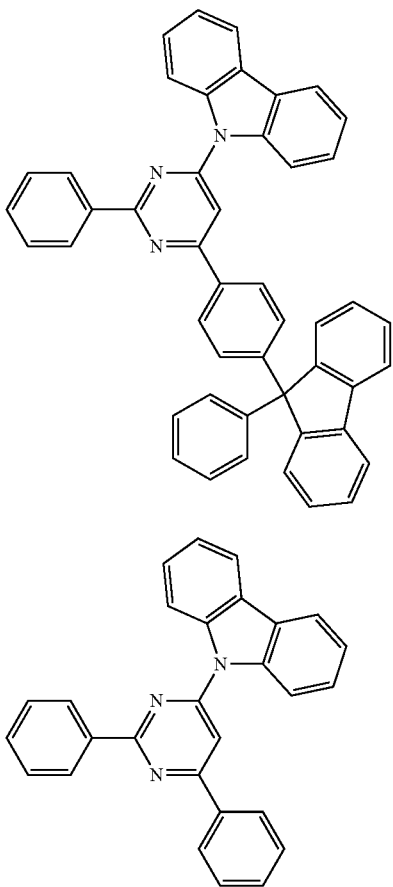

E27

Especially in the embodiment of the present invention, from the viewpoint of efficiently transferring charges to the luminescent material, it is desirable that the luminescent material contains at least one electron-transporting material and at least one hole-transporting material. This is because, in the luminescent element containing three or more kinds of luminescent materials, when any one type of transporting material is contained, then charges could not uniformly transfer to the luminescent materials and positive or negative charges would reach only a part of the luminescent materials thereby having some negative influence on the light emission efficiency of the element.

Further, in a case where the luminescent layer is formed according to a wet film formation method, the constituent materials could not be uniformly mixed owing to the difference in solubility between the charge-transporting material and the luminescent material, or the materials could not precipitate uniformly in film formation or drying, and as a result, there is a possibility that the individual materials would aggregate and the light emission efficiency of the element would be thereby lowered. The problem can be solved in the present invention by using the charge-transporting material having the common partial structure represented by the above-mentioned formula (2-A) or (2-B). The reason could be presumed as follows. Owing to the presence of the similar or common point in the partial structure, use of two or more different kinds of charge-transporting materials not differing so much in point of the solubility thereof can solve the problem; or use of two or more different kinds of charge-transporting materials which originally differ in point of the structure thereof and therefore differ also in point of the solubility thereof, but which, however, as having a specific similar or common partial structure, can uniformly mix together even though they differ in solubility can solve the problem in that only any one alone would not precipitate in coating and drying and therefore a uniform film can be formed.

However, even in a case where two or more different kinds of charge-transporting materials are used, they could not mix uniformly owing to the difference in solubility between them and any other materials such as luminescent materials, or there may form a concentration distribution during film formation, therefore bringing about some problems of poor light emission efficiency, etc. In particular, in a case where a white emission element is produced according to a wet film formation method, using different kinds of dopants and in accordance with the combination of emission wavelengths and when the materials do not mix and precipitate uniformly, it is considered that not only the light emission efficiency but also the emission spectrum and the repetitive reproducibility would be thereby negatively affected.

Because of the above reasons, it is desirable that both a hole-transporting material and an electron-transporting material are used as the charge-transporting material in the present invention. Preferably, the chemical structure of the hole-transporting material and that of the electron-transporting material contain the partial structure represented by the above-mentioned formula (2-A) or (2-B), from the viewpoint of preventing aggregation and crystallization without lowering the charge transportability to give a uniform film. More preferably, at least one T in the formula (2-A) or (2-B) contained in the molecules of both the hole-transporting material and the electron-transporting material is a 6-5-6-membered ring selected from —O—, —S— and —N—. Even more preferably, T in the formula (2-A) or (2-B) contained in the molecules of both the hole-transporting material and the electron-transporting material is a 6-5-6-membered ring selected from —O—, —S— and —N—. Most preferably, the partial structure contained in the molecules of both the hole-transporting material and the electron-transporting material contains the same skeleton selected from the formula (2-A) or (2-B).

<Formation of Luminescent Layer>

In the organic electroluminescent element of the present invention, the luminescent layer is formed according to a wet film formation method.

"Wet film formation method" as referred to in the present invention is a method of forming a film using an ink containing a solvent, such as a spin coating method, a dip coating method, a die coating method, a bar coating method, a blade coating method, a roll coating method, a spray coating method, a capillary coating method, a nozzle printing method, an inkjet method, a screen printing method, a gravure printing method, a flexographic printing method, an offset printing method, etc. From the viewpoint of easiness in patterning, preferred is a nozzle printing method, a die coating method, a roll coating method, a spray coating method, an inkjet method, a gravure coating method or a flexographic printing method. From the viewpoint of securing uniform film quality, especially preferred is a nozzle printing method, an inkjet method, a gravure printing method or a flexographic printing method.

The luminescent layer is formed according to the above-mentioned wet film formation method using a luminescent layer-forming composition to be mentioned below, which contains the above-mentioned luminescent material and charge-transporting material and a solvent.

A luminescent layer-forming composition is formed into a film through wet film formation, then the resultant coating film is dried and the solvent is removed, thereby giving a luminescent layer. Concretely, the method is the same as that to be described below for formation of a hole injection layer. The mode of the wet film formation method is not specifically defined so far as the advantageous effects of the present invention is not thereby significantly worsened, and any of the above-mentioned modes is employable herein.

Not significantly detracting from the advantageous effects of the present invention, the thickness of the luminescent layer may be any one, but is generally 3 nm or more, preferably 5 nm or more, and is generally 200 nm or less, preferably 100 nm or less. When the thickness of the luminescent layer is too small, then the film may have defects; but when too large, then the driving voltage would increase.

<Solvent>

Not specifically defined, the solvent for the luminescent layer-forming composition for use in forming the luminescent layer according to a wet film formation method may be any one capable of well dissolving the above-mentioned luminescent material and charge-transporting material.

Regarding the solubility in the solvent, it is desirable that the solvent may dissolve the luminescent material and the charge-transporting material at room temperature and under normal pressure generally in an amount of 0.01% by weight or more, preferably 0.05% by weight or more, more preferably 0.1% by weight or more.

Specific examples of the solvent are given below, however, not detracting from the advantageous effects of the present invention, the solvent is not limited to the following.

For example, there are mentioned alkanes such as n-decane, cyclohexane, ethylcyclohexane, decalin, bicyclohexane, etc.; aromatic hydrocarbon such as toluene, xylene, mesitylene, cyclohexylbenzene, tetralin, etc.; halogenoaromatic hydrocarbons such as chlorobenzene, dichlorobenzene, trichlorobenzene, etc.; aromatic ethers such as 1,2-dimethoxybenzene, 1,3-dimethoxybenzene, anisole, phenetol, 2-methoxytoluene, 3-methoxytoluene, 4-methoxytoluene, 2,3-dimethylanisole, 2,4-dimethylanisole, diphenyl ether, etc.; aromatic esters such as phenyl acetate, phenyl propionate, methyl benzoate, ethyl benzoate, propyl benzoate, n-butyl benzoate, etc.; alicyclic ketones such as cyclohexanone, cyclooctanone, fenchone, etc.; alicyclic alcohols such as cyclohexanol, cyclooctanol, etc.; aliphatic ketones such as methyl ethyl ketone, dibutyl ketone, etc.; aliphatic alcohols such as butanol, hexanol, etc.; aliphatic ethers such as ethylene glycol dimethyl ether, ethylene glycol diethyl ether, propylene glycol-1-monomethyl ether acetate (PG-MEA), etc.

Of those, preferred are alkanes and aromatic hydrocarbons.

One alone or two or more different kinds of those solvents may be used here either singly or as combined in any desired manner and in any desired ratio.

For obtaining a more uniform film, it is desirable that the solvent can be evaporated away at a suitable speed from the liquid film just after film formation. Consequently, the boiling point of the solvent is generally 80° C. or higher, preferably 100° C. or higher, more preferably 120° C. or higher, and is generally 300° C. or lower, preferably 270° C. or lower, more preferably 250° C. or lower. When the boiling point of the solvent is too low, then the drying speed would be too high and the film quality may worsen. On the other hand, when the boiling point of the solvent is too high, then the temperature in the drying step must be high but such a high temperature would have some negative influence on the other layers and the substrate.

The amount of the solvent to be used may be any one not significantly detracting from the advantageous effects of the present invention, but is preferably 10% by weight or more relative to the luminescent layer-forming composition, more preferably 50% by weight or more, even more preferably 80% by weight or more, and is preferably 99.95% by weight or less, more preferably 99.9% by weight or less, even more preferably 99.8% by weight or less. When the content of the solvent in the luminescent layer-forming composition is lower than the above-mentioned lower limit, then the viscosity of the composition would increase too much and the film formation operability may thereby worsen. On the other hand, when the content is more than the upper limit, then the thickness of the film to be formed by removing the solvent after the film formation would not be enough and therefore the film formation would be difficult.

In case where two or more kinds of solvents are used, as mixed therein, in the luminescent layer-forming composition to be mentioned below, the total amount of the solvents shall satisfy the range.

<Luminescent Layer-Forming Composition>

In the present invention, the composition containing the above-mentioned solvent, luminescent material and charge-transporting material is referred to as a luminescent layer-forming composition.

The luminescent layer-forming composition contains the luminescent material generally in an amount of $10^{-3}$% by weight or more, preferably $5 \times 10^{-3}$% by weight or more, more preferably 0.01% by weight or more, and generally in an amount of 5% by weight or less, preferably 1% by weight or less, more preferably 0.5% by weight or less.

In the luminescent layer-forming composition, the content ratio of the luminescent material to the charge-transporting material (luminescent material/charge-transporting material) is generally 0.001 or more, preferably 0.005 or more and is generally 0.5 or less, preferably 0.2 or less.

Not detracting from the advantageous effects of the present invention, the luminescent layer-forming composition in the present invention may additionally contain a coating improver such as a leveling agent, a defoaming agent, a tackifier, etc.; a charge transportation auxiliary agent such as an electron-accepting compound, an electron-donating compound, etc.; a binder resin, etc. The content of these components in the luminescent layer-forming composition is generally 50% by weight or less from the viewpoint that they do not significantly detract from charge transfer in the formed thin film, do not detract from light emission of the luminescent material, and do not worsen the film quality of the thin film.

[Configuration of Organic Electroluminescent Element]

The organic electroluminescent element of the present invention contains, on a substrate, an anode, a cathode and a luminescent layer between the anode and the cathode, in which, as described above, the luminescent layer contains a luminescent material and a charge-transporting material and is formed according to a wet film formation method, and a hole injecting and transporting layer is arranged between the luminescent layer and the anode and adjacent to the luminescent layer.

The layer configuration of the organic electroluminescent element of the present invention and a general production method for the element are described hereinunder with reference to FIG. 1.

FIG. 1 is a schematic view of a cross section showing a configuration example of the organic electroluminescent element of the present invention.

In FIG. 1, 1 indicates a substrate, 2 indicates an anode, 3 indicates a hole injection layer, 4 indicates a hole transport layer, 5 indicates a luminescent layer, 6 indicates a hole-blocking layer, 7 indicates an electron transport layer, 8 indicates an electron injection layer, and 9 indicates a cathode.

Specifically, it is desirable that the organic electroluminescent element of the present invention has two or more hole injecting and transporting layers, and FIG. 1 shows an example in which, as the two or more hole injecting and transporting layers, the hole injection layer 3 and the hole transport layer 4 are formed.

In the organic electroluminescent element of the present invention, it is desirable that the hole injecting and transporting layer adjacent to the luminescent layer, or that is, in FIG. 1, the hole transport layer 4 contains an arylamine polymer compound. The arylamine polymer compound is preferably a conjugated or nonconjugated arylamine polymer compound. The conjugated compound is preferably an arylamine polymer compound that has a repeating unit having a partial structure represented by the following formula (10-C) (hereinafter this may be referred to as "partial structure (10-C)") and a repeating unit having a crosslinking group. Also preferably, the nonconjugated compound is an arylamine polymer compound that has a repeating unit having a partial structure represented by the following formula (10-A) (hereinafter this may be referred to as "partial structure (10-A)") and a repeating unit having a crosslinking group. (Hereinafter the arylamine polymer compound including both the conjugated one and the nonconjugated one may be referred to as "arylamine polymer compound (10)").

In a case where a white emission element that contains a luminescent material for blue or blue-green phosphorescent emission generally having a high triplet state is produced, it is considered that use of an arylamine polymer derivative capable of maintaining a high triplet level would enable energy transfer to the other luminescent material without energy deactivation of the phosphorescent blue-emitting material, and in addition, since broad band gap planning is possible, light emission from the blue-emitting material would be hardly absorbed, and as a result, it is considered that the white-emitting element of the type can secure high efficiency for white emission. Accordingly, in general, arylamine polymer derivatives are preferred, and conjugated arylamine polymer derivatives having the repeating unit having the partial structure (10-C) are preferred in which the main chain is conjugated and therefore hole transfer is hardly blocked. More preferred are nonconjugated arylamine polymer derivatives having the repeating unit having the partial structure (10-A) in which the conjugated moiety is short and therefore the band gap is broad and which hardly absorb light emission from the blue-emitting material. Even more preferred are nonconjugated arylamine polymer derivatives having the repeating unit having the partial structure (10-B) in which the branched moiety enables molecular planning for high hole mobility. General formulae of these compounds are described below.

(i) Partial Structure (10-C)

The arylamine polymer compound (10) preferably contains a repeating unit having the partial structure represented by the following general formula (10-C) (hereinafter this may be referred to as "partial structure (10-C)"). Specifically, the arylamine polymer compound (10) more preferably contains a repeating unit having the partial structure (10-C) and a repeating unit having a crosslinking group. In this, the repeating unit having a crosslinking group is preferably a repeating unit having the partial structure (10-C) that has a crosslinking group.

In this case, between the repeating units, $Ar^a$ and $Ar^b$ may differ from each other.

[Chem. 48]

(10-C)

(In the formula (10-C), $Ar^a$ and $Ar^b$ each independently represent an aromatic ring group optionally having a substituent.)

The aromatic ring group optionally having a substituent of $Ar^a$ and $Ar^b$ includes, for example, a 6-membered single ring or 2- to 5-condensed ring having a monovalent or divalent free atomic valence of a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, a fluorene ring or the like, and a group formed by bonding two or more of these rings via a direct bond. Further mentioned are a 5- or 6-membered, single ring or 2- to 4-condensed ring having a monovalent or divalent free atomic valence of a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, an azulene ring or the like, and a group formed by bonding two or more of these rings via a direct bond.

From the viewpoint of solubility and heat resistance, it is preferable that $Ar^a$ and $Ar^b$ each are independently a ring selected from a group consisting of a benzene ring, a naphthalene ring, an anthracene ring, a phenanthrene ring, a triphenylene ring, a pyrene ring, a thiophene ring, a pyridine ring and a fluorene ring and having a monovalent or divalent free atomic valence, or a group formed by bonding two or more benzene rings (for example, a biphenyl group (a biphenyl group) or a terphenylene group (terphenylene group)).

Above all, preferred is a group derived from a benzene ring (phenyl group), a group formed by bonding two benzene rings (biphenyl group) or a group derived from a fluorene ring (fluorenyl group), each having a monovalent free atomic valence.

The substituent that the aromatic ring group of $Ar^a$ and $Ar^b$ may have includes an alkyl group, an alkenyl group, an alkynyl group, an alkoxy group, an aryloxy group, an alkoxycarbonyl group, a dialkylamino group, a diarylamino group, an acyl group, a halogen atom, a haloalkyl group, an alkylthio group, an arylthio group, a silyl group, a siloxy group, a cyano group, an aromatic ring group, etc.

<Regarding Formula Weight of Partial Structure (10-C)>

The formula weight of the partial structure (10-C) is generally 300 or more and generally 3000 or less, and is especially preferably 2000 or less. When the formula weight of the partial structure (10-C) is too large, then the solubility of the polymer before crosslinking in solvent may lower. However, for introducing the necessary structure into the formula (10-C), the formula weight of the partial structure (10-C) is generally not lower than the above-mentioned lower limit.

(ii) Partial Structure (10-A)

Preferably, the arylamine polymer compound (10) contains a repeating unit that has the partial structure represented by the following formula (10-A) (hereinafter this may be referred to as "partial structure (10-A)"). Specifically, it is more desirable that the arylamine polymer compound (10) contains a repeating unit having the partial structure (10-A), a repeating unit having the partial structure (10-B) to be mentioned below, and a repeating unit having a crosslinking group, in which the repeating unit having a crosslinking group is preferably the repeating unit having the partial structure (10-A) that has a crosslinking group.

[Chem. 49]

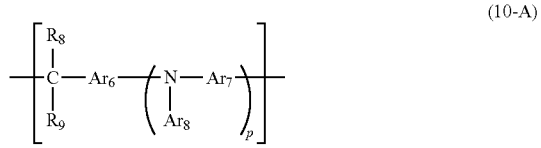

(10-A)

(In the formula (10-A), $Ar_6$ and $Ar_7$ each independently represent an aromatic ring group having two free atomic valences and optionally having a substituent, $Ar_8$ represents an aromatic ring group having one free atomic valence and optionally having a substituent, $R_8$ and $R_9$ each independently represent a hydrogen atom, an alkyl group having one free atomic valence and optionally having a substituent, an alkoxy group having one free atomic valence and optionally having a substituent, or an aromatic ring group having one free atomic valence and optionally having a substituent.

$R_8$ and $R_9$ may bond to each other to form a ring.

p indicates an integer of from 1 to 5.

When the formula (10-A) has plural $Ar_6$'s to $Ar_8$'s, $R_8$'s and $R_9$'s, these plural substituents may be the same or different.)

<Structural Characteristics>

The formula (10-A) has a methylene group. Containing the methylene group that is not rigid in the main chain thereof, the arylamine polymer compound (10) is, even after crosslinked to be insoluble in an organic solvent, able to still maintain high charge transportability and oxidation reduction stability. In addition, as containing the methylene group capable of preventing the π-conjugated system from expanding in the main chain thereof, the arylamine polymer compound (10) is, even after crosslinked to be insoluble in an organic solvent, able to still maintain a high singlet excitation level and a high triplet excitation level. Consequently, in a case where the arylamine polymer compound (10) having the partial structure (10-A) is crosslinked to form a layer of the resultant network-structure polymer, the layer can pass a current therethrough even at a low voltage and hardly deactivates excitons.

In addition, the formula (10-A) has a methylene group and the π-conjugation does not expand therein, and therefore holes move through the polymer chain while hopping therethrough. In the case where holes move while hopping and when the polymer has a branched structure of the flexible partial structure (10-A), such is more desirable since there may readily occur intermolecular/intramolecular polymer chain interaction to thereby greatly increase the hole mobility.

<Regarding $Ar_6$ to $Ar_8$>

The aromatic ring group having two free atomic valences and optionally having a substituent, which constitutes $Ar_6$ and $Ar_7$, is the same as the aromatic ring group having two free atomic valences and optionally having a substituent in $Ar_1$, and $Ar_3$ to $Ar_5$ in the partial structure (10-B), and specific examples and preferred embodiments thereof are the same as those of the latter.

The aromatic ring group optionally having a substituent to constitute $Ar_8$ is the same as the aromatic ring group optionally having a substituent in $Ar_2$ in the partial structure (10-B), and specific examples and preferred embodiments thereof are the same as those of the latter.

<Regarding $R_8$ and $R_9$>

The alkyl group optionally having a substituent, the alkoxy group optionally having a substituent and the aromatic ring group optionally having a substituent to constitute $R_8$ and $R_9$ are the same as the alkyl group optionally having a substituent, the alkoxy group optionally having a substituent and the aromatic ring group optionally having a substituent in $R_2$ to $R_7$ in the partial structure (10-B), and specific examples and preferred embodiments thereof are the same as those of the latter.

$R_8$ and $R_9$ may bond to each other to form a ring.

<Regarding p> p indicates an integer of from 1 to 5.

When p is too large the solubility of the polymer in solvent may lower, and therefore, p is preferably from 1 to 3, more preferably 1 or 2.

When the formula (10-A) has plural $Ar_6$'s to $Ar_8$'s, $R_8$'s and $R_9$'s, these plural substituents may be the same or different.

<Regarding Formula Weight of Partial Structure (10-A)>

The formula weight of the partial structure (10-A) is generally 300 or more and generally 3000 or less, and is especially preferably 2000 or less. When the formula weight of the partial structure (10-A) is too large, then the solubility of the polymer before crosslinking in solvent may lower. However, for introducing the necessary structure into the formula (10-A), the formula weight of the partial structure (10-A) is generally not lower than the above-mentioned lower limit.

<Examples of Partial Structure (10-A)>

Specific examples of the partial structure (10-A) are shown below, however, the partial structure (10-A) in the present invention is not whatsoever limited to the following.

The arylamine polymer compound (10) may have a repeating unit having one partial structure (10-A), or may have a repeating unit having two or more partial structures (10-A).

[Chem. 50]
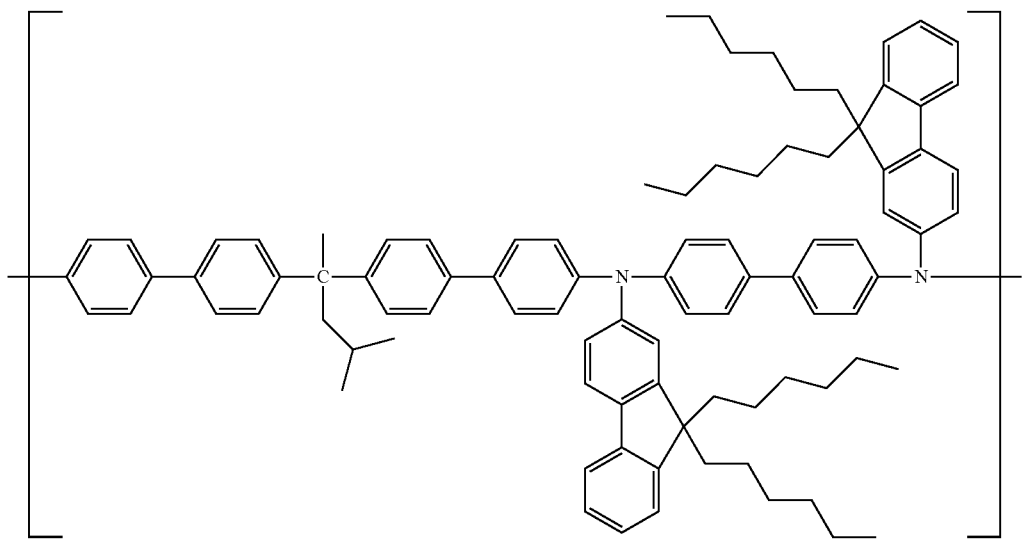
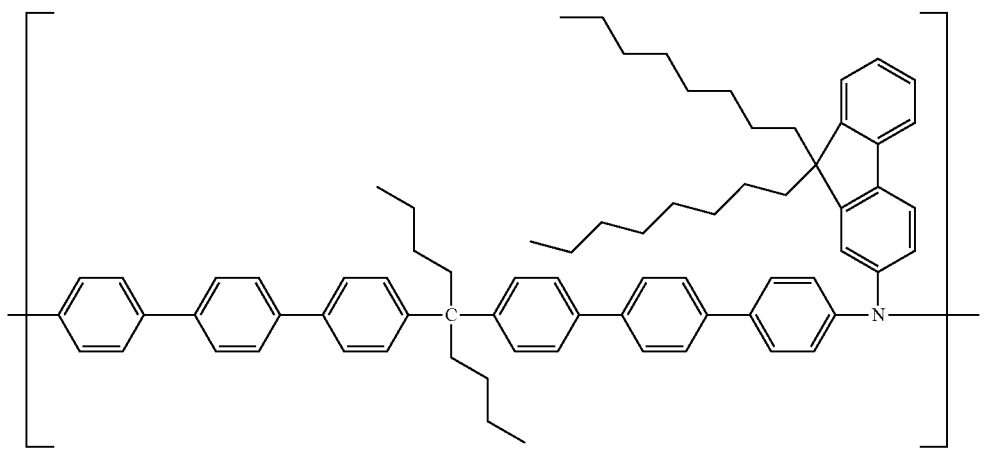
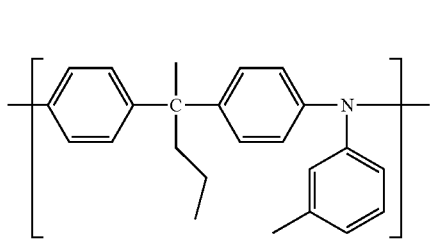
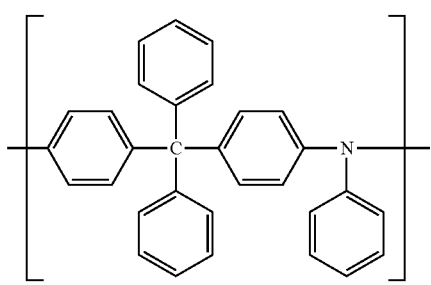
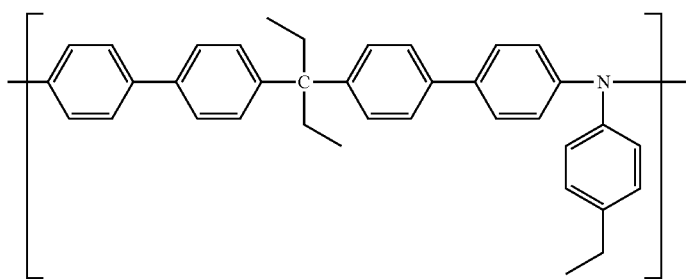

-continued
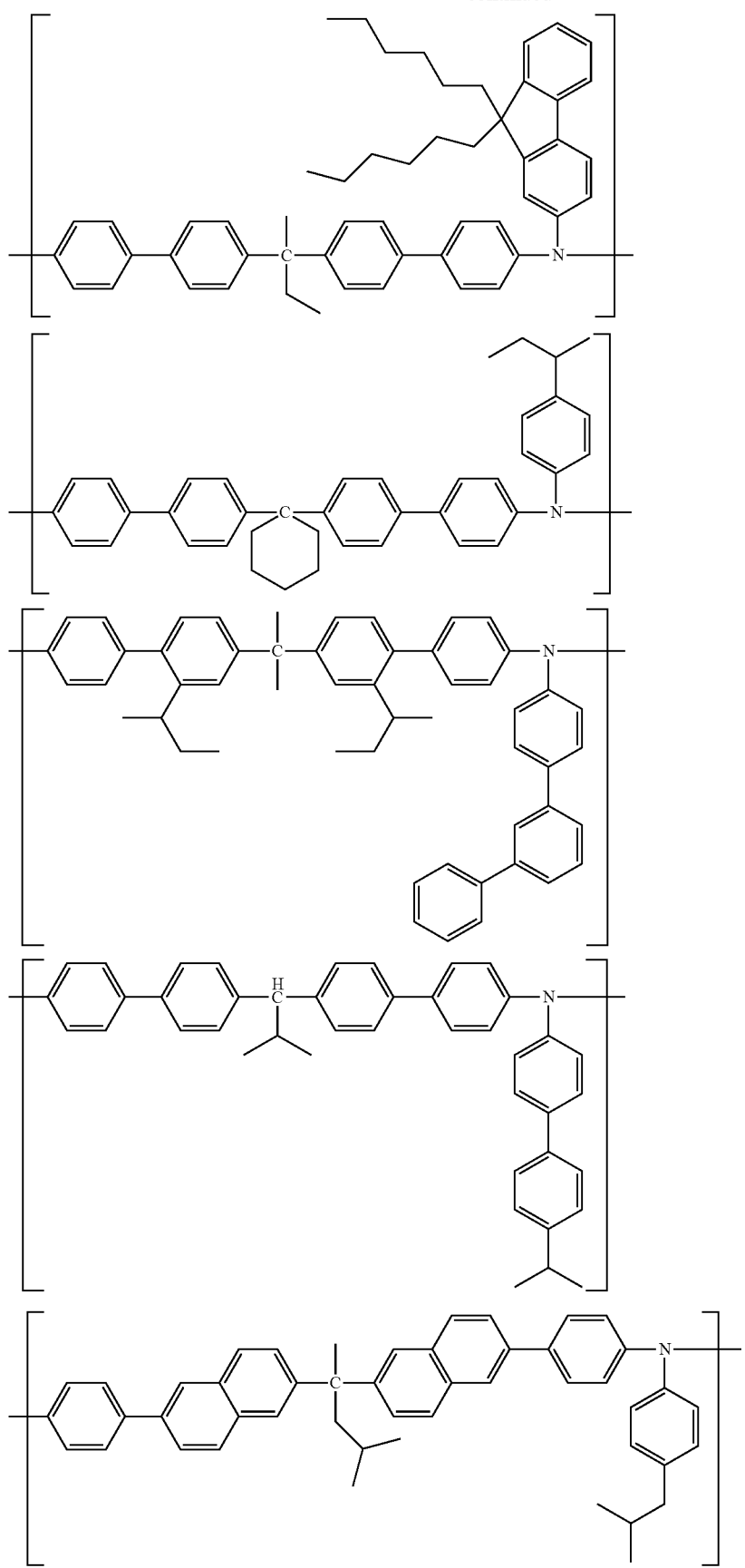

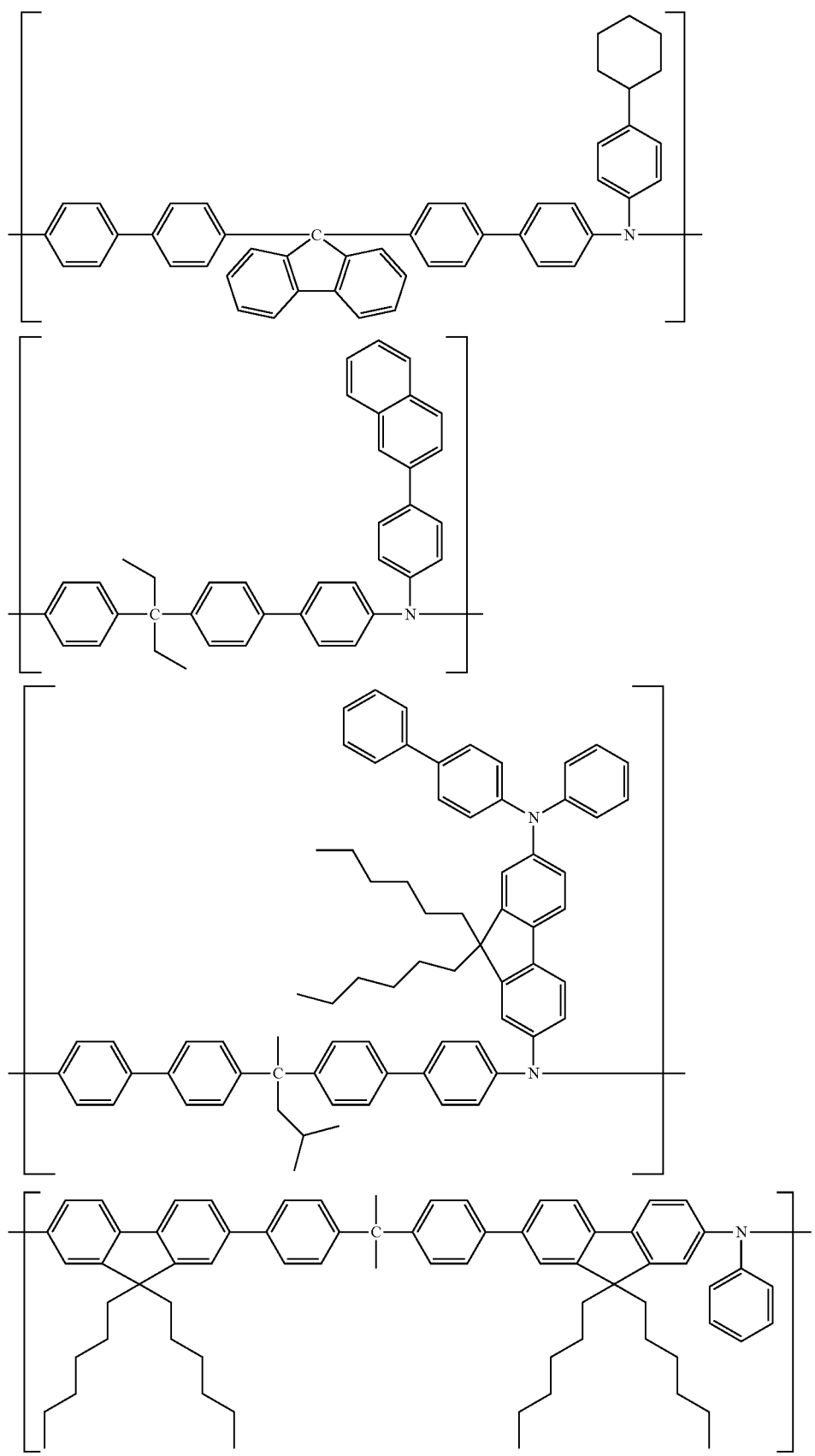

137
-continued
138
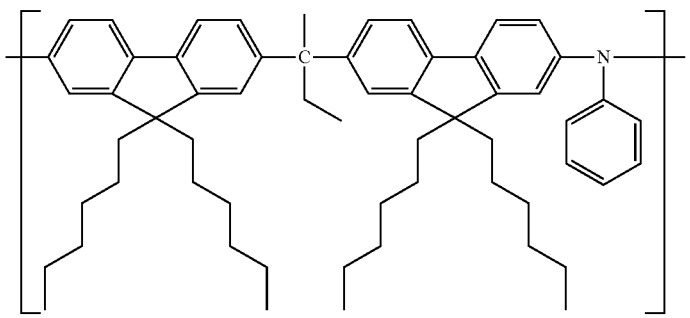
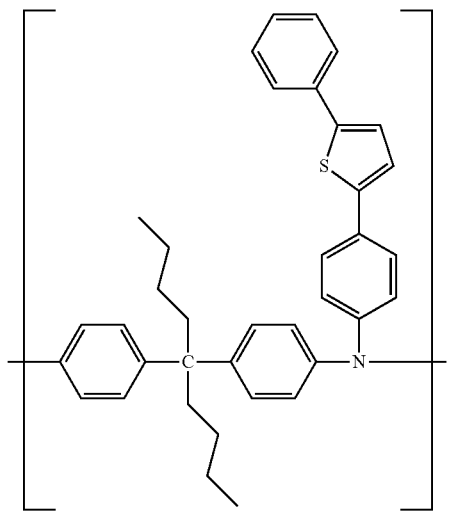
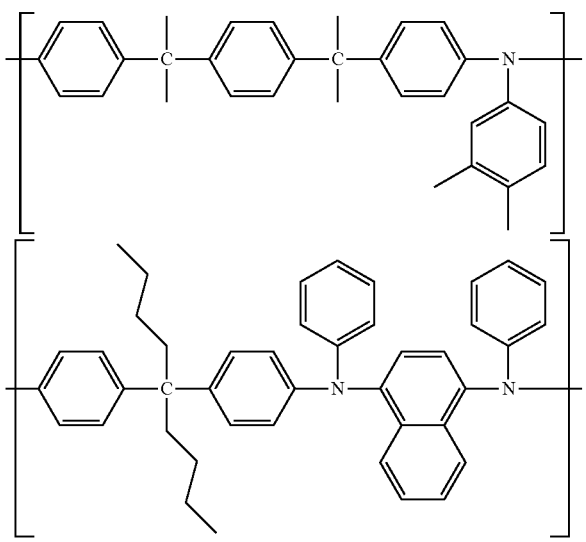
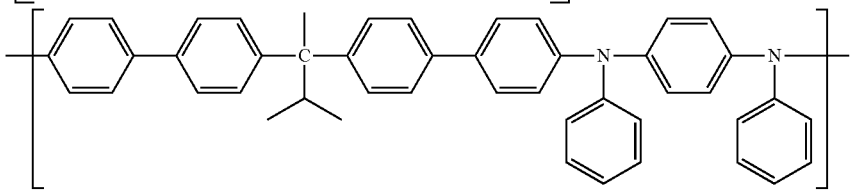
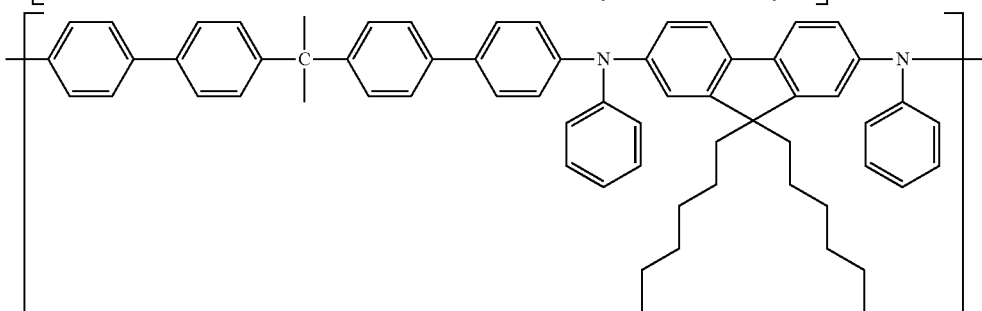
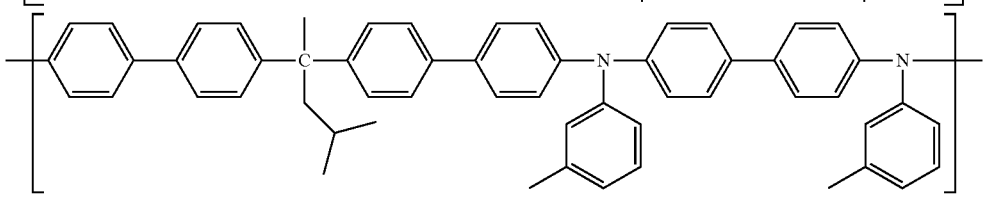

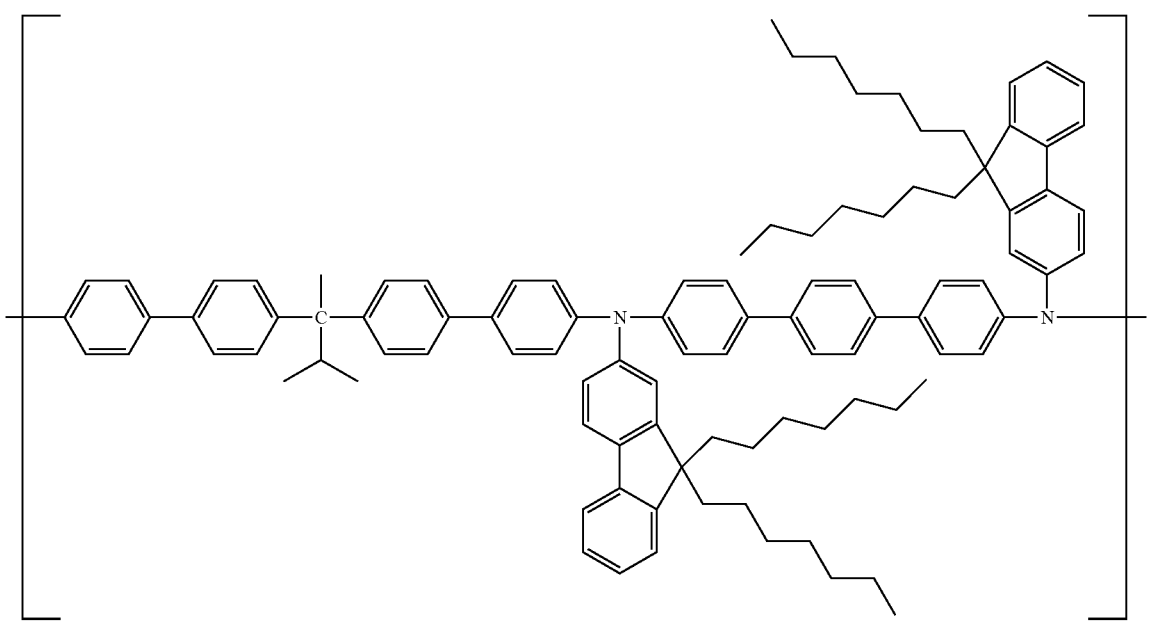
[Chem. 51]
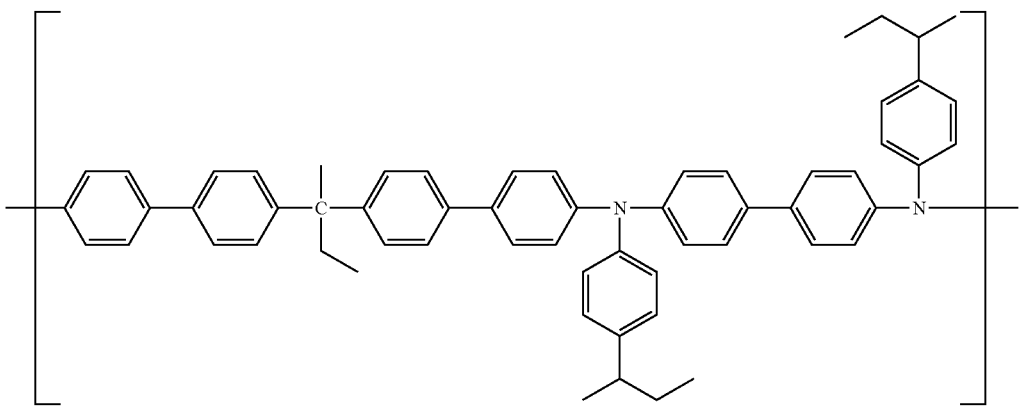
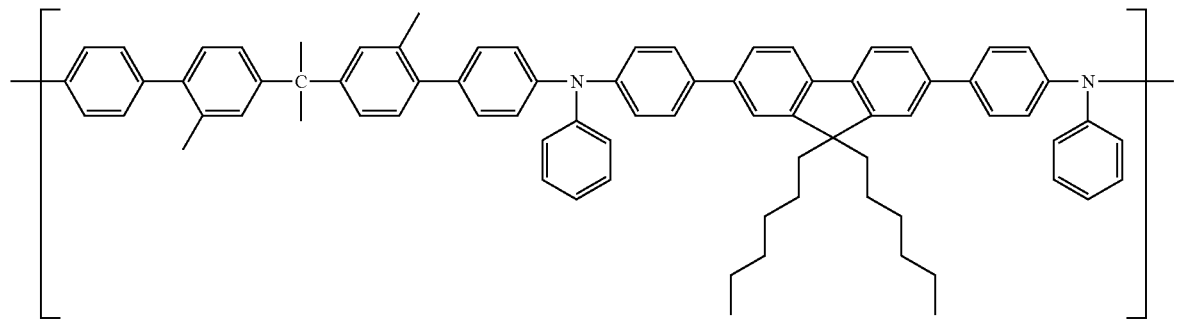

-continued
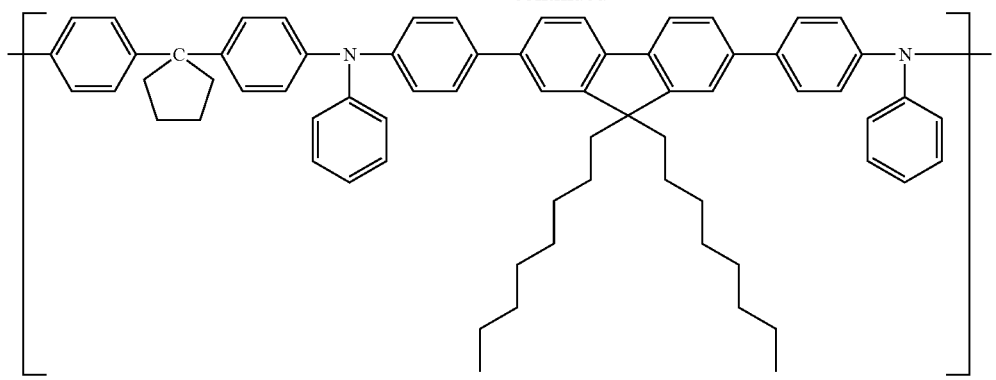
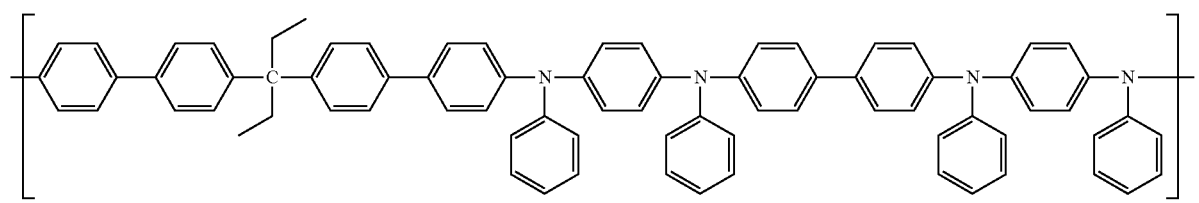
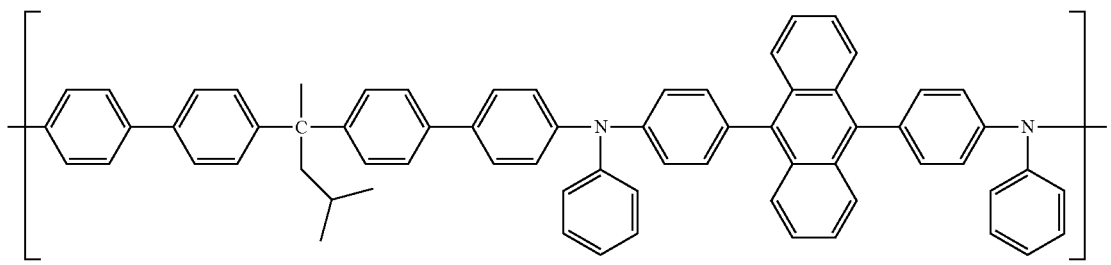
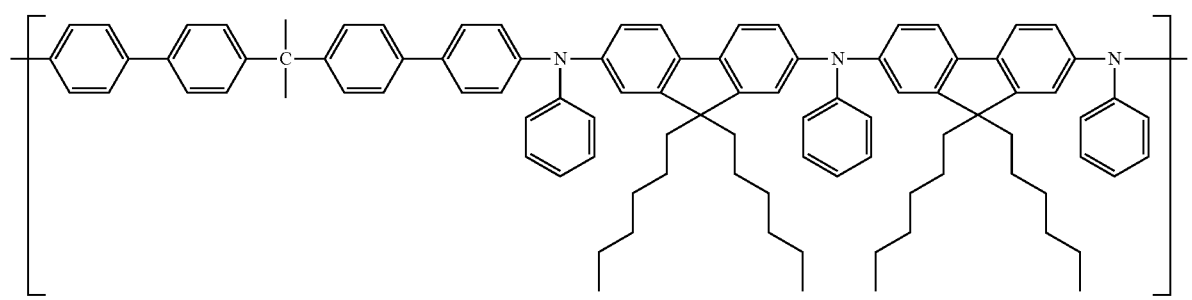
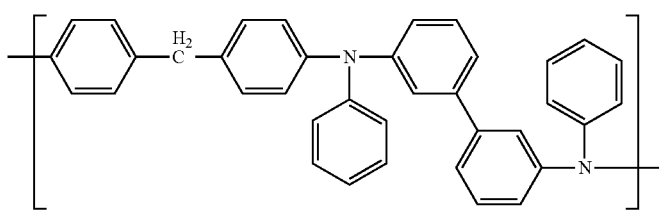
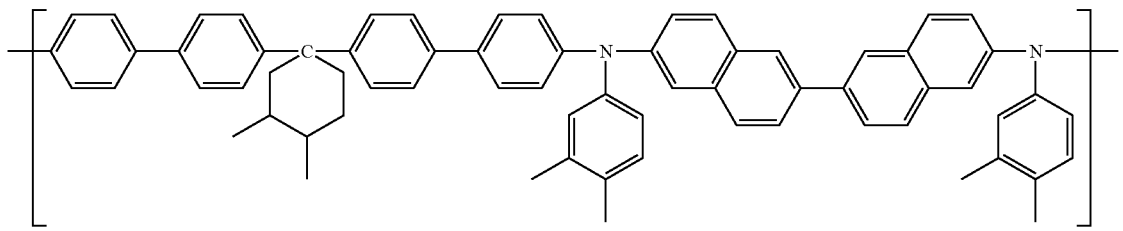

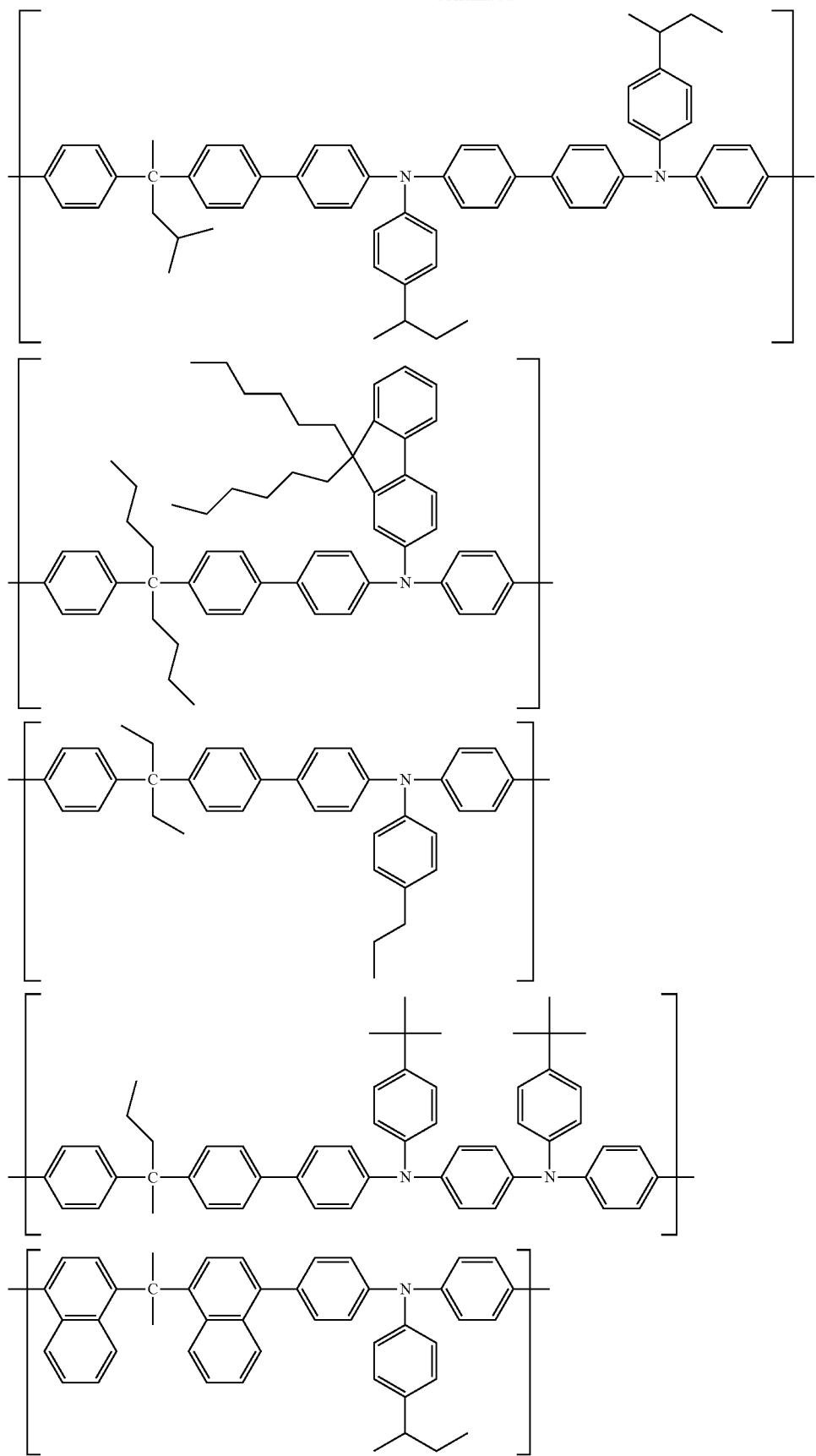

-continued
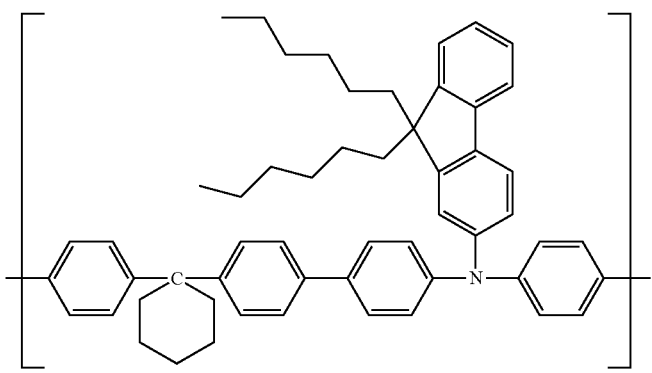
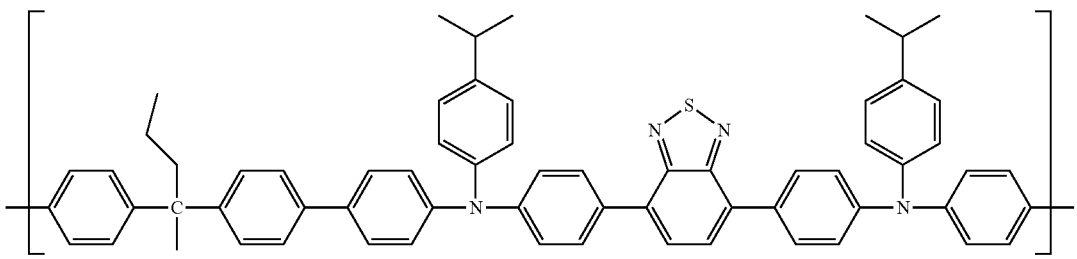
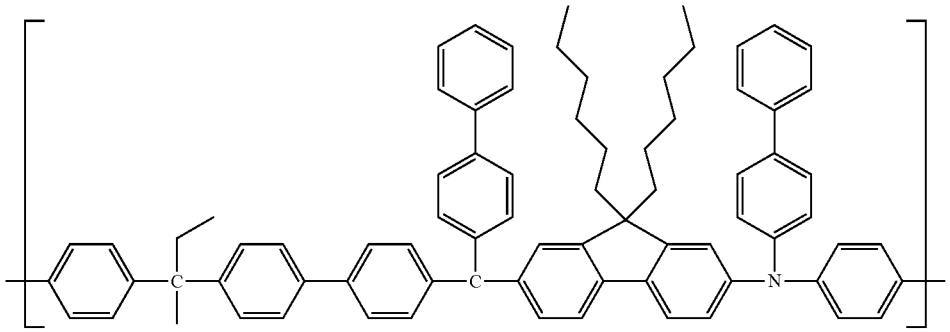
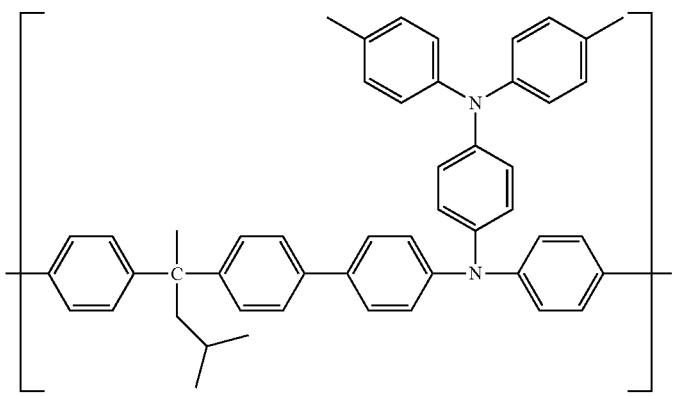
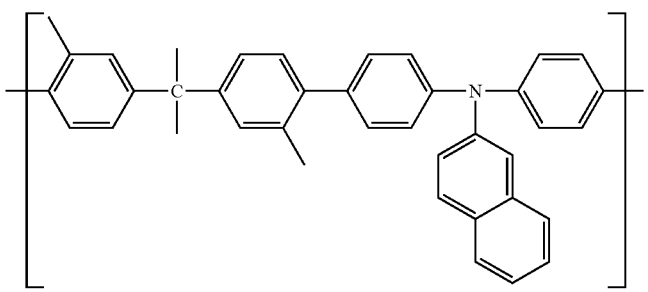

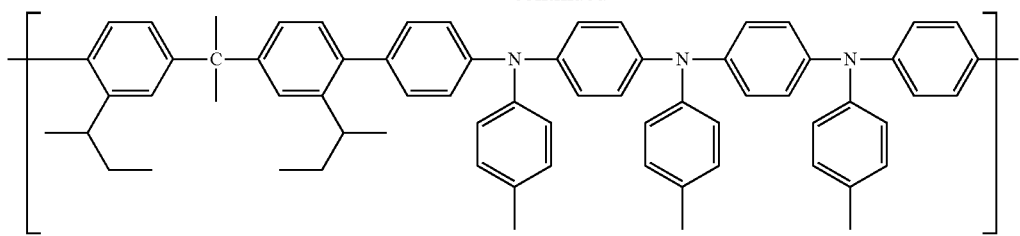
[Chem. 52]
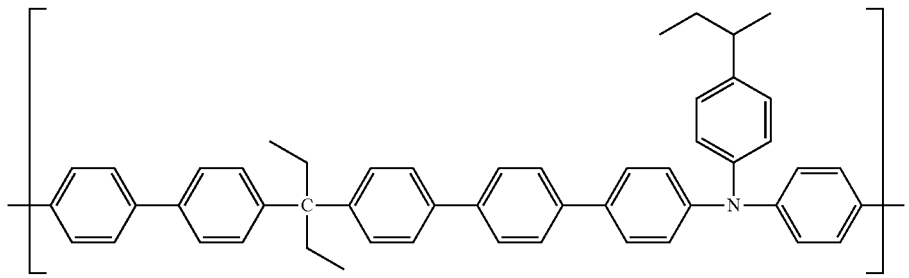
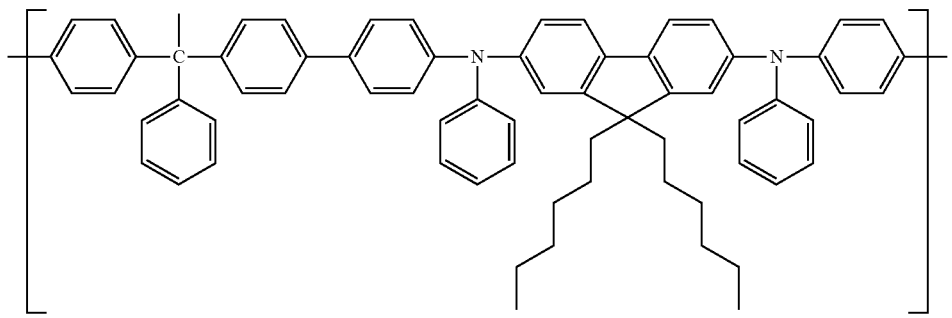
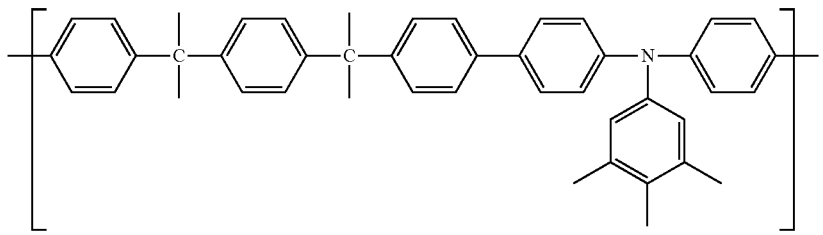
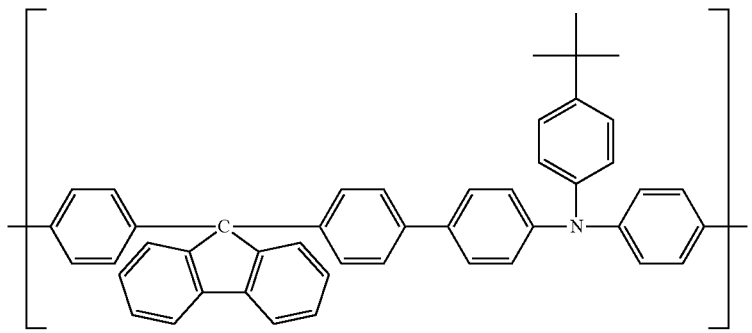
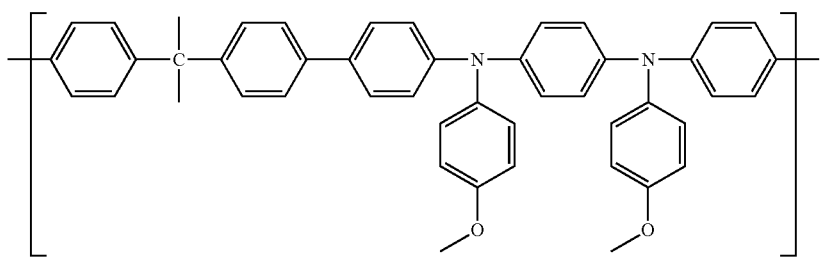

-continued
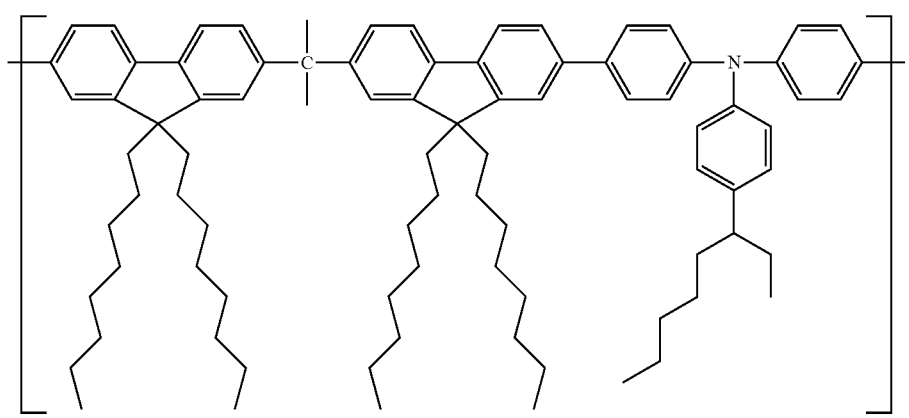
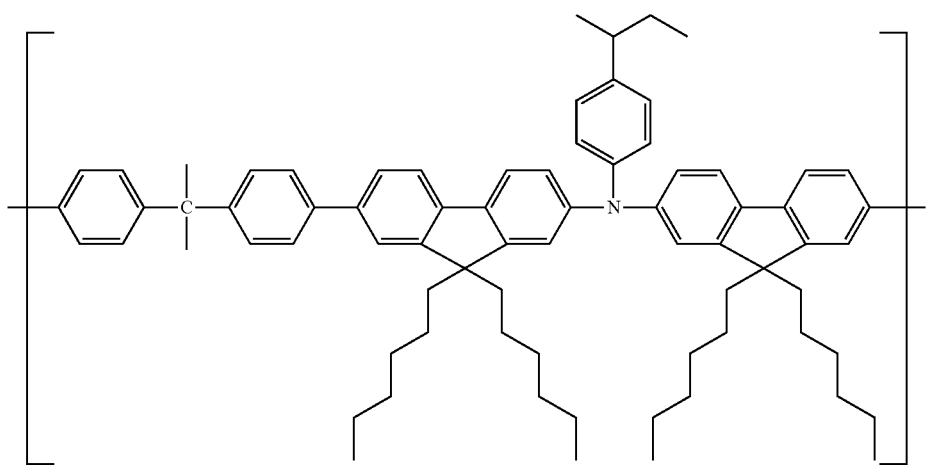
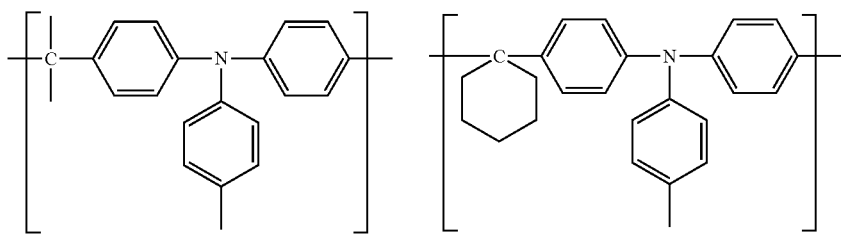
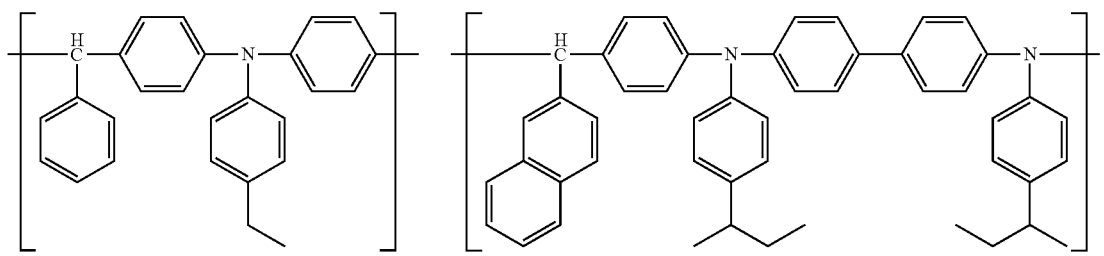

(iii) Partial Structure (10-B)

Preferably, the arylamine polymer compound (10) contains a repeating unit having a partial structure represented by the following formula (10-B) (hereinafter this may be referred to as "partial structure (10-B)"). Specifically, the arylamine polymer compound (10) preferably has a repeating unit having the partial structure (10-A), a repeating unit having the following partial structure (10-B), and a repeating unit having a crosslinking group, in which the repeating unit having a crosslinking unit is preferably a repeating unit having the partial structure (10-B) that has a crosslinking group.

[Chem. 53]

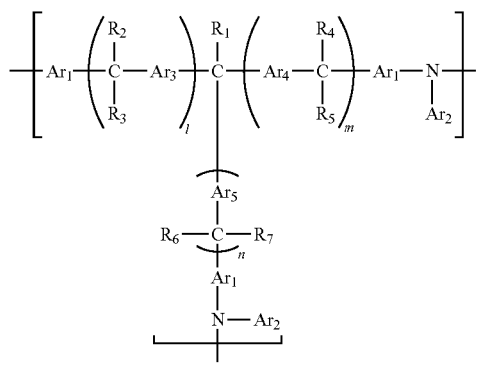

(10-B)

(In the formula (10-B), $Ar_1$, $Ar_3$, $Ar_4$ and $Ar_5$ each independently represent an aromatic ring group having two free atomic valences and optionally having a substituent, $Ar_2$ represents an aromatic ring group having one free atomic valence and optionally having a substituent, $R_1$ represents an alkyl group having one free atomic valence and optionally having a substituent, or an alkoxy group optionally having a substituent. $R_2$ to $R_7$ each independently represent a hydrogen atom, an alkyl group having one free atomic valence and optionally having a substituent, an alkoxy group optionally having a substituent, or an aromatic ring group optionally having a substituent.

$R_2$ and $R_3$ may bond to each other to form a ring. $R_4$ and $R_5$ may bond to each other to form a ring. $R_6$ and $R_7$ may bond to each other to form a ring.

l, m and n each independently indicate an integer of from 0 to 2.

When the formula (10-B) has plural $Ar_1$'s to $Ar_5$', $R_1$'s to $R_7$'s, these plural substituents may be the same or different.)
(Arylamine Polymer Compound (10))}
(i) Partial Structure (10-B)
<Structural Characteristics>

The partial structure (10-B) is a flexible branched structure which is branched on the sp³ carbon therein and in which the sp³ carbon has $R_1$ of an alkyl group or an alkoxy group. The arylamine polymer compound (10) that contains such a partial structure (10-B) as the repeating unit therein facilitates intermolecular polymer chain interaction and facilitates intermolecular hole transfer. Consequently, the film formed of the arylamine polymer compound (10) has a high hole mobility and, therefore, the organic electroluminescent element having a layer formed of the arylamine polymer compound (10) requires a low driving voltage for operation thereof.

The layer formed of the arylamine polymer compound (10) hardly traps holes and hardly accumulates charges, and therefore the material hardly decomposes. Consequently, the organic electroluminescent element having a layer formed of the arylamine polymer compound (10) requires a low driving voltage for operation thereof and provides a high emission efficiency.

<Regarding $Ar_1$ to $Ar_5$>

Of the aromatic ring group optionally having a substituent to constitutes $Ar_1$ to $Ar_5$, the aromatic hydrocarbon ring group includes a 6-membered single ring or 2- to 5-condensed ring such as a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, a fluorene ring or the like each having one (for $Ar_2$) or two (for $Ar_1$, $Ar_3$ to $Ar_5$) free atomic valences.

Of the aromatic ring group optionally having a substituent to constitutes $Ar_1$ to $Ar_5$, the aromatic heterocyclic group includes a 5- or 6-membered single ring or 2- to 4-condensed ring such as a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, an azulene ring or the like each having one (for $Ar_2$) or two (for $Ar_1$, $Ar_3$ to $Ar_5$) free atomic valences.

Above all, from the viewpoint of solubility and heat resistance, $Ar_1$ to $Ar_5$ each are preferably a ring selected from a group consisting of a benzene ring, a naphthalene ring, an anthracene ring, a phenanthrene ring, a triphenylene ring, a pyrene ring, a thiophene ring, a pyridine ring or a fluorene ring each having one (for $Ar_2$) or two (for $Ar_1$, $Ar_3$ to $Ar_5$) free atomic valences.

In the formula (10-B), $Ar_1$ to $Ar_5$ each may be a group formed by bonding two or more aromatic ring groups optionally having a substituent. The group of the type includes a biphenylene group, a terphenylene group and the like for $Ar_1$, $Ar_3$ to $Ar_5$, and is preferably a 4,4'-biphenylene group. For $Ar_2$, the group of the type includes a biphenyl group, a terphenyl group, etc., and preferred is a p-phenylphenyl group.

The substituent that the aromatic ring group for $Ar_1$ to $Ar_5$ may have is not specifically defined. For example, the substituent includes those selected from the following family of substituents Z. $Ar_1$ to $Ar_5$ may have one substituent or may have two or more substituent. When they have two or more substituents, the substituents may be the same type or may be a combination of two or more different kinds of substituents as combined in any desired manner and in any desired ratio.
(Family of Substituents Z)

The substituents include:
an alkyl group having generally one or more and generally 24 or less but preferably 12 or less carbon atoms, for example, a methyl group, an ethyl group, etc.;
an alkenyl group having generally 2 or more and generally 24 or less but preferably 12 or less carbon atoms, for example a vinyl group, etc.;
an alkynyl group having generally 2 or more and generally 24 or less but preferably 12 or less carbon atoms, for example an ethynyl group, etc.;
an alkoxy group having generally 1 or more and generally 24 or less but preferably 12 or less carbon atoms, for example, a methoxy group, an ethoxy group, etc.;

an aryloxy group having generally 4 or more, preferably 5 or more and generally 36 or less, preferably 24 or less carbon atoms, for example, a phenoxy group, a naphthoxy group, a pyridyloxy group, etc.;

an alkoxycarbonyl group having generally 2 or more and generally 24 or less but preferably 12 or less carbon atoms, for example, a methoxycarbonyl group, an ethoxycarbonyl group, etc.;

a dialkylamino group having generally 2 or more and generally 24 or less but preferably 12 or less carbon atoms, for example, a dimethylamino group, a diethylamino group, etc.;

a diarylamino group having generally 10 or more, preferably 12 or more and is generally 36 or less, preferably 24 or less carbon atoms, for example, a diphenylamino group, a ditolylamino group, an N-carbazolyl group, etc.;

an arylalkylamino group having generally 7 or more and generally 36 or less but preferably 24 or less carbon atoms, for example, a phenylmethylamino group, etc.;

an acyl group having generally 2 or more and generally 24 or less but preferably 12 or less carbon atoms, for example, an acetyl group, a benzoyl group, etc.;

a halogen atom, for example a fluorine atom, a chlorine atom, etc.;

a haloalkyl group having generally 1 or more and generally 12 or less but preferably 6 or less carbon atoms, for example, a trifluoromethyl group, etc.;

an alkylthio group having generally 1 or more and generally 24 or less but preferably 12 or less carbon atoms, for example, a methylthio group, an ethylthio group, etc.;

an arylthio group having generally 4 or more, preferably 5 or more and generally 36 or less, preferably 24 or less carbon atoms, for example, a phenylthio group, a naphthylthio group, a pyridylthio group, etc.;

a silyl group having generally 2 or more, preferably 3 or more and generally 36 or less, preferably 24 or less carbon atoms, for example, a trimethylsilyl group, a triphenylsilyl group, etc.;

a siloxy group having generally 2 or more, preferably 3 or more and generally 36 or less, preferably 24 or less carbon atoms, for example, a trimethylsiloxy group, a triphenylsiloxy group, etc.;

a cyano group;

an aromatic hydrocarbon ring group having generally 6 or more and generally 36 or less but preferably 24 or less carbon atoms, for example a phenyl group, a naphthyl group, etc.;

an aromatic heterocyclic group having generally 3 or more, preferably 4 or more and generally 36 or less, preferably 24 or less carbon atoms, such as a thienyl group, a pyridyl group, etc.

Of those substituents, preferred is an alkyl group having from 1 to 12 carbon atoms and an alkoxy group having from 1 to 12 carbon atoms, from the viewpoint of solubility.

The above-mentioned substituents may further have a substituent, and as examples of the substituent include those exemplified hereinabove for the family of substituents Z.

The formula weight of the group represented by $Ar_1$ to $Ar_5$ is, including the substituent, if any, generally 65 or more, preferably 75 or more and is generally 500 or less, preferably 300 or less, more preferably 250 or less, even more preferably 200 or less. When the formula weight of the group represented by $Ar_1$ to $Ar_5$ is too large, then the charge transportability of the polymer may lower, and the solubility of the polymer before crosslinking in solvent may greatly lower.

<Regarding $R_1$>

$R_1$ represents an alkyl group optionally having a substituent, or an alkoxy group optionally having a substituent.

Introducing an alkyl group or an alkoxy group into the sp3 carbon of the branched part of the arylamine polymer compound (10) improves the solubility of the polymer before crosslinking in a solvent, as compared with the case where an aromatic hydrocarbon ring group or an aromatic heterocyclic group is introduced thereinto, and therefore the polymer of the type can readily form a homogeneous film.

The alkyl group optionally having a substituent to constitute $R_1$ includes a straight-chain or branched chain-like alkyl group having generally 1 or more and generally 24 or less carbon atoms, for example, methyl, ethyl, n-propyl, 2-propyl, n-butyl, isobutyl, tert-butyl groups, etc. Of those, more preferred is an alkyl group having 1 or more and 12 or less, especially 6 or less carbon atoms, from the viewpoint of durability and solubility.

The alkoxy group optionally having a substituent to constitute $R_1$ includes a straight-chain or branched chain-like alkoxy group having generally 1 or more and generally 24 or less carbon atoms, for example, methoxy, ethoxy, butoxy groups, etc. Of those more preferred is an alkoxy group having generally 1 or more and 12 or less, especially 6 or less carbon atoms, from the viewpoint of durability and solubility.

Further, the substituent that the alkyl group or the alkoxy group of $R_1$ may have includes, though not specifically defined, for example, those selected from the above-mentioned family of substituents Z. $R_1$ may have one substituent or two or more substituents. When $R_1$ have two or more substituents, the substituents may be the same type, or may be a combination of two or more different kinds of substituents as combined in any desired manner and in any desired ratio.

In case where the alkyl group or the alkoxy group of $R_1$ has a substituent for efficiently securing the effect of $R_1$ in the present invention, or that is, for securing the effect thereof to facilitate interaction of polymer chains, the substituent is preferably an aromatic hydrocarbon ring group having 12 or less carbon atoms, but especially preferably, the alkyl group or the alkoxy group of $R_1$ does not have a substituent.

The formula weight of $R_1$ is, including the substituent, if any, preferably 500 or less, more preferably 200 or less. When the formula weight of the group of $R_1$ is too large, then as the case may be, the effect of facilitating the interaction of polymer chains could not be secured sufficiently.

<Regarding $R_2$ to $R_7$>

As the alkyl group optionally having a substituent or the alkoxy group optionally having a substituent to constitute $R_2$ to $R_7$, there are mentioned those exemplified hereinabove as the alkyl group optionally having a substituent or the alkoxy group optionally having a substituent to constitute $R_1$.

As the aromatic ring group optionally having a substituent to constitute $R_2$ to $R_7$, there are mentioned those exemplified hereinabove as the aromatic ring group optionally having a substituent to constitute $Ar_2$.

$R_2$ and $R_3$, $R_4$ and $R_5$, and $R_6$ and $R_7$ may bond to each other to form a ring.

Of those, preferred is a straight chain or branched chain-like alkyl group having generally 1 or more and generally 12 or less carbon atoms, such as methyl, ethyl, n-propyl, 2-propyl, n-butyl, isobutyl, tert-butyl groups and the like, is preferred as $R_2$ to $R_7$, from the viewpoint of durability and solubility.

The substituent that the alkyl group, the alkoxy group and the aromatic ring group to constitute these $R_2$ to $R_7$ may have includes, though not specifically defined, for example, those selected from the above-mentioned family of substituents Z. $R_2$ to $R_7$ may have one substituent or two or more substituents. When they have two or more substituents, the substituents may be the same type, or may be a combination of two or more different kinds of substituents as combined in any desired manner and in any desired ratio.

The formula weight of the group of $R_2$ to $R_7$ is, including the substituent, if any, generally 15 or more and generally 500 or less, preferably 300 or less, more preferably 250 or less, even more preferably 200 or less. When the formula weight of $R_2$ to $R_7$ is too large, then the solubility of the polymer before crosslinking in solvent may greatly lower.

<Regarding l, m, n> l, m and n each independently indicates an integer of from 0 to 2. When at least one of l, m and n differs from any other, or that is, when they are not l=m=n, such a case is more preferred since the symmetry of the branched structure is lowered and the solubility of the polymer in solvent increases, and therefore a more homogeneous film can be formed.

In case where the formula (10-B) has plural $Ar_1$'s to $Ar_5$'s and $R_1$'s to $R_7$'s, these substituents may be the same or different.

<Regarding Formula Weight of Partial Structure (10-B)>

The formula weight of the partial structure (10-B) is generally 400 or more and generally 3000 or less but preferably 2000 or less. When the formula weight of the partial structure (10-B) is too large, then the solubility of the polymer before crosslinking may lower. However, for introducing the necessary structure into the formula (10-B), the formula weight of the partial structure (10-B) is generally not lower than the above-mentioned lower limit.

<Examples of Partial Structure (10-B)>

Specific examples of the partial structure (10-B) are shown below, however, the partial structure (10-B) in the present invention is not whatsoever limited to the following.

The arylamine polymer compound (10) may have a repeating unit having one type of the partial structure (10-B), or may have a repeating unit having two or more kinds of the partial structure (10-B).

[Chem. 54]

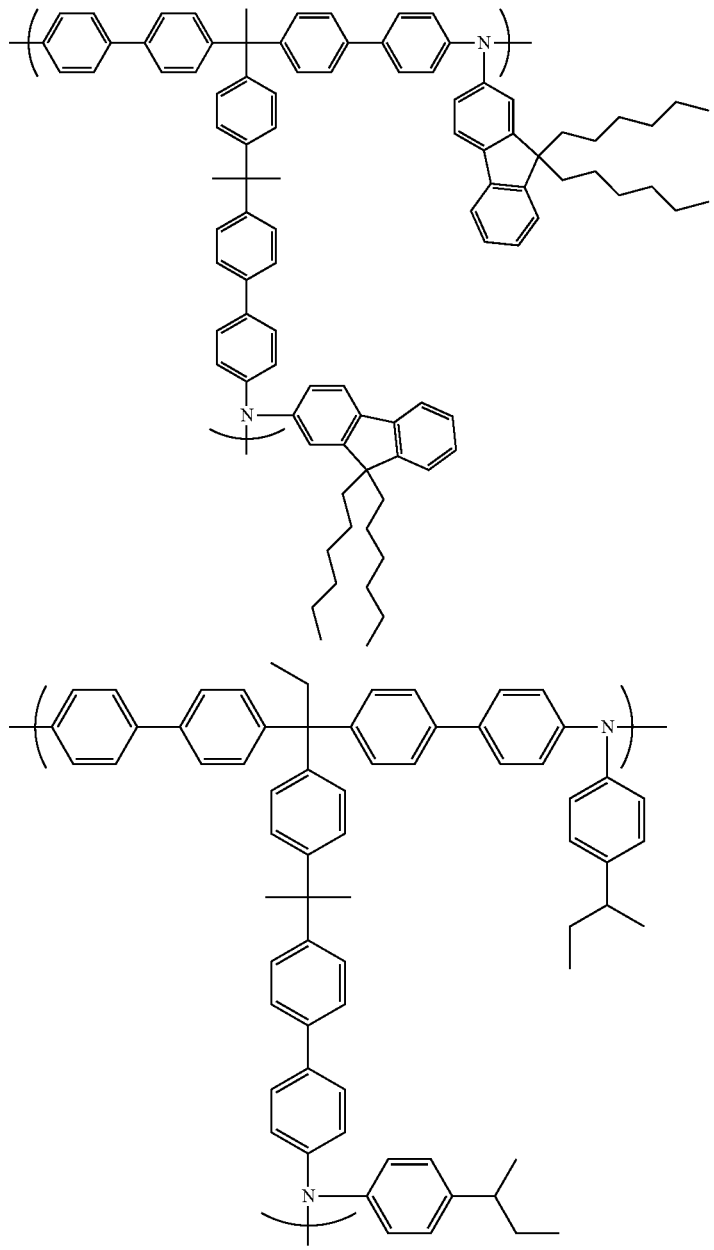

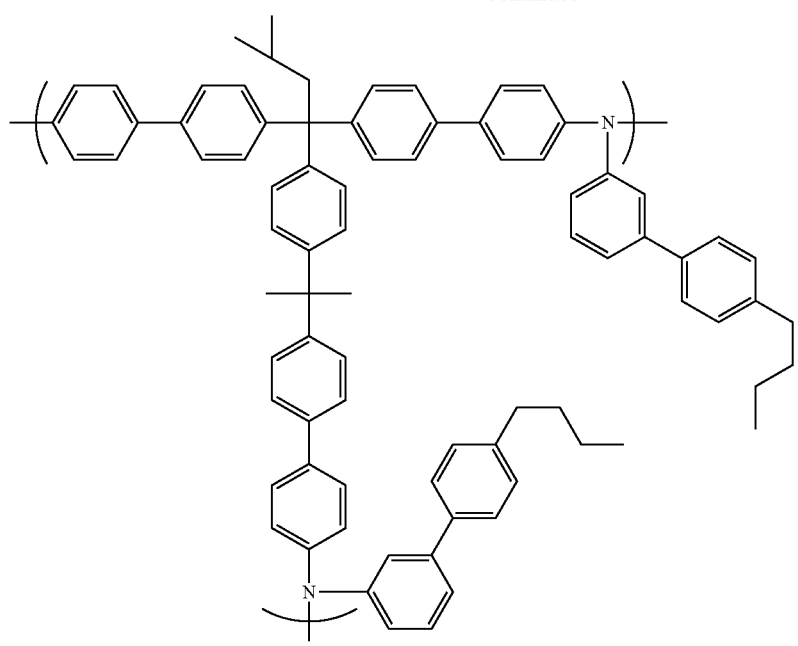
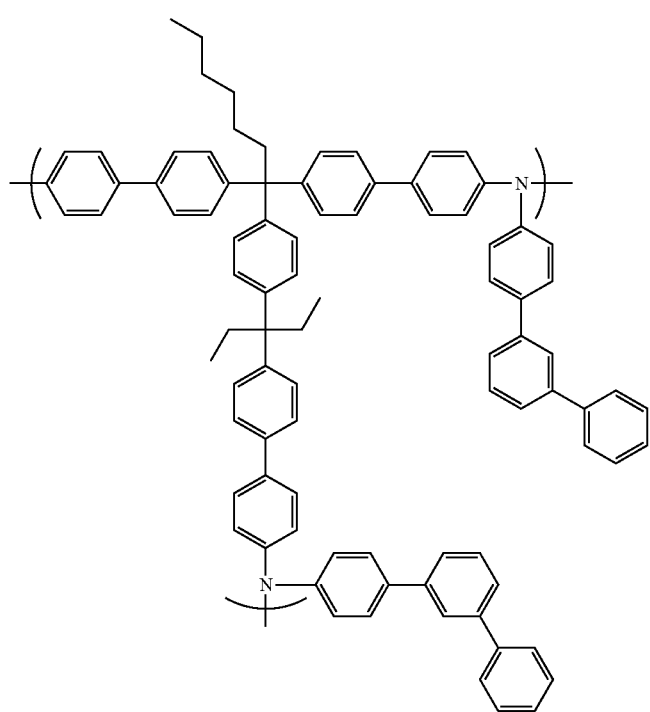

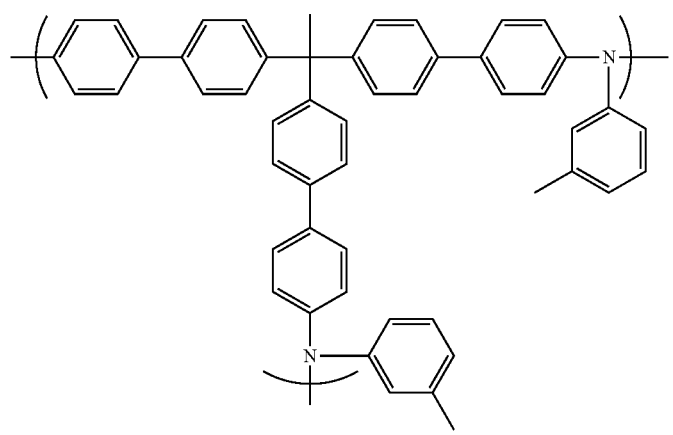
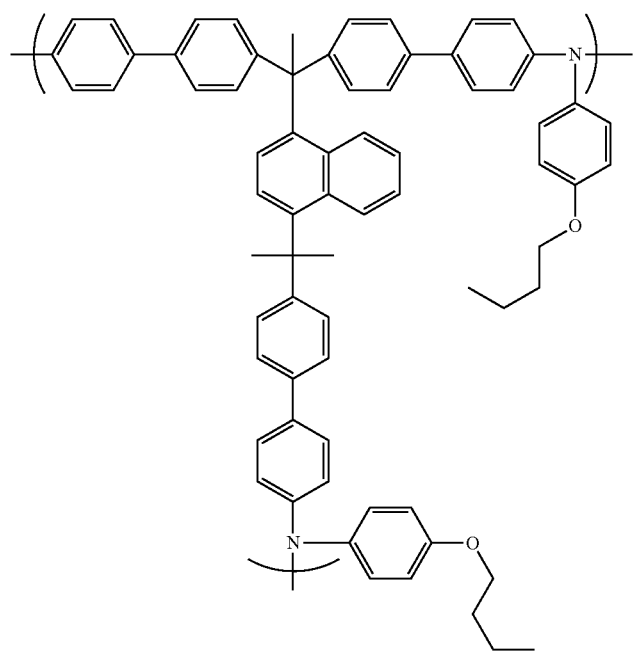

[Chem. 55]
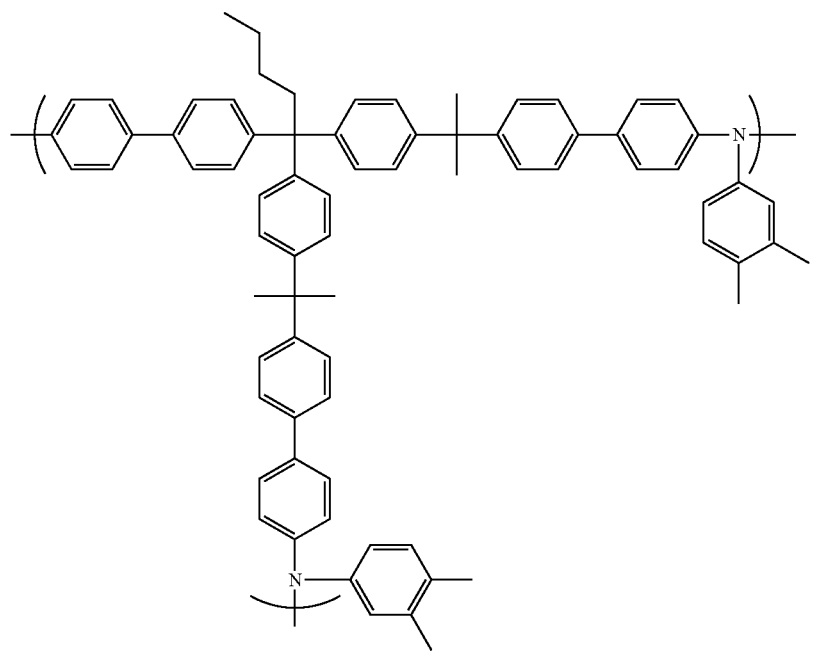
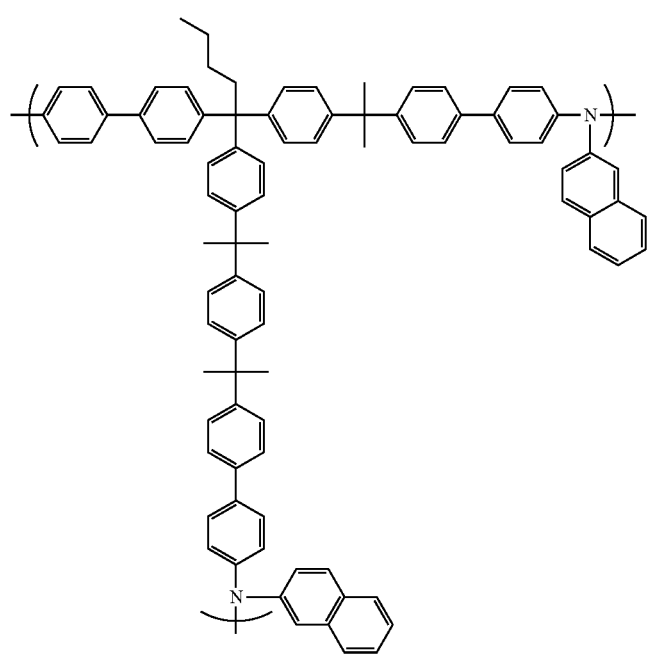

-continued
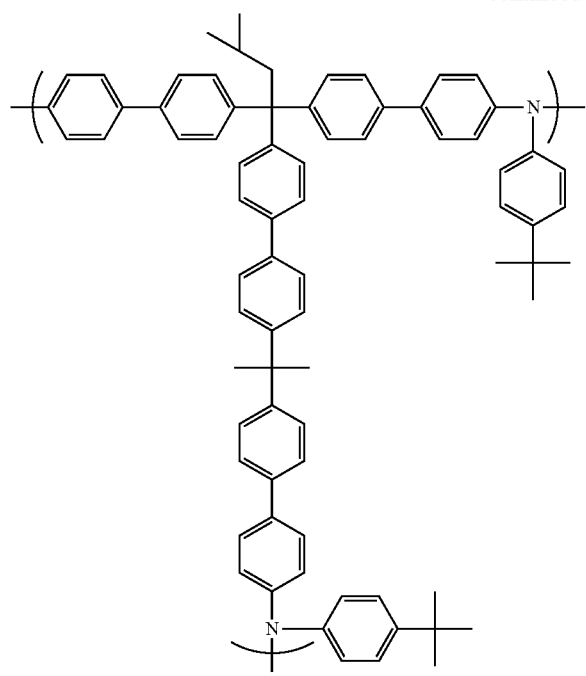
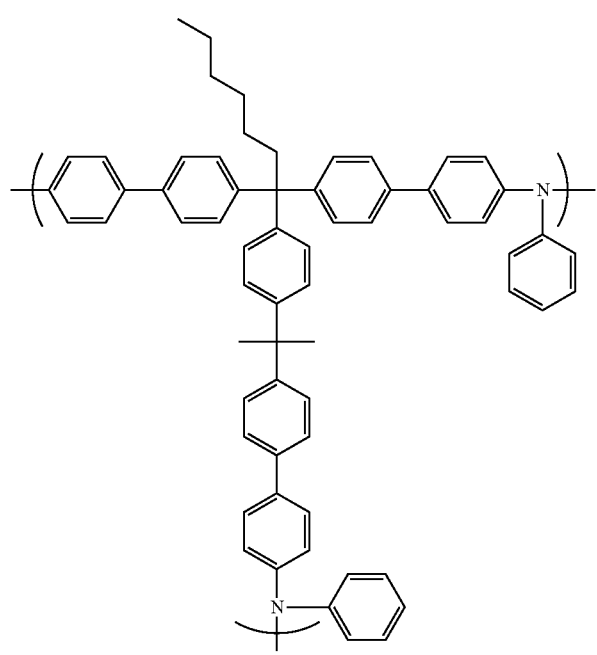

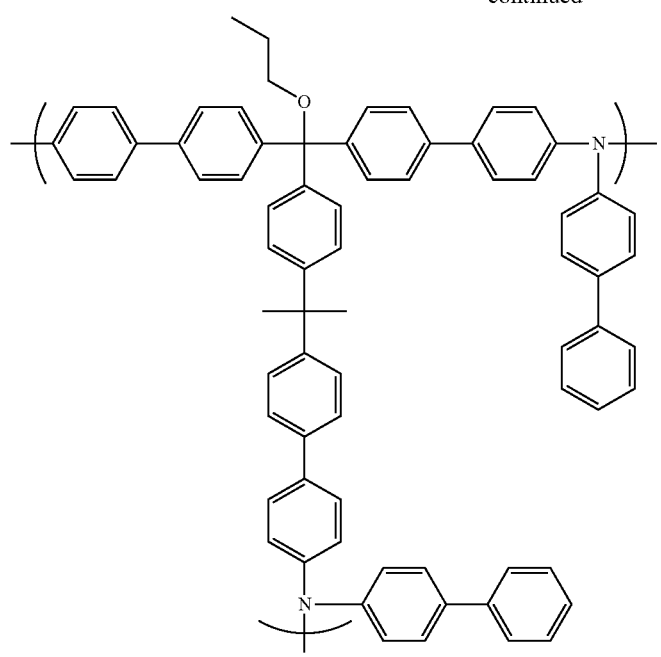
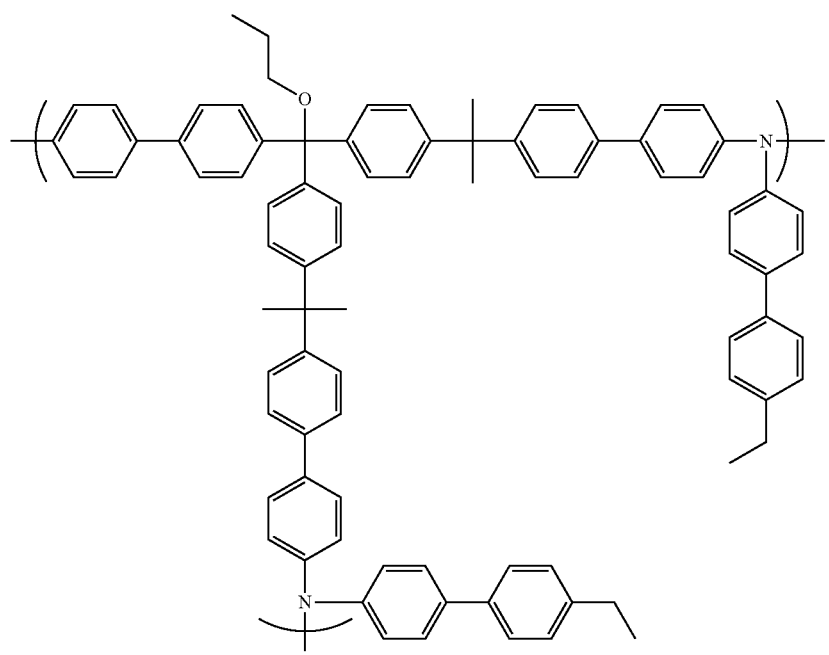

[Chem. 56]
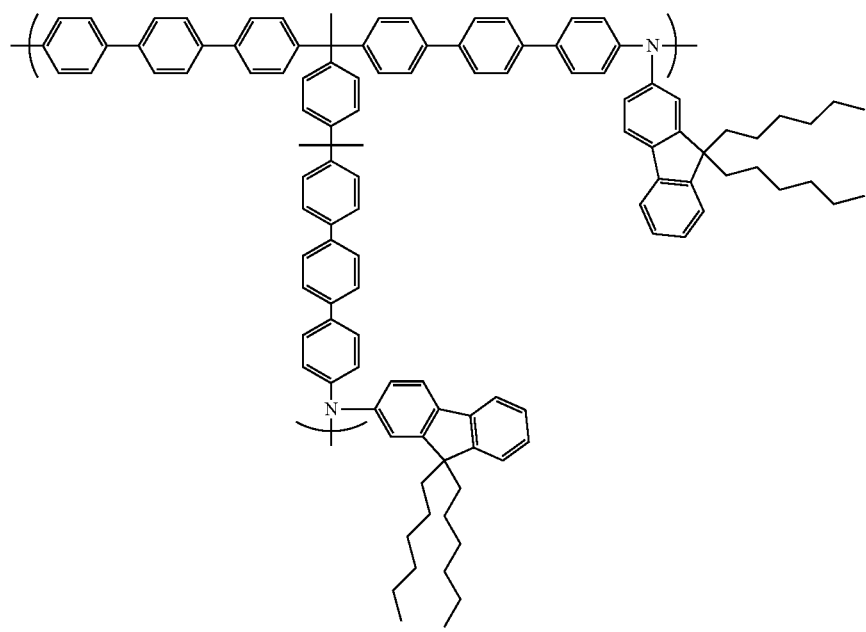
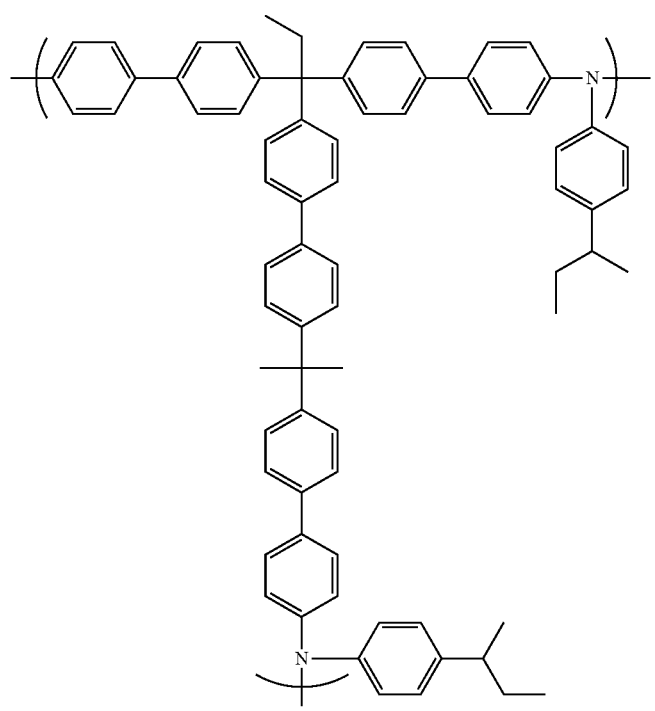

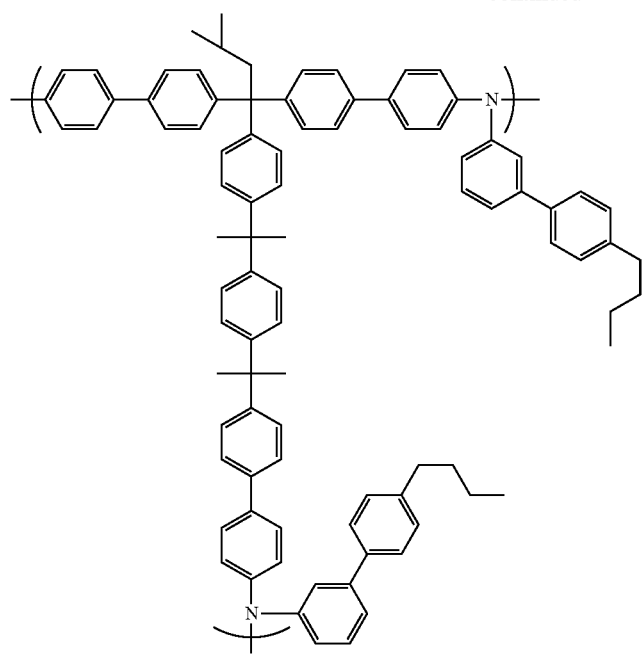
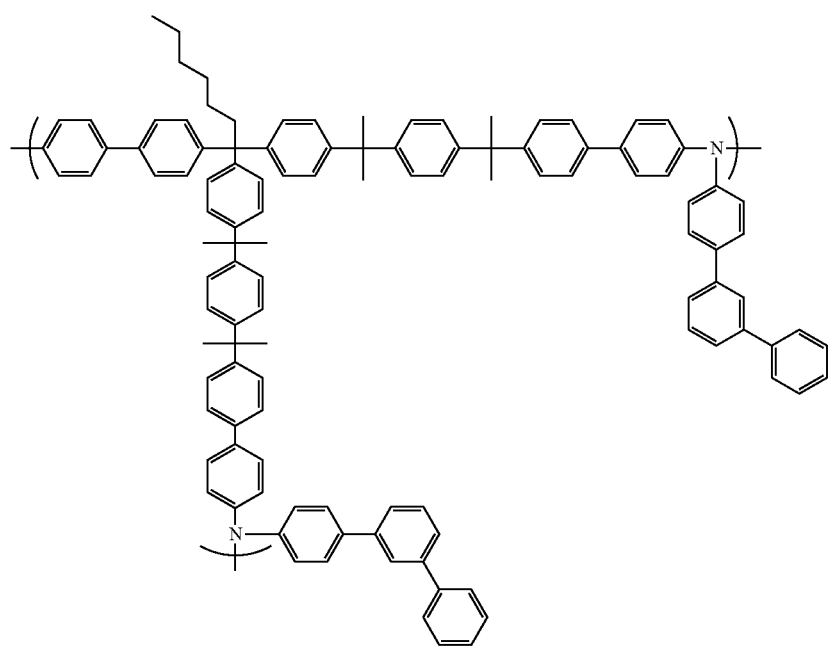

[Chem. 57]
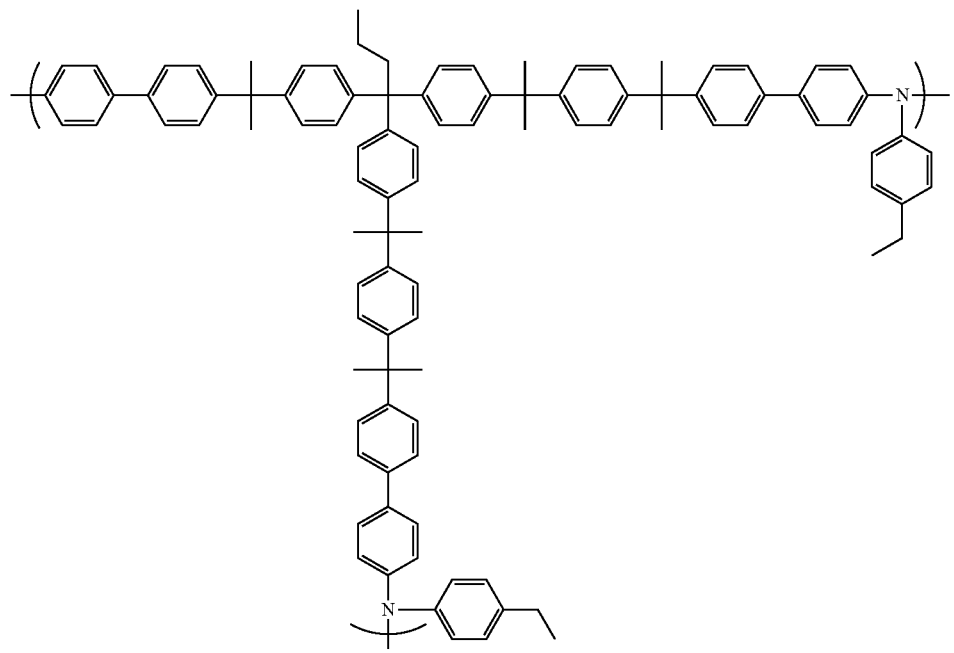
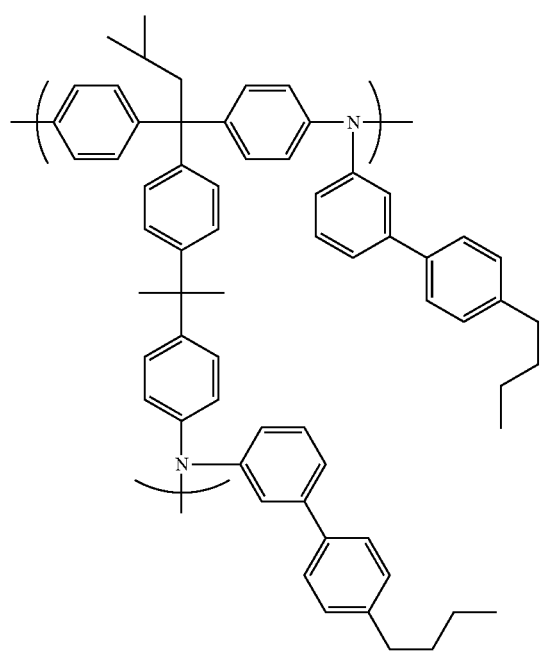

-continued
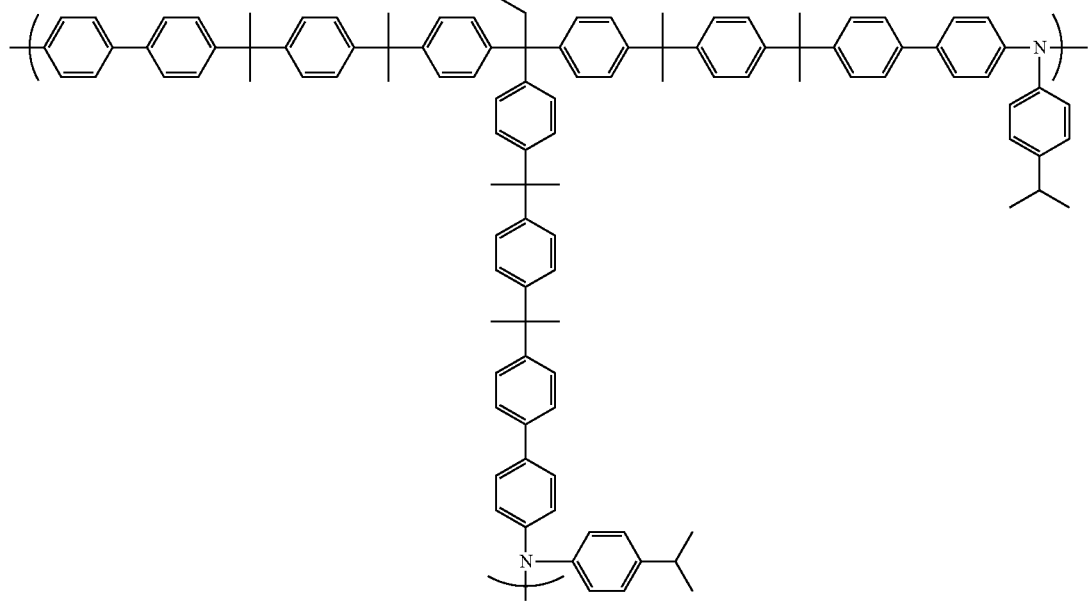
[Chem. 58]
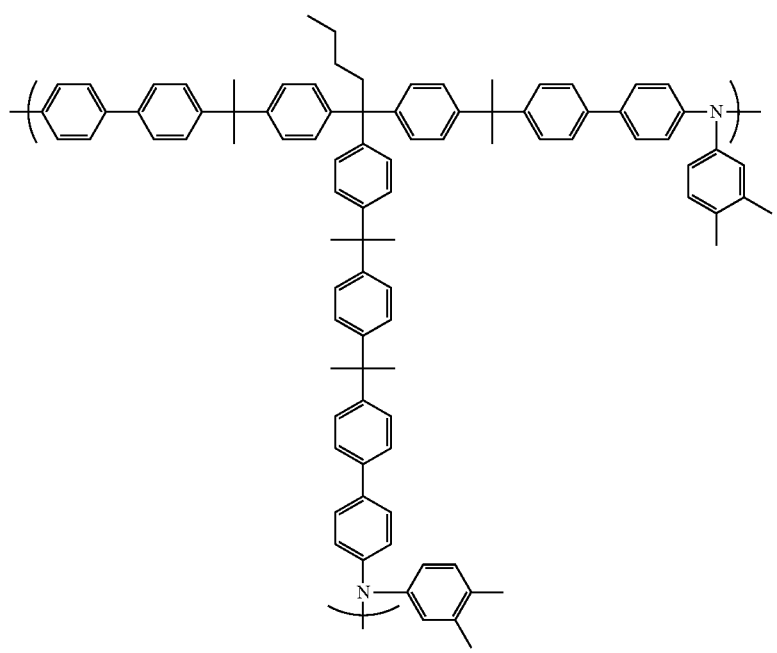

-continued

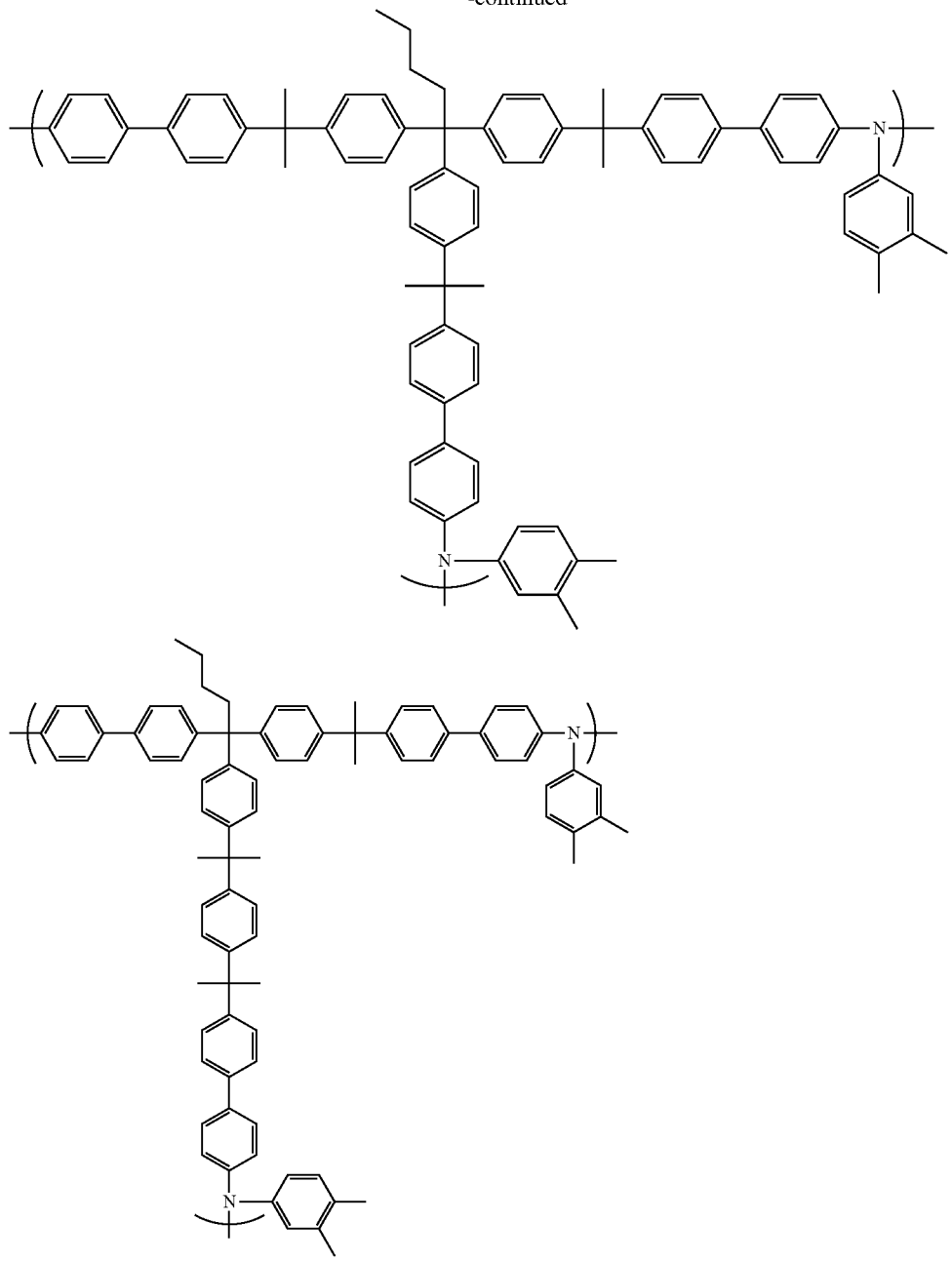

(ii) Crosslinking Group

Containing a repeating unit that has a crosslinking group, the arylamine polymer compound (10) can bring about a great difference in solubility thereof in an organic solvent before and after the reaction to be caused by irradiation with heat and/or active energy rays (insolubilization reaction).

The crosslinking group is a group that reacts with the same or different group of any other molecule existing in the vicinity thereof by irradiation with heat and/or active energy rays, thereby forming a new chemical bond.

The crosslinking group includes, for example, those of the following family of crosslinking groups T that are readily crosslinkable.

[Chem. 59]

<Family of Crosslinking Groups T>

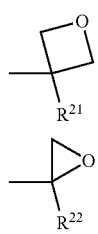

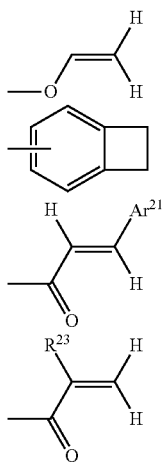

(In the formulae, $R^{21}$ to $R^{23}$ each independently represent a hydrogen atom or an alkyl group. $Ar^{21}$ represents an aromatic ring group optionally having a substituent.)

The alkyl group for $R^{21}$ to $R^{23}$ is preferably a straight chain or branched chain-like alkyl group having generally 6 or less carbon atoms, including, for example, a methyl group, an ethyl group, an n-propyl group, a 2-propyl group, an n-butyl group, an isobutyl group, etc. Especially preferred is a methyl group or an ethyl group. When $R^{21}$ to $R^{23}$ are too bulky, then they may sterically interfere with crosslinking reaction and therefore the film could hardly be insolubilized.

The aromatic ring group optionally having a substituent for $Ar^{21}$ includes, for example, a 6-membered single ring or 2- to 5-condensed ring such as a benzene ring, a naphthalene ring or the like having one free atomic valence. Especially preferred is a benzene ring having one free atomic valence. $Ar^{21}$ may also be a group formed by bonding two or more such aromatic ring groups optionally having a substituent. The group of the type includes a biphenylene group, a terphenylene group, etc. Preferred is a 4,4'-biphenylene group.

Of those, more preferred is a group that is crosslinkable through cationic polymerization, for example, a cyclic ether group such as an epoxy group, an oxetane group or the like, or a vinyl ether group or the like, as having high reactivity to readily bring about insolubilization through crosslinking. Above all, an oxetane group is especially preferred from the viewpoint of the ability to readily control the speed of cationic polymerization. A vinyl ether group is also preferred from the viewpoint that it hardly forms a hydroxyl group that may worsen the element during cationic polymerization.

Also preferred is an arylvinylcarbonyl group such as a cinnamoyl group or the like, or a group that reacts through cyclization addition such as a benzocyclobutene ring having a monovalent free atomic valence or the like, because of the ability thereof to further improve the electrochemical stability of the element.

Of the crosslinking groups, especially preferred is a benzocyclobutene ring having a monovalent free atomic valence from the viewpoint that the structure thereof after crosslinking is especially stable.

As the crosslinking group, concretely, preferred is a benzocyclobutene ring having a monovalent free atomic valence represented by the following formula (X). The benzocyclobutene ring of the formula (X) is unsubstituted, however, a benzocyclobutene ring having a substituent is also preferred herein. The substituents may bond to each other to form a ring.

[Chem. 60]

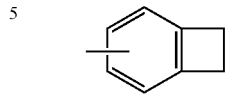

(X)

In the arylamine polymer compound (10), the crosslinking group may directly bond to the aromatic ring group, or may directly bond to any other group than the aromatic ring group, or may bond to any of these groups via any arbitrary divalent linking group. The arbitrary divalent group is preferably a group formed by linking from 1 to 30 groups selected from a group —O—, a group —C(=O)— and a group —CH$_2$— (optionally having a substituent) in any desired order. As preferred examples of the crosslinking group formed by bonding the groups via such a divalent group, for example, there are mentioned those listed in the following <Family of Groups Containing Crosslinking Group G3>. However, the present invention is not limited to these.

<Family of Groups Containing Crosslinking Group G3>

[Chem. 61]

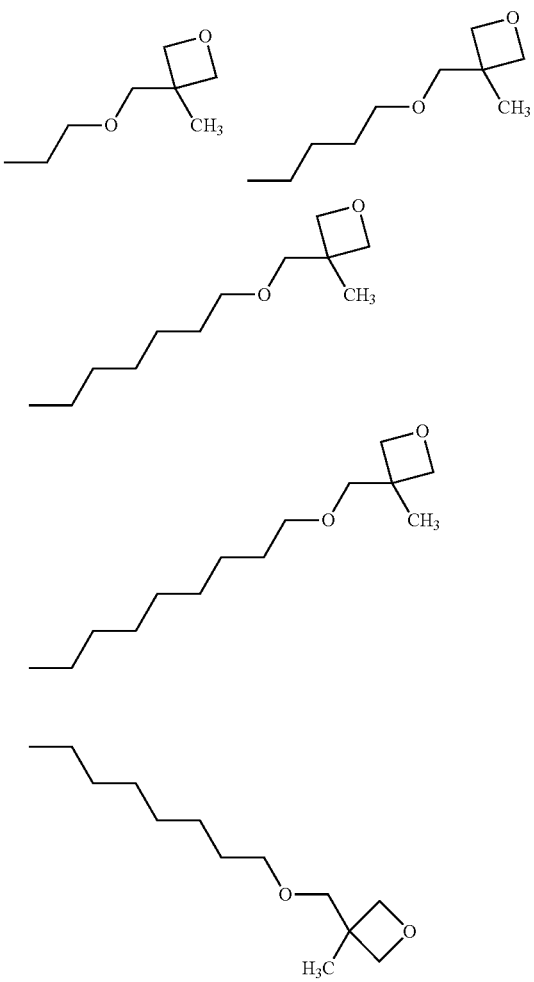

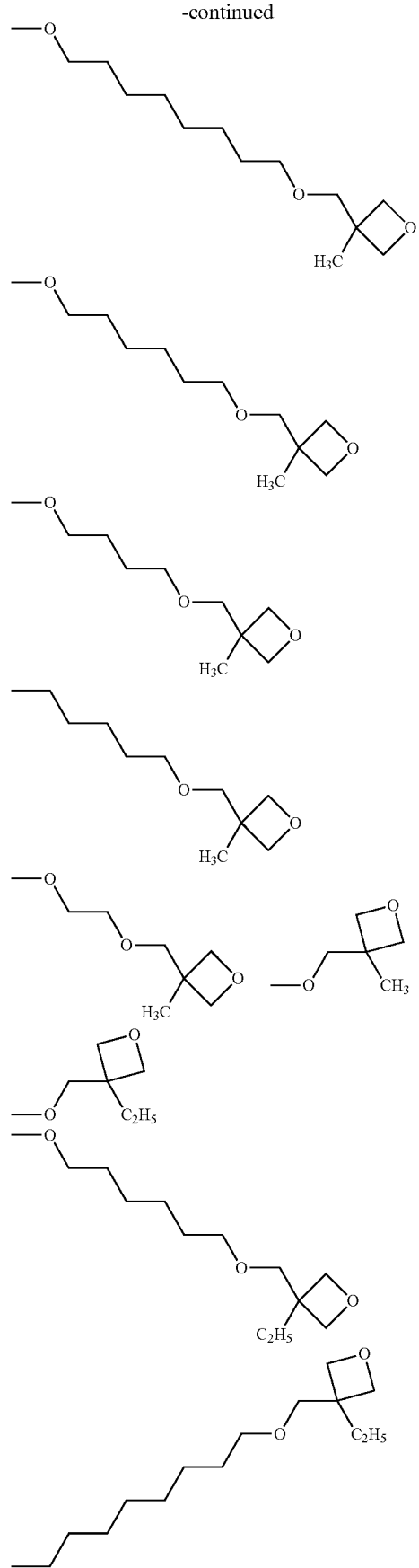
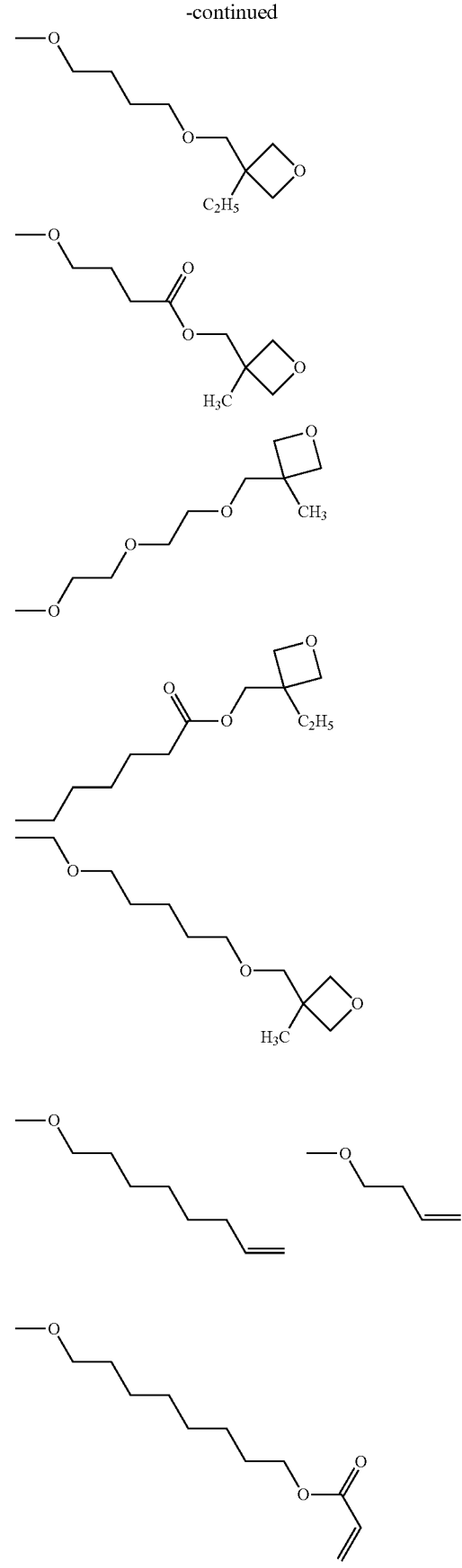

181
-continued
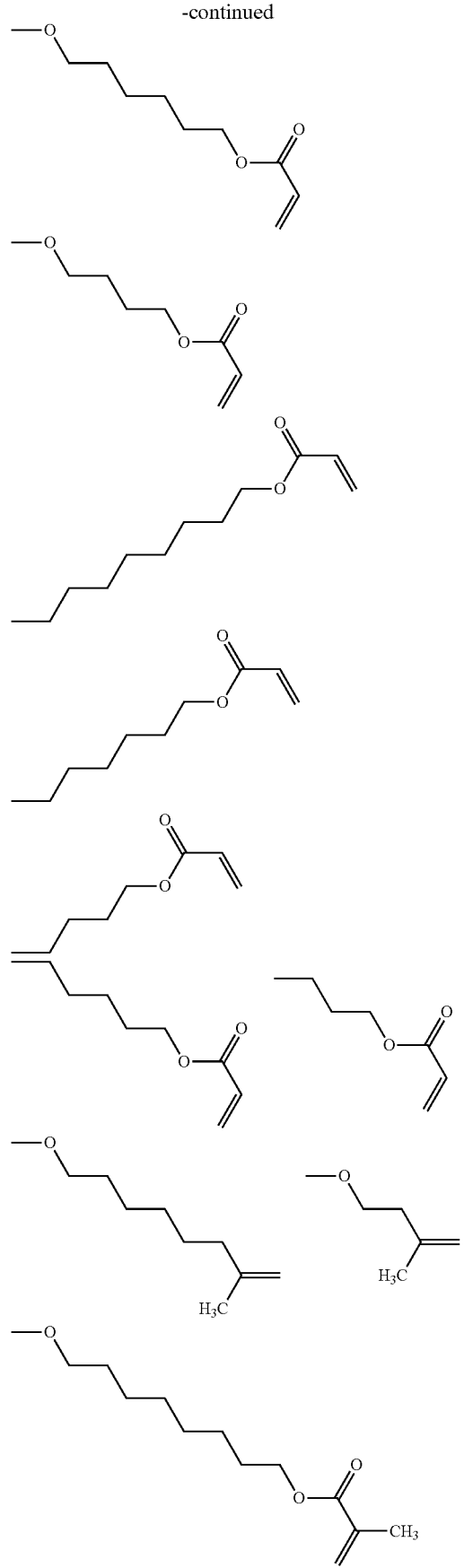
182
-continued
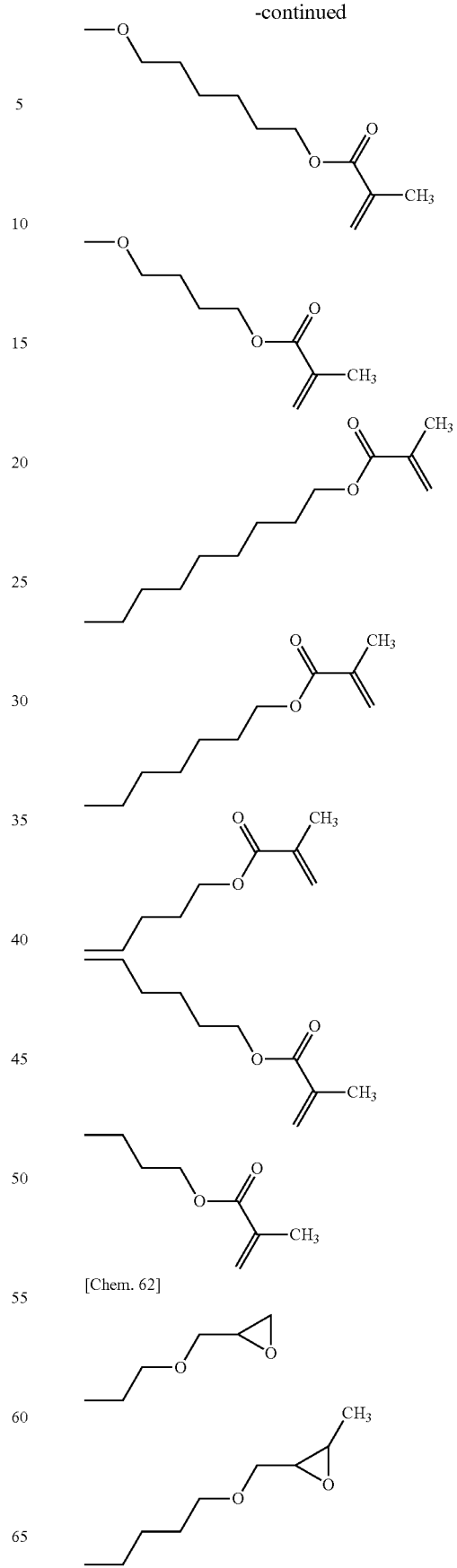
[Chem. 62]

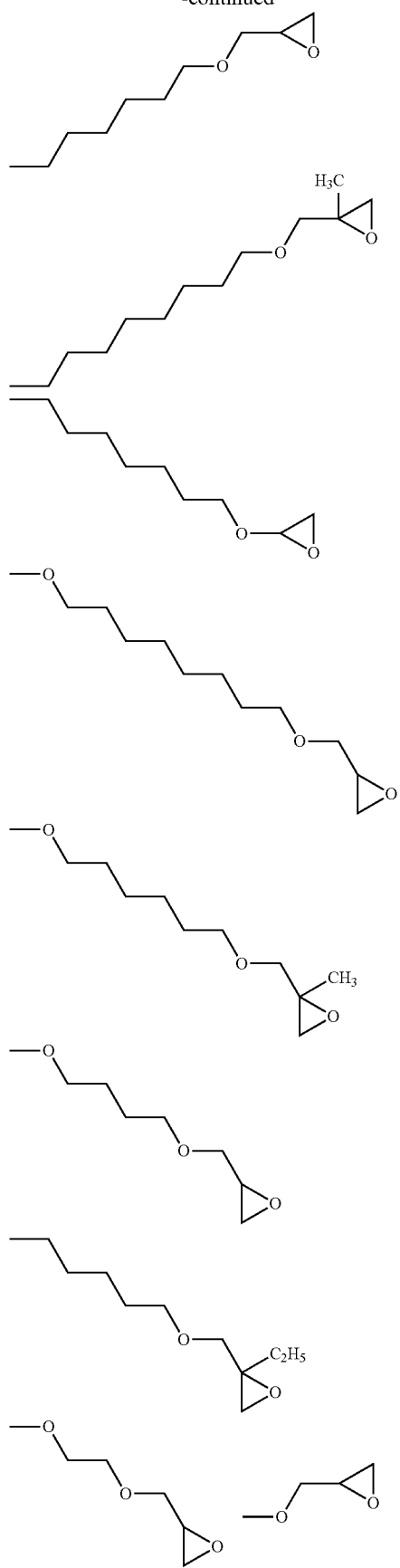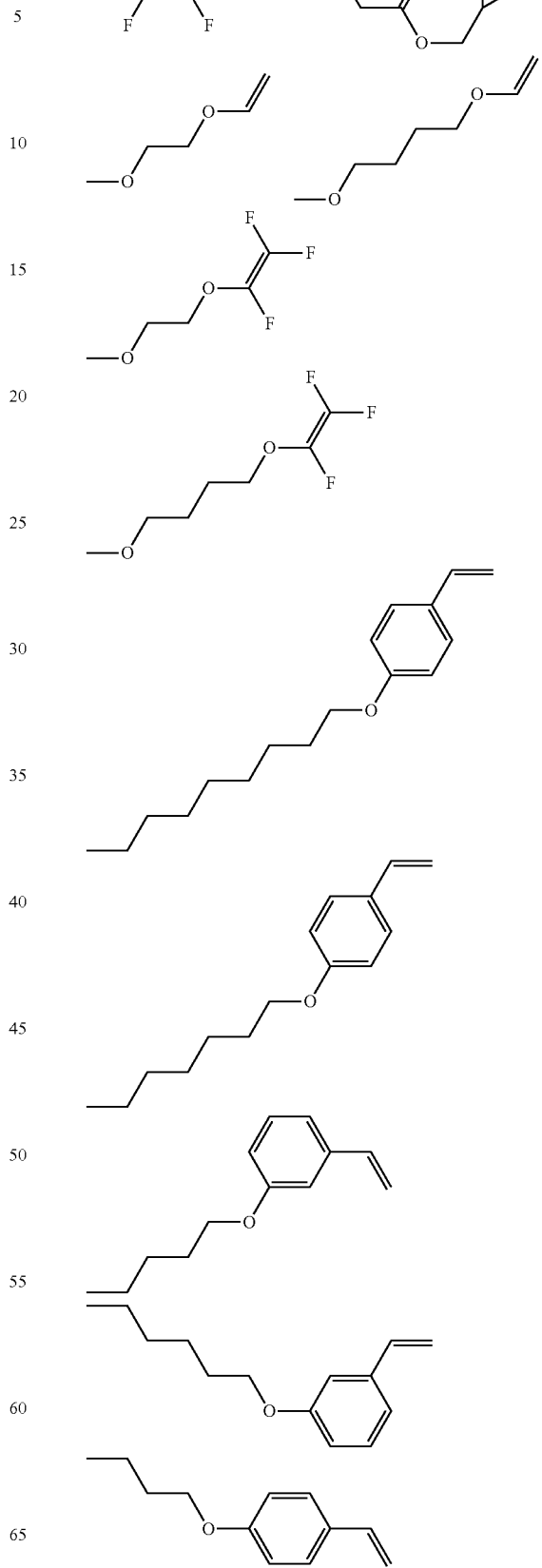

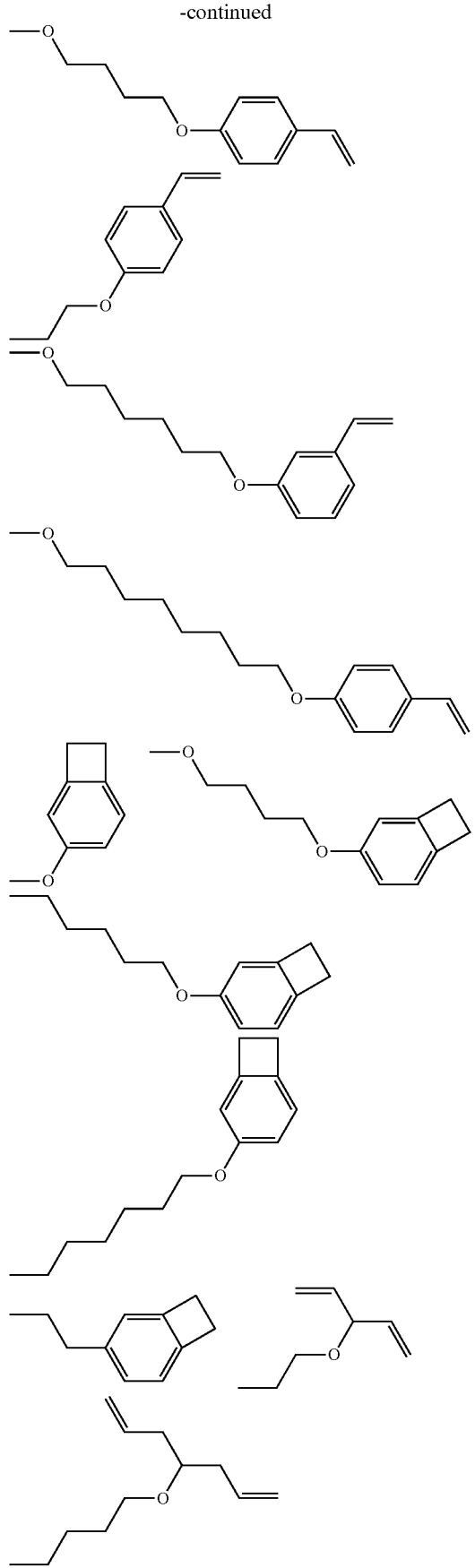
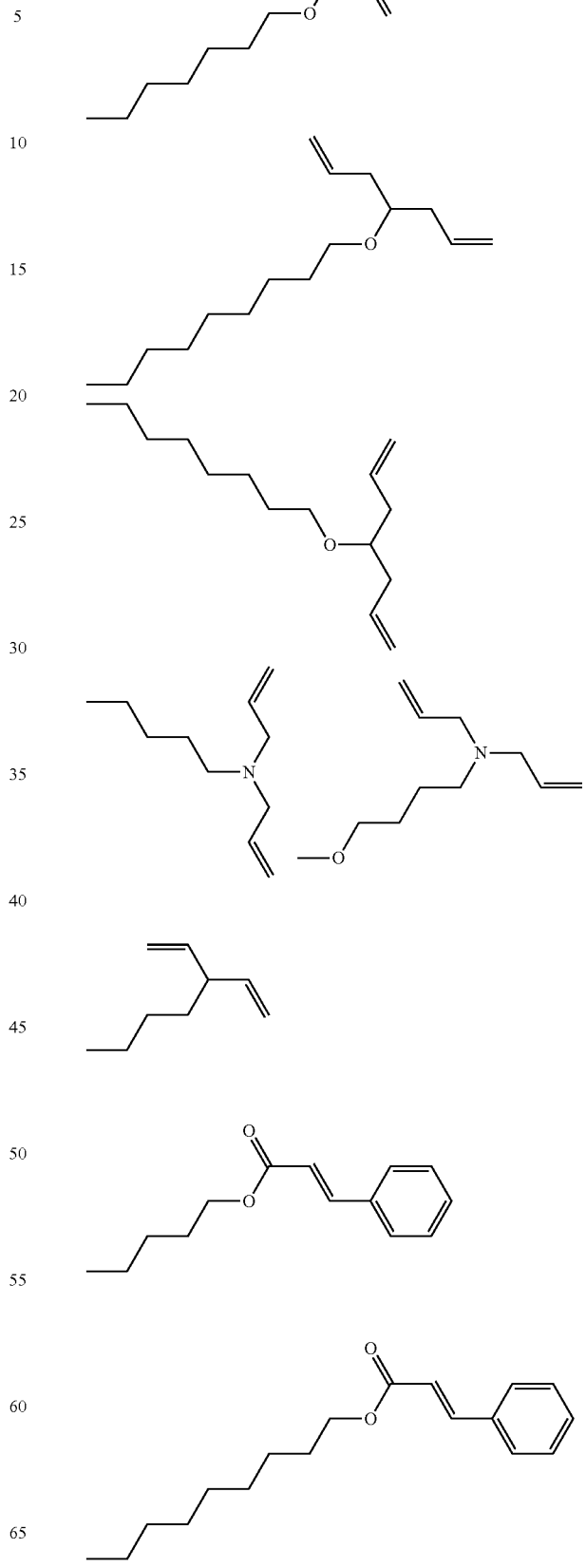

-continued

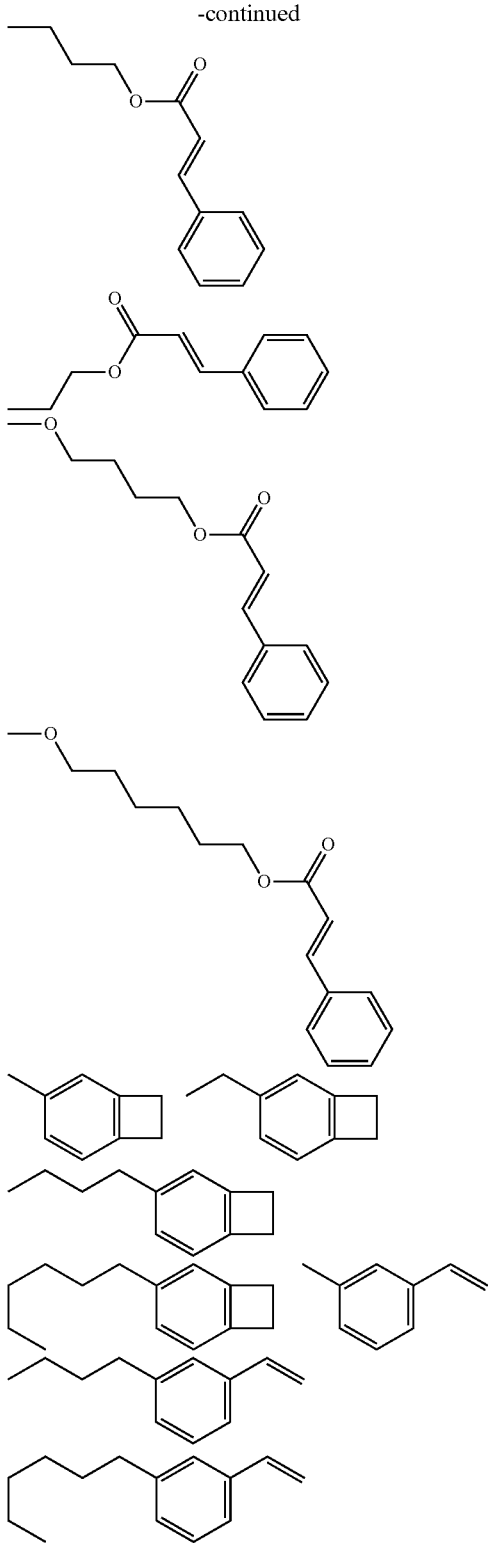

Not detracting from the advantageous effects of the present invention, the position of the crosslinking group in the arylamine polymer compound (10) is not specifically defined. From the viewpoint of good crosslinkability, it is especially desirable that the crosslinking group exists as a substituent on the aromatic ring of $Ar_8$ in the formula (10-A) or $Ar_2$ in the formula (10-B).

When 1 in the formula (10-B) is 2 or more, two or more $Ar_2$'s contained in the partial structure (10-B) may be the same or different, as described above. Accordingly, in the formula, one repeating unit may have $Ar_2$ having a crosslinking group as the substituent therein and $Ar_2$ not having a crosslinking group.

Regarding the number of the crosslinking groups that the arylamine polymer compound (10) has, it is desirable that the number of the groups is larger from the viewpoint that the compound could be fully insolubilized through crosslinking and it is easy to form any other layer thereon according to a wet film formation method; but on the other hand, from the viewpoint that the formed layer is hardly cracked and the unreacted crosslinking groups hardly remain and therefore the organic electroluminescent element could readily have a long life, the number of the groups is smaller.

The number of the crosslinking group existing in one polymer chain of the arylamine polymer compound (10) is preferably 1 or more on average, more preferably 2 or more on average, and is preferably 200 or less, more preferably 100 or less.

The number of the crosslinking groups that the arylamine polymer compound (10) has may be expressed as the number thereof per the molecular weight 1000 of the polymer.

When the number of the crosslinking groups that the arylamine polymer compound (10) has is expressed as the number thereof per the molecular weight 1000 of the polymer, the number is generally 3.0 or less per the molecular weight 1000, preferably 2.0 or less, more preferably 1.0 or less, and is generally 0.01 or more, preferably 0.05 or more.

When the number of the crosslinking groups falls within the above range, then cracks may hardly form and a flat film is easy to form and the crosslinking density is suitable, and therefore since the number of the unreacted crosslinking groups to remain in the crosslinked layer may be small, the groups would hardly have some negative influence on the life of the element to be obtained.

Further, after crosslinking reaction, the difficult solubility of the compound in an organic solvent is satisfactory and therefore, a multilayer laminate structure is easy to form according to a wet film formation method.

Here, the number of the crosslinking groups per the molecular weight 1000 of the arylamine compound (10) may be calculated by removing the terminal groups from the arylamine polymer compound (10) and calculating from the molar ratio of the monomers blended in synthesis and the structural formula of the compound.

For example, a case of the compound (HIT-4) used in Example 8 to be described below is referred to here. In the compound (HIT-4), the molecular weight of the repeating unit after removal of the terminal groups is 731.8805 on average, and the number of the crosslinking groups is 0.0639 on average per one repeating unit. These are calculated through simple proportion, and the number of the crosslinking groups per the molecular weight 1000 is 0.087.

(iv) Proportion of Partial Structure (10-A) and Partial Structure (10-B)

The proportion of the partial structure (10-A) and the partial structure (10-B) contained in the arylamine polymer compound (10) is preferably such that the partial structure (10-A) accounts for from 0 to 99.9 mol %, more preferably from 80 to 99.5 mol % relative to the total 100 mol % of the partial structure (10-A) and the partial structure (10-B). Having the partial structure (10-A), as described above, the polymer exhibits the effects of improving the charge transportability, maintaining the oxidation reduction stability and improving the hole mobility.

(v) Molecular Weight of Arylamine Polymer Compound (10)

The weight-average molecular weight of the arylamine polymer compound (10) is generally 3,000,000 or less, preferably 1,000,000 or less, more preferably 500,000 or less, even more preferably 200,000 or less, and is generally 1,000 or more, preferably 2,500 or more, more preferably 5,000 or more, even more preferably 20,000 or more.

When the weight-average molecular weight of the arylamine polymer compound (10) is more than the above-mentioned upper limit, then the solubility thereof in solvent may lower, and therefore the film formability thereof may worsen. When the weight-average molecular weight of the arylamine polymer compound (10) is less than the lower limit, then the glass transition temperature, the melting point and the vaporization temperature of the arylamine polymer compound (10) may lower and therefore the heat resistance thereof may also lower.

The number-average molecular weight (Mn) of the arylamine polymer compound (10) is generally 2,500,000 or less, preferably 750,000 or less, more preferably 400,000 or less, and is generally 500 or more, preferably 1,500 or more, more preferably, 3,000 or more.

Further, the dispersion degree (Mw/Mn) of the arylamine polymer compound (10) is preferably 3.5 or less, more preferably 2.5 or less, even more preferably 2.0 or less. The value of the dispersion degree is preferably smaller, and therefore the lower limit thereof is ideally 1. When the dispersion degree of the polymer is lower than the upper limit, then the purification thereof may be easy and the solubility thereof in solvent and the charge transportability thereof may be good.

In general, the weight-average molecular weight of the arylamine polymer compound (10) is determined through SEC (size exclusion chromatography). In SEC measurement, a component having a higher molecular weight takes a shorter elution time, while a component having a lower molecular weight takes a longer elution time. Using a calibration curve calculated from the elution time of polystyrene having a known molecular weight (standard sample), the elution time of the sample is converted into the molecular weight thereof, and the weight-average molecular weight can be thereby calculated.

(vi) Examples of Arylamine Polymer Compound (10)

Specific examples of the arylamine polymer compound (10) are shown below, however, the arylamine polymer compound (10) is not limited to these.

[Chem. 63]

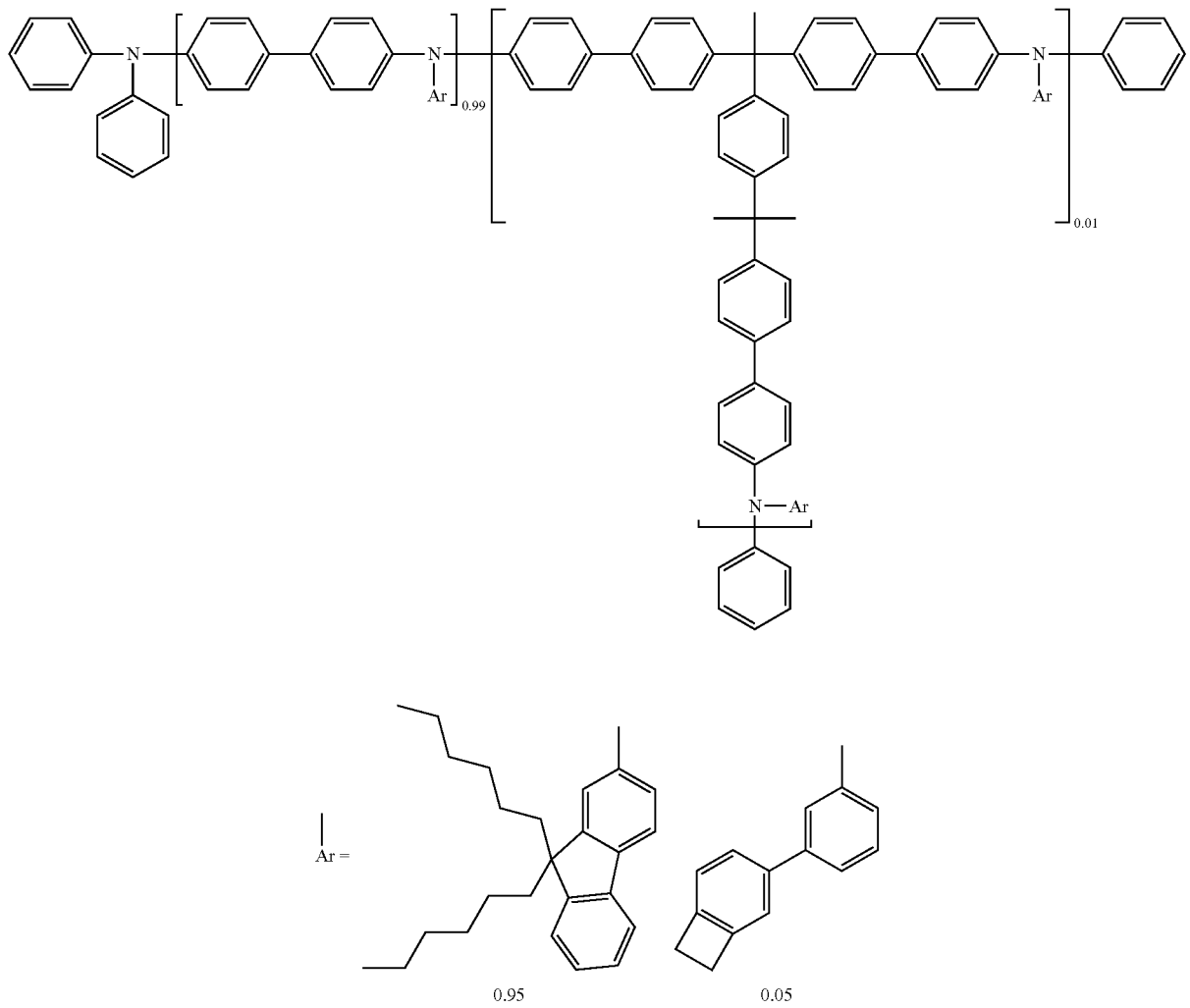

191
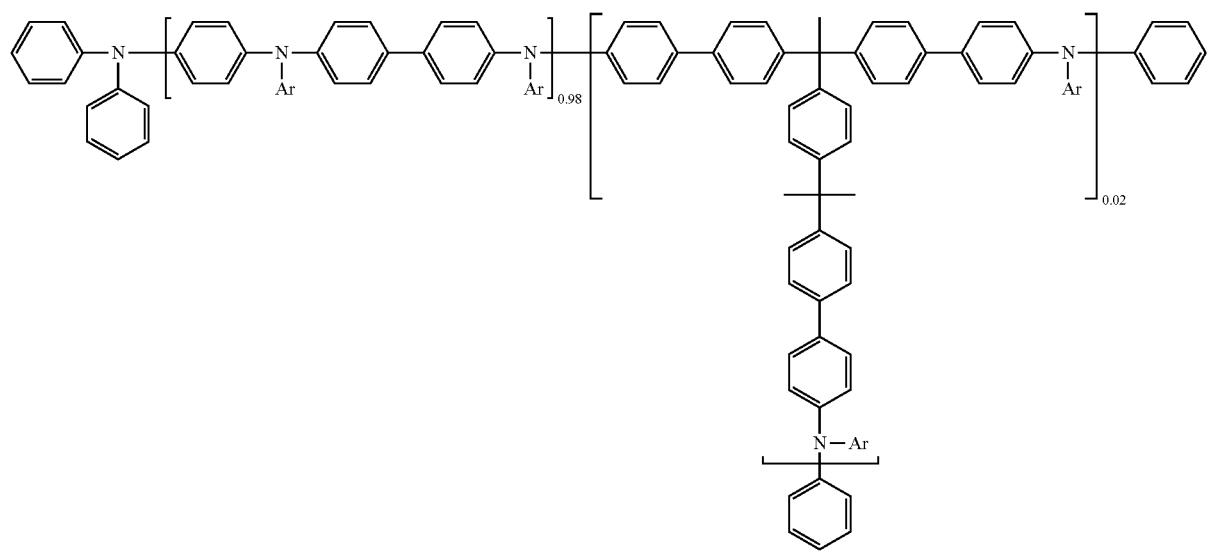
-continued
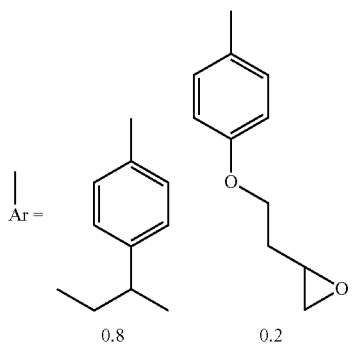
192
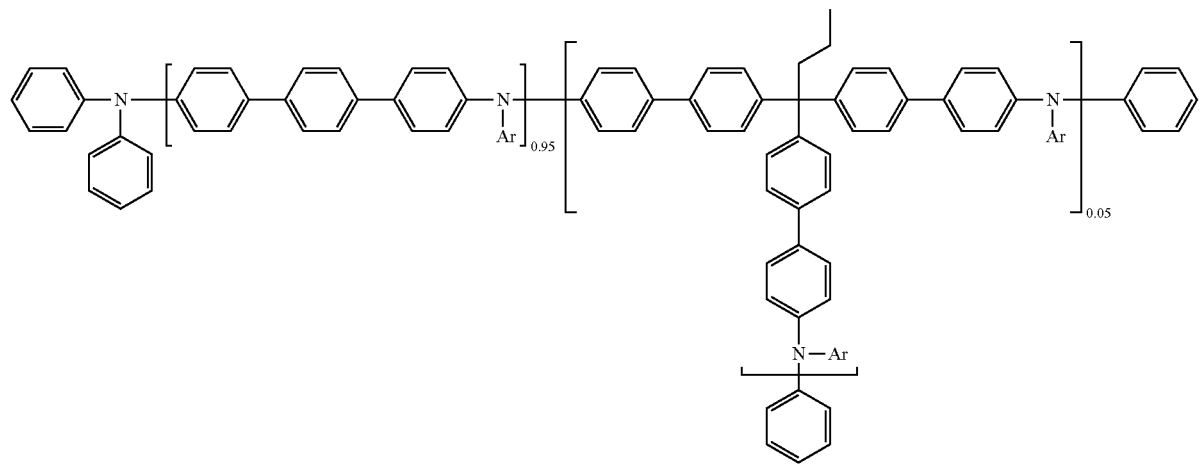

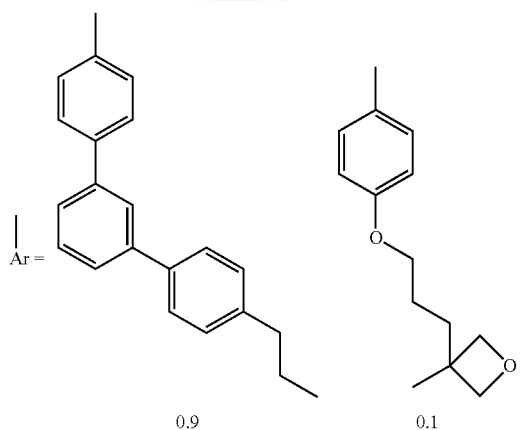
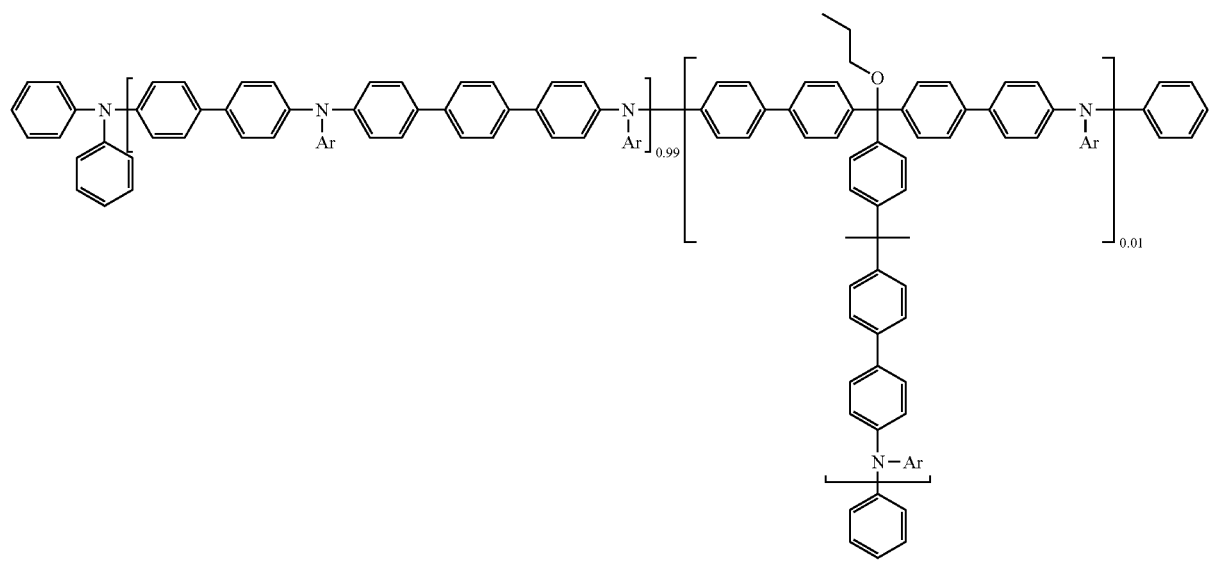
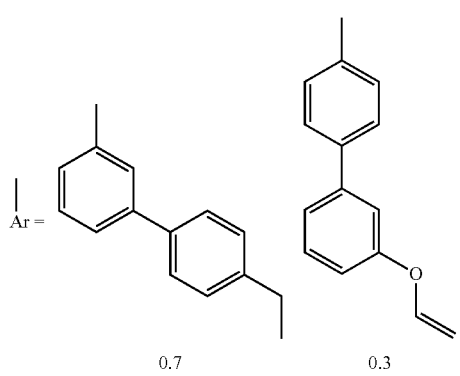

[Chem. 64]
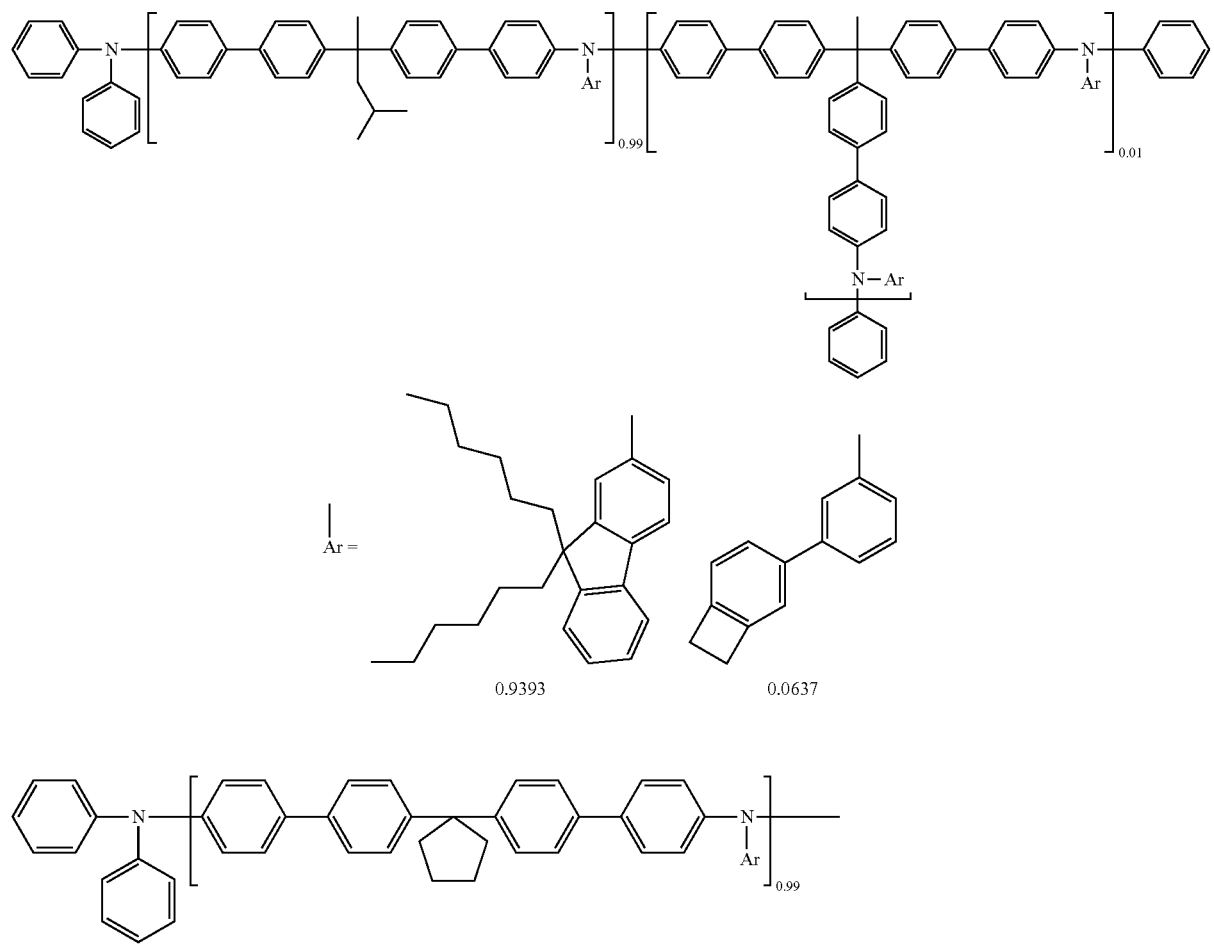
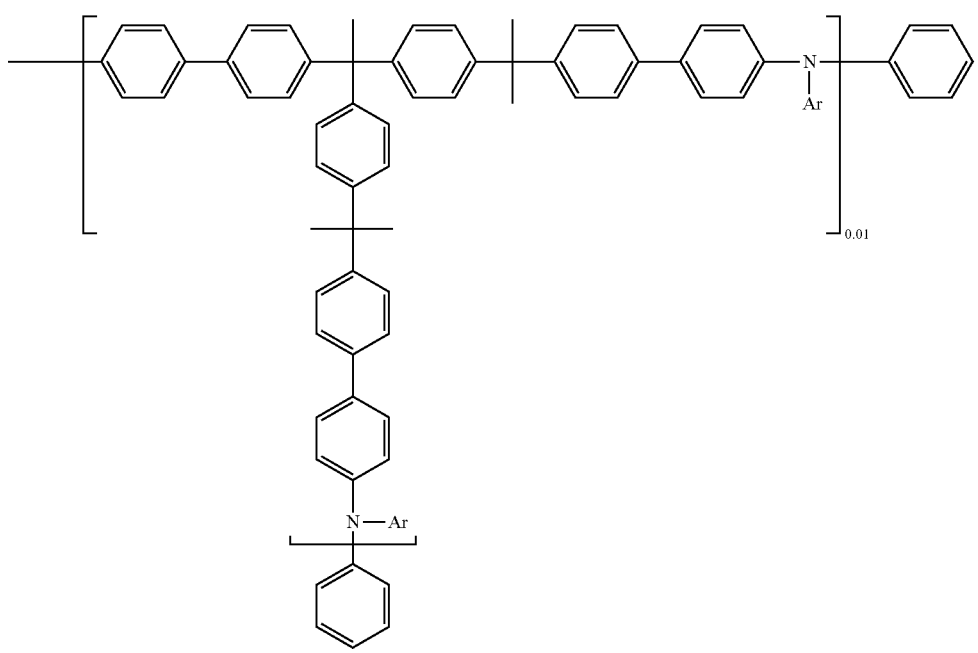

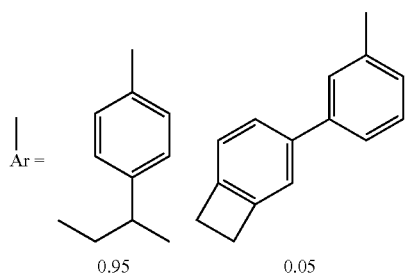
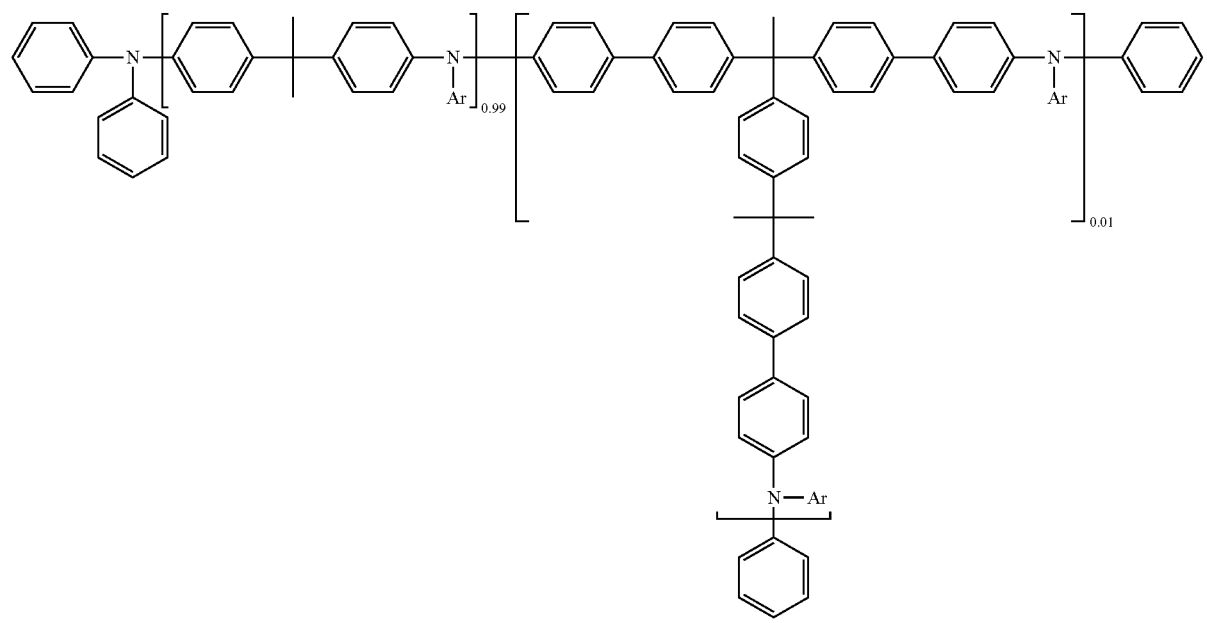
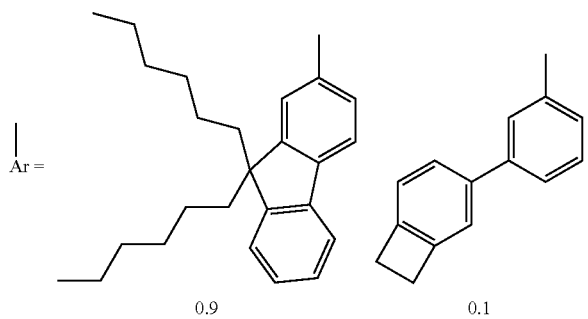
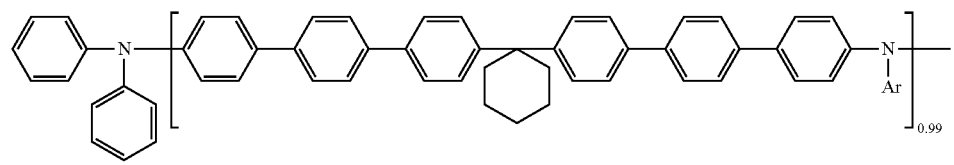

-continued
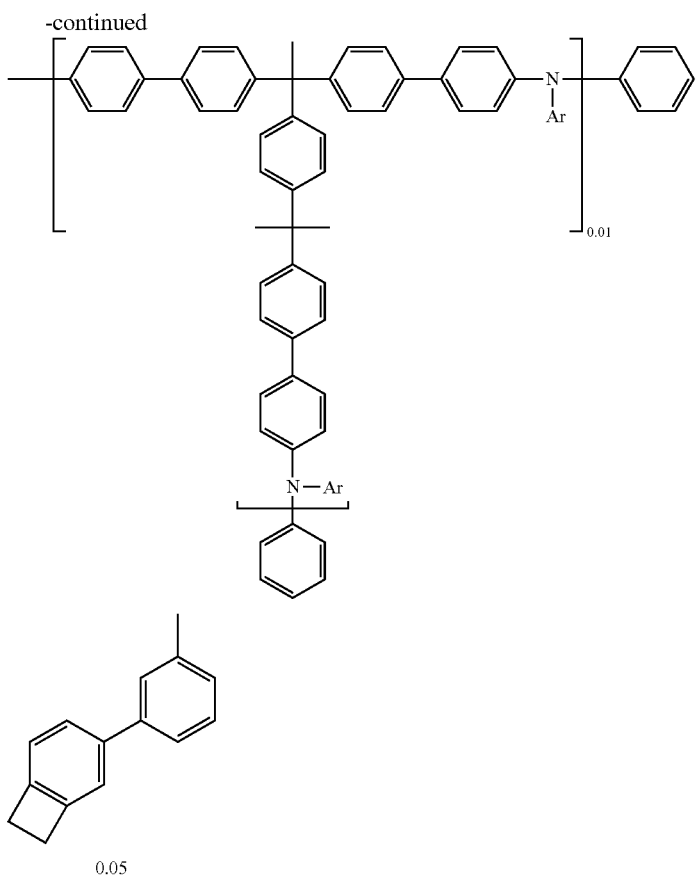
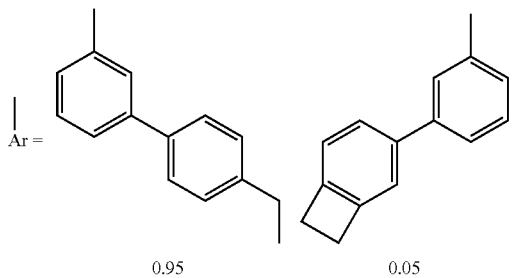
[Chem. 65]
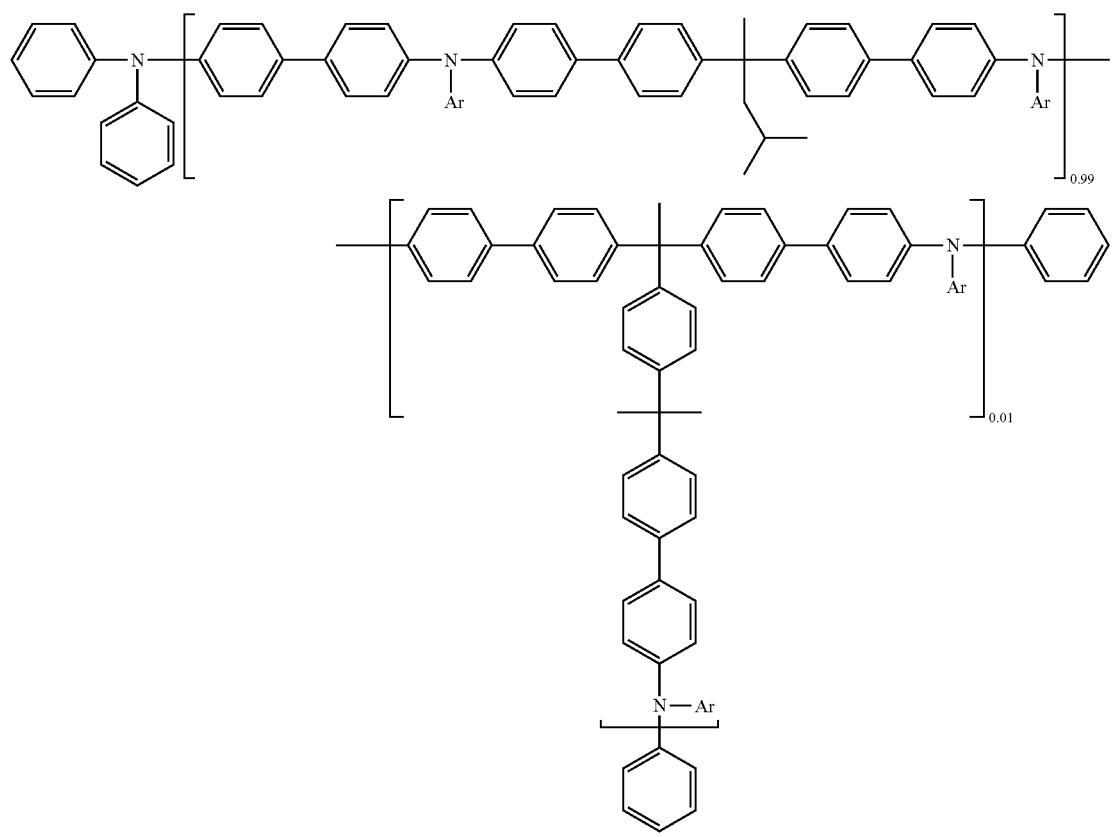

-continued
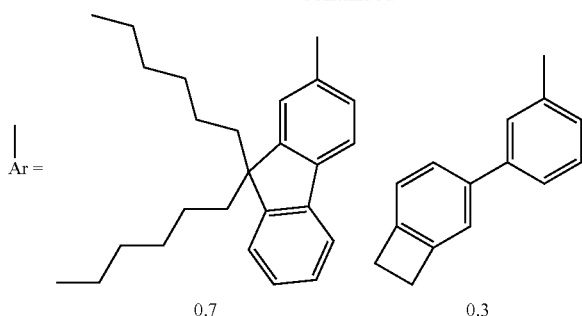
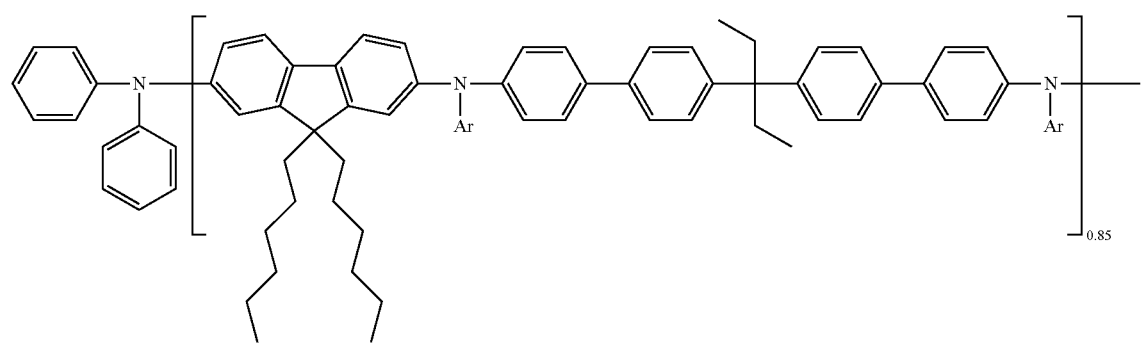
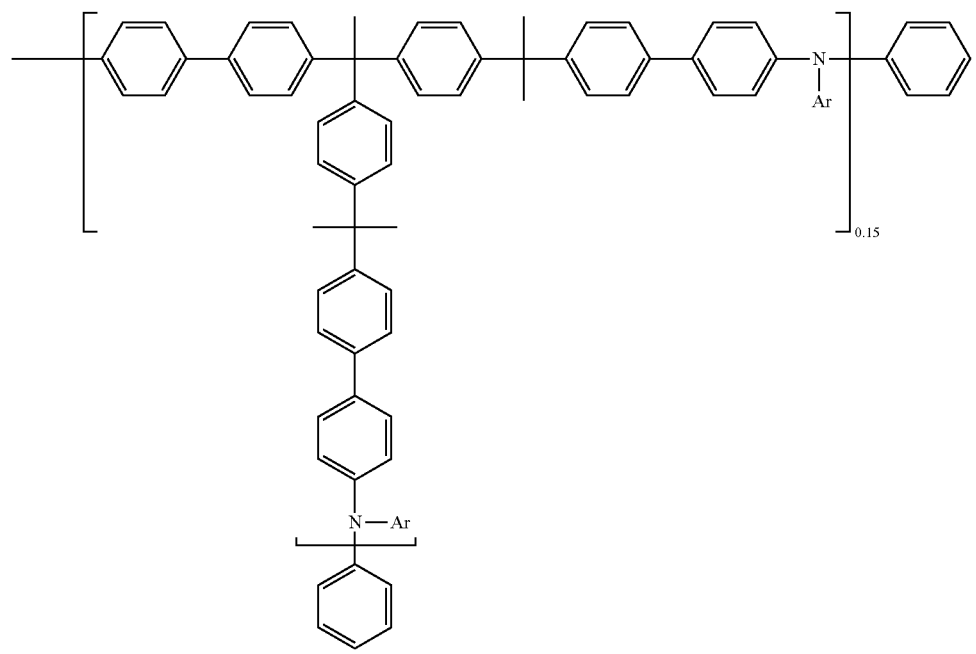
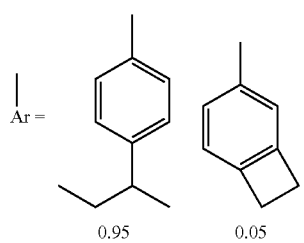

203
-continued
204
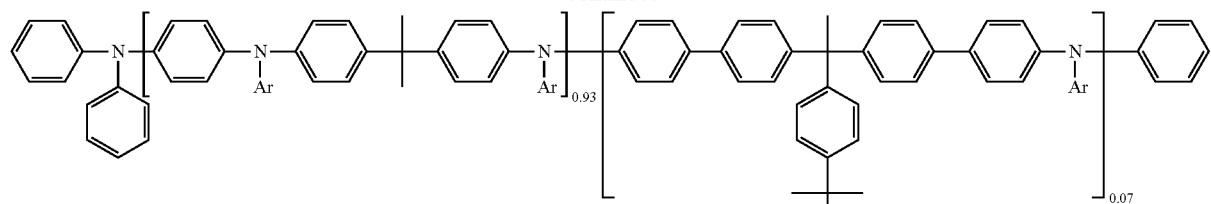
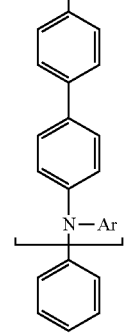
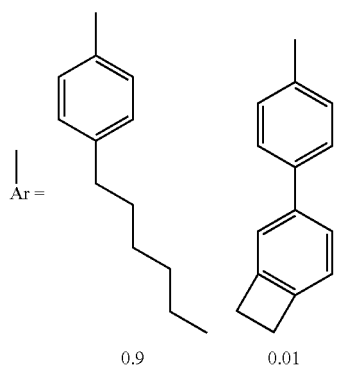
Ar =
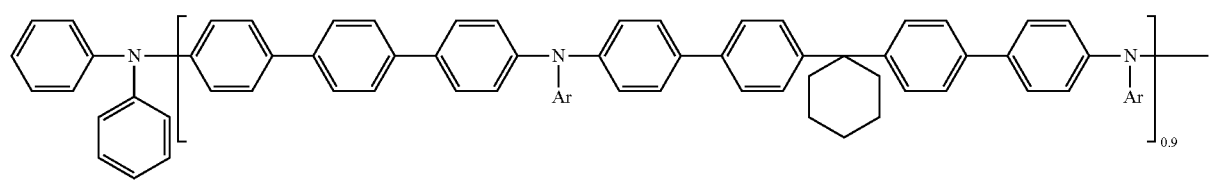
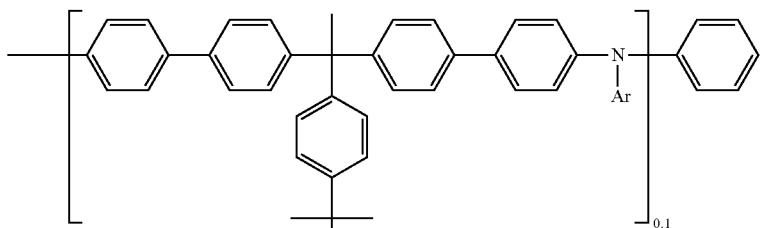
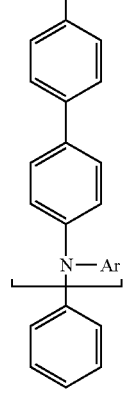

-continued
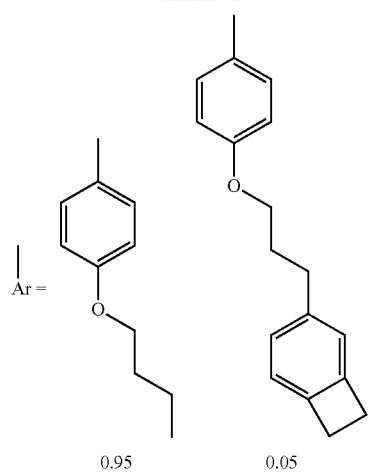
[Chem. 66]
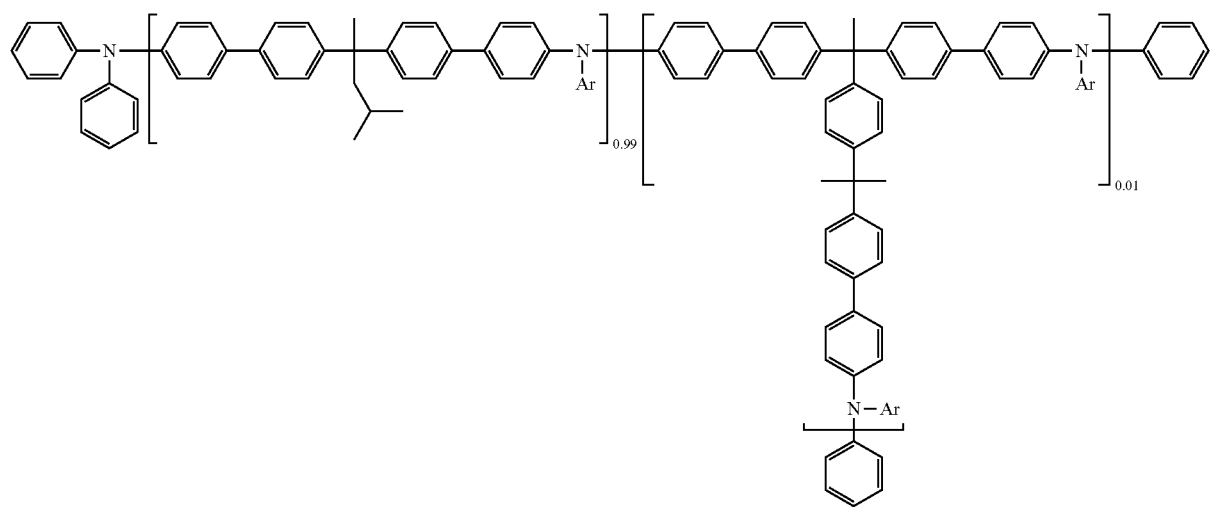
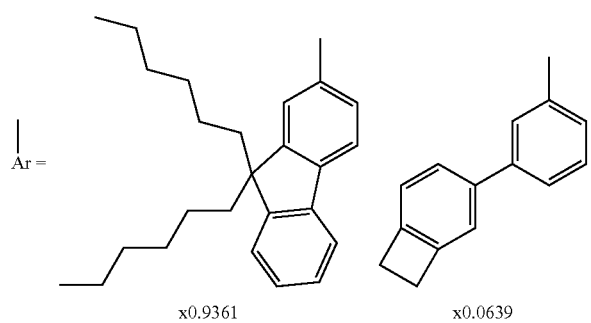

207 208
-continued
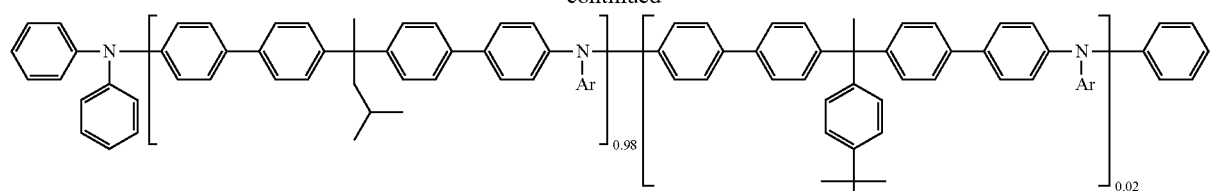
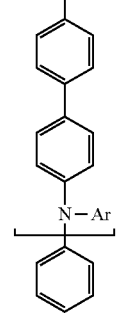
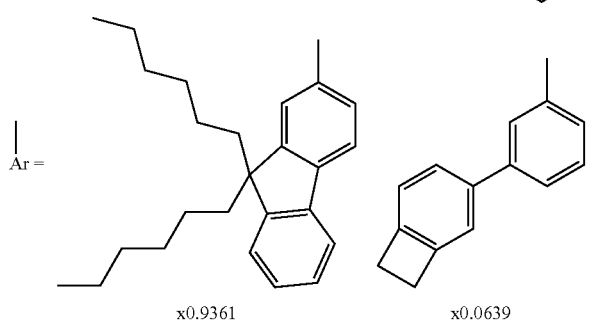
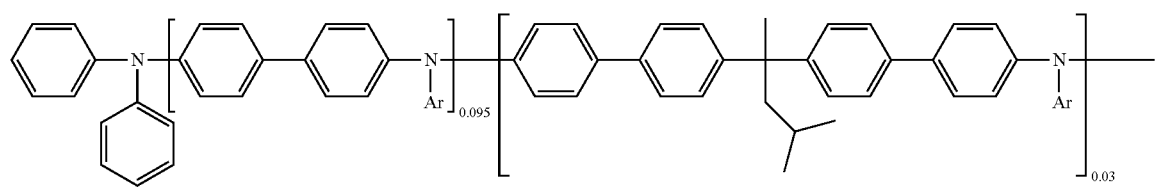
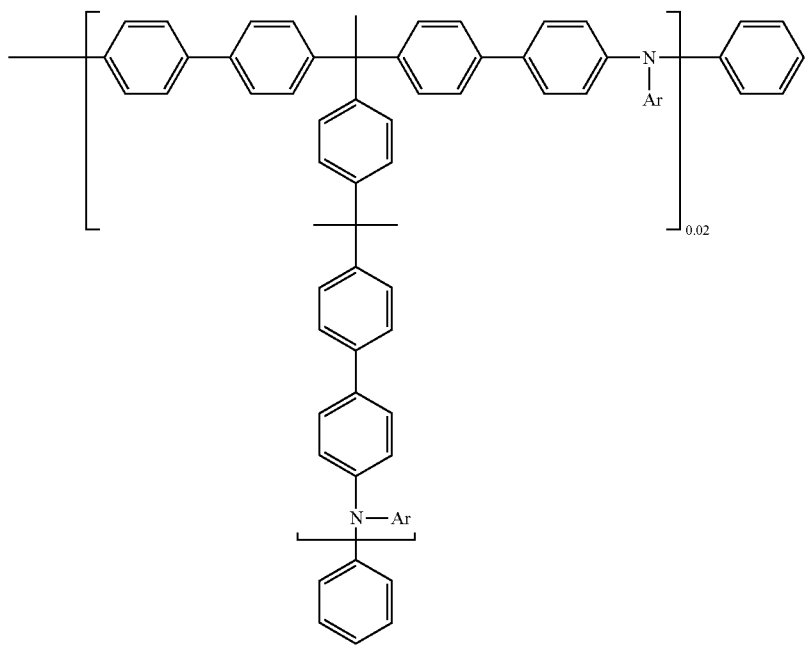

-continued
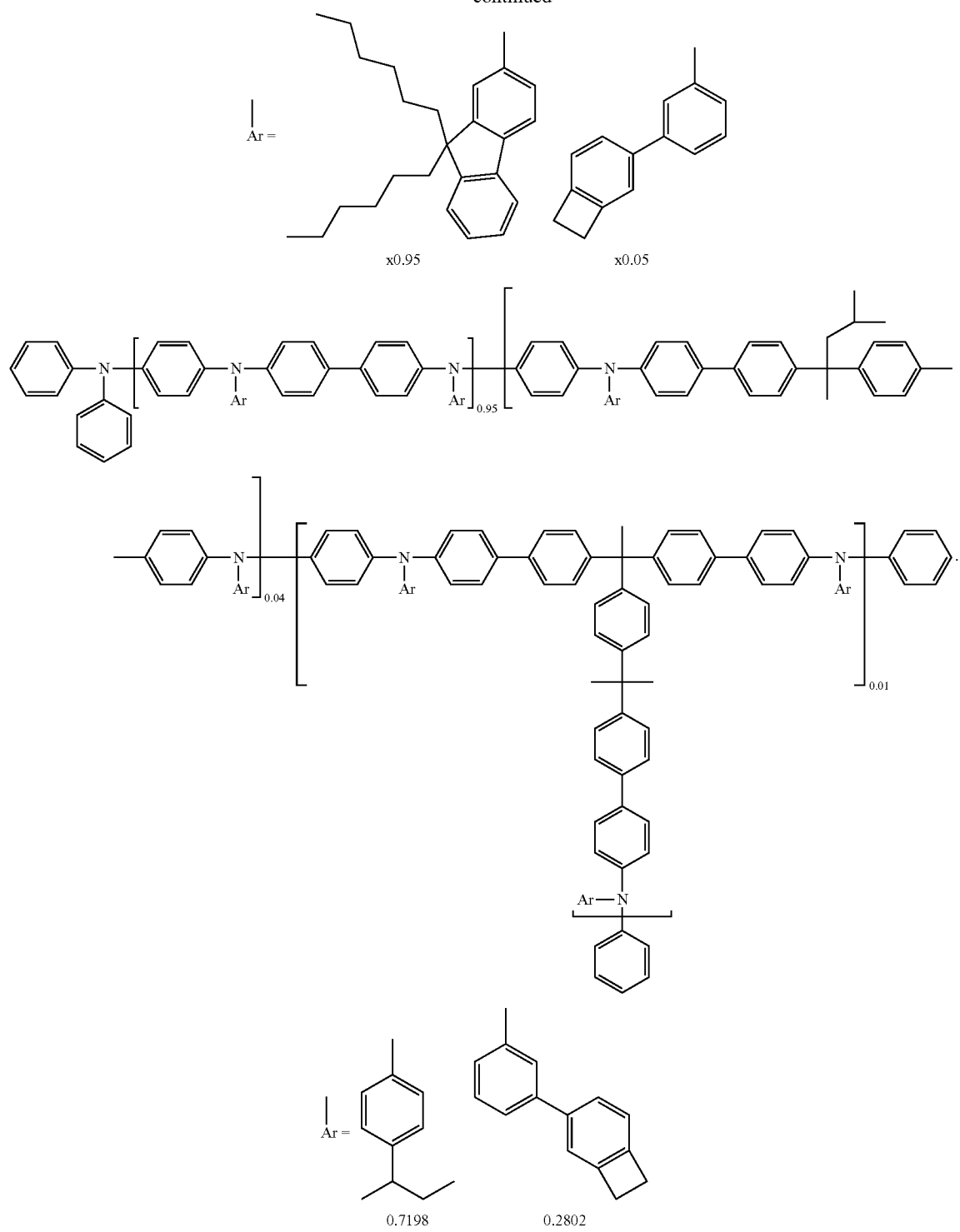
[Chem. 67]
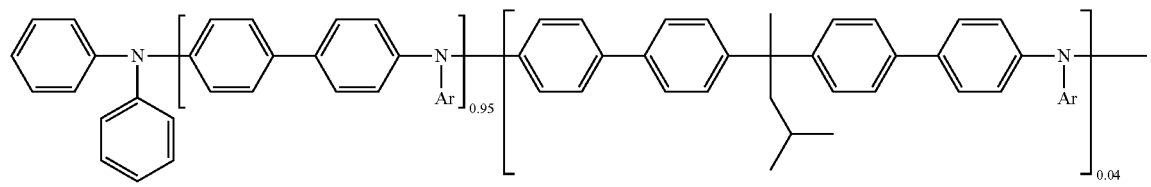

-continued
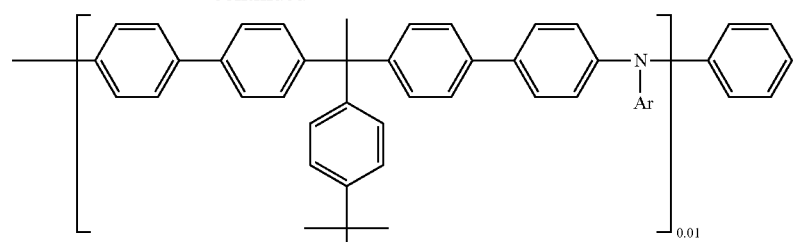
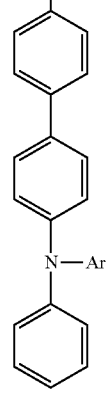
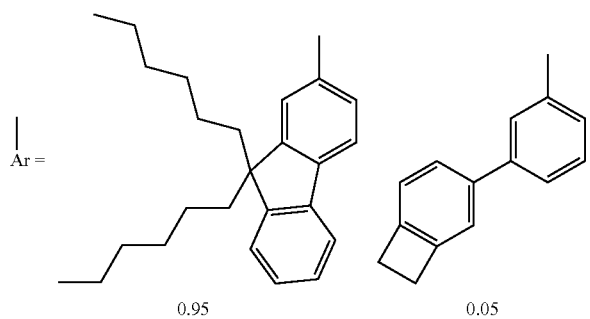
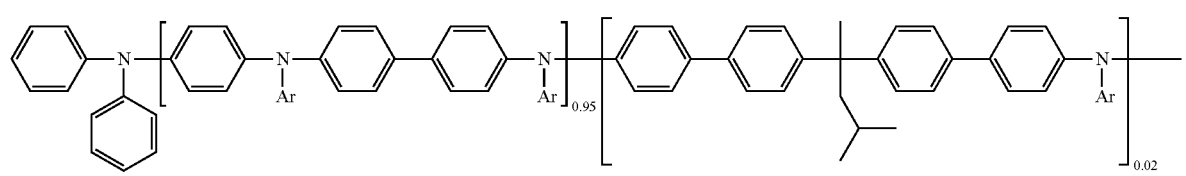
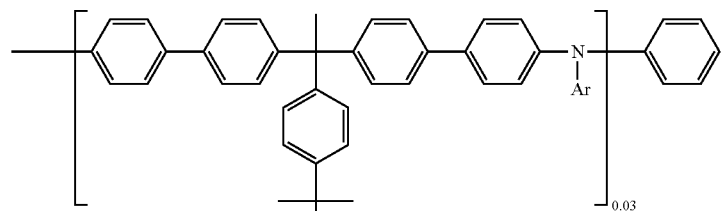
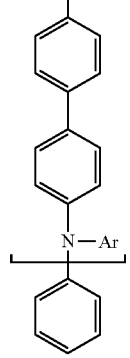

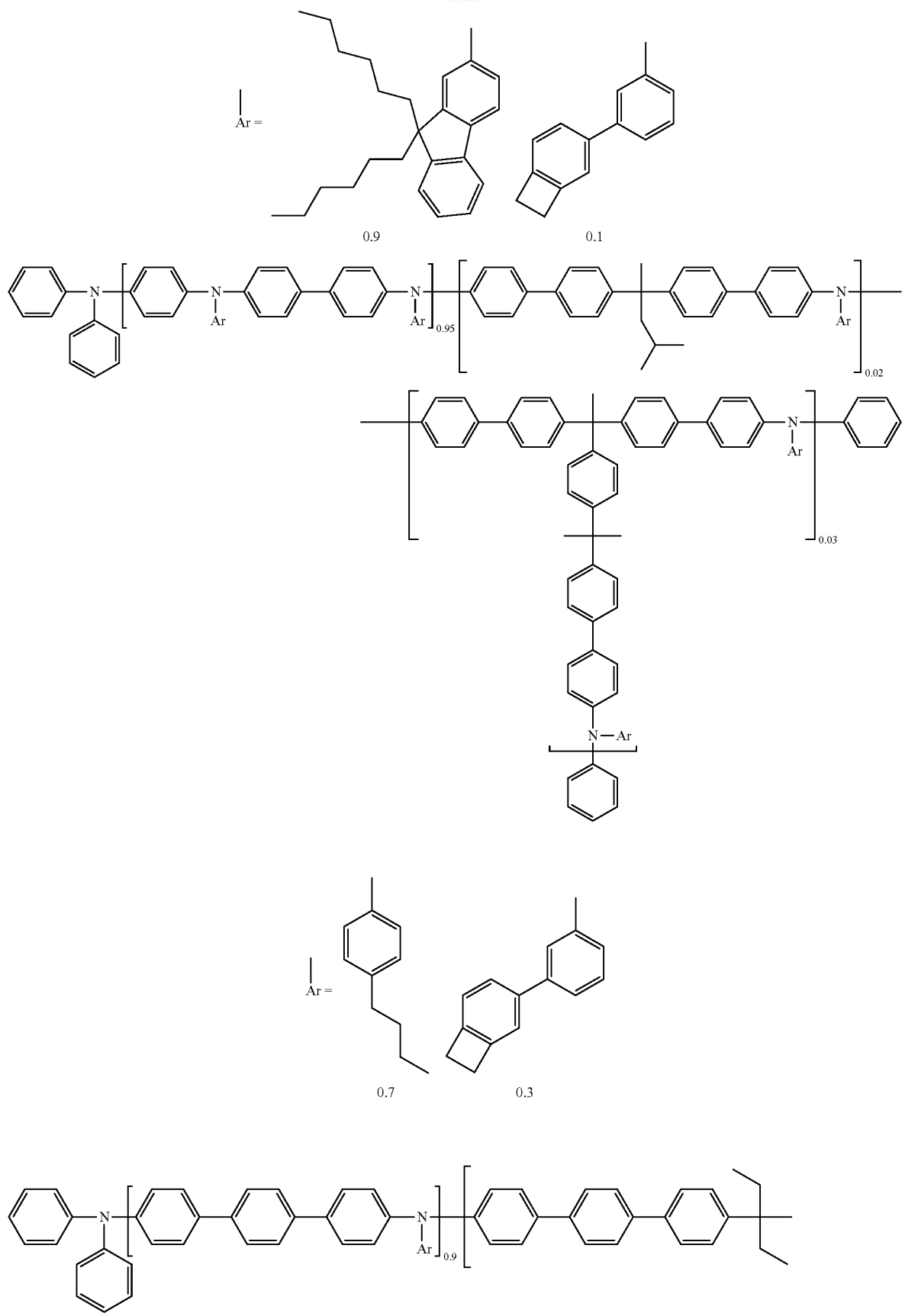

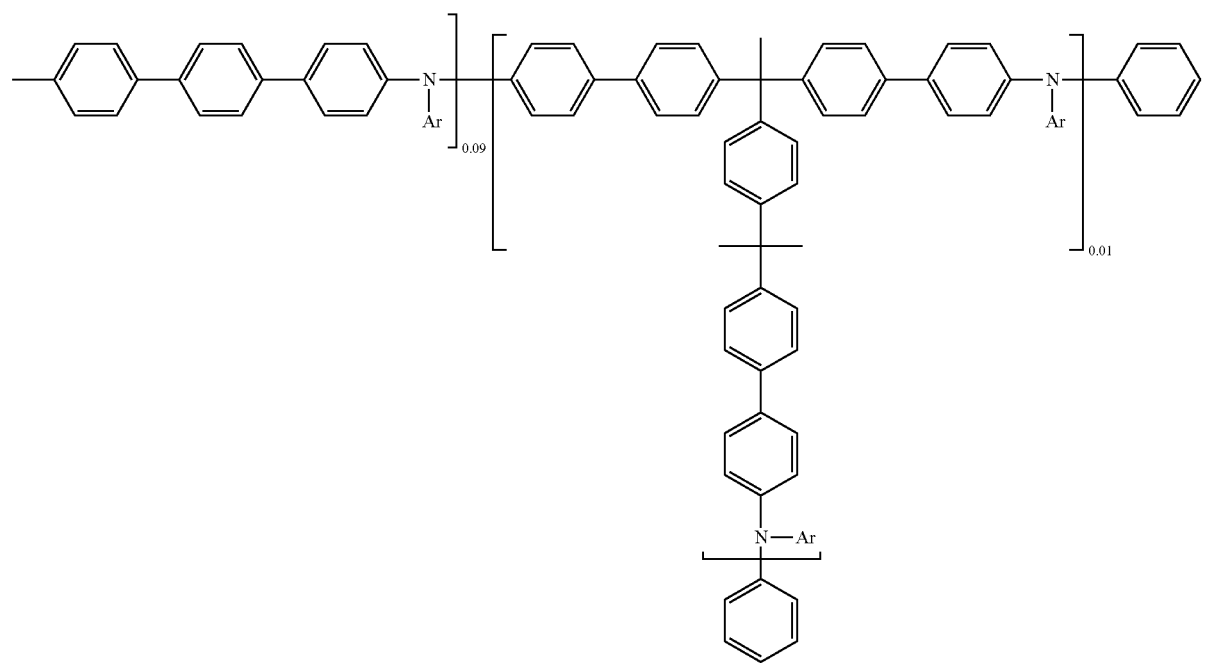
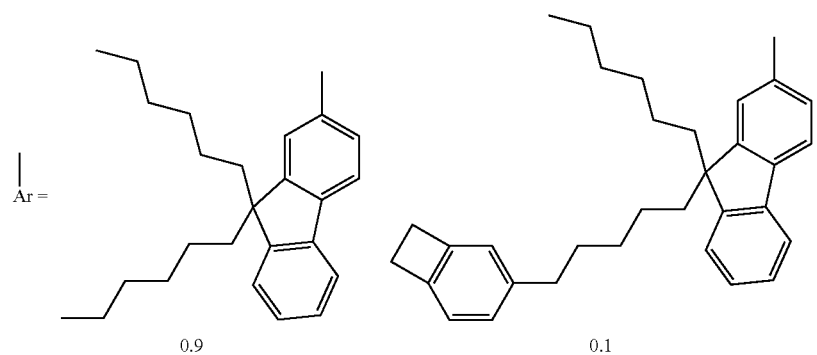
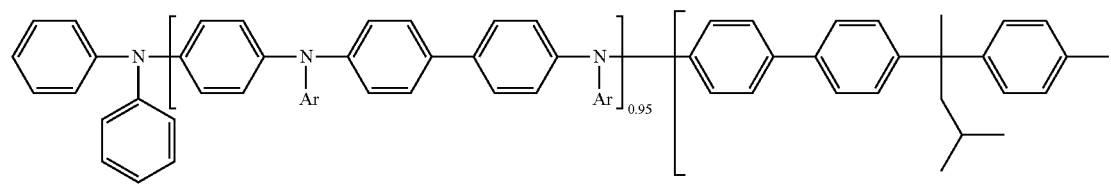

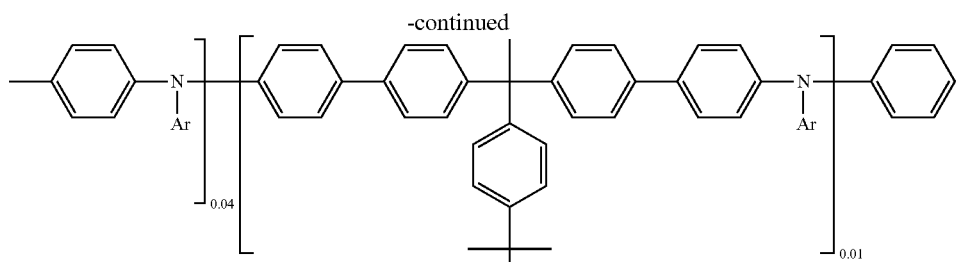

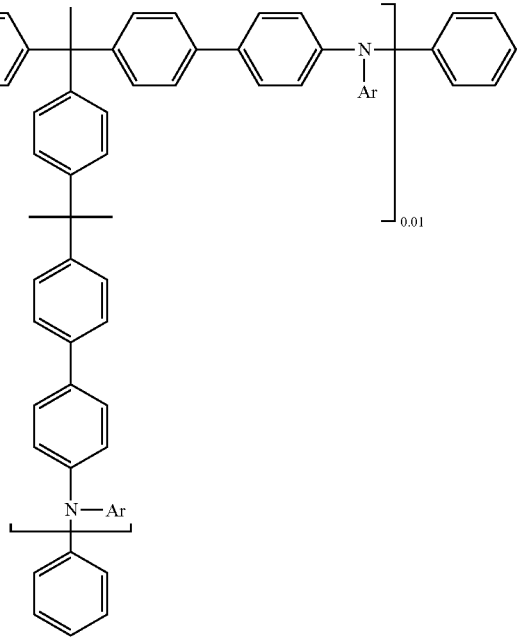

(vii) Physical Properties of Arylamine Polymer Compound (10)

The glass transition temperature of the arylamine polymer compound (10) is generally 50° C. or higher, preferably 80° C. or higher, more preferably 100° C. or higher, and is generally 300° C. or lower.

Falling within the above range is preferred, since the heat resistance of the polymer is excellent and the driving life of the element to be obtained may be prolonged.

The ionization potential of the arylamine polymer compound (10) is generally 4.5 eV or more, preferably 4.8 eV or more, and is generally 6.0 eV or less, preferably 5.7 eV or less.

Falling within the above range is preferred, since the hole transportability of the arylamine polymer compound (10) is excellent and the driving voltage for the element to be obtained may lower.

(viii) Production Method for Arylamine Polymer Compound (10)

The production method for the arylamine polymer compound (10) is not specifically defined, and may be any one for producing the arylamine polymer compound (10). For example, the polymer may be produced according to a polymerization method through Suzuki reaction, a polymerization method through Grignard reaction, a polymerization method through Yamamoto reaction, a polymerization method through Ullmann reaction, a polymerization method through Buchwald-Hartwig reaction, etc.

In the case of the polymerization method through Ullmann reaction and the polymerization method through Buchwald-Hartwig reaction, for example, an aryl trihalide represented by the following formula (10-Ba) (where X represents a halogen atom such as I, Br, Cl, F, etc.) is reacted with a primary aminoaryl or a secondary diaminoaryl represented by the formula (10-Aa) to produce the arylamine polymer compound (10).

[Chem. 68]

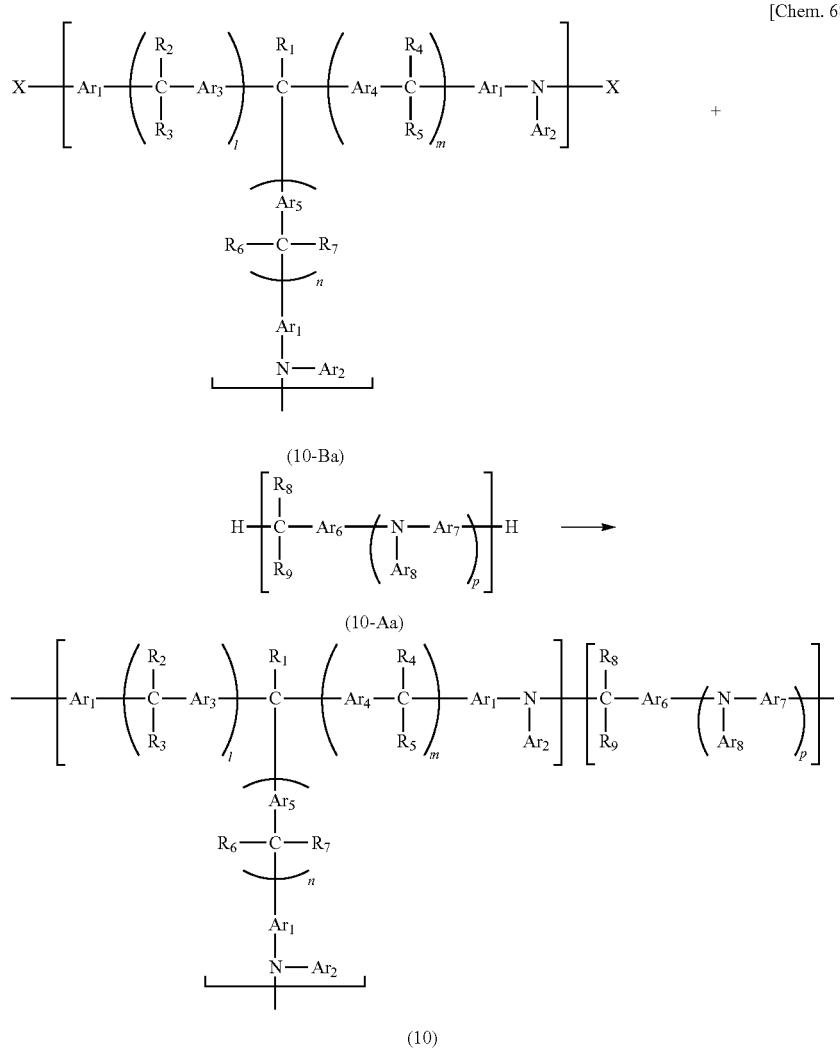

(In the above formulae, $Ar_1$ to $Ar_7$ and $R_1$ to $R_9$, l, m, n and p are the same as in the above-mentioned formulae (10-A) and (10-B).)

In the above-mentioned polymerization method, in general, the reaction to form the N-aryl bond is carried out in the presence of a base such as, for example, potassium carbonate, sodium tert-butoxide, triethylamine, etc. In addition, the reaction may also be carried out in the presence of a transition metal catalyst such as, for example, a copper or palladium complex, etc.

In the case of the polymerization method through Suzuki reaction, for example, a boron derivative (R is an arbitrary substituent, and is generally a hydroxyl group or an alkoxy group that may form a ring) is reacted with an aryl dihalide to produce the arylamine polymer compound (10).

In the polymerization method, in general, the reaction step of the boron derivative and the dihalide is carried out in the presence of a base such as, for example, potassium carbonate, sodium tert-butoxide, triethylamine, etc. If desired, the reaction may be carried out in the presence of a transition metal catalyst such as, for example, a copper or palladium complex, etc. Further in the reaction step with the boron derivative, for example, the reaction may be carried out in the presence of a base such as for example, potassium carbonate, potassium phosphate, sodium tert-butoxide, triethylamine, etc., and a transition metal catalyst such as a palladium complex, etc.

Further, the arylamine polymer compound (10) may also be produced through polymerization of a carbonyl compound or a divinyl compound with a triarylamine in which the p-position of the amino group is a hydrogen atom, in the presence of an acid catalyst such as trifluoromethanesulfonic acid, sulfuric acid, etc.

{Substrate}

The substrate 1 is to be a support of the organic electroluminescent element, for which used is a plate of quartz or glass, a metal plate or a metal foil, or a plastic film, sheet or the like. In particular, preferred are a glass plate, and a transparent synthetic resin plate of polyester, polymethacrylate, polycarbonate, polysulfone, etc. In case where a synthetic resin plate is used, attention should be paid to the gas barrier property thereof. When the gas barrier property of the substrate is poor, then the organic electroluminescent element may be degraded by air having passed through the substrate. Consequently, a method of providing a dense silicon oxide film or the like on at least one surface of such a synthetic resin substrate to secure the gas barrier property of the substrate is one preferred method.

221

{Anode}

The anode 2 plays a role of hole injection into the layer on the side of the luminescent layer.

In general, the anode 2 is formed of a metal such as aluminium, gold, silver, nickel, palladium, platinum, etc.; a metal oxide such as indium and/or tin oxide, etc.; a metal halide such as copper iodide, etc.; carbon black; or a conductive polymer such as poly(3-methylthiophene), polypyrrole, polyaniline, etc.

In general, the anode 2 is formed according to a sputtering method, a vacuum vapor deposition method or the like. On the other hand, in a case where the anode 2 is formed using metal fine particles of silver or the like, fine particles of copper iodide or the like, carbon black, conductive metal oxide fine particles, conductive polymer fine powder or the like, the material may be dispersed in a suitable binder resin solution and may be applied onto the substrate 1 by coating to form the anode 2 thereon. Further, in a case of using a conductive polymer, a thin film may be formed directly on the substrate 1 through electrolytic polymerization, or a conductive polymer may be applied onto the substrate 1 by coating to form the anode 2 thereon (Appl. Phys. Lett., Vol. 60, p. 2711, 1992).

The anode 2 generally has a single-layer structure, but if desired, may have a laminate structure comprising different kinds of materials.

The thickness of the anode 2 may vary depending on the needed transparency. In case where the transparency is needed, it is desirable that the visible light transmittance is generally 60% or more, preferably 80% or more. In this case, the thickness of the anode 2 is generally 5 nm or more, preferably 10 nm or more, and is generally 1000 nm or less, preferably 500 nm or less or so. In case where the anode 2 may be nontransparent, the thickness thereof may be any arbitrary one, and the anode 2 may be the same as the substrate 1. Further, any different conductive material may be layered on the anode 2.

For the purpose of improving the hole injectability by removing the impurities having adhered to the anode 2 and by controlling the ionization potential, it is desirable that the surface of the anode 2 is processed through ultraviolet (UV)/ozone treatment, oxygen plasma treatment or argon plasma treatment.

{Hole Injection Layer}

The hole injection layer 3 is a layer for transporting holes from the anode 2 to the luminescent layer 5 and is, in general, formed on the anode 2.

The method for forming the hole injection layer 3 in the present invention may be a vacuum vapor deposition method or a wet film formation method, and is not specifically defined. From the viewpoint of reducing dark spots, it is desirable that the hole injection layer 3 is formed according to a wet film formation method.

The thickness of the hole injection layer 3 is in a range of generally 5 nm or more, preferably 10 nm or more, and is generally 1000 nm or less, preferably 500 nm or less.

<Formation of Hole Injection Layer according to Wet Film Formation Method>

In case where the hole injection layer 3 is formed according to a wet film formation method, in general, materials to constitute the hole injection layer 3 are mixed with a suitable solvent (solvent for hole injection layer) to prepare a composition for film formation (composition for forming hole injection layer), and the composition for forming hole injection layer is applied onto a layer that corresponds to an underlayer below the hole injection layer 3 (in general, anode) for film formation thereon according to a suitable method, and dried to form the hole injection layer 3.

222

<Hole-Transporting Compound>

The composition for forming hole injection layer generally contains a hole-transporting compound as a constitutive material of the hole injection layer, and a solvent.

The hole-transporting compound may be a compound having hole transportability that is generally used for forming a hole injection layer of organic electroluminescent elements, including a high-molecular compound such as polymer or the like as well as a low-molecular compound such as monomer or the like, but is preferably a polymer compound.

As the hole-transporting compound, preferred is a compound having an ionization potential of from 4.5 eV to 6.0 eV, from the viewpoint of the barrier against charge injection from the anode 2 to the hole injection layer 3. Examples of the hole-transporting compound include aromatic amine derivatives, phthalocyanine derivatives, porphyrin derivatives, oligothiophene derivatives, polythiophene derivatives, benzylphenyl derivatives, compounds with a tertiary amine bonded via a fluorene group, hydrazone derivatives, silazane derivatives, silanamine derivatives, phosphamine derivatives, quinacridone derivatives, polyaniline derivatives, polypyrrole derivatives, polyphenylenevinylene derivatives, polythienylenevinylene derivatives, polyquinoline derivatives, polyquinoxaline derivatives, carbon, etc.

Derivatives as referred to in the present invention are as follows. Described as one example, aromatic amine derivatives include aromatic amines themselves and compounds having an aromatic amine as the main skeleton thereof, and may be either polymers or monomers.

The hole-transporting compound for use as the material of the hole injection layer 3 may contain any one alone of those compounds, or may contain two or more different kinds of those compounds. In case where the layer contains two or more different kinds of such hole-transporting materials, the combination thereof is not specifically defined. Preferably, the layer contains one or more aromatic tertiary amine polymer compounds and one or more other hole-transporting compounds, as combined.

Of the above-exemplified ones, preferred are aromatic amine compounds from the viewpoint of the non-crystallinity and the visible light transmittance thereof, and more preferred are aromatic tertiary amine compounds. Here, the aromatic tertiary amine compounds are compounds having an aromatic tertiary amine structure and include compounds having an aromatic tertiary amine-derived group.

The aromatic tertiary amine compounds are not specifically defined in point of the type thereof, but from the viewpoint of uniform light emission owing to the surface-smoothing effect thereof, more preferred are polymer compounds having a weight-average molecular weight of 1000 or more and 1000000 or less (polymerization-type compounds with continuing repeating units). As preferred examples of the aromatic tertiary amine polymer compound, mentioned are polymer compounds having a repeating unit represented by the following formula (I).

[Chem. 69]

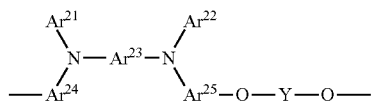

(I)

(In the formula (I), $Ar^{21}$ and $Ar^{22}$ each independently represent an aromatic ring group optionally having a substituent.

Ar²³ to Ar²⁵ each independently represent an aromatic ring group optionally having a substituent. Y represents a linking group selected from the following family of linking groups. Of Ar²¹ to Ar²⁵, two groups bonding to the same N atom may bond to each other to form a ring.)

[Chem. 70]

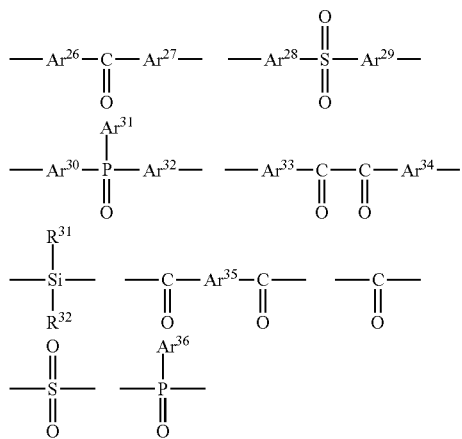

(In the above formulae, $Ar^{26}$ to $Ar^{36}$ each independently represent an aromatic ring group optionally having a substituent. $R^{31}$ and $R^{32}$ each independently represent a hydrogen atom or an arbitrary substituent.)

As the aromatic ring group for $Ar^{21}$ to $Ar^{36}$, preferred are a benzene ring, a naphthalene ring, a phenanthrene ring, a thiophene ring and a pyridine ring each having one or two free atomic valences, from the viewpoint of the solubility, the heat resistance and the hole injection/transport capability of the polymer compounds; and more preferred are a benzene ring and a naphthalene ring each having one or two free atomic valences.

The aromatic ring group for $Ar^{21}$ to $Ar^{36}$ may further have a substituent. The molecular weight of the substituent is, in general, preferably 400 or less, more preferably 250 or less or so. As the substituent, preferred are an alkyl group, an alkenyl group, an alkoxy group, an aromatic hydrocarbon ring group, an aromatic heterocyclic group, etc.

In case where $R^{31}$ and $R^{32}$ each are a substituent, the substituent includes an alkyl group, an alkenyl group, an alkoxy group, a silyl group, a siloxy group, an aromatic hydrocarbon ring group, an aromatic heterocyclic group, etc.

As specific examples of the aromatic tertiary amine polymer compounds having the repeating unit represented by the formula (I), there are mentioned those described in WO2005/089024.

As the hole-transporting compound, also preferred is a conductive polymer (PEDOT/PSS) which is a polythiophene derivative and which is prepared through polymerization of 3,4-ethylenedioxythiophene in a high-molecular-weight polystyrenesulfonic acid. The end of the polymer may be capped with methacrylate or the like for use herein.

The concentration of the hole-transporting compound in the composition for forming hole injection layer may be any one, not markedly detracting from the advantageous effects of the present invention. The concentration is generally 0.01% by weight or more, preferably 0.1% by weight or more, more preferably 0.5% by weight or more and is generally 70% by weight or less, preferably 60% by weight or less, more preferably 50% by weight or less, from the viewpoint of the uniformity of the film thickness. When the concentration is too high, then the film thickness may be uneven; but when too low, then the hole injection layer formed would have defects.

<Electron-Accepting Compound>

Preferably, the composition for forming hole injection layer contains an electron-accepting compound as the constitutive material of the hole injection layer. Here, the electron-accepting compound is preferably a compound having an oxidation power and having the ability to accept one electron from the above-mentioned hole-transporting compound. Concretely, preferred is a compound having an electron affinity of 4 eV or more, more preferably 5 eV or more.

As the electron-accepting compound of the type, for example, there are mentioned one or more compounds selected from a group consisting of triarylboron compounds, metal halides, Lewis acids, organic acids, onium salts, salts of arylamine and metal halide, and salts of arylamine and Lewis acid. More concretely, the electron-accepting compounds include onium salts substituted with an organic group, such as 4-isopropyl-4'-methyldiphenyliodonium tetrakis(pentafluorophenyl)borate, triphenylsulfonium tetrafluoroborate, etc. (WO2005/089024); high-valent inorganic compounds such as iron(III) chloride (JP-A 11-251067), ammonium peroxodisulfate, etc.; cyano compounds such as tetracyanoethylene, etc.; aromatic boron compounds such as tris(pentafluorophenyl)borane (JP-A 2003-31365), etc.; fullerene derivatives; iodine; sulfonate ions such as polystyrenesulfonate ions, alkylbenzenesulfonate ions, camphorsulfonate ions, etc.

These electron-accepting compounds may increase the electroconductivity of the hole injection layer, as oxidizing the hole-transporting compound in the layer.

The content of the electron-accepting compound relative to the hole-transporting compound in the hole injection layer or in the composition for forming hole injection layer is generally 0.1 mol % or more, preferably 1 mol % or more, and is generally 100 mol % or less, preferably 40 mol % or less.

<Other Constituent Materials>

Regarding the materials of the hole injection layer, the layer may contain any other component in addition to the above-mentioned hole-transporting compound and electron-accepting compound, not significantly detracting from the advantageous effects of the present invention. Examples of the other additives include various kinds of luminescent materials, electron-transporting compound, binder resins, coating improvers, etc. One alone or two or more such other additives may be used here either singly or as combined in any desired manner and in any desired ratio.

<Solvent>

At least one solvent in the composition for forming hole injection layer that is used in a wet film formation method is preferably a compound capable of dissolving the constitutive materials of the hole injection layer. The boiling point of the solvent is generally 110° C. or higher, preferably 140° C. or higher, more preferably 200° C. or higher, and is generally 400° C. or lower, preferably 300° C. or lower. When the boiling point of the solvent is too low, then the drying speed would be too high so that the film quality may worsen. On the other hand, when the boiling point of the solvent is too high, then the temperature in the drying step must be high, therefore often having some negative influence on the other layers and the substrate.

As the solvent, for example, there are mentioned ether solvents, ester solvents, aromatic hydrocarbon solvents, amide solvents, etc.

The ether solvents include, for example, aliphatic ethers such as ethylene glycol dimethyl ether, ethylene glycol diethyl ether, propylene glycol 1-monomethyl ether acetate (PGMEA), etc.; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, etc.

The ester solvents include, for example, aromatic esters such as phenyl acetate, phenyl propionate, methyl benzoate, ethyl benzoate, propyl benzoate, n-butyl benzoate, etc.

The aromatic hydrocarbon solvents include, for example, toluene, xylene, cyclohexylbenzene, 3-isopropylbiphenyl, 1,2,3,4-tetramethylbenzene, 1,4-diisopropylbenzene, cyclohexylbenzene, methylnaphthalene, etc.

The amide solvents include, for example, N,N-dimethylformamide, N,N-dimethylacetamide, etc.

In addition, dimethyl sulfoxide or the like is also usable here.

One alone or two or more different kinds of those solvents may be used here either singly or as combined in any desired manner and in any desired ratio.

[Method of Film Formation]

After the composition for forming hole injection layer has been prepared, the composition is applied onto the layer that corresponds to the underlayer below the hole injection layer 3 (in general, anode 2) for film formation thereon according to wet film formation, and dried to form the hole injection layer 3.

The temperature in the film formation step is preferably 10° C. or higher and is preferably 50° C. or lower for preventing the film from having defects owing to crystal formation in the composition.

The relative humidity in the film formation step is not specifically defined so far as it does not markedly detract from the advantageous effects of the present invention, but is generally 0.01 ppm or more and is generally 80% or less.

After the film formation, the film of the composition for forming hole injection layer is dried generally by heating or the like. Examples of the heating means for use in the heating step include clean oven, hot plate, IR rays, halogen heater, microwave irradiation, etc. Above all, preferred is clean oven and hot plate for uniformly giving heat to the entire film.

The heating temperature in the heating step may be any one not markedly detracting from the advantageous effects of the present invention, and preferably, the coating film is heated at a temperature not lower than the boiling point of the solvent used in the composition for forming hole injection layer. In case where a mixed solvent of two or more different kinds of solvents are used for the hole injection layer, it is desirable that the coating film is heated at a temperature not lower than the boiling point of at least one solvent of the mixed solvent. In consideration of boiling point elevation of the solvent, it is desirable that the coating film is heated at 120° C. or higher and at 410° C. or lower in the heating step.

In the heating step, the heating time is not specifically defined so far as the heating temperature is not lower than the boiling point of the solvent in the composition for forming hole injection layer and the coating film is not sufficiently insolubilized; however, the heating time is preferably 10 seconds or more and is generally 180 minutes or less. When the heating time is too long, then the components of the other layers may diffuse; but when too short, the hole injection layer would be inhomogeneous. The heating may be carried out two times.

<Formation of Hole Injection Layer according to Vacuum Vapor Deposition Method>

In case where the hole injection layer 3 is formed through vacuum vapor deposition, one or more of the constitutive materials of the hole injection layer 3 (above-mentioned hole-transporting compound, electron-accepting compound, etc.) are put into the crucibles set in a vacuum chamber (in case where two or more different kinds of materials are used, the materials are individually put in different crucibles), the vacuum chamber is degassed down to $10^{-4}$ Pa or so via a suitable vacuum pump, then the crucibles are heated (in case where two or more different kinds of materials are used, the respective crucibles are heated) to thereby evaporate the solvent under control of the evaporation amount thereof (in case where two or more different kinds of materials are used, each material is evaporated under independent control of the evaporation amount thereof), and thus the hole injection layer 3 is formed on the anode 2 on the substrate put to face the crucibles. In case where two or more different kinds of materials are used, a mixture thereof may be put in one crucible, and may be heated and evaporated to form the hole injection layer 3.

Not markedly detracting from the advantageous effects of the present invention, the vacuum degree in evaporation is not specifically defined. The vacuum degree in evaporation is typically $0.1 \times 10^{-6}$ Torr ($0.13 \times 10^{-4}$ Pa) or more and $9.0 \times 10^{-6}$ Torr ($12.0 \times 10^{-4}$ Pa) or less. Not markedly detracting from the advantageous effects of the present invention, the evaporation rate is not specifically defined. The evaporation rate is typically 0.1 angstrom/sec or more and is 5.0 angstrom/sec or less. Also not markedly detracting from the advantageous effects of the present invention, the film formation temperature in vapor deposition is preferably 10° C. or higher and is preferably 50° C. or lower.

{Hole Transport Layer}

Not specifically defined, the hole transport layer 4 in the invention may be formed according to any of a vacuum vapor deposition method or a wet film formation method. From the viewpoint of reducing dark spots, the hole transport layer 4 is preferably formed according to a wet film formation method.

The hole transport layer 4 may be formed on the hole injection layer 3 when the hole injection layer is present, but when the hole injection layer 3 is absent, the hole transport layer 4 may be formed on the anode 2. The organic electroluminescent element of the present invention may have a configuration not having the hole transport layer.

The material for forming the hole transport layer 4 is preferably a material having high hole transportability and capable of efficiently transporting the injected holes. Consequently, it is desirable that the material for forming the hole transport layer has a small ionization potential, is highly transparent to visible light, has a large hole mobility, is excellent in stability and generates few impurities to be traps in production and during use. Kept in adjacent to the luminescent layer 5, in many cases, it is desirable that the hole transport layer does not quench the emission from the luminescent layer 5 and does not form an exciplex with the luminescent layer 5 to lower the light emission efficiency.

The material for the hole transport layer 4 may be any and every material heretofore used as the constitutive material for hole transport layer, and includes, for example, those exemplified as the hole-transporting compound for use in the above-mentioned hole injection layer 3. As the material, in addition, there are further mentioned arylamine derivatives, fluorene derivatives, spiro derivatives, carbazole derivatives, pyridine derivatives, pyrazine derivatives, pyrimidine derivatives, triazine derivatives, quinoline derivatives, phenanthroline derivatives, phthalocyanine derivatives, porphyrin derivatives, silol derivatives, oligothiophene derivatives, condensed polycyclic aromatic derivatives, metal complexes, etc.

In addition, for example, there are further mentioned polyvinylcarbazole derivatives, polyarylamine derivatives, polyvinyltriphenylamine derivatives, polyfluorene derivatives, polyarylene derivatives, tetraphenylbenzidine-containing polyarylene ether sulfone derivatives, polyarylenevinylene derivatives, polysiloxane derivatives, polythiophene derivatives, poly(p-phenylenevinylene) derivatives, etc. These may be any of alternate copolymers, random polymers, block polymers or graft copolymers. In addition, also employable are polymers and so-called dendrimers having a branched main chain and having 3 or more end parts.

Above all, preferred are polyarylamine derivatives and polyarylene derivatives.

As polyarylamine derivatives, preferred is use of the above-mentioned arylamine polymer compound (10).

As polyarylene derivatives, there are mentioned polymers of the above-mentioned formula (10-C) that have, in the repeating unit therein, an arylene group such as an aromatic ring group optionally having a substituent, as exemplified as $Ar^a$ and $Ar^b$.

As polyarylene derivatives, preferred are polymers having a repeating unit of the following formula (10-D) and/or the following formula (10-E).

[Chem. 71]

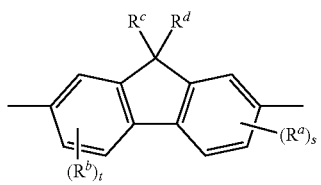

(10-D)

(In the formula (10-D), $R^a$, $R^b$, $R^c$ and $R^d$ each independently represent an alkyl group, an alkoxy group, a phenylalkyl group, a phenylalkoxy group, a phenyl group, a phenoxy group, an alkylphenyl group, an alkoxyphenyl group, an alkylcarbonyl group, an alkoxycarbonyl group, or a carboxy group. t and s each independently indicate an integer of from 0 to 3. When t or s is 2 or more, then plural $R^a$'s or $R^b$'s contained in one molecule may be the same or different, and the neighboring $R^a$'s or $R^b$'s may form a ring.)

[Chem. 72]

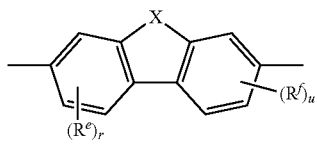

(10-E)

(In the formula (10-E), $R^e$ and $R^f$ each independently have the same meaning as those of $R^a$, $R^b$, $R^c$ or $R^d$ in the formula (10-D). r and u each independently indicate an integer of from 0 to 3. When r or u is 2 or more, then plural $R^e$'s or $R^e$'s contained in one molecule may be the same or different, and the neighboring $R^e$'s or $R^f$'s may form a ring. X represents an atom or an atomic group to constitute a 5-membered ring or a 6-membered ring.)

Specific examples of X include —O—, —BR—, —NR—, —SiR$_2$—, —PR—, —SR—, —CR$_2$— or a group formed by bonding any of these. Here, R means a hydrogen atom or an arbitrary organic group. The arbitrary organic group in the present invention is a group containing at least one carbon atoms.

As polyarylene derivatives, also preferred are those further having a repeating unit represented by the following formula (10-F), in addition to the repeating unit of the above-mentioned formula (10-D) and/or the above-mentioned formula (10-E).

[Chem. 73]

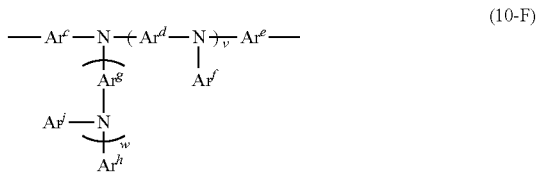

(10-F)

(In the formula (10-F), $Ar^c$ to $Ar^j$ each independently represent an aromatic ring group having one or two free atomic valences and optionally having a substituent. v and w each independently indicate 0 or 1.)

Specific examples of $Ar^c$ to $Ar^j$ are the same as those of $Ar^a$ and $Ar^b$ in the formula (10-C).

As specific examples of the above-mentioned formulae (10-D) to (10-F) and specific examples of polyarylene derivatives, there are mentioned those described in JP-A 2008-98619.

In case where the hole transport layer 4 is formed according to a wet film formation method, a composition for forming hole transport layer is first prepared, then processed for wet film formation and dried, like in the case of forming the above-mentioned hole injection layer 3.

The composition for forming hole transport layer contains a solvent in addition to the above-mentioned hole-transporting material. The solvent to be used is the same as that used in the composition for forming hole injection layer. In addition, the film formation condition and the drying condition are also the same as in the case of forming the hole injection layer 3.

When the hole transport layer 4 is formed according to a vacuum vapor deposition method, the film formation condition and others are also the same as in the case of forming the hole injection layer 3.

The hole transport layer 4 may contain various kinds of luminescent material, electron-transporting compound, binder resin, coating improver and the like, in addition to the above-mentioned hole-transporting material.

The hole transport layer 4 may be a layer formed by crosslinking a crosslinking compound. The crosslinking compound is a compound having a crosslinking group, and crosslinks to form a network polymer compound.

Examples of the crosslinking group include cyclic ethers such as oxetane, epoxy and the like having a monovalent free atomic valence; unsaturated double bond-derived groups such as a vinyl group, a trifluorovinyl group, a styryl group, ab acryl group, methacryloyl, cinnamoyl, etc.; benzocyclobutane having a monovalent free atomic valence.

The crosslinking compound may be any of monomer, oligomer and polymer. One alone or two or more different kinds of crosslinking compounds may be used here either singly or as combined in any desired manner and in any desired ratio.

As the crosslinking compound, preferably used here is a hole-transporting material having a crosslinking group. The hole-transporting material includes those exemplified hereinabove; and the hole-transporting material having a crosslinking group includes those hole-transporting materials and having a crosslinking group bonding to the main chain or the side chain thereof. In particular, the crosslinking group preferably bonds to the main chain via a linking group such as an alkylene group or the like. Also preferably, the hole-transporting material is a polymer that contains a repeating unit having a crosslinking group. In particular, the hole-transporting material is preferably a polymer of the above-mentioned formula (10-C) or formulae (10-D) to (10-F) having a repeating unit with a crosslinking group bonding thereto directly or via a linking group.

As the crosslinking compound, preferred is use of a hole-transporting material having a crosslinking group. Examples of the hole-transporting material include nitrogen-containing aromatic compound derivatives such as pyridine derivatives, pyrazine derivatives, pyrimidine derivatives, triazine derivatives, quinoline derivatives, phenanthroline derivatives, carbazole derivatives, phthalocyanine derivatives, porphyrin derivatives, etc.; triphenylamine derivatives; silol derivatives, oligothiophene derivatives, condensed polycyclic aromatic derivatives, metal complexes, etc. Above all, as the hole-transporting compound, preferred are nitrogen-containing aromatic derivatives such as pyridine derivatives, pyrazine derivatives, pyrimidine derivatives, triazine derivatives, quinoline derivatives, phenanthroline derivatives, carbazole derivatives, etc.; triphenylamine derivatives, silol derivatives, condensed polycyclic aromatic derivatives, metal complexes, etc.; and more preferred are triphenylamine derivatives.

For forming the hole transport layer 4 by crosslinking the crosslinking compound, in general, a composition for forming hole transport layer is prepared by dissolving or dispersing the crosslinking compound in a solvent, then the composition is formed into a film through wet film formation and then crosslinked.

The composition for forming hole transport layer may contain an additive for promoting crosslinking reaction in addition to the crosslinking compound therein. Examples of the additive for promoting crosslinking reaction include a polymerization initiator and a polymerization promoter such as alkylphenone compounds, acylphosphine oxide compounds, metallocene compounds, oxime ester compounds, azo compounds, onium salts, etc.; an optical sensitizer such as condensed polycyclic hydrocarbons, porphyrin compounds, diarylketone compounds, etc.

The composition for forming hole transport layer may further contain a coating improver such as a leveling agent, a defoaming agent, etc.; an electron-accepting compound; a binder resin, etc.

The composition for forming hole transport layer contains the arylamine polymer compound (10) and the crosslinking compound such as those mentioned above, in an amount of generally 0.01% by weight or more, preferably 0.05% by weight or more, more preferably 0.1% by weight or more. The composition for forming hole transport layer contains the crosslinking compound in an amount of generally 50% by weight or less, preferably 20% by weight or less, more preferably 10% by weight or less.

In general, a network polymer compound is formed by applying the hole transport layer-forming composition that contains a crosslinking compound in the concentration as above to an underlayer (generally hole injection layer 3) to form a film thereon, followed by crosslinking the crosslinking compound through irradiation with active energy of heat and/or light.

The condition such as temperature and humidity in film formation is the same as that in the case of wet film formation for the hole injection layer.

The heating method after film formation is not specifically defined. The heating temperature condition is generally 120° C. or hither, and is preferably 400° C. or lower.

The heating time is generally 1 minute or more and is preferably 24 hours or less. The heating means is not specifically defined. The laminate having the formed layer may be put on a hot plate, or may be heated in an oven. Regarding the heating method, for example, the laminate may be heated on a hot plate at 120° C. or higher for 1 minute or more.

Regarding the method for active energy irradiation in the case of crosslinking the crosslinking compound through active energy irradiation with light or the like, there are mentioned a method of direct irradiation with a light source such as an ultra-high-pressure mercury lamp, a high-pressure mercury lamp, etc.; a method of irradiation using a mask aligner or a conveyor-type photoirradiation apparatus that has the above-mentioned light source as a built-in device inside it, etc. For active energy irradiation with any other than light, for example, there is mentioned a method of irradiation using an apparatus for radiating microwaves generated by a magnetron, or that is, a so-called microwave oven.

Regarding the irradiation time, preferably, the condition necessary for lowering the film solubility is set, and in general, the irradiation time is 0.1 seconds or more and is preferably 10 hours or less.

For the heating and the active energy irradiation such as irradiation of light, the methods and the conditions may be selected singly or may be combined. When combined, the sequence of the methods is not specifically defined.

The thickness of the hole transport layer 4 thus formed is generally 5 nm or more, preferably 10 nm or more, and is generally 300 nm or less, preferably 100 nm or less.

{Luminescent Layer}

The luminescent layer 5 is, as sandwiched between the electrodes given an electric field, excited though recombination of the holes injected thereinto from the anode 2 and the electrons injected thereinto from the cathode 9, and is a layer to be a main luminescent source in the element. When the element has the hole transport layer 4, in general, the luminescent layer 5 is formed on the hole transport layer 4, but when the element does not have the hole transport layer 4 but has the hole injection layer 3, the luminescent layer is formed on the hole injection layer 3.

The constituent materials of the luminescent layer and the formation method for the layer are as described above.

{Hole-Blocking Layer}

The hole-blocking layer 6 may be provided between the luminescent layer 5 and the electron injection layer 8 to be mentioned below. The hole-blocking layer 6 is a layer laminated or the luminescent layer 5 to be adjacent to the interface on the side of the cathode 9 of the luminescent layer 5.

The hole-blocking layer 6 plays a role in blocking the holes moving from the anode 2 from reaching the cathode 9 and a role in efficiently transporting the electrons injected from the electron cathode 9 toward the luminescent layer 5.

Regarding the necessary physical properties thereof, the material to constitute the hole-blocking layer 6 is desired to have a high electron mobility, a low hole mobility, a large energy gap (difference between HOMO and LUMO) and a high excitation triplet energy level (T1).

The hole-blocking layer material satisfying the requirements includes mixed ligand complexes such as bis(2-methyl-8-quinolinolato)(phenolato)aluminium, bis(2-methyl-8-quinolinolato)(triphenylsilanolato)aluminium, etc.; metal complexes such as bis(2-methyl-8-quinolato)aluminium-p-oxo-bis(2-methyl-8-quinolinolato)aluminium binuclear metal complex, etc.; styryl compounds such as distyrylbiphenyl derivatives, etc. (JP-A 11-242996); triazole derivatives such as 3-(4-biphenylyl)-4-phenyl-5(4-tert-butylphenyl)-1,2,4-triazole, etc. (JP-A 7-41759); phenanthroline derivatives such as bathocuproin, etc. (JP-A 10-79297), etc. Further, compounds having at least one pyridine ring substituted at the 2,4,6-positions, as described in WO2005/022962, are also preferred as the material for the hole-blocking layer 6.

One alone or two or more different kinds of the materials may be used for the hole-blocking layer 6 either singly or as combined in any desired manner and in any desired ratio.

The formation method for the hole-blocking layer 6 is not specifically defined. Accordingly, the layer may be formed according to a wet film formation method, a vapor deposition method or any other method.

The thickness of the hole-blocking layer 6 is not specifically defined so far as it does not significantly detract from the advantageous effects of the present invention. The thickness is generally 0.3 nm or more, preferably 0.5 nm or more, and is generally 100 nm or less, preferably 50 nm or less.

In place of the hole-blocking layer, a hole relaxation layer may be arranged in the element.

{Electron Transport Layer}

The electron transport layer 7 may be arranged between the luminescent layer 5 and the electron injection layer 8 to be mentioned below.

The electron transport layer 7 is arranged for the purpose of further improving the light emission efficiency of the element, and is formed of a compound capable of transporting the electrons injected from the cathode 9 efficiently toward the luminescent layer 5 between the electrodes given an electric field.

The electron-transporting compound to be used for the electron transport layer 7 is a compound having a high electron injection efficiency from the cathode 9 or the electron injection layer 8, having a high electron mobility, and capable of efficiently transporting the injected electrons. The compound satisfying the requirements includes metal complexes such as aluminium complex of 8-hydroxyquinoline, etc. (JP-A 59-194393), 10-hydroxybenzo[h]quinoline metal complexes, oxadiazole derivatives, distyrylbiphenyl derivatives, silol derivatives, 3-hydroxyflavone metal complexes, 5-hydroxyflavone metal complexes, benzoxazole metal complexes, benzothiazole metal complexes, trisbenzimidazolylbenzene (U.S. Pat. No. 5,645,948), quinoxaline compounds (JP-A 6-207169), phenanthroline derivatives (JP-A 5-331459), 2-t-butyl-9,10-N,N'-dicyanoanthraquinonediimine, n-type hydrogenated amorphous silicon carbide, n-type zinc sulfide, n-type zinc selenide, etc.

One alone or two or more different kinds of materials may be used for the electron transport layer 7 either singly or as combined in any desired manner and in any desired ratio.

The formation method for the electron transport layer 7 is not limited. Therefore, the layer may be formed according to a wet film formation method, a vapor deposition method or any other method.

The thickness of the electron transport layer 7 may be any one not markedly detracting from the advantageous effects of the present invention. In general, the thickness is 1 nm or more, preferably 5 nm or more, and is generally 300 nm or less, preferably 100 nm or less.

{Electron Injection Layer}

The electron injection layer 8 plays a role in efficiently injecting the electrons injected from the cathode 9, into the luminescent layer 5. For efficient electron injection, the material to form the electron injection layer 8 is preferably a metal having a low work function. For example, used here are alkali metals such as sodium, cesium, etc., and alkaline earth metals such as barium, calcium, etc. For example, there are mentioned lithium fluoride (LiF), magnesium fluoride ($MgF_2$), lithium oxide ($Li_2O$), cesium(II) carbonate ($CsCO_3$), etc. (see Applied Physics Letters, 1997, Vol 70, p. 152; JP-A 10-74586; IEEE Transactions on Electron Devices, 1997, Vol. 44, p. 1245; SID 04 Digest, p. 154, etc.).

The thickness of the layer is generally 0.1 nm or more and is preferably 5 nm or less.

In addition, also preferred is doping an organic electron-transporting compound such as typically a nitrogen-containing heterocyclic compound such as basophenanthroline or the like, or a metal complex such as an aluminium complex of 8-hydroxyquinoline or the like, with an alkali metal such as sodium, potassium, cesium, lithium, rubidium or the like (as described in JP-A 10-270171, 2002-100478, 2002-100482, etc.), as capable of satisfying both good electron injection/transport capability and excellent film quality. In this case, the film thickness is generally 5 nm or more, preferably 10 nm or more and is generally 200 nm or less, preferably 100 nm or less.

One alone or two or more kinds of materials may be used for the electron injection layer 8 either singly or as combined in any desired manner and in any desired ratio.

The formation method for the electron injection layer 8 is not specifically defined. Therefore, the layer may be formed according to a wet film formation method, a vapor deposition method or any other method.

{Cathode}

The cathode 9 plays a role in injecting electrons into the layer on the side of the luminescent layer 5 (electron injection layer 8, luminescent layer 5, etc.).

As the material for the cathode 9, the material for use for the above-mentioned anode 2 may be used; however, for efficient electron injection, preferred is a metal having a low work function. Suitable metals such as tin, magnesium, indium, calcium, aluminium or silver or their alloys may be used. Specific examples are low-work-function alloy electrodes of magnesium-silver alloy, magnesium-indium alloy, aluminium-lithium alloy, etc.

One alone or two or more kinds of materials may be used for the cathode 9 either singly or as combined in any desired manner and in any desired ratio.

The thickness of the cathode 9 is generally the same as that of the anode 2.

For the purpose of protecting the cathode 9 formed of a low-work-function metal, a metal layer having a high work function and is stable to air is preferably layered on the cathode, whereby the stability of the element could increase. For this purpose, metals are used, such as aluminium, silver, copper, nickel, chromium, gold, platinum, etc. One alone or two or more kinds of these materials may be sued either singly or as combined in any desired manner and in any desired ratio.

{Other Constituent Layers}

Within the range not overstepping the scope and the spirit thereof, the organic electroluminescent element of the present invention may have any other configuration. For example, not detracting from the performance thereof, the element may have any other layer than those mentioned above between the anode 2 and the cathode 9, or some of the constituent layers therebetween may be omitted.

The optional layer includes, for example, an electron-blocking layer. The electron-blocking layer may be provided between the hole injection layer 3 or the hole transport layer 4 and the luminescent layer 5, and plays a role in blocking the electrons moving from the luminescent layer 5 from reaching the hole injection layer 3, thereby increasing the probability of recombination between the holes and the electrons in the luminescent layer 5 and trapping the formed excitons in the luminescent layer 5, and a role in efficiently transporting the holes injected from the hole injection layer 3 toward the luminescent layer 5. In particular, in case where a phosphorescent material or a blue-emitting material is used as the luminescent material, it is effective to arrange the electron-blocking layer.

Regarding the necessary properties thereof, the electron-blocking layer is desired to have a high hole transportability, a large energy gap (difference between HOMO and LUMO) and a high excitation triplet energy level (T1). In case where the luminescent layer 5 is formed according to a wet film formation method, the electron-blocking layer is also desired to be compatible with wet film formation. As the material for use for the electron-blocking layer of the type, there are mentioned copolymers of dioctylfluorene and triphenylamine such as typically F8-TFB (WO2004/084260), etc.

One alone or two or more kinds of the materials may be used for the electron-blocking layer either singly or as combined in any desired manner and in any desired ratio.

The formation method for the electron-blocking layer is not specifically defined. Therefore, the layer may be formed according to a wet film formation method, a vapor deposition method or any other method.

In the above-described layer configuration, the constituent elements except the substrate may be laminated in reverse order. For example, the layer configuration of FIG. 1 is referred to. On the substrate 1, the other constituent elements may be arranged in an order of a cathode 9, an electron injection layer 8, an electron transport layer 7, a hole-blocking layer 6, a luminescent layer 5, a hole transport layer 4, a hole injection layer 3 and an anode 2.

Further, between two substrates at least one of which is transparent, the other constituent elements than the substrates may be laminated to construct the organic electroluminescent element of the present invention.

Further, the present invention may employ a layered structure comprising a plurality of constituent elements (light emission units) than substrates (laminate structure of plural light emission units). In this case, in place of the interlayer between the unit layer constructions (light emission units) (when the anode is ITO and the cathode is Al, in place of both the two layers), for example, vanadium pentoxide ($V_2O_5$) or the like may be used as a charge generation layer (CGL), and this is favorable from the viewpoint of luminescent efficiency/driving voltage since the barrier between the units may be reduced.

Further, the organic electroluminescent element of the present invention may be formed as a single element, or may be applied to a configuration where plural elements are arranged in an array, or may also be applied to a configuration where the anode and the cathode are arranged in an X-Y matrix.

Not markedly detracting from the advantageous effects of the present invention, the above-mentioned layers may contain any other material than those mentioned above.

[Organic EL Display Device]

The organic EL display device of the present invention uses the organic electroluminescent element of the present invention mentioned above. The type and the configuration of the organic EL display device of the present invention are not specifically defined. The organic EL display device of the present invention can be constructed using the organic electroluminescent element of the present invention according to an ordinary method.

For example, the organic EL display device of the present invention can be constructed according to the method described in "Organic EL Display" (by Ohm, issued on Aug. 20, 2004, written by Shizuo Tokito, Chihaya Adachi, Hideyuki Murata).

[Organic EL Lighting Device]

The organic EL lighting device of the present invention uses the organic electroluminescent element of the present invention mentioned above. The type and the configuration of the organic EL lighting device of the present invention are not specifically defined. The lighting device can be constructed using the organic electroluminescent element of the present invention and according to an ordinary method.

EXAMPLES

Next, the present invention is described more concretely with reference to Examples. However, the present invention is not limited to the following Examples, not overstepping the scope and the spirit thereof.

Example 1

An organic electroluminescent element was produced according to the process mentioned below.

On a glass substrate 1 having, as deposited thereon by sputtering film formation, an indium tin oxide (ITO) transparent conductive film, an anode 2 was formed by patterning thereon in stripes each having a width of 2 mm, according to ordinary photolithography combined with hydrochloric acid etching. The thus-patterned ITO substrate was ultrasonically washed with an aqueous surfactant solution, washed with ultrapure water, ultrasonically washed with ultrapure water and then washed with ultrapure water in that order, then dried and further washed with UV ozone.

Next, a composition for forming hole injection layer was prepared, which has the following formulation and contains an arylamine polymer shown by the following structural formula (P-1), 4-isopropyl-4'-methyldiphenyliodonium tetrakis (pentafluorophenyl)borate shown by the structural formula (A-1) and ethyl acetate. The hole injection layer-forming composition was applied onto the anode 2 according to a spin coating method under the condition mentioned below, thereby forming a hole injection layer 3 having a thickness of 40 nm.

[Chem. 74]

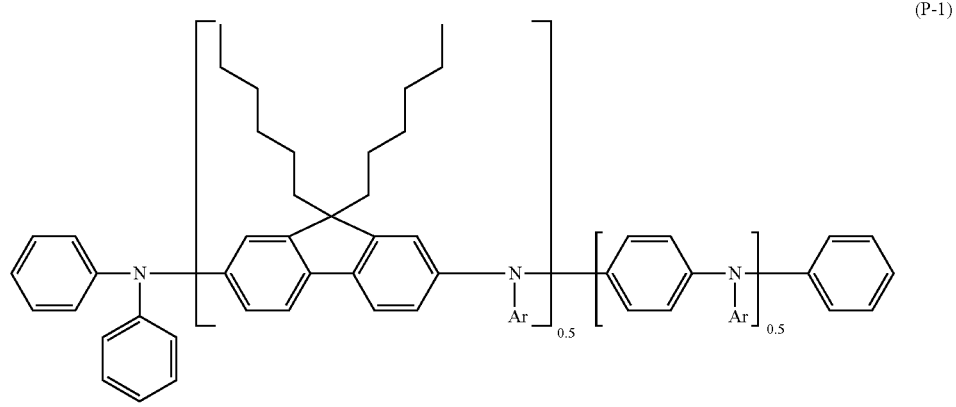

(P-1)

—Ar = 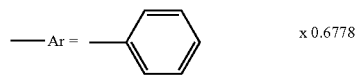 x 0.6778

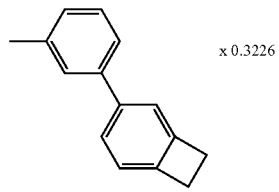 x 0.3226

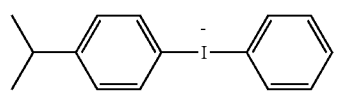

(A-1)

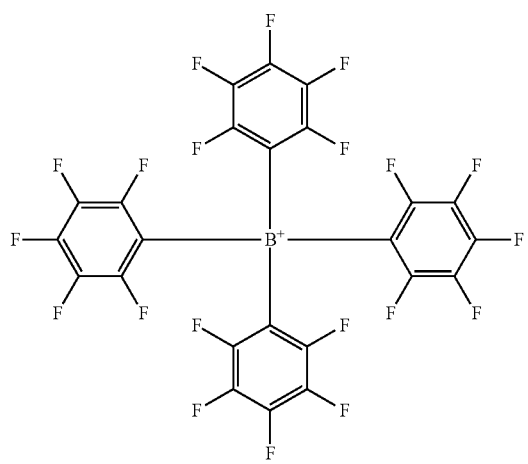

<Formulation of Composition for Forming Hole Injection Layer>

| <Formulation of Composition for Forming Hole Injection Layer> | |
|---|---|
| Solvent | ethyl benzoate |
| Composition concentration | P-1: 2.5 wt % |
| | A-1: 0.5 wt % |

| <Film Formation Condition for Hole Injection Layer 3> | |
|---|---|
| Spinner rotation time | 2000 rpm, 30 seconds |
| A spin coating atmosphere | in air |
| Heating Condition | in air, 230° C., 1 hour |

Subsequently, a composition for forming hole transport layer, containing a compound having the following structural formula (HIT-2) was prepared, and this was applied onto the hole injection layer 3 according to a spin coating method under the condition mentioned below, and polymerized by heating to form a hole transport layer 4 having a thickness of 15 nm.

[Chem. 75]

(HIT-2)

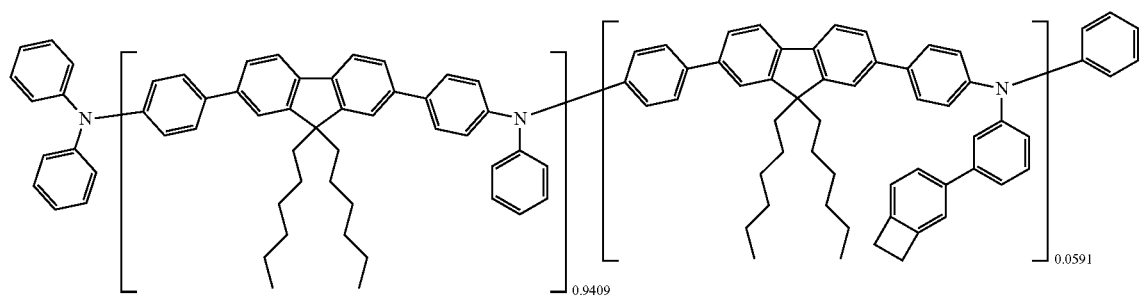

| <Composition for Forming Hole Transport Layer> | |
|---|---|
| Solvent | cyclohexylbenzene |
| Concentration | HIT-2: 1.0 wt % |

| <Film Formation Condition for Hole Transport Layer 4> | |
|---|---|
| Spinner rotation time | 1500 rpm, 120 seconds |
| Heating Condition | 230° C., 1 hour |

Next prepared was a composition for forming luminescent layer, containing the following compound (H-1) and (E-1) as charge-transporting materials and compounds having the structural formula (R1), (G1) and (B1), respectively, as luminescent materials, and the composition was applied onto the hole transport layer 4 according to a spin coating method under the condition mentioned below and then heated to form thereon a luminescent layer 5 having a thickness of 45 nm.

[Chem. 76]

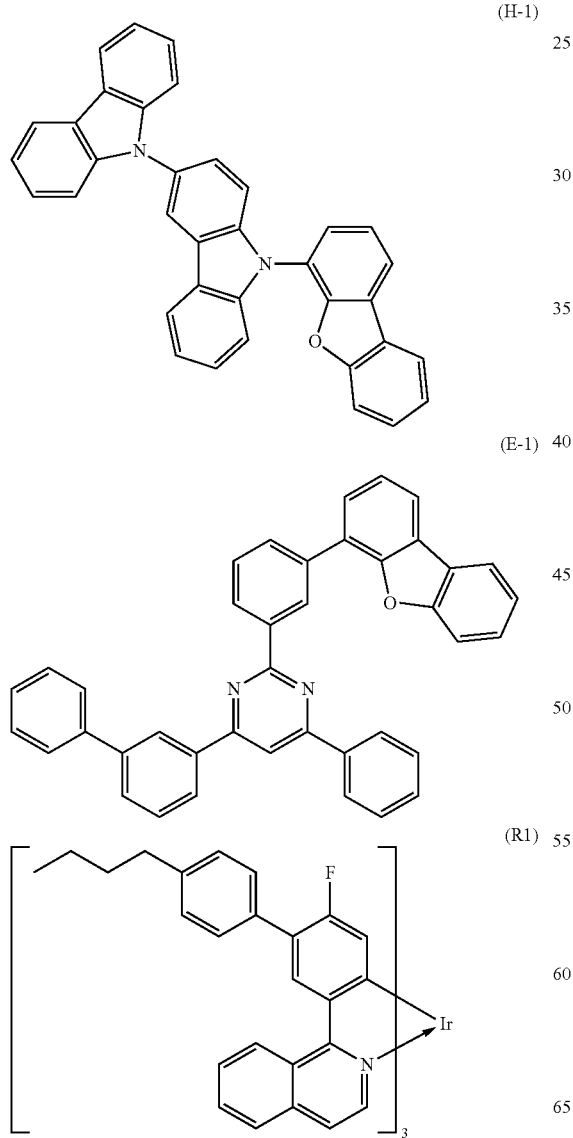

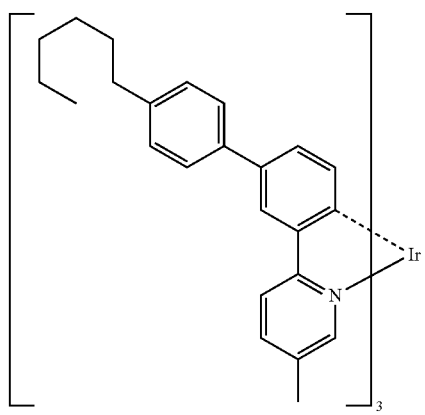

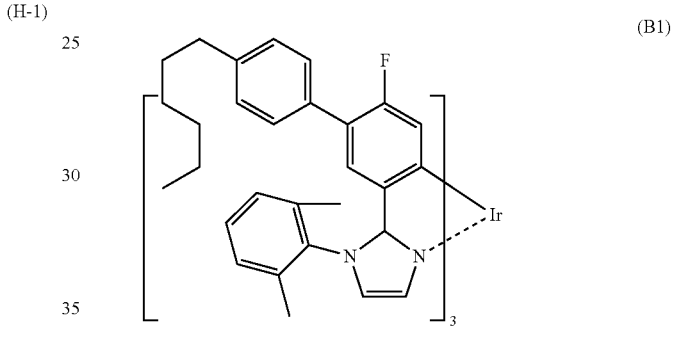

| <Composition for Forming Luminescent Layer> | |
|---|---|
| Solvent | cyclohexylbenzene |
| Composition concentration | H-1: 2.625 wt % |
| | E-1: 0.875 wt % |
| | R1: 0.035 wt % |
| | G1: 0.0245 wt % |
| | B1: 0.35 wt % |

| <Film Formation Condition for Luminescent Layer 5> | |
|---|---|
| Spinner rotation time | 1500 rpm, 120 seconds |
| Heating Condition | 100° C., 10 minutes |

The substrate thus layered up to the luminescent layer 5 was transferred into a vacuum evaporation chamber, the chamber was then degassed to have a vacuum degree of $2.0 \times 10^4$ Pa or less, and thereafter a compound having the following structural formula (HB-1) was deposited on the luminescent layer 5 according to a vacuum vapor deposition method at a vapor deposition rate of from 0.8 to 1.2 angstrom/sec, thereby forming thereon a hole-blocking layer 6 having a thickness of 10 nm.

[Chem. 77]

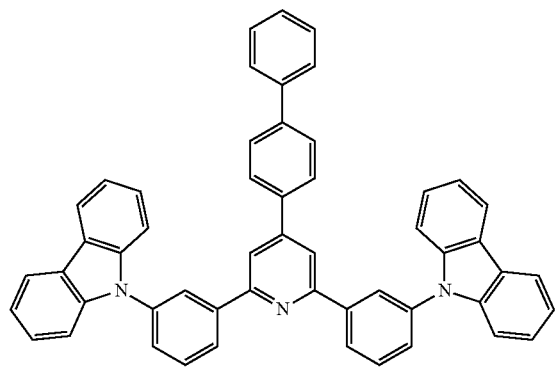

(HB-1)

Further, an organic compound (Y1) having the following structure was deposited on the hole-blocking layer 6 according to a vacuum vapor deposition method at a vapor deposition rate of from 0.8 to 1.2 angstrom/sec, thereby forming thereon an electron transport layer 7 having a thickness of 20 nm.

[Chem. 78]

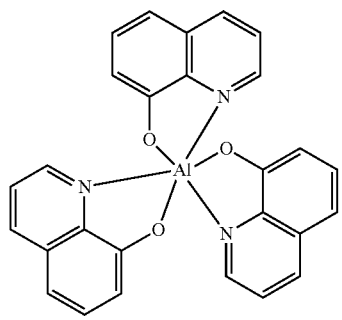

(Y1)

Here, a stripy shadow mask in which each stripe has a width of 2 mm, as a mask for cathode vapor deposition was airtightly stuck to the electron transport layer 7 of the substrate thus layered through vapor deposition up to the electron transport layer 7, in such a manner that the stripe pattern of the mask could be orthogonal to the ITO stripe pattern of the anode 2, then the substrate was transferred into a vacuum evaporation chamber, which was then degassed to have a vacuum degree of $2.0 \times 10^{-4}$ Pa or less.

As an electron injection layer 8, first, lithium fluoride (LiF) was formed on the electron transport layer 7 using a molybdenum boat and at a vapor deposition rate of from 0.1 to 0.4 angstrom/sec, thereby having a thickness of 0.5 nm. Next, as a cathode 9, aluminium was heated similarly in a molybdenum boat and evaporated at a vapor deposition rate of from 0.7 to 5.3 angstrom/sec, thereby forming an aluminium layer having a thickness of 80 nm.

Subsequently, for preventing the element from being degraded by moisture or the like in air during storage, the element was sealed up according to the method mentioned below. In a nitrogen glove box, a photocurable resin (Three Bond's 30Y-437) was applied to the outer peripheral part of a glass plate having a size of 23 mm×23 mm, in a width of 1 mm therearound, and a moisture getter sheet (by Dynic) was put in the center part of the plate. To this, the substrate that had been layered to have the cathode thereon was stuck in such a manner that the vapor-deposited surface thereof could face the desiccant sheet. Subsequently, only the region coated with the photocurable resin was irradiated with UV rays to cure the resin.

In the manner as above, an organic electroluminescent element having a light emission area part size of 2 mm×2 mm was produced.

The characteristics of the element are shown in Table 1.

Example 2

An organic electroluminescent element was produced in the same manner as in Example 1, except that a composition for forming luminescent layer containing the following compound (H-2) in addition to the compounds (H-1) and (E-1) as the charge-transporting materials therein and prepared to have the formulation mentioned below was used. The characteristics of the element are shown in Table 1.

[Chem. 79]

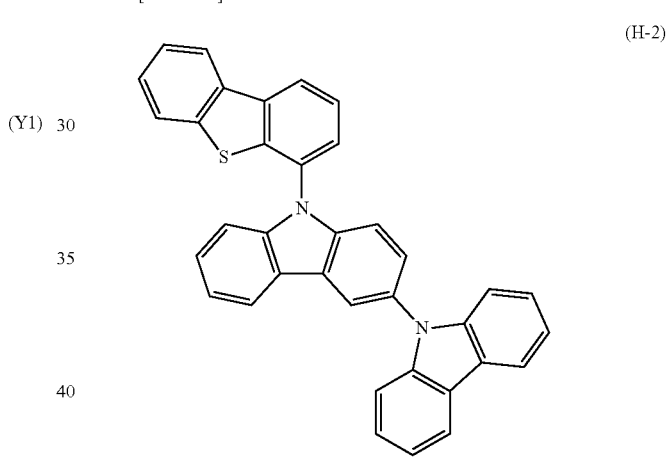

(H-2)

| <Composition for Forming Luminescent Layer> | |
| --- | --- |
| Solvent | cyclohexylbenzene |
| Composition concentration | H-1: 1.313 wt % |
| | H-2: 1.313 wt % |
| | E-1: 0.875 wt % |
| | R1: 0.035 wt % |
| | G1: 0.0245 wt % |
| | B1: 0.35 wt % |

Example 3

An organic electroluminescent element was produced in the same manner as in Example 1, except that a composition for forming luminescent layer containing the following compound (H-3) in addition to the compounds (H-1) and (E-1) as the charge-transporting materials therein and prepared to have the formulation mentioned below using the following compound (B2) in place of the compound (B1) as the luminescent material was used. The characteristics of the element are shown in Table 1.

[Chem. 80]

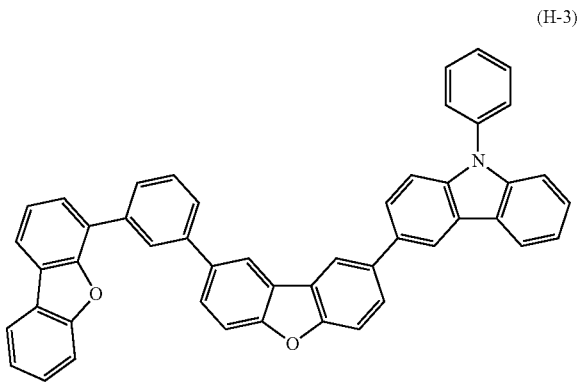
(H-3)

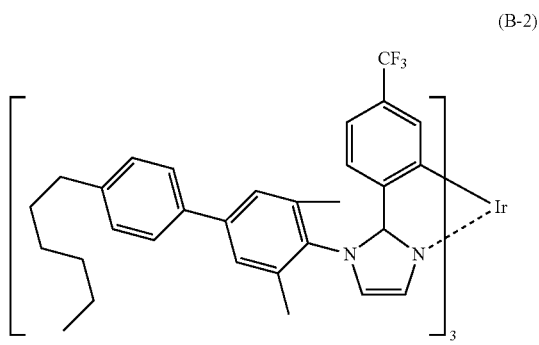
(B-2)

| <Composition for Forming Luminescent Layer> | |
|---|---|
| Solvent | cyclohexylbenzene |
| Composition concentration | H-1: 1.313 wt % |
| | H-3: 1.313 wt % |
| | E-1: 0.875 wt % |
| | R1: 0.035 wt % |
| | G1: 0.0245 wt % |
| | B2: 0.35 wt % |

Comparative Example 1

An organic electroluminescent element was produced in the same manner as in Example 1, except that a composition for forming luminescent layer not containing the compound (H-1) as the charge-transporting material but having the formulation mentioned below was used. The characteristics of the element are shown in Table 1.

| <Composition for Forming Luminescent Layer> | |
|---|---|
| Solvent | cyclohexylbenzene |
| Composition concentration | E-1: 3.5 wt % |
| | R1: 0.035 wt % |
| | G1: 0.0245 wt % |
| | B1: 0.35 wt % |

Comparative Example 2

An organic electroluminescent element was produced in the same manner as in Example 1, except that a composition for forming luminescent layer not containing the compound (E-1) as the charge-transporting material but having the formulation mentioned below was used. The characteristics of the element are shown in Table 1.

| <Composition for Forming Luminescent Layer> | |
|---|---|
| Solvent | cyclohexylbenzene |
| Composition concentration | H-1: 3.5 wt % |
| | R1: 0.035 wt % |
| | G1: 0.0245 wt % |
| | B1: 0.35 wt % |

The meanings of the terms in the following Tables 1 to 3 are as follows.

Efficiency Factor:

This means a relative efficiency based on the efficiency on 10 mA current impression in Comparative Example 1 (Table 1), Comparative Example 3 (Table 2) and Comparative Example 4 (Table 3) standardized as 1.00 cd/W.

Maximum Light Emission Wavelength:

This is the maximum wavelength in the spectrum appearing between 400 nm and 800 nm during constant voltage impression.

TABLE 1

| | Efficiency Factor | Maximum Light Emission Wavelength (nm) | | |
|---|---|---|---|---|
| Example 1 | 1.41 | 594 | 514 | 464 |
| Example 2 | 1.41 | 598 | 514 | 462 |
| Example 3 | 2.44 | 598 | 518 | 490 |
| Comparative Example 1 | 1.00 | 594 | 516 | 458 |
| Comparative Example 2 | 0.49 | 596 | 512 | 462 |

Example 4

An organic electroluminescent element was produced in the same manner as in Example 1, except that the following compound HIT-3) was used in place of the compound (HIT-2) in the composition for forming hole transport layer. The characteristics of the element are shown in Table 2.

[Chem. 81]

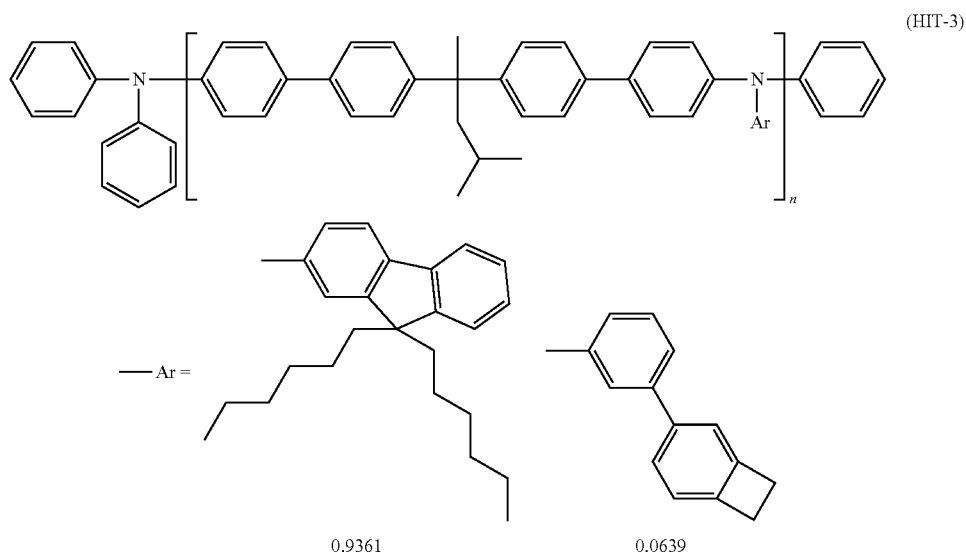

(HIT-3)

| <Composition for Forming Luminescent Layer> | |
|---|---|
| Solvent | cyclohexylbenzene |
| Composition concentration | H-1: 2.625 wt % |
|  | E-1: 0.875 wt % |
|  | R1: 0.035 wt % |
|  | G1: 0.0245 wt % |
|  | B1: 0.35 wt % |

Example 5

An organic electroluminescent element was produced in the same manner as in Example 4, except that a composition for forming luminescent layer was prepared to have the following formulation containing the following compounds (H-4), (E-2) and (B3) in place of the compounds (H-1), (E-1) and (B1). The characteristics of the element are shown in Table 2.

[Chem. 82]

(H-4)

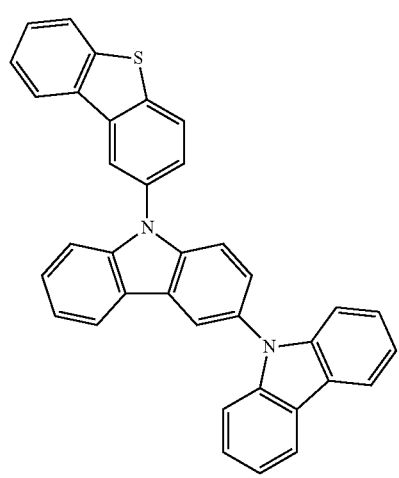

-continued (E-2)

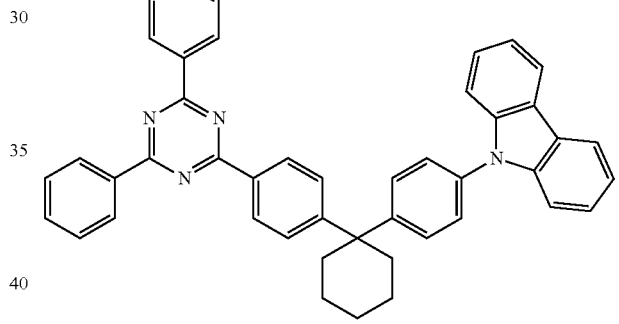

(B3)

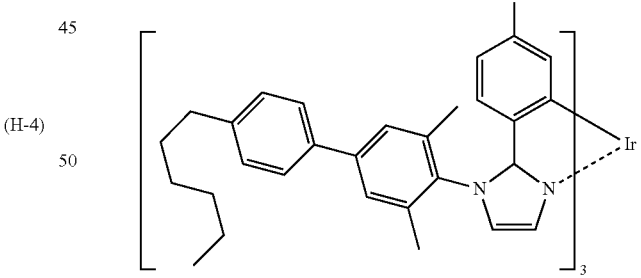

| <Composition for Forming Luminescent Layer> | |
|---|---|
| Solvent | cyclohexylbenzene |
| Composition concentration | H-4: 2.625 wt % |
|  | E-2: 0.875 wt % |
|  | R1: 0.035 wt % |
|  | G1: 0.0245 wt % |
|  | B3: 0.35 wt % |

Example 6

An organic electroluminescent element was produced in the same manner as in Example 5, except that a composition for forming luminescent layer, as prepared to have the following formulation containing the compound (H-3) and the following compound (E-3) in place of the compounds (H-4) and (E-2), was used. The characteristics of the element are shown in Table 2.

| <Composition for Forming Luminescent Layer> | |
|---|---|
| Solvent | cyclohexylbenzene |
| Composition concentration | H-3: 2.625 wt % |
| | E-3: 0.875 wt % |
| | R1: 0.035 wt % |
| | G1: 0.0245 wt % |
| | B3: 0.35 wt % |

[Chem. 83]

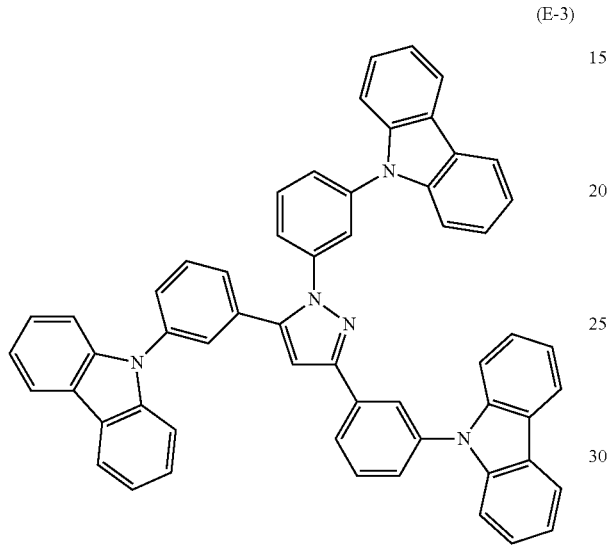

(E-3)

Example 7

An organic electroluminescent element was produced in the same manner as in Example 4, except that a compound (HIT-5) was used in place of the compound (HIT-2) for the hole transport layer 4 and a compound (H-4) was used in place of the compound (H-3) for the luminescent layer. The characteristics of the element are shown in Table 2.

[Chem. 84]

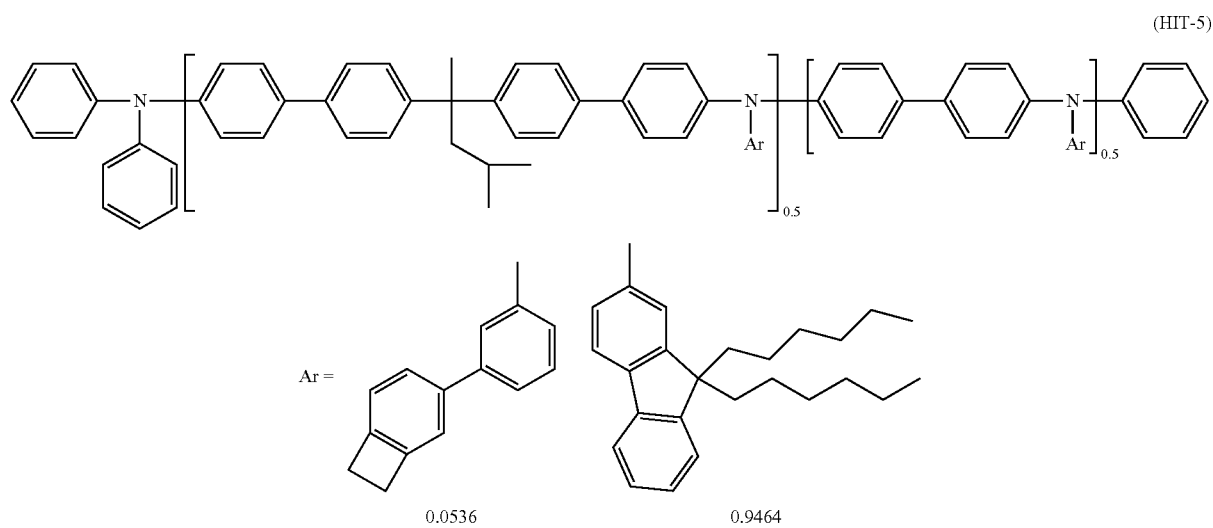

(HIT-5)

<Composition for Forming Luminescent Layer>

| Solvent | cyclohexylbenzene |
|---|---|
| Composition concentration | H-4: 2.625 wt % |
| | E-1: 0.875 wt % |
| | R1: 0.035 wt % |
| | G1: 0.0245 wt % |
| | B1: 0.35 wt % |

Comparative Example 3

An organic electroluminescent element was produced in the same manner as in Example 5, except that the following composition for forming luminescent layer was used. The characteristics of the element are shown in Table 2.

<Composition for Forming Luminescent Layer>

| Solvent | cyclohexylbenzene |
|---|---|
| Composition concentration | H-4: 3.5 wt % |
| | R1: 0.035 wt % |
| | G1: 0.0245 wt % |
| | B1: 0.35 wt % |

Comparative Example 4

An organic electroluminescent element was produced in the same manner as in Example 4, except that the following composition for forming luminescent layer was used. The characteristics of the element are shown in Table 2.

<Composition for Forming Luminescent Layer>

| Solvent | cyclohexylbenzene |
|---|---|
| Composition concentration | H-1: 3.5 wt % |
| | R1: 0.035 wt % |
| | G1: 0.0245 wt % |
| | B1: 0.35 wt % |

TABLE 2

| | Efficiency Factor | Maximum Light Emission Wavelength (nm) | | |
|---|---|---|---|---|
| Example 4 | 1.56 | 594 | 514 | 464 |
| Example 5 | 1.93 | 596 | 516 | — |
| Example 6 | 1.03 | 596 | 516 | 464 |
| Example 7 | 1.58 | 596 | 516 | 464 |
| Comparative Example 3 | 1.00 | 598 | 514 | 462 |
| Comparative Example 4 | 0.91 | 598 | 514 | 462 |

Example 8

An organic electroluminescent element was produced in the same manner as in Example 1, except that a compound (HIT-4) shown below was used in place of the compound (HIT-2) in the composition for forming hole transport layer. The characteristics of the element are shown in Table 3.

[Chem. 85]

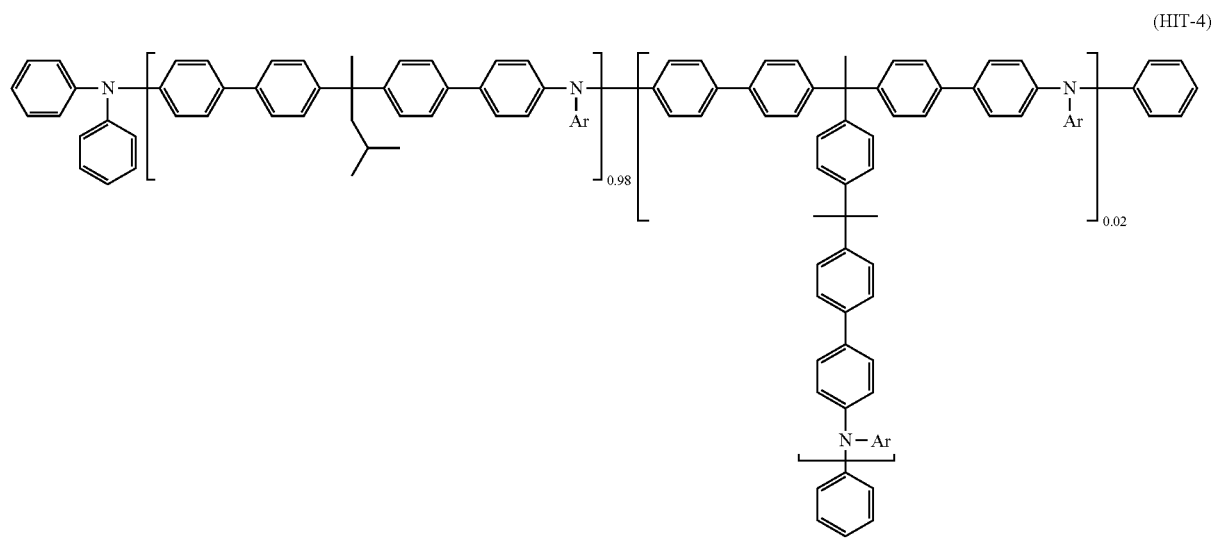

(HIT-4)

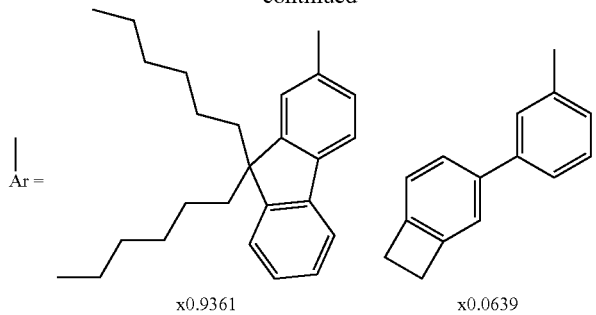

| <Composition for Forming Luminescent Layer> | |
|---|---|
| Solvent | cyclohexylbenzene |
| Composition concentration | H-1: 2.625 wt % |
| | E-1: 0.875 wt % |
| | R1: 0.035 wt % |
| | G1: 0.0245 wt % |
| | B1: 0.35 wt % |

Example 9

An organic electroluminescent element was produced in the same manner as in Example 8, except that the composition for forming luminescent layer, as prepared to have the following formulation containing the following compound (H-4), compound (E-4) and compound (B3) in place of the compounds (H-1), (E-1) and (B1), was used. The characteristics of the element are shown in Table 3.

[Chem. 86]

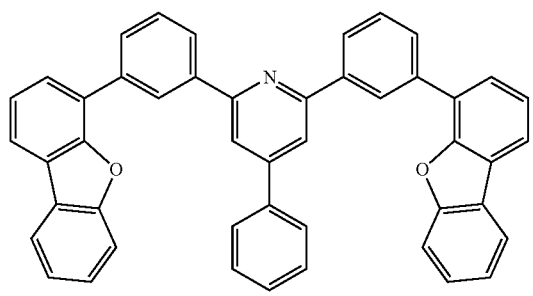

(E-4)

| <Composition for Forming Luminescent Layer> | |
|---|---|
| Solvent | cyclohexylbenzene |
| Composition concentration | H-4: 2.625 wt % |
| | E-4: 0.875 wt % |
| | R1: 0.035 wt % |
| | G1: 0.0245 wt % |
| | B3: 0.35 wt % |

Comparative Example 5

An organic electroluminescent element was produced in the same manner as in Example 8, except that the following composition for forming luminescent layer was used. The characteristics of the element are shown in Table 3.

| <Composition for Forming Luminescent Layer> | |
|---|---|
| Solvent | cyclohexylbenzene |
| Composition concentration | E-4: 3.5 wt % |
| | R1: 0.035 wt % |
| | G1: 0.0245 wt % |
| | B1: 0.35 wt % |

Comparative Example 6

An organic electroluminescent element was produced in the same manner as in Example 8, except that the following composition for forming luminescent layer was used. The characteristics of the element are shown in Table 3.

| <Composition for Forming Luminescent Layer> | |
|---|---|
| Solvent | cyclohexylbenzene |
| Composition concentration | H-4: 3.5 wt % |
| | R1: 0.035 wt % |
| | G1: 0.0245 wt % |
| | B3: 0.35 wt % |

TABLE 3

| | Efficiency Factor | Maximum Light Emission Wavelength (nm) | | |
|---|---|---|---|---|
| Example 8 | 1.36 | 594 | 516 | 464 |
| Example 9 | 1.05 | 598 | 514 | 458 |
| Comparative Example 5 | 1.00 | 596 | 516 | 458 |
| Comparative Example 6 | 0.88 | 598 | 514 | 460 |

From the above results, it is known that all the elements of Examples using both a hole-transporting material and an electron-transporting material as the charge-transporting materials in the luminescent layer and using at least three luminescent materials each had at least two maximum light emission wavelengths, and as compared with those of Comparative Examples, the elements of Examples have an increased efficiency.

While the present invention has been described in detail with reference to specific embodiments thereof, it will be apparent to one skilled in the art that various changes and modifications can be made therein without departing from the spirit and scope thereof. The present application is based on a Japanese patent application (Application No. 2012-118717) filed on May 24, 2012, the contents of which are incorporated herein by reference.

REFERENCE SIGNS LIST

1 Substrate
2 Anode
3 Hole Injection Layer
4 Hole Transport Layer
5 Luminescent Layer
6 Hole-Blocking Layer
7 Electron Transport Layer
8 Electron Injection Layer
9 Cathode
10 Organic Electroluminescent Element

The invention claimed is:

1. An organic electroluminescent element, comprising:
an anode;
a cathode; and
a luminescent layer between the anode and the cathode,
wherein at least the luminescent layer is formed according to a wet film formation method, and contains a charge-transporting material and a luminescent material, in which the charge-transporting material includes a hole-transporting material and an electron-transporting material each having a partial structure represented by formula (2-A) or formula (2-B),
wherein the luminescent material includes three or more kinds of luminescent materials of phosphorescent organic metal complex compounds, and the combination of the basic skeleton of the ligands in the individual organic metal complex compounds have differs between the three or more kinds of the organic metal complex compounds,
wherein the luminescent material has an emission spectrum having at least two kinds of emission maximums, and
wherein the organic electroluminescent element comprises a hole injecting and transporting layer provided between the anode and the luminescent layer and adjacent to the luminescent layer:

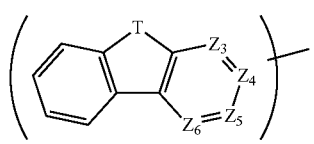

(2-A)

wherein, in formula (2-A):
T represents an atom or an atomic group selected from —O—, —S—, —C(Ar$^{21}$)(Ar$^{22}$)—, —N(Ar$^{23}$)—, and —Si(Ar$^{24}$)(Ar$^{25}$)—, wherein Ar$^{21}$ to Ar$^{25}$ each independently represent a hydrogen atom, or an aromatic ring group having from 3 to 30 carbon atoms and optionally having a substituent, (Ar$^{21}$ and Ar$^{22}$) and (Ar$^{24}$ and Ar$^{25}$) may bond to each other to form a ring structure; and $Z_3$ to $Z_6$ each independently represent a group =CH— or a group =N—

[Chem. 2]

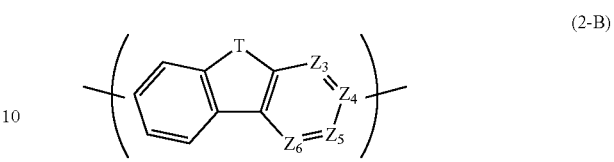

(2-B)

wherein, in formula (2-B):
T represents an atom or an atomic group selected from —O—, —S—, —C(Ar$^{26}$)(Ar$^{27}$)—, —N(Ar$^{28}$)—, and —Si(Ar$^{29}$)(Ar$^{30}$)—, wherein Ar$^{26}$ to Ar$^{30}$ each independently represent a hydrogen atom, or an aromatic ring group having from 3 to 30 carbon atoms and optionally having a substituent, (Ar$^{26}$ and Ar$^{27}$) and (Ar$^{29}$ and Ar$^{30}$) may bond to each other to form a ring structure; and
$Z_3$ to $Z_6$ each independently represent a group =CH— or a group =N—.

2. The organic electroluminescent element of claim 1, wherein the hole-transporting material and the electron-transporting material have the same partial structure, and the same partial structure is a structure represented by the formula (2-A) or the formula (2-B).

3. The organic electroluminescent element of claim 1, wherein all the organic metal complex compounds have a ligand having a basic skeleton represented by formula (IIIg), each of which may differ,

[Chem. 3]

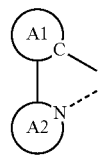

(IIIg)

wherein, in formula (IIIg):
the ring A1 represents any of a benzene ring, a naphthalene ring, a benzothiophene ring or a phenanthrene ring; and
the ring A2 represents any of a pyridine ring, a quinoline ring, an isoquinoline ring, a quinoxaline ring, a quinazoline ring, a pyrrole ring, an imidazole ring, a benzothiazole ring or a benzisoquinoline ring.

4. The organic electroluminescent element of claim 1, wherein at least one basic skeleton of the ligands of the organic metal complex compounds is selected from a group consisting of a phenylpyridine skeleton, a phenylquinoline skeleton, a phenylisoquinoline skeleton and a phenylimidazole skeleton.

5. The organic electroluminescent element of claim 1, wherein all the basic skeletons of the ligands of at least two organic metal complex compounds of the three or more organic metal complex compounds are selected from a phenylpyridine skeleton, a phenylquinoline skeleton, a phenylisoquinoline skeleton and a phenylimidazole skeleton.

6. The organic electroluminescent element of claim 1, wherein the hole injecting and transporting layer adjacent to the luminescent layer contains an arylamine polymer compound.

7. The organic electroluminescent element of claim 6, wherein the arylamine polymer compound contains a repeating unit having a partial structure represented by formula (10-C):

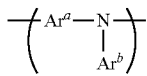

(10-C)

wherein, in formula (10-C):

$Ar^a$ and $Ar^b$ each independently represent an aromatic ring group optionally having a substituent, and in each of the repeating units, $Ar^a$ and $Ar^b$ may differ from each other.

8. The organic electroluminescent element of claim 6, wherein the arylamine polymer compound contains a repeating unit having a partial structure represented by formula (10-A):

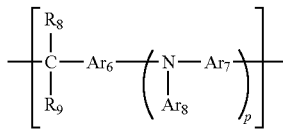

(10-A)

wherein, in formula (10-A):

$Ar_6$ and $Ar_7$ each independently represent a divalent aromatic ring group optionally having a substituent;

$Ar_8$ represents an aromatic ring group optionally having a substituent;

$R_8$ and $R_9$ each independently represent a hydrogen atom, an alkyl group optionally having a substituent, an alkoxy group optionally having a substituent, or an aromatic ring group optionally having a substituent;

$R_8$ and $R_9$ may bond to each other to form a ring;

p indicates an integer of from 1 to 5; and when formula (10-A) has plural $Ar_6$'s to $Ar_8$'s, $R_8$'s and $R_9$'s, these plural substituents may be the same or different.

9. The organic electroluminescent element of claim 6, wherein the arylamine polymer compound contains a repeating unit having a partial structure represented by formula (10-B):

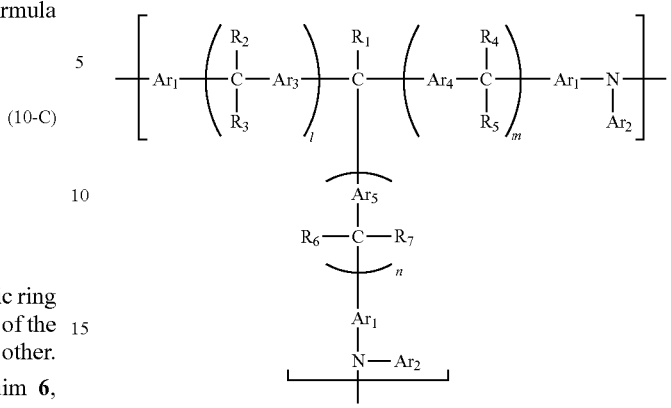

(10-B)

wherein, in formula (10-B);

$Ar_1$, $Ar_3$, $Ar_4$ and $Ar_5$ each independently represent a divalent aromatic ring group optionally having a substituent;

$Ar_2$ represents an aromatic ring group optionally having a substituent;

$R_1$ represents an alkyl group optionally having a substituent or an alkoxy group optionally having a substituent;

$R_2$ to $R_7$ each independently represent a hydrogen atom, an alkyl group optionally having a substituent, an alkoxy group optionally having a substituent, or an aromatic ring group optionally having a substituent, $R_2$ and $R_3$ may bond to each other to form a ring;

$R_4$ and $R_5$ may bond to each other to form a ring;

$R_6$ and $R_7$ may bond to each other to form a ring;

l, m and n each independently indicate an integer of from 0 to 2; and when formula (10-B) has plural $Ar_1$'s to $Ar_5$', $R_1$'s to $R_7$'s, these plural substituents may be the same or different.

10. The organic electroluminescent element of claim 1, which comprises at least two hole injecting and transporting layers between the anode and the luminescent layer.

11. A display device comprising the organic electroluminescent element of claim 1.

12. A lighting device comprising the organic electroluminescent element of claim 1.

13. The organic electroluminescent element of claim 1, wherein the luminescent material has at least three maximum emission wavelengths, wherein a first maximum emission wavelength is in the region of from 440 to 500 nm, a second maximum emission wavelength is in the region of from 510 to 590 nm, and a third maximum emission wavelength is in the region of from 570 to 660 nm.

* * * * *